US012708661B2

(12) United States Patent
Kalinichev

(10) Patent No.: US 12,708,661 B2
(45) Date of Patent: Aug. 18, 2026

(54) TREATMENT OF BRAIN DAMAGE

(71) Applicant: Ipsen Biopharm Limited, Wrexham (GB)

(72) Inventor: Mikhail Kalinichev, Wrexham (GB)

(73) Assignee: Ipsen Biopharm Limited, Wrexham (GB)

( * ) Notice: Subject to any disclaimer, the term of this patent is extended or adjusted under 35 U.S.C. 154(b) by 323 days.

(21) Appl. No.: 18/261,402

(22) PCT Filed: Jan. 14, 2022

(86) PCT No.: PCT/GB2022/050077
§ 371 (c)(1),
(2) Date: Jul. 13, 2023

(87) PCT Pub. No.: WO2022/153057
PCT Pub. Date: Jul. 21, 2022

(65) Prior Publication Data

US 2024/0082368 A1 Mar. 14, 2024

(30) Foreign Application Priority Data

Jan. 15, 2021 (GB) ..................................... 2100566

(51) Int. Cl.
*A61K 38/48* (2006.01)

(52) U.S. Cl.
CPC .. *A61K 38/4893* (2013.01); *C12Y 304/24069* (2013.01)

(58) Field of Classification Search
CPC .... A61K 38/4893; A61K 39/00; A61K 39/08; A61K 35/30
See application file for complete search history.

(56) References Cited

U.S. PATENT DOCUMENTS

| | | | | |
|---|---|---|---|---|
| 6,306,403 | B1 | 10/2001 | Donovan | |
| 10,780,149 | B2 | 9/2020 | Marinelli et al. | |
| 2001/0005337 | A1 | 6/2001 | Jung | |
| 2001/0053370 | A1 | 12/2001 | Donovan | |
| 2003/0021112 | A1 | 1/2003 | Gladnick | |
| 2003/0211121 | A1 | 11/2003 | Donovan | |
| 2006/0286127 | A1* | 12/2006 | Van Schaack | A61P 29/00 424/239.1 |
| 2007/0218084 | A1 | 9/2007 | Caleo et al. | |
| 2019/0224288 | A1 | 7/2019 | Marinelli et al. | |

FOREIGN PATENT DOCUMENTS

| | | | |
|---|---|---|---|
| EP | 2246065 | A1 | 11/2010 |
| RU | 2299674 | C2 | 5/2007 |
| WO | 0178760 | A2 | 10/2001 |
| WO | 0195924 | A2 | 12/2001 |
| WO | WO 2007/044809 | A2 * | 4/2007 |
| WO | 2014113539 | A1 | 7/2014 |
| WO | WO 2017191315 | A1 * | 11/2017 |
| WO | 2020115490 | A1 | 6/2020 |
| WO | 2021/007165 | A1 | 1/2021 |
| WO | 2021/064369 | A1 | 4/2021 |
| WO | 2022153057 | A1 | 7/2022 |

OTHER PUBLICATIONS

Traumatic brain injury; Mayo Clinic, https://www.mayoclinic.org/diseases-conditions/traumatic-brain-injury/diagnosis-treatment/drc-20378561#treatment; Feb. 4, 2021 (Year: 2021).*

Neurologic complications; Barrow Neurological Institute, https://www.barrowneuro.org/condition/neurologic-complications-of-cancer/#neurologic-complications-of-cancer-treatments, accessed Sep. 5, 2025, (Year: 2025).*

Neurodegenerative diseases, The Cleveland Clinic, https://my.clevelandclinic.org/health/diseases/24976-neurodegenerative-diseases#management-and-treatment, May 10, 2023 (Year: 2023).*

Sara Marinelli et al., The Analgesic Effect on Neuropathic Pain of Retrogradely Transported Botulinum Neurotoxin A Involves Schwann Cells and Astrocytes, 7 PLOS One e47977 (2012).

Cesare Montecucco & Giampietro Schiavo, Mechanism of Action of Tetanus and Botulinum Neurotoxins, 13 Molecular Microbiology 1 (1994).

ISR for International Application No. PCT/GB2022/050077, mailed Mar. 25, 2022.

"Neuroimmune Communication", Nat Neurosci. (Editorial), vol. 20, No. 2, Feb. 2017, p. 127, DOI: 10.1038/nn.4496 (1 page).

"Pharmacology", Textbook [in Russian w/ English Translation], Ed. A.A. Svistunov and V. V. Tarasov, Moscow: Laboratory of Knowledge, 2017, pp. 55-56 (6 pages).

Davis, Benjamin M., et al., "Characterizing microglia activation: A spatial statistics approach to maximize information extraction", Sci Rep., vol. 7, No. 1, May 2017, Article ID 1576, DOI: 10.1038/s41598-017-01747-8 (12 pages).

Grishanova, T. G., et al., "Pathogenesis, Markers of Brain Injury and Integral Evaluation of Condition of Patients with Severe Combined Traumas", Meditsina v Kuzbasse [in Russian], No. 3, 2010, pp. 3-8 (6 pages), abstract translated only.

Kharkevich, D. A., "Pharmacology [Farmakologiya]", Textbook [in Russian w/ English Translation], 10th Ed., Moscow: GEOTAR-Media, 2010, pp. 73-74 (8 pages pages).

Legland, David, et al., "MorphoLibJ: Integrated library and plugins for mathematical morphology with ImageJ", Bioinformatics, vol. 32, No. 22, Nov. 2016, pp. 3532-3534, DOI: 10.1093/bioinformatics/btw413 (3 pages).

Marinelli, Sara, et al., "The analgesic effect on neuropathic pain of retrogradely transported botulinum neurotoxin A involves Schwann cells and astrocytes", PLoS One, vol. 7, No. 10, Oct. 2012, Article ID e47977, DOI: 10.1371/journal.pone.0047977 (12 pages).

Montecucco, Cesare, et al., "Mechanism of action of tetanus and botulinum neurotoxins", Mol Microbiol., vol. 13, No. 1, Jul. 1994, pp. 1-8, DOI: 10.1111/j.1365-2958.1994.tb00396.x (9 pages).

Nimmerjahn, Axel, et al., "Resting microglial cells are highly dynamic surveillants of brain parenchyma in vivo", Science, vol. 308, No. 5726, May 2005, pp. 1314-1318, DOI: 10.1126/science.1110647 (6 pages).

(Continued)

*Primary Examiner* — Brian Gangle
*Assistant Examiner* — Lakia J Jackson-Tongue
(74) *Attorney, Agent, or Firm* — Proskauer Rose LLP

(57) ABSTRACT

The present invention provides a clostridial neurotoxin for use in a method of treating a brain disorder in a patient by promoting a neuroimmune response.

20 Claims, 3 Drawing Sheets

Specification includes a Sequence Listing.

(56) References Cited

OTHER PUBLICATIONS

Semenova, V. G., et al., "Multiple causes in cases of death from trauma and poisoning", Social Aspects of Population Health [in Russian w/ English Translation], vol. 53, No. 1, 2017, DOI: 10.21045/2071-5021-2017-53-1-7 (56 pages).

Sychyova, M. A., et al., "Organic Lesions of the Brain", Textbook [in Russian w/ English Translation], Novosibirsk: NSU Publishing Center, 2015, pp. 3-4, ISBN: 978-5-4437-0392-3 (6 pages).

Szalay, Gergely, et al., "Microglia protect against brain injury and their selective elimination dysregulates neuronal network activity after stroke", Nat Commun., vol. 7, Article ID 11499, May 2016, DOI: 10.1038/ncomms11499 (13 pages).

* cited by examiner

TREATMENT OF BRAIN DAMAGE

FIELD OF THE INVENTION

The present invention relates to the treatment of brain disorders, more particularly by promoting activity of a neuroimmune response at a site of brain tissue damage.

BACKGROUND

Brain disorders typically result from damage or injury to neural tissue, and such damage can be a principal cause of the symptoms underlying or defining a neurological disorder. By way of example, when a patient suffers a stroke, a blood vessel in the brain becomes blocked or bursts (e.g. hemorrhages). Thus, nerve cells in the brain tissue, depleted of oxygen, which would otherwise be provided by a healthy blood supply, become injured or die, impairing nerve cell activity. Such lack of nerve activity can lead to symptoms including muscle weakness, paralysis, lost sensation on one side of the body, difficulty speaking, confusion, problems with vision, dizziness, loss of balance and coordination, and, in some hemorrhagic strokes, a sudden, severe headache.

In a further example, infectious disease of the brain can lead to cell death underlying brain tissue damage. In bacterial meningitis, bacteria such as *Streptococcus pneumoniae* can invade the meninges (membranes that help protect brain and spinal cord tissue from injury), with subsequent damage to the meninges resulting in nerve cell death. If a virus reaches and affects the brain, nerve tissue damage can be caused by virus lytic effects on brain cells (e.g. in the case of cytomegalovirus), induced apoptosis (e.g. in the case of vesicular stomatitis virus, VSV), or secondary damage due to release of glutamate, DNA, and other inducers of brain damage.

In a patient suffering brain cancer, tumors can cause physical damage to nerve tissue in the brain by pressing against and applying pressure to nerve cells. Damage can also be caused by tumor movement in metastatic cases.

While there exist treatment options to alleviate patient symptoms arising from such nerve damage, comparatively few of these function in a way that promote repair (else facilitates said repair) of the actual damage to the nerve tissue. For example, in stroke, the only therapeutic options are local recanalization and systemic thrombolysis (which aim to restore blood flow to mitigate nerve damage). However, such therapeutic options are not suitable for all patients, and/or may cause yet further damage.

The present invention solves one or more of the above-mentioned problems.

SUMMARY OF THE INVENTION

In more detail, the present invention is predicated upon the surprising finding that a clostridial neurotoxin, when administered to a patient suffering brain disorder-induced damage to tissue of the nervous system, promotes immune cell (e.g. neuroimmune cell) activity in the area of neural tissue damage. In other words, a clostridial neurotoxin may surprisingly by used to promote neuroimmune activity as a means to prevent/repair damage to neural tissue in a patient suffering a brain disorder.

More particularly, it is demonstrated herein that the activity of microglia (located in the vicinity of an area of brain tissue damage) is promoted in a patient that has received a dose of clostridial neurotoxin. Microglia are key macrophages of the brain involved in clearing damaged nerve tissue and foreign bodies. This represents a surprising utility of clostridial neurotoxins, which are introduced below.

Bacteria in the genus Clostridia produce highly potent and specific protein toxins, which can (temporarily) impair function of neurons and other cells to which they are delivered. Examples of such clostridial toxins include the neurotoxins produced by *C. tetani* (TeNT) and by *C. botulinum* (BoNT) serotypes A-G, and X (see WO 2018/009903 A2), as well as those produced by *C. baratii* and *C. butyricum.*

Among the clostridial neurotoxins are some of the most potent toxins known. By way of example, botulinum neurotoxins have median lethal dose ($LD_{50}$) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Clostridial neurotoxins provide non-cytotoxic protease activity. Non-cytotoxic proteases act by proteolytically cleaving intracellular transport proteins known as SNARE proteins (e.g. SNAP-25, VAMP, or Syntaxin). The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins.

In view of the ubiquitous nature of SNARE proteins, clostridial neurotoxins such as botulinum toxin have been successfully employed in a wide range of therapies. The inventors have demonstrated a surprising utility of clostridial neurotoxins in treating brain disorders by promoting neuroimmune activity.

A common feature of brain disorders is that the host's own neuroimmune response reacts to insults underlying the brain disorder by clearing and/or preventing brain tissue damage. In the case of infectious disease, there may be (for example) an innate response in which macrophages (e.g. microglia) migrate to a site of infection and phagocytose the invading pathogen. Macrophages are a type of white blood cell of the immune system that engulf and digest cellular debris, foreign substances, microbes, cancer cells, and other non-host agents, in a process called phagocytosis.

When neuronal cell death occurs, microglia react by migrating to the lesion (damage) site, where they phagocytose cellular debris. Thus, microglia can be reactive to brain disorders by removing brain tissue caused by physical damage (e.g. brain tumors). For example, microglial phagocytosis may clear dead cells, which might otherwise release noxious substances into their environment and thereby exacerbate tissue damage. It has also been reported that microglia play a role in the defense against brain tumors directly. Furthermore, microglia have been reported to be involved in 'synaptic pruning' in which they engulf synaptic material helping to prevent synaptic abnormalities seen in some neurodevelopmental disorders.

Thus, by promoting neuroimmune activity in response to neural tissue damage, clostridial neurotoxin administration advantageously finds utility in treating brain disorders.

DETAILED DESCRIPTION

Broad aspects of the invention provide any of the following:

- a clostridial neurotoxin for use in a method of treating a brain disorder;
- a method of treating a brain disorder in a patient, the method comprising administering a clostridial neurotoxin to the patient;
- use of a clostridial neurotoxin in the manufacture of a medicament to treat a brain disorder in a patient.

Broad aspects of the invention provide any of the following:

- a clostridial neurotoxin for use in a method of treating brain tissue damage (e.g. neural tissue damage);
- a method of treating brain tissue damage (e.g. neural tissue damage) in a patient, the method comprising administering a clostridial neurotoxin to the patient;
- use of a clostridial neurotoxin in the manufacture of a medicament to treat brain tissue damage (e.g. neural tissue damage) in a patient.

Broad aspects of the invention provide any of the following:

- a clostridial neurotoxin for use in a method of treating a brain infection;
- a method of treating a brain infection in a patient, the method comprising administering a clostridial neurotoxin to the patient;
- use of a clostridial neurotoxin in the manufacture of a medicament to treat a brain infection in a patient.

The clostridial neurotoxin may treat the brain disorder by promoting a neuroimmune (e.g. microglial) response. For example, the clostridial neurotoxin may be for use in a method of treating a brain disorder by promoting the neuroimmune (e.g. microglial) response to treat the brain disorder. The clostridial neurotoxin may treat the brain tissue damage (e.g. neural tissue damage) by promoting a neuroimmune (e.g. microglial) response. For example, the clostridial neurotoxin may be for use in a method of treating brain tissue damage (e.g. neural tissue damage) by promoting the neuroimmune (e.g. microglial) response to treat the brain tissue damage (e.g. neural tissue damage).

The clostridial neurotoxin may treat the brain disorder by promoting microglial activity (e.g. in response to neural tissue damage). For example, the clostridial neurotoxin may be for use in a method of treating a brain disorder by promoting microglia activity to treat the brain disorder. The clostridial neurotoxin may treat the brain tissue damage (e.g. neural tissue damage) by promoting a microglial activity (e.g. in response to neural tissue damage). For example, the clostridial neurotoxin may be for use in a method of treating brain tissue damage (e.g. neural tissue damage) by promoting the microglia activity to treat the brain tissue damage (e.g. neural tissue damage).

The clostridial neurotoxin may treat the brain disorder by promoting microglial migration to a site of brain tissue damage (e.g. to neural tissue damage). For example, the clostridial neurotoxin may be for use in a method of treating a brain disorder by promoting microglial migration to a site of brain tissue damage. The clostridial neurotoxin may treat the brain tissue damage (e.g. neural tissue damage) by promoting microglial migration to a site of brain tissue damage (e.g. to neural tissue damage). For example, the clostridial neurotoxin may be for use in a method of treating brain tissue damage (e.g. neural tissue damage) by promoting microglial migration to a site of brain tissue damage (e.g. neural tissue damage) to treat the brain tissue damage.

The clostridial neurotoxin may treat the brain disorder by promoting microglia cell phagocytic activity at a site of brain tissue damage (e.g. neural tissue damage). For example, the clostridial neurotoxin may be for use in a method of treating a brain disorder by promoting microglia cell phagocytic activity at a site of brain tissue damage (e.g. neural tissue damage). The clostridial neurotoxin may treat the brain tissue damage (e.g. neural tissue damage) by promoting microglia cell phagocytic activity at a site of brain tissue damage (e.g. neural tissue damage). For example, the clostridial neurotoxin may be for use in a method of treating brain tissue damage (e.g. neural tissue damage) by promoting microglia cell phagocytic activity at a site of brain tissue damage (e.g. neural tissue damage) to treat the brain tissue damage.

The clostridial neurotoxin may treat the brain disorder by promoting microglial clearance of cellular debris at a site of brain tissue damage (e.g. neural tissue damage). For example, the clostridial neurotoxin may be for use in a method of treating a brain disorder by promoting microglial clearance of cellular debris at a site of brain tissue damage (e.g. neural tissue damage). The clostridial neurotoxin may treat the brain tissue damage (e.g. neural tissue damage) by promoting microglial clearance of cellular debris at a site of brain tissue damage (e.g. neural tissue damage). For example, the clostridial neurotoxin may be for use in a method of treating brain tissue damage (e.g. neural tissue damage) by promoting microglial clearance of cellular debris at a site of brain tissue damage (e.g. neural tissue damage) to treat the brain tissue damage.

The clostridial neurotoxin may treat the brain disorder by promoting a microglia response to an infection. For example, the clostridial neurotoxin may be for use in a method of treating a brain disorder by promoting the microglia response to an infection to treat the brain disorder. The clostridial neurotoxin may treat the brain tissue damage (e.g. neural tissue damage) by promoting a microglia response to an infection. For example, the clostridial neurotoxin may be for use in a method of treating brain tissue damage (e.g. neural tissue damage) by promoting a microglia response to an infection to treat the brain tissue damage (e.g. neural tissue damage).

The clostridial neurotoxin may treat a brain infection by promoting a neuroimmune (e.g. microglial) response. For example, the clostridial neurotoxin may be for use in a method of treating a brain infection by promoting the neuroimmune (e.g. microglial) response to treat the brain infection. The clostridial neurotoxin may treat the brain infection by promoting a neuroimmune (e.g. microglial) response. For example, the clostridial neurotoxin may be for use in a method of treating a brain infection by promoting the neuroimmune (e.g. microglial) response to treat the brain infection.

The clostridial neurotoxin may treat a brain infection by promoting microglia cell activity (e.g. in response to infection). For example, the clostridial neurotoxin may be for use in a method of treating a brain infection by promoting microglia cell activity to treat the brain infection. The clostridial neurotoxin may treat the brain infection by promoting microglia cell activity (e.g. in response to infection). For example, the clostridial neurotoxin may be for use in a method of treating a brain infection by promoting microglia cell activity to treat the brain infection.

The clostridial neurotoxin may treat a brain infection by promoting microglia cell migration to a site of a brain infection. For example, the clostridial neurotoxin may be for use in a method of treating a brain infection by promoting microglia cell migration to a site of a brain infection. The clostridial neurotoxin may treat a brain infection by promoting microglial migration to a site of a brain infection. For example, the clostridial neurotoxin may be for use in a method of treating a brain infection by promoting microglia cell migration to a site of brain infection to treat the brain infection.

The clostridial neurotoxin may treat a brain infection by promoting microglia cell phagocytic activity at a site of brain infection. For example, the clostridial neurotoxin may be for use in a method of treating a brain infection by promoting microglia cell phagocytic activity at a site of brain infection. The clostridial neurotoxin may treat a brain infection by promoting microglia cell phagocytic activity at a site of brain infection. For example, the clostridial neurotoxin may be for use in a method of treating a brain infection by promoting microglia cell phagocytic activity at a site of brain infection to treat the brain infection.

The clostridial neurotoxin may treat a brain infection by promoting microglial clearance of cellular debris at a site of brain infection. For example, the clostridial neurotoxin may be for use in a method of treating a brain infection by promoting microglial clearance of cellular debris at a site of brain infection. The clostridial neurotoxin may treat the brain infection by promoting microglial clearance of cellular debris at a site of brain infection. For example, the clostridial neurotoxin may be for use in a method of treating a brain infection by promoting microglial clearance of cellular debris at a site of brain infection to treat the brain infection.

The clostridial neurotoxin may treat a brain infection by promoting a microglia response to an infection. For example, the clostridial neurotoxin may be for use in a method of treating a brain infection by promoting the microglia response to an infection to treat the brain disorder. The clostridial neurotoxin may treat the brain infection by promoting a microglia response to an infection. For example, the clostridial neurotoxin may be for use in a method of treating a brain infection by promoting a microglia response to an infection to treat the brain infection.

In one aspect there is provided a clostridial neurotoxin for use in a method of treating brain disorder in a patient by promoting a neuroimmune response. In other words, one aspect provides a clostridial neurotoxin for use in promoting a neuroimmune response to treat a brain disorder.

In a related aspect there is provided a method of treating a brain disorder in a patient by promoting a neuroimmune response, the method comprising administering a clostridial neurotoxin to the patient. In other words, one aspect provides a method for promoting a neuroimmune response to treat a brain disorder in a patient, the method comprising administering a clostridial neurotoxin to the patient.

In a further aspect there is provided use of a clostridial neurotoxin in the manufacture of a medicament to treat a brain disorder in a patient, by promoting a neuroimmune response. In other words, one aspect provides use of a clostridial neurotoxin in the manufacture of a medicament for promoting a neuroimmune response to treat a brain disorder in a patient.

Thus, the clostridial neurotoxin described herein promotes a neuroimmune response. As such, clostridial neurotoxin(s) find utility in treating a brain disorder. The term "brain disorder" (which may be used herein synonymously with the term "brain damage") as used herein is a disorder that can be treated by promoting a neuroimmune response in a patient. The brain disorder may be caused by brain tissue damage (e.g. neural tissue damage). Additionally or alternatively, the brain disorder may cause neural tissue damage. As such, the promotion of neuroimmune response activity may have the effect of promoting repair of neural tissue damage, thus enhancing recovery from the brain disorder.

The term "brain tissue damage" may be used synonymously herein with the term "brain tissue injury". Similarly, the term "neural tissue damage" may be used synonymously herein with the term "neural tissue injury".

In one embodiment, the neuroimmune response may be defined as a microglial response. Thus, the clostridial neurotoxin promotes microglial activity in the brain.

Microglia represent a population of macrophage-like cells in the central nervous system (particularly the brain). They are typically considered immune sentinels that are capable of orchestrating a potent inflammatory response. Microglia are also involved in synaptic organization, trophic neuronal support during development, phagocytosis of apoptotic cells in the developing brain, myelin turnover, control of neuronal excitability, phagocytic debris removal as well as brain protection and repair.

In one aspect there is provided a clostridial neurotoxin for use in a method of treating a brain disorder in a patient by promoting microglia activity (e.g. in the brain). In other words, one aspect provides a clostridial neurotoxin for use in promoting microglia activity (e.g. in the brain) to treat a brain disorder. In the context of brain tissue (e.g. neural tissue) damage, microglia activity may be promoted to repair (or clear) damaged tissue. A non-limiting example of microglial cell (e.g. macrophages) activity includes phagocytic activity (e.g. clearance of cellular debris) at a site of the nerve or brain tissue damage.

Thus, without wishing to be bound by theory, one observed effect on which the present invention is predicated is the ability to promote the neuroimmune response's role in responding to neural damage (which may be caused by, or indeed causing, the brain disorder), to clear/repair such damage. Thus, while an individual's endogenous neuroimmune response may already come into action and work to combat neural damage as a matter of course, the present invention provides an advantageous 'boost' to such response, which may correlate with faster onset of the neuroimmune response, increased recruitment of neuroimmune cells to a site of neural damage and/or increased activity of neuroimmune cells toward treating the damage. As an outcome, enhanced recovery from injury (e.g. neural tissue injury) may follow.

To demonstrate such technical effects, the inventors coupled "two-photon" imaging and laser technology with a transgenic mouse model allowing for high-resolution tracking of the activity of the animal's own microglia cells, directly within the in vivo brain setting. The animal model (CX3CR1-GFP mice) express GFP within their microglia cells, allowing the cells to imaging and tracked via fluorescent light microscopy.

In order to induce neural damage representative of that which occurs in a 'brain disorder' (e.g. in a brain infection) described herein, the inventor employed two-photon microscopy technology to provide a distinct focal point of laser-induced injury in the brain. In more detail, a micrometre-size region of interest (ROI) was selected in the focal plane at the depth of 25-35 micrometres from the cortical surface and the laser intensity was applied to this focal region to provide a localised, distinct region of damaged brain tissue. Such distinct region of brain tissue damage emulates that which may occur due to brain hypoxia (e.g. following a stroke), due to a growing brain tumor and/or due to swelling (e.g. encephalitis) following infection, while also allowing investigations of microglia cells around a distinct, space-controlled area of induce tissue damage.

As demonstrated in the examples section, the microglia responded to this damage via migration to the particular site of damage, and adopting a phenotype consistent with phagocytic activity. However, surprisingly, such activity was significantly increased in mice to which a clostridial neurotoxin (e.g. BoNT/A) was administered, demonstrating an unexpected technical effect for clostridial neurotoxins in promoting a patient's neuroimmune response to brain damage.

Thus, the clostridial neurotoxins find utility in enhancing recovery from brain (e.g. neural tissue) damage, and thus can be used to treat a distinct clinical subset of patient requiring brain damage repair. Advantageously, such repair is orchestrated by the patient's own neuroimmune response, which is enhanced/promoted following administration of a clostridial neurotoxin. The step(s) toward providing this effect, namely administration of the clostridial neurotoxin through routes such as intracortical injection, are comparatively (vs brain surgery) achievable and non-invasive techniques. Thus, need for complex surgical intervention (brain surgery) can be mitigated.

Following on from the note that patients suffering brain damage are particularly suited to treatment by the present invention, a yet further clinical subset (or sub-subset) of such patients may be represented by those patients in which the 'endogenous' level of neuroimmune response activity is insufficient to treat the tissue damage. In other words, the presently demonstrated technical effect(s) provided by administration of a clostridial neurotoxin provide particular clinical utility in patients that would benefit from a 'boost' in their neuroimmune response (to injury) in order to improve their prognosis vs that which would follow when relying on the patients' endogenous level of neuroimmune response.

Such utility contrasts with the purported function of clostridial neurotoxins in prior art methods employing such neurotoxins for treating brain disorders. Since clostridial neurotoxins function to cleave SNARE proteins and suppress neurotransmitter secretion (as explained in detail elsewhere herein), prior art methods have sought to suppress neuronal activity in the brain via administration of clostridial neurotoxin, in order to effect neurotoxin-mediated prevention of neurotransmitter release. For example, it has been proposed to target neurotoxins to regions of the brain showing 'abnormal' activity in epilepsy, in order to suppress such abnormal activity which may otherwise correlate with seizure. Other prior art has proposed to target (and suppress) otherwise hyperactive inhibitory cholinergic neurons (e.g. present in the striatum of brain) to suppress neural activity correlating with movement disorders.

However, such prior art methods did not involve repair of tissue damage, let alone via clostridial neurotoxin-induced promotion of neuroimmune cell activity. Instead of suppressing neuronal activity, the present invention is directed to removal/repair of damaged neurons. Thus, the invention is directed to treating brain disorders via treating brain tissue damage; more particularly, via promoting neuroimmune cell activity in treating such damage.

Thus, not only has the present inventor identified a new technical field of application (i.e. brain disorders associated with brain tissue damage) for clostridial neurotoxins, but also identified an unexpected technical effect within said field (i.e. promotion of the neuroimmune response). In a related aspect there is provided a method of treating a brain disorder in a patient by promoting microglia activity (e.g. in the brain), the method comprising administering a clostridial neurotoxin to the patient. In other words, one aspect provides a method for promoting microglia activity (e.g. in the brain) to treat a brain disorder in a patient, the method comprising administering a clostridial neurotoxin to the patient.

In a further aspect there is provided use of a clostridial neurotoxin in the manufacture of a medicament to treat a brain disorder in a patient, by promoting microglia activity (e.g. in the brain). In other words, one aspect provides use of a clostridial neurotoxin in the manufacture of a medicament for promoting microglia activity (e.g. in the brain) to treat a brain disorder in a patient.

Thus, the clostridial neurotoxin described herein promotes a neuroimmune response. As such, clostridial neurotoxin(s) find utility in treating a brain disorder. The term "brain disorder" (which may be used herein synonymously with the term "brain damage") as used herein is a disorder that can be treated by promoting a neuroimmune response in a patient.

The term "neuroimmune response" refers to the response of a patient's neuroimmune system to a brain disorder. For example, the term "neuroimmune response" as used herein may refer to the response of the neuroimmune system to brain tissue damage (e.g. neural tissue damage) in the brain, infection in the brain and/or a brain tumor (said neural damage may be caused by infection in the brain and/or a brain tumor). The neuroimmune response may be to prevent brain tissue damage (e.g. neural tissue damage). Additionally or alternatively, the neuroimmune response may be to repair brain tissue damage (e.g. neural tissue damage). The term "neuroimmune response" is not intended to be limited to a response to infection, and additionally embraces response of the neuroimmune system to brain tissue damage (e.g. neural tissue damage) cause by alternative disorders (e.g. stroke). Indeed, physical injury and necrosis can also cause a neuroimmune response. In embodiments where the brain disorder is (or is caused by) and infectious disease, the neuroimmune response may be a response to infection.

The neuroimmune system is composed primarily of glial cells, including astrocytes, microglia, and oligodendrocytes, with microglia cells (e.g. macrophages) in particular representing key immune cells of this system in the brain. As described above, the neuroimmune response as referred to herein may be defined as a microglial response.

The term "promotes a neuroimmune response" may mean that the clostridial neurotoxin (or fragment thereof) of the invention initiates a neuroimmune response in the patient having a brain disorder, for example where a neuroimmune response was not occurring or where the 'endogenous' neuroimmune response was not sufficiently strong to overcome the brain disorder (e.g. neural tissue damage). Thus, while the invention is predicated on administration of a clostridial neurotoxin in the methods described herein, it may be more accurate to say that the "neuroimmune response" (preferably microglial cells) effect the treatment e.g. of brain tissue damage; in this context, the clostridial neurotoxin promotes the role of the neuroimmune response (e.g. microglia cells) in treating brain tissue damage.

The term "promotes a neuroimmune response" may mean that the clostridial neurotoxin of the invention accelerates the onset of a neuroimmune response in the patient having a brain disorder, for example where a neuroimmune response was not occurring. In preferable embodiments, the term "promotes a neuroimmune response" may mean that the clostridial neurotoxin increases the level of the neuroimmune response. Said increase may be an increase when compared to the level of the neuroimmune response in the absence of the clostridial neurotoxin of the invention. In one embodiment, the neuroimmune response may remove damaged brain tissue (e.g. damaged neural tissue or a nerve) allowing for the rebuilding of damaged neuronal circuits, thereby restoring activity and/or neuronal communication in a network or population of neurons.

In an embodiment, the neuroimmune response comprises activation of microglial cell(s) (e.g. macrophages), as measured by 1) changes in the density of microglial cells at a site of brain tissue damage (e.g. neural tissue damage), 2) changes in the level of microglia cell migration (e.g. changes in sphericity of microglia cells) to a site of brain tissue damage (e.g. neural tissue damage), 3) changes in the level of microglia process extension toward a site of brain tissue damage (e.g. neural tissue damage), and/or 4) changes in the level of microglia cell phagocytic activity (e.g. clearance of cellular debris) at a site of brain tissue damage (e.g. neural tissue damage) in the presence of a clostridial neurotoxin of the invention when compared to microglia activity in the absence of the clostridial neurotoxin of the invention.

It should be noted that neuroimmune cell (notably microglia cell) activity is expected to increase also in an 'untreated' (e.g. untreated with an agent such as a clostridial neurotoxin) brain in response to neural tissue damage, consistent with such cells' role in central nervous system repair after injury. Notwithstanding this, the 'control' experiments provided by the present application (e.g. vehicle-only control) demonstrate that administration of a clostridial neurotoxin provides for levels of injury-induced activation of neuroimmune cell activity that goes above-and-beyond a level otherwise endogenous to the subject (even in the presence of precisely the same type of injury). Thus, in promoting neuroimmune cell activity (responsive to damage), the present invention can be utilised to 'boost' such cell's efforts to combat/repair damage caused by a brain disorder, further enhancing patient healing and mitigating further insults caused by the presence of damaged tissue (e.g. necrotic material). For example, methods of the invention may be utilised to treat patients whose 'normal' (or 'endogenous') level of neuroimmune cell activity (responsive to damage) is insufficient to combat/repair neural tissue injury underlying (or caused by) the brain disorder.

By 'promoting' the neuroimmune response to increase its activity by a certain level, there may a concomitant increase in the level of 'damage repair'. As a positive outcome, a subsequent (e.g. correlating) increase in the patient's prognosis for recovery (or survival) may follow. For example, by 'promoting' the neuroimmune response to increase its activity by say 5%, there may a concomitant 5% increase the level of 'damage repair'; and a subsequent 5% increase in the patient's prognosis for recovery (or survival) may follow.

For instance, the neuroimmune response may be increased by at least 1%, 2%, 3%, 4%, 5%, 6%, 7%, 8%, 9% or 10% (preferably at least 5%) or more in the presence of a clostridial neurotoxin of the invention when compared to the neuroimmune response in the absence of the clostridial neurotoxin of the invention (or in the presence of an alternative polypeptide).

The neuroimmune response may be increased by at least 5%, 10%, 20%, 30%, 40%, 50%, 60% or 70% (preferably at least 30%) in the presence of a clostridial neurotoxin of the invention when compared to the neuroimmune response in the absence of the clostridial neurotoxin of the invention (or in the presence of an alternative polypeptide). In some embodiments the neuroimmune response may be increased by at least 100%, 150% or 200% in the presence of a clostridial neurotoxin of the invention when compared to the neuroimmune response in the absence of the clostridial neurotoxin of the invention (or in the presence of an alternative polypeptide).

The neuroimmune response may refer to microglia activity. For example, the neuroimmune response referred to herein may preferably comprise or consist of microglia activity. In one embodiment, the clostridial neurotoxin promotes microglia activity in the brain. For instance, the microglia activity may be increased by at least 1%, 2%, 3%, 4%, 5%, 6%, 7%, 8%, 9% or 10% (preferably at least 5%) or more in the presence of a clostridial neurotoxin of the invention when compared to microglia activity in the absence of the clostridial neurotoxin of the invention (or in the presence of an alternative polypeptide).

For example, microglia activity may be increased by at least 5%, 10%, 20%, 30%, 40%, 50%, 60% or 70% (preferably at least 30%) in the presence of a clostridial neurotoxin of the invention when compared to microglia activity in the absence of the clostridial neurotoxin of the invention (or in the presence of an alternative polypeptide). In some embodiments, microglial activity may be increased by at least 100%, 150% or 200% in the presence of a clostridial neurotoxin of the invention when compared to microglial activity in the absence of the clostridial neurotoxin of the invention (or in the presence of an alternative polypeptide).

The term "microglia activity" (aka "microglia cell activity" or "microglial activity") as used refers to functions undertaken by microglia cells against the presence of an insult such as brain tissue damage, infection, and/or a tumour. Microglia are sensitive to neural tissue damage, and such damage by an injury/infection/neurotoxicant etc. stimulates microglia (e.g. to become activated) which migrate to the site of damage. Stronger microglia responses typically correlate with higher numbers of microglial cells migrating to a lesion (site of damage), such that the density of microglial cells at a site of injury may increase in line with the rate/level of the response.

In one embodiment, microglia activity may be measured based on the density of microglial cells at a site of brain tissue damage (e.g. neural tissue damage). The clostridial neurotoxin may promote "microglia cell density level" at a site of brain tissue damage (e.g. neural tissue damage), for example brain tissue damage caused by a brain disorder described herein.

The term "microglia cell density level" refers to the number of microglia cells at a given site/in a given area, with increasing density correlating with increasing numbers of cells.

The clostridial neurotoxin may promote a microglia cell density level at a site of infection (e.g. a site of brain tissue damage caused by infection). The clostridial neurotoxin may promote a microglia cell density level at a site of a brain tumor (or a site of brain tissue damage caused by a brain tumor). The clostridial neurotoxin may promote a microglia cell density level at a site of a stroke (or a site of brain tissue damage caused by a stroke). For instance, the microglia cell density level may be increased by at least 1%, 2%, 3%, 4%, 5%, 6%, 7%, 8%, 9% or 10% (preferably at least 5%) or more in the presence of a clostridial neurotoxin of the invention when compared to the microglia cell density level in the absence of the clostridial neurotoxin of the invention (or in the presence of an alternative polypeptide).

For example, said microglia cell density level (in any embodiment described herein) may be increased by at least 5%, 10%, 20%, 30%, 40%, 50%, 60% or 70% (preferably at least 30%) in the presence of a clostridial neurotoxin of the invention when compared to microglia cell density level in the absence of the clostridial neurotoxin of the invention (or in the presence of an alternative polypeptide). In some embodiments, said microglia cell density level may be increased by at least 100%, 150% or 200% in the presence of a clostridial neurotoxin of the invention when compared to microglia cell density in the absence of the clostridial neurotoxin of the invention (or in the presence of an alternative polypeptide).

By increasing microglia cell density level, as such, at a site of damage (neural injury), the number of microglia cells that are 'available' to combat/repair the injury is increased. For example, due to an increased number of microglia being present at the site of damage/injury, the amount of microglial phagocytosis of damaged tissue (and/or pathogen) can follow. A concomitant increase in the level of repair (of the injury) can therefore follow, following which treatment of the brain disorder is provided.

In one embodiment, microglia activity may be measured based on a level of "microglia cell migration" to a site of brain tissue damage (e.g. neural tissue damage). In one embodiment, the clostridial neurotoxin promotes microglia cell migration to a site of brain tissue damage (e.g. neural tissue damage). The clostridial neurotoxin may promote microglia cell migration to a site of infection (or a site of brain tissue damage caused by infection). The clostridial neurotoxin may promote microglia cell migration to a site of a brain tumor (or a site of brain tissue damage caused by a brain tumor). The clostridial neurotoxin may promote a microglia cell density level at a site of a stroke (or a site of brain tissue damage caused by a stroke).

The term "microglia cell migration" refers to the active (directional) movement microglia cells moving toward a site described herein (e.g. site of brain tissue damage, infection, tumour), for example responsive to a stimulant release from dying cells. The term "microglia cell migration" may be used synonymously with the term "microglial migration" herein.

For instance, said microglia cell migration may be increased by at least 1%, 2%, 3%, 4%, 5%, 6%, 7%, 8%, 9% or 10% (preferably at least 5%) in the presence of a clostridial neurotoxin of the invention when compared to the microglia cell density level in the absence of the clostridial neurotoxin of the invention (or in the presence of an alternative polypeptide). For example, said microglia cell migration (in any embodiment described herein) may be increased by at least 5%, 10%, 20%, 30%, 40%, 50%, 60% or 70% (preferably at least 30%) in the presence of a clostridial neurotoxin of the invention when compared to microglia cell migration in the absence of the clostridial neurotoxin of the invention (or in the presence of an alternative polypeptide). In some embodiments, said microglia cell migration may be increased by at least 80%, 90% or 100% in the presence of a clostridial neurotoxin of the invention when compared to microglia cell migration in the absence of the clostridial neurotoxin of the invention (or in the presence of an alternative polypeptide). In some embodiments, said microglia cell migration may be increased by at least 110%, 125% or 150% in the presence of a clostridial neurotoxin of the invention when compared to microglia cell migration in the absence of the clostridial neurotoxin of the invention (or in the presence of an alternative polypeptide).

By increasing microglia cell migration toward a site described herein (e.g. site of brain tissue damage, infection, tumour), the number of microglia cells that are 'available' to combat/repair the injury (or infection) is increased. For example, due to an increased number of microglia being present at the site of damage/injury, the amount of microglial phagocytosis of damaged tissue (and/or pathogen) can follow. A concomitant increase in the level of repair (of the injury) can therefore follow, following which treatment of the brain disorder is provided.

A suitable readout of cell migration is the sphericity of microglia cells. Thus, a sphericity index for a microglial cell (more typically a mean sphericity index for microglial cells) may be detected, where a decrease in sphericity index correlates with an increased elongation (elongated shape) of the microglial cell(s), e.g. because they have become motile and are migrating in the direction of the site of brain damage. The sphericity index can be defined as the ratio of the squared volume (V) of a microglial cell over the cube of the surface area(S) covered by the microglial cell:

$$\text{sphericity} = 36\pi\frac{V^2}{S^3}$$

For example, the sphericity of microglial cell(s) may be decreased by at least 1%, 2%, 5%, 10%, 15%, 20%, 25% or 30% (preferably at least 10%) in the presence of a clostridial neurotoxin of the invention when compared to sphericity of microglial cell(s) in the absence of the clostridial neurotoxin of the invention (or in the presence of an alternative polypeptide). In some embodiments, sphericity of microglial cell(s) may be decreased by at least 35%, 40% or 50% in the presence of a clostridial neurotoxin of the invention when compared to sphericity of microglial cell(s) in the absence of the clostridial neurotoxin of the invention (or in the presence of an alternative polypeptide).

Microglia are highly dynamic cells that interact with neurons and nonneuronal cells. Microglia patrol the brain parenchyma via continuous process extension and retraction. For instance, microglia can extend their processes toward damaged areas, for example in response to stimulation of the metabotropic ATP receptor P2Y (12) by ATP released from damaged tissue.

In one embodiment, microglia activity may be measured based on a level of microglia process extension toward a site of brain tissue damage (e.g. neural tissue damage). In one embodiment, the clostridial neurotoxin promotes microglia process extension toward a site of brain tissue damage (e.g.

neural tissue damage). The clostridial neurotoxin may promote microglia process extension toward a site of infection (or a site of brain tissue damage cause by infection). The clostridial neurotoxin may promote microglia process extension toward a site of a brain tumor (or a site of brain tissue damage caused by a brain tumor). The clostridial neurotoxin may promote microglia process extension toward a site of a stroke (or a site of brain tissue damage caused by a stroke).

The term "microglia process extension" refers to an extension in length of the microglia cell's elongated processes, said processes enabling, amongst other functions, the cells to migrate such as via chemotaxis. For example, the number and/or length of microglial processes may be increased in methods of the invention.

For instance, said microglia process extension may be increased by at least 1%, 2%, 3%, 4%, 5%, 6%, 7%, 8%, 9% or 10% (preferably at least 5%) in the presence of a clostridial neurotoxin of the invention when compared to the microglia cell density level in the absence of the clostridial neurotoxin of the invention (or in the presence of an alternative polypeptide). For example, said microglia process extension (in any embodiment described herein) may be increased by at least 5%, 10%, 20%, 30%, 40%, 50%, 60% or 70% (preferably at least 60%) in the presence of a clostridial neurotoxin of the invention when compared to microglia process extension in the absence of the clostridial neurotoxin of the invention (or in the presence of an alternative polypeptide). In some embodiments, said microglia process extension may be increased by at least 80%, 90% or 100% in the presence of a clostridial neurotoxin of the invention when compared to microglia process extension in the absence of the clostridial neurotoxin of the invention (or in the presence of an alternative polypeptide). In some embodiments, said microglia process extension may be increased by at least 125%, 150% or 200% in the presence of a clostridial neurotoxin of the invention when compared to microglia process extension in the absence of the clostridial neurotoxin of the invention (or in the presence of an alternative polypeptide).

In one embodiment, microglia activity may be measured based on a level of microglia cell phagocytic activity at a site of brain tissue damage (e.g. neural tissue damage). The clostridial neurotoxin may promote microglia cell phagocytic activity at a site of brain tissue damage (e.g. neural tissue damage). The clostridial neurotoxin may promote microglia cell phagocytic activity at a site of infection (or. a site of brain tissue damage caused by infection). The clostridial neurotoxin may promote microglia cell phagocytic activity at a site of a brain tumor (or a site of brain tissue damage caused by a brain tumor). The clostridial neurotoxin may promote microglia cell phagocytic activity a site of a stroke (or a site of brain tissue damage caused by a stroke).

The term "microglia cell phagocytic activity" (aka "microglial phagocytic activity") refers to engulfment of cellular material by microglia (embracing engulfment of cell debris following brain tissue damage, as well as foreign bodies such as microorganism). When engulfing cell debris, the term "microglia cell phagocytic activity" may be used synonymously with the term "microglial clearance of cellular debris" herein. Phagocytic activity may be measured by detecting clearance of cell debris at a site of brain tissue damage.

The term "cell debris" preferably refers to cellular components released from a dead neuron.

For example, said microglia cell phagocytic activity (in any embodiment described herein) may be increased by at least 10%, 20%, 30%, 40%, 50%, 60% or 70% (preferably at least 30%) in the presence of a clostridial neurotoxin of the invention when compared to microglia cell phagocytic activity in the absence of the clostridial neurotoxin of the invention (or in the presence of an alternative polypeptide). In some embodiments, said microglia cell phagocytic activity may be increased by at least 80%, 90% or 100% in the presence of a clostridial neurotoxin of the invention when compared to microglia cell phagocytic activity in the absence of the clostridial neurotoxin of the invention (or in the presence of an alternative polypeptide). In some embodiments, said microglia cell phagocytic activity may be increased by at least 125%, 150% or 200% in the presence of a clostridial neurotoxin of the invention when compared to microglia cell phagocytic activity in the absence of the clostridial neurotoxin of the invention (or in the presence of an alternative polypeptide).

The inventors have surprisingly demonstrated that the clostridial neurotoxin-mediated promotion of a neuroimmune response can occur rapidly i.e. can promote early onset of the response to damage. Furthermore, the promoted response may be acute e.g. abating once the tissue damage/invading insult has been cleared, mitigating any negative effect of a long-term 'hyperactive' response.

In one embodiment, the neuroimmune response is promoted ≤2 minutes, ≤4 minutes, ≤6 minutes, ≤8 minutes, ≤10 minutes, ≤12 minutes, ≤14 minutes, ≤16 minutes, ≤18 minutes or ≤20 minutes following the occurrence of brain tissue damage (e.g. neuron tissue damage). In a preferable embodiment, the neuroimmune response is promoted ≤10 minutes following the occurrence of brain tissue damage.

The term "brain tissue damage" (e.g. neuron tissue damage) may be damage that is caused by a brain disorder described herein. For example, where the brain disorder is an infection, the brain tissue damage may be caused by a microbial infection.

In one embodiment, the neuroimmune response is promoted ≤2 minutes, ≤4 minutes, ≤6 minutes, ≤8 minutes, ≤10 minutes, ≤12 minutes, ≤14 minutes, ≤16 minutes, ≤18 minutes or ≤20 minutes following administration of the clostridial neurotoxin. In a preferable embodiment, the neuroimmune response is promoted ≤10 minutes following administration of the clostridial neurotoxin.

The neuroimmune response may be promoted for ≤48 hours, ≤36 hours, ≤24 hours, or ≤12 hours (preferably ≤24 hours) following the occurrence of brain tissue damage. For example, there may be no clostridial neurotoxin-mediated promotion of the neuroimmune after said time period;

in other words, there may be no clostridial neurotoxin-mediated promotion of the neuroimmune response after 48 hours, 36 hours, 24 hours, or 48 hours (preferably 24 hours) following the occurrence of brain tissue damage. In such embodiments, the clostridial neurotoxin may be said to promote an acute neuroimmune response. The term "no clostridial neurotoxin-mediated promotion" means that there is substantially no increase in the neuroimmune response, for example "substantially no increase" suitably meaning the increase in the neuroimmune response may be less than 5%, 3%, or 1% (preferably 0%, where there is no increase in the neuroimmune response at all).

As described above, a brain disorder/brain damage herein is a disorder that can be treated by promoting a neuroimmune response in a patient.

Such disorders may originate from within or outside the brain, and include disorders associated with bodily insults that cause brain tissue damage. By way of example, in stroke, a blockage of the blood vessels may interrupt or reduce the supply of blood to the brain, leading to oxygen depletion in the brain and thus nerve cell death. The nerve damage thus caused may underly symptoms suffered by a patient that has said brain disorder.

Thus, a clostridial neurotoxin of the invention may be for treating a brain disorder that causes brain tissue damage (e.g. neural tissue damage), e.g. by promoting a neuroimmune response.

Examples of brain disorders embraced by the invention include any one (or more) of traumatic brain injury, cancer (e.g. a brain tumour), infectious disease, stroke, a neurodegenerative disorder, brain aneurysm, multiple sclerosis, anoxic injury, toxic injury and metabolic injury.

The "brain disorder" may refer more specifically to brain tissue damage (e.g. neural tissue damage). In such cases, it may be said that the brain disorder is caused by any one (or more) of traumatic brain injury, cancer (e.g. a brain tumour), infectious disease, stroke, a neurodegenerative disorder, brain aneurysm, multiple sclerosis, anoxic injury, toxic injury and metabolic injury.

In a preferable embodiment, the brain disorder is caused by a non-traumatic brain injury. A non-traumatic brain injury can be the result of an illness, oxygen deprivation, metabolic disorders, aneurysms, and/or cardiac arrest. A non-traumatic brain injury may be distinguished from a "traumatic brain injury" (TBI), which is typically caused by as physical blow or jolt to the head or a penetrating head injury that disrupts the function of the brain.

In one embodiment, the brain disorder is not caused by a "traumatic brain injury" (TBI).

A non-traumatic brain injury may be defined by one or more selected from: cancer (e.g. a brain tumour), infectious disease, stroke, a neurodegenerative disorder, brain aneurysm, multiple sclerosis, anoxic injury, toxic injury and metabolic injury (preferably cancer, infectious disease, and stroke; more preferably infectious disease).

Preferable examples of a brain disorder of the invention may be selected from brain disorder by cancer, infectious disease, and stroke. In other words, the brain disorder may be caused by cancer, infectious disease, and/or stroke.

A particularly suitable brain disorder is infectious disease. In other words, the brain disorder may be caused by infectious disease.

Infections can cause inflammation of the brain (encephalitis). Viruses are the most common causes of encephalitis. Infections can also cause inflammation of the layers of tissue (meninges) that cover the brain, the resulting condition being called meningitis. Often, bacterial meningitis spreads to the brain itself, causing encephalitis. Similarly, viral infections that cause encephalitis often also cause meningitis. When both the brain and the meninges are infected, the disorder is called meningoencephalitis. However, infection that affects mainly the meninges is usually called meningitis, and infection that affects mainly the brain is usually called encephalitis.

The infectious disease may refer to an infection with a microorganism, for example a microorganism selected from a bacterium, virus, fungus, a parasite and a protist (more preferably selected from a bacterium and a fungus). Thus, the infectious disease may be caused by an infectious agent which contains nucleic acids (DNA, RNA or both), which may contrast an agent of a prion protein infection. The infectious disease may thus be distinguished from a prion disease.

In one embodiment, the infectious disease is selected from encephalitis, meningitis, and a brain abscess (preferably encephalitis, and meningitis). Thus, in one embodiment, the brain disorder may be encephalitis. In one embodiment, the brain disorder may be meningitis.

In one embodiment, the brain disorder is caused by a neurodegenerative disease. Said neurodegenerative disease may be selected from: Alzheimer's disease, Parkinson's disease, Parkinson's disease related disorders, motor neuron disease (e.g. amyotrophic lateral sclerosis), prion disease, Huntington's disease, spinocerebellar ataxia, ataxia, Hallervorden-Spatz disease, and frontotemporal lobar degeneration.

In one embodiment, the brain disorder is caused by stroke. Said stroke may be ischemic stroke (e.g. lack of blood flow to brain) or hemorrhagic stroke (e.g. bleeding within the brain).

A "patient" (which may be used synonymously with the term "subject") as used herein may be a mammal, such as a human or other mammal. Preferably "patient" means a human subject.

The patient may be a patient having a lower than average (basal) neuroimmune response, e.g. a patient receiving an alternative therapy, such as chemotherapy, which may suppress the immune system. For example, the patient may be immunocompromised. The patient may be immunocompromised due to any underlying condition, or due to an elderly state (e.g. patients >60 or 70 years old). Additionally or alternatively, the patient may be immunocompromised due to administration of an alternatives therapy (for example, as mentioned above, chemotherapy). The latter represents a distinct subset of patients in which the state of being immunocompromised is 'induced', and such patients may benefit in particular from the treatment described herein.

The term "disorder" as used herein also encompasses a "disease". In one embodiment the disorder is a disease.

The term "treat" or "treating" as used herein encompasses prophylactic treatment (e.g. to prevent onset of a disorder) as well as corrective treatment (treatment of a subject already suffering from a disorder). Preferably "treat" or "treating" as used herein means corrective treatment.

The term "treat" or "treating" as used herein refers to the disorder and/or a symptom thereof.

Therefore, a clostridial neurotoxin of the invention may be administered to a patient in a therapeutically effective amount or a prophylactically effective amount. Preferably a clostridial neurotoxin of the invention is administered to a patient in a therapeutically effective amount.

A "therapeutically effective amount" is any amount of the clostridial neurotoxin, which when administered alone or in combination, with another agent, to a patient for treating said disorder (or a symptom thereof) is sufficient to effect such treatment of the disorder, or symptom thereof.

A "prophylactically effective amount" is any amount of the clostridial neurotoxin that, when administered alone or in combination to a patient inhibits or delays the onset or reoccurrence of a disorder (or a symptom thereof). In some embodiments, the prophylactically effective amount prevents the onset or reoccurrence of a disorder entirely. "Inhibiting" the onset means either lessening the likelihood of a disorder's onset (or symptom thereof), or preventing the onset entirely.

The clostridial neurotoxins of the invention may be formulated in any suitable manner for administration to a subject, for example as part of a pharmaceutical composition. Thus, in one aspect, the invention provides a pharmaceutical composition for any method of treatment described herein, the pharmaceutical composition comprising a clostridial neurotoxin of the invention and a pharmaceutically acceptable carrier, excipient, adjuvant, propellant and/or salt.

In some embodiments, the clostridial neurotoxin of the invention may be in a single-chain form, while in other embodiments the clostridial neurotoxin may be in a di-chain form, e.g. where the two chains are linked by a di-sulphide bridge. Preferably the clostridial neurotoxin is in a di-chain form.

The clostridial neurotoxins of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of a clostridial neurotoxin that is to be delivered locally, the clostridial neurotoxin may be formulated as a cream (e.g. for topical application), or for subdermal injection.

Local delivery means may include an aerosol, or other spray (e.g. a nebuliser). In this regard, an aerosol formulation of a clostridial neurotoxin enables delivery to the lungs and/or other nasal and/or bronchial or airway passages.

Clostridial neurotoxins of the invention may be administered to a subject by intrathecal or epidural injection in the spinal column at the level of the spinal segment involved in the innervation of an affected organ.

A route of administration may be via or localised injection. In one embodiment a clostridial neurotoxin of the invention is administered at or near to a site of injury, preferably at a site of injury. In one embodiment the route of administration of a clostridial neurotoxin of the invention may be perineural, intraneural, intraspinal, and/or intrathecal.

The clostridial neurotoxin may be administered subcutaneously and/or intracranially. For example, the clostridial neurotoxin may be administered intracranially (e.g. to any appropriate region of the brain in which neural damage is present). For instance, the clostridial neurotoxin may be administered by intracortical administration (e.g. intracortical injection). The clostridial neurotoxin may be administered into the somatosensory cortex. The clostridial neurotoxin may be administered into the frontal cortex.

Intracranial administration (such as intracranial injection) may be used to allow for direct administration to the brain.

The dosage ranges for administration of the clostridial neurotoxins of the present invention are those to produce the desired therapeutic and/or prophylactic effect. It will be appreciated that the dosage range required depends on the precise nature of the clostridial neurotoxin or composition, the route of administration, the nature of the formulation, the age of the subject, the nature, extent or severity of the subject's condition, contraindications, if any, and the judgement of the attending physician. Variations in these dosage levels can be adjusted using standard empirical routines for optimisation.

In one embodiment a dosage of the clostridial neurotoxin is a flat dose. A flat dose may be in the range of 50 μg to 250 μg, preferably 100 μg to 100 μg. In one embodiment a flat dose may be at least 50 μg, 100 pg, 500 μg, 1 ng, 50 ng, 100 ng, 500 ng, 1 μg or 50 μg. Said dose may be a single flat dose.

Fluid dosage forms are typically prepared utilising the clostridial neurotoxin and a pyrogen-free sterile vehicle. The clostridial neurotoxin, depending on the vehicle and concentration used, can be either dissolved or suspended in the vehicle. In preparing solutions the clostridial neurotoxin can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for an administration route described herein, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition(s) to facilitate uniform distribution of the components.

Administration in accordance with the present invention may take advantage of a variety of delivery technologies including microparticle encapsulation, or high-pressure aerosol impingement.

The clostridial neurotoxin may be administered prior to, simultaneous or subsequent to the onset of brain tissue damage (e.g. neural tissue damage) caused by a brain disorder described herein. For example, where the brain disorder is caused by an infection, the clostridial neurotoxin may be administered subsequent to detection of the infection to promote neuroimmune response-mediated clearance of the infection.

In one embodiment, the clostridial neurotoxin may be administered prior to brain tissue damage (e.g. neural tissue damage). In other words, the clostridial neurotoxin may be administered before brain tissue damage (e.g. neural tissue damage) occurs.

Reference to "administering the clostridial neurotoxin before brain tissue damage (e.g. neural tissue damage) occurs" embraces the situation where brain tissue damage has previously occurred. For example, the clostridial neurotoxin may be administered to promote a neuroimmune response to treat or prevent further brain tissue damage. This is advantageous in the context of a brain disorder described herein, where (further) tissue damage can be anticipated.

In one embodiment, the clostridial neurotoxin is administered up to 4 days before brain tissue damage (e.g. neural tissue damage). The clostridial neurotoxin may be administered between 1-3 days before brain tissue damage (e.g. neural tissue damage) occurs. The clostridial neurotoxin may be administered 3 days before brain tissue damage (e.g. neural tissue damage). In a preferable embodiment, the clostridial neurotoxin may be administered ≤24 hours before brain tissue damage (e.g. neural tissue damage).

The inventors have demonstrated that administration of a clostridial neurotoxin may lead to a rapid promotion of the neuroimmune response. Thus, the clostridial neurotoxin may be administered at a time that brain tissue damage has occurred and/or is occurring (or is suspected to have occurred and/or be occurring) to promote the neuroimmune response to respond to the damage.

In one embodiment, the clostridial neurotoxin is administered within 48 hours (e.g. in less than or equal to 4 h hours) following the occurrence of brain tissue (e.g. neural tissue) damage. For example, the clostridial neurotoxin may be administered ≤10 minutes, ≤30 minutes, ≤1 hour, ≤2 hours, ≤5 hours, ≤12 hours, ≤34 hours, ≤3 h hours or ≤48 hours following the occurrence of brain tissue damage (e.g. neural tissue damage). Preferably, the clostridial neurotoxin may be administered ≤2 hours following the occurrence of brain tissue damage (e.g. neural tissue damage). More preferably, the clostridial neurotoxin may be administered within 1-10 minutes following the occurrence of brain tissue damage (e.g. neural tissue damage).

As explained in more detail elsewhere in this disclosure, the term "clostridial neurotoxin" embraces a clostridial neurotoxin fragment thereof.

Further information on clostridial neurotoxins, and suitable neurotoxins for use in the invention, is now provided below.

In one embodiment the present invention encompasses the use of full-length clostridial neurotoxins comprising a clostridial neurotoxin L-chain and a clostridial neurotoxin H-chain, optionally with the proviso that said clostridial neurotoxin L-chain is catalytically inactive.

The term "clostridial neurotoxin" embraces toxins produced by *C. botulinum* (botulinum neurotoxin serotypes A, B, C1, D, E, F, G, and X), *C. tetani* (tetanus neurotoxin), *C. butyricum* (botulinum neurotoxin serotype E), and *C. baratii* (botulinum neurotoxin serotype F), as well as modified clostridial neurotoxins or derivatives derived from any of the foregoing.

Botulinum neurotoxin (BoNT) is produced by *C. botulinum* in the form of a large protein complex, consisting of BoNT itself complexed to a number of accessory proteins. There are at present eight different classes of botulinum neurotoxin, namely: botulinum neurotoxin serotypes A, B, C1, D, E, F, G, and X all of which share similar structures and modes of action. Different BONT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are absorbed in the gastrointestinal tract, and, after entering the general circulation, bind to the presynaptic membrane of cholinergic nerve terminals and prevent the release of their neurotransmitter acetylcholine. BoNT/B, BoNT/D, BONT/F and BONT/G cleave synaptobrevin/vesicle-associated membrane protein (VAMP); BoNT/C1, BoNT/A and BoNT/E cleave the synaptosomal-associated protein of 25 kDa (SNAP-25); and BoNT/C1 cleaves syntaxin. BoNT/X has been found to cleave SNAP-25, VAMP1, VAMP2, VAMP3, VAMP4, VAMP5, Ykt6, and syntaxin 1.

Tetanus toxin is produced in a single serotype by *C. tetani*. *C. butyricum* produces BoNT/E, while *C. baratii* produces BoNT/F.

The term "clostridial neurotoxin" is intended to encompass both full length neurotoxins (comprising a clostridial neurotoxin L-chain and a clostridial neurotoxin H-chain), as well as fragments thereof. For example, the "clostridial neurotoxin" may refer to a polypeptide that comprises or consists of a clostridial neurotoxin L-chain, a clostridial neurotoxin translocation domain ($H_N$) and/or a clostridial neurotoxin receptor binding domain ($H_C$) domain. The "clostridial neurotoxin" may refer to a polypeptide that comprises or consists of a clostridial neurotoxin L-chain, a clostridial neurotoxin translocation domain ($H_N$) and/or a clostridial neurotoxin receptor binding domain ($H_C$) domain, wherein when the polypeptide comprises a clostridial neurotoxin L-chain, the L-chain is a catalytically inactive.

Advantageously, the use of a clostridial neurotoxin fragment allows for the use of non-toxic (or substantially non-toxic) fragments of clostridial neurotoxins, which given the smaller size (compared to the full-length H-chain or full-length clostridial neurotoxin), are less likely to provoke an adverse immune response (against the fragment) in a subject administered said fragments. Moreover, the non-toxic (or substantially non-toxic) fragments are less expensive and/or less complex to manufacture than full-length clostridial neurotoxins. Additionally, the non-toxic (or substantially non-toxic) fragments constitute a more well-defined therapeutic than the full-length clostridial toxins, and given the shorter length of the polypeptides there is a reduced probability of, for example, cysteine shuffling between domains.

In embodiments which refer to a particular domain of a clostridial neurotoxin, the molecule may conveniently be referred to as a "polypeptide". That is, the term "clostridial neurotoxin" may be substituted for the term "polypeptide".

Thus, the clostridial neurotoxin referred to herein may be a polypeptide that comprises (or consists of) a clostridial neurotoxin light-chain (L-chain), a clostridial neurotoxin translocation domain ($H_N$ domain) and/or a clostridial neurotoxin receptor binding domain ($H_C$ domain). The clostridial neurotoxin referred to herein may be a polypeptide that comprises (or consists of) a clostridial neurotoxin light-chain (L-chain), a clostridial neurotoxin translocation domain ($H_N$ domain) and/or a clostridial neurotoxin receptor binding domain ($H_C$ domain), wherein when the polypeptide comprises a clostridial neurotoxin L-chain, the L-chain is catalytically inactive.

It follows, therefore, that aspects of the invention provide any of the following:

a polypeptide for use in a method of treating a brain disorder (e.g. by promoting a neuroimmune response);

a method of treating a brain disorder in a patient (e.g. by promoting a neuroimmune response), the method comprising administering a polypeptide to the patient;

use of a polypeptide in the manufacture of a medicament to treat a brain disorder in a patient (e.g. by promoting a neuroimmune response);

wherein said peptide comprises (or consists of) a clostridial neurotoxin light-chain (L-chain), a clostridial neurotoxin translocation domain ($H_N$ domain) and/or a clostridial neurotoxin receptor binding domain ($H_C$ domain); optionally wherein when the polypeptide comprises a clostridial neurotoxin L-chain, the L-chain is catalytically inactive.

In one embodiment, a clostridial neurotoxin of the invention may be encoded by a nucleotide sequence having at least 70% sequence identity to any one of SEQ ID NOs: 1, 3, 5, 7, 9, 11, 13, 15, 17, 19, 21, 23, 25, 27, 29, 31, 33, 35, 37, 39, 41, 43, 45, 47, 49, or 60. In one embodiment, a clostridial neurotoxin of the invention may be encoded by a nucleotide sequence having at least 80%, 90%, 95% or 98% sequence identity to any one of SEQ ID NOs: 1, 3, 5, 7, 9, 11, 13, 15, 17, 19, 21, 23, 25, 27, 29, 31, 33, 35, 37, 39, 41, 43, 45, 47, 49, or 60. Preferably, a clostridial neurotoxin of the invention may be encoded by a nucleotide sequence comprising any one of SEQ ID NOs: 1, 3, 5, 7, 9, 11, 13, 15, 17, 19, 21, 23, 25, 27, 29, 31, 33, 35, 37, 39, 41, 43, 45, 47, 49, or 60.

In one embodiment a clostridial neurotoxin of the invention may comprise a clostridial neurotoxin sequence having at least 70% sequence identity to any one of SEQ ID NOs: 2, 4, 6, 8, 10, 12, 14, 16, 18, 20, 22, 24, 26, 28, 30, 32, 34, 36, 38, 40, 42, 44, 46, 48, 50, 51, 52, 53, 54, 55, 56, 57, 58, 59, 61, 62, 63, 64 or 65. In one embodiment a clostridial neurotoxin of the invention may comprise a clostridial neurotoxin sequence having at least 80%, 90%, 95% or 98% sequence identity to any one of SEQ ID NOs: 2, 4, 6, 8, 10, 12, 14, 16, 18, 20, 22, 24, 26, 28, 30, 32, 34, 36, 38, 40, 42, 44, 46, 48, 50, 51, 52, 53, 54, 55, 56, 57, 58, 59, 61, 62, 63, 64 or 65. Preferably, a clostridial neurotoxin of the invention may comprise a clostridial neurotoxin sequence of any one of SEQ ID NOs: 2, 4, 6, 8, 10, 12, 14, 16, 18, 20, 22, 24, 26, 28, 30, 32, 34, 36, 38, 40, 42, 44, 46, 48, 50, 51, 52, 53, 54, 55, 56, 57, 58, 59, 61, 62, 63, 64 or 65.

In one embodiment a clostridial neurotoxin of the invention may comprise a clostridial neurotoxin sequence having at least 70% sequence identity to any one of SEQ ID NOs: 51, 52, 53, 54, 55, 56, 57, 58, or 59 (preferably SEQ ID NOs: 51, 52, 53, 54, 55, 56, 57, or 59). In one embodiment a clostridial neurotoxin of the invention may comprise a clostridial neurotoxin sequence having at least 80%, 90%, 95% or 98% sequence identity to any one of SEQ ID NOs: 51, 52, 53, 54, 55, 56, 57, 58, or 59 (preferably SEQ ID NOs: 51, 52, 53, 54, 55, 56, 57, or 59). Preferably, a clostridial neurotoxin of the invention may comprise a clostridial neurotoxin sequence of any one of SEQ ID NOs: 51, 52, 53, 54, 55, 56, 57, 58, or 59 (preferably SEQ ID NOs: 51, 52, 53, 54, 55, 56, 57, or 59). In one embodiment a clostridial neurotoxin of the invention may comprise a clostridial neurotoxin sequence having at least 70% sequence identity to SEQ ID NO: 51. In one embodiment a clostridial neurotoxin of the invention may comprise a clostridial neurotoxin sequence having at least 80%, 90%, 95% or 98% sequence identity to SEQ ID NO: 51. Preferably, a clostridial neurotoxin of the invention may comprise a clostridial neurotoxin sequence of SEQ ID NO: 51.

The term "clostridial neurotoxin" is also intended to embrace modified clostridial neurotoxins and derivatives thereof, including but not limited to those described below. A modified clostridial neurotoxin or derivative may contain one or more amino acids that has been modified as compared to the native (unmodified) form of the clostridial neurotoxin, or may contain one or more inserted amino acids that are not present in the native (unmodified) form of the clostridial neurotoxin. By way of example, a modified clostridial neurotoxin may have modified amino acid sequences in one or more domains relative to the native (unmodified) clostridial neurotoxin sequence. Such modifications may modify functional aspects of the toxin, for example biological activity or persistence. Thus, in one embodiment, the clostridial neurotoxin of the invention is a modified clostridial neurotoxin, or a modified clostridial neurotoxin derivative, or a clostridial neurotoxin derivative.

A modified clostridial neurotoxin may have one or more modifications in the amino acid sequence of the heavy chain (such as a modified $H_C$ domain), wherein said modified heavy chain binds to target nerve cells with a higher or lower affinity than the native (unmodified) clostridial neurotoxin. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified clostridial neurotoxins are described in WO 2006/027207 and WO 2006/114308, both of which are hereby incorporated by reference in their entirety.

A modified clostridial neurotoxin may have one or more modifications in the amino acid sequence of the light chain, for example modifications in the substrate binding or catalytic domain which may alter or modify the SNARE protein specificity of the modified L-chain. Examples of such modified clostridial neurotoxins are described in WO 2010/120766 and US 2011/0318385, both of which are hereby incorporated by reference in their entirety.

A modified clostridial neurotoxin may comprise one or more modifications that increases or decreases the biological activity and/or the biological persistence of the modified clostridial neurotoxin. For example, a modified clostridial neurotoxin may comprise a leucine-or tyrosine-based motif, wherein said motif increases or decreases the biological activity and/or the biological persistence of the modified clostridial neurotoxin. Suitable leucine-based motifs include xDxxxLL, xExxxLL, xExxxIL, and xExxxLM (wherein x is any amino acid). Suitable tyrosine-based motifs include Y-x-x-Hy (wherein Hy is a hydrophobic amino acid). Examples of modified clostridial neurotoxins comprising leucine-and tyrosine-based motifs are described in WO 2002/08268, which is hereby incorporated by reference in its entirety.

As described above, a modified clostridial neurotoxin (or clostridial neurotoxin fragment) may be one that comprises one or more modifications that increases the isoelectric point of the clostridial neurotoxin when compared to an equivalent unmodified clostridial neurotoxin lacking said one or more modifications. Suitable modified clostridial neurotoxins are described above and in WO 2015/004461 A1 and WO 2016/110662 A1, which are incorporated herein by reference. Exemplary sequences include SEQ ID NOs: 61 and 42 described herein.

A modified clostridial neurotoxin may preferably comprise or consist of a sequence of SEQ ID No: 61.

The term "clostridial neurotoxin" is intended to embrace hybrid and chimeric clostridial neurotoxins. A hybrid clostridial neurotoxin comprises at least a portion of a light chain from one clostridial neurotoxin or subtype thereof, and at least a portion of a heavy chain from another clostridial neurotoxin or clostridial neurotoxin subtype. In one embodiment the hybrid clostridial neurotoxin may contain the entire light chain of a light chain from one clostridial neurotoxin subtype and the heavy chain from another clostridial neurotoxin subtype. In another embodiment, a chimeric clostridial neurotoxin may contain a portion (e.g. the binding domain) of the heavy chain of one clostridial neurotoxin subtype, with another portion of the heavy chain being from another clostridial neurotoxin subtype. Similarly or alternatively, the therapeutic element may comprise light chain portions from different clostridial neurotoxins. Such hybrid or chimeric clostridial neurotoxins are useful, for example, as a means of delivering the therapeutic benefits of such clostridial neurotoxins to subjects who are immunologically resistant to a given clostridial neurotoxin subtype, to subjects who may have a lower than average concentration of receptors to a given clostridial neurotoxin heavy chain binding domain, or to subjects who may have a protease-resistant variant of the membrane or vesicle toxin substrate (e.g., SNAP-25, VAMP and syntaxin). Hybrid and chimeric clostridial neurotoxins are described in U.S. Pat. No. 8,071,110, which publication is hereby incorporated by reference in its entirety. Thus, in one embodiment, the clostridial neurotoxin (or fragment thereof) of the invention is a hybrid clostridial neurotoxin, or a chimeric clostridial neurotoxin.

In a particularly preferred embodiment, a polypeptide of the invention may be a chimeric clostridial neurotoxin comprising (preferably consisting of) a BoNT/A light-chain and translocation domain, and a BoNT/B receptor binding domain ($H_C$ domain) or a portion thereof (e.g. BoNT/A $LH_N$-BoNT/B $H_C$). A suitable chimeric and/or hybrid clostridial neurotoxin may be one taught in WO 2017/191315 A1, which is incorporated herein by reference. Such preferred sequences include SEQ ID NOs: 44, 63, and 64.

For example, a chimeric clostridial neurotoxin may comprise (preferably consist of) a sequence of SEQ ID NO: 64 (which may be said to comprise a catalytically inactive L-chain).

In a preferable embodiment, a chimeric clostridial neurotoxin may comprise (preferably consist of) a sequence of SEQ ID NO: 63.

The BoNT/A $LH_N$ domain may be covalently linked to the BoNT/B $H_C$ domain. Said chimeric BoNT/A is also referred to herein as "BoNT/AB" or a "BoNT/AB chimera".

The C-terminal amino acid residue of the $LH_N$ domain may correspond to the first amino acid residue of the $3_{10}$ helix separating the $LH_N$ and $H_C$ domains of BoNT/A, and the N-terminal amino acid residue of the $H_C$ domain may correspond to the second amino acid residue of the $3_{10}$ helix separating the $LH_N$ and $H_C$ domains in BoNT/B.

Reference herein to the "first amino acid residue of the $3_{10}$ helix separating the $LH_N$ and $H_C$ domains of BoNT/A" means the N-terminal residue of the $3_{10}$ helix separating the $LH_N$ and $H_C$ domains.

Reference herein to the "second amino acid residue of the $3_{10}$ helix separating the $LH_N$ and $H_C$ domains of BoNT/B" means the amino acid residue following the N-terminal residue of the $3_{10}$ helix separating the $LH_N$ and $H_C$ domains.

A "$3_{10}$ helix" is a type of secondary structure found in proteins and polypeptides, along with α-helices, β-sheets and reverse turns. The amino acids in a $3_{10}$ helix are arranged in a right-handed helical structure where each full turn is completed by three residues and ten atoms that separate the intramolecular hydrogen bond between them. Each amino acid corresponds to a 120° turn in the helix (i.e., the helix has three residues per turn), and a translation of 2.0 Å (=0.2 nm) along the helical axis, and has 10 atoms in the ring formed by making the hydrogen bond. Most importantly, the N—H group of an amino acid forms a hydrogen bond with the C=O group of the amino acid three residues earlier; this repeated $i+3 \rightarrow i$ hydrogen bonding defines a $3_{10}$ helix. A $3_{10}$ helix is a standard concept in structural biology with which the skilled person is familiar.

This $3_{10}$ helix corresponds to four residues which form the actual helix and two cap (or transitional) residues, one at each end of these four residues. The term "$3_{10}$ helix separating the $LH_N$ and $H_C$ domains" as used herein consists of those 6 residues.

Through carrying out structural analyses and sequence alignments, a $3_{10}$ helix separating the $LH_N$ and $H_C$ domains was identified. This $3_{10}$ helix is surrounded by an α-helix at its N-terminus (i.e. at the C-terminal part of the $LH_N$ domain) and by a β-strand at its C-terminus (i.e. at the N-terminal part of the $H_C$ domain). The first (N-terminal) residue (cap or transitional residue) of the $3_{10}$ helix also corresponds to the C-terminal residue of this α-helix.

The $3_{10}$ helix separating the $LH_N$ and $H_C$ domains can be for example determined from publicly available crystal structures of botulinum neurotoxins, for example 3BTA and 1EPW for botulinum neurotoxins A1 and B1 respectively.

In silico modelling and alignment tools which are publicly available can also be used to determine the location of the $3_{10}$ helix separating the $LH_N$ and $H_C$ domains in other neurotoxins, for example the homology modelling servers LOOPP (Learning, Observing and Outputting Protein Patterns), PHYRE (Protein Homology/analogY Recognition Engine) and Rosetta, the protein superposition server SuperPose, the alignment program Clustal Omega, and a number of other tools/services listed at the Internet Resources for Molecular and Cell Biologists. In particular that the region around the "$H_N/H_{CN}$" junction is structurally highly conserved which renders it an ideal region to superimpose different serotypes.

For example, the following methodology may be used to determine the sequence of this $3_{10}$ helix in other neurotoxins:

1. The structural homology modelling tool LOOP was used to obtain a predicted structure of other BoNT serotypes based on the BoNT/A1 crystal structure (3BTA.pdb);
2. The structural (pdb) files thus obtained were edited to include only the N-terminal end of the $H_{CN}$ domain and about 80 residues before it (which are part of the $H_N$ domain), thereby retaining the "$H_N/H_{CN}$" region which is structurally highly conserved;
3. The protein superposition server SuperPose was used to superpose each serotype onto the 3BTA.pdb structure;
4. The superposed pdb files were inspected to locate the $3_{10}$ helix at the start of the $H_C$ domain of BoNT/A1, and corresponding residues in the other serotype were then identified;
5. The other BoNT serotype sequences were aligned with Clustal Omega in order to check that corresponding residues were correct.

Examples of $LH_N$, $H_C$ and $3_{10}$ helix domains determined by this method are presented below:

| Neurotoxin | Accession Number (Plus Sequence Version after Decimal) | $LH_N$ | $H_C$ | $3_{10}$ helix |
|---|---|---|---|---|
| BoNT/A1 (SEQ ID NO: 62) | A5HZZ9.1 | 1-872 | 873-1296 | $^{872}$NIINTS$^{877}$ |
| BoNT/A2 | X73423.3 | 1-872 | 873-1296 | $^{872}$NIVNTS$^{877}$ |
| BoNT/A3 | DQ185900.1 (aka Q3LRX9.1) | 1-872 | 873-1292 | $^{872}$NIVNTS$^{877}$ |
| BoNT/A4 | EU341307.1 (aka Q3LRX8.1) | 1-872 | 873-1296 | $^{872}$NITNAS$^{877}$ |
| BoNT/A5 | EU679004.1 (aka C1IPK2.1) | 1-872 | 873-1296 | $^{872}$NIINTS$^{877}$ |
| BoNT/A6 | FJ981696.1 | 1-872 | 873-1296 | $^{872}$NIINTS$^{877}$ |
| BoNT/A7 | JQ954969.1 (aka K4LN57.1) | 1-872 | 873-1296 | $^{872}$NIINTS$^{877}$ |
| BoNT/A8 | KM233166.1 | 1-872 | 873-1297 | $^{872}$NITNTS$^{877}$ |
| BoNT/B1 (a.k.a. SEQ ID NO: 52) | B1INP5.1 | 1-859 | 860-1291 | $^{859}$EILNNI$^{864}$ |
| BoNT/B2 | AB084152.1 (aka Q8GR96.1) | 1-859 | 860-1291 | $^{859}$EILNNI$^{864}$ |
| BoNT/B3 | EF028400.1 (aka A2I2S2.1) | 1-859 | 860-1291 | $^{859}$EILNNI$^{864}$ |
| BoNT/B4 | EF051570.1 (aka A2I2W0.1) | 1-859 | 860-1291 | $^{859}$EILNNI$^{864}$ |
| BoNT/B5 | EF033130.1 (aka A2I2U6.1) | 1-859 | 860-1291 | $^{859}$DILNNI$^{864}$ |
| BoNT/B6 | AB302852.1 (aka A8R089.1) | 1-859 | 860-1291 | $^{859}$EILNNI$^{864}$ |
| BoNT/B7 | JQ354985.1 (aka H9CNK9.1) | 1-859 | 860-1291 | $^{859}$EILNNI$^{864}$ |

-continued

| Neurotoxin | Accession Number (Plus Sequence Version after Decimal) | $LH_N$ | $H_C$ | $3_{10}$ helix |
|---|---|---|---|---|
| BoNT/B8 | JQ964806.1 (aka I6Z8G9.1) | 1-859 | 860-1292 | $^{859}$EILNNI$^{864}$ |

Using structural analysis and sequence alignments, it was found that the β-strand following the $3_{10}$ helix separating the $LH_N$ and $H_C$ domains is a conserved structure in all botulinum and tetanus neurotoxins and starts at the 8th residue when starting from the first residue of the $3_{10}$ helix separating the $LH_N$ and $H_C$ domains (e.g., at residue 879 for BoNT/A1).

A BONT/AB chimera may comprise an $LH_N$ domain from BoNT/A covalently linked to a $H_C$ domain from BoNT/B, wherein the C-terminal amino acid residue of the $LH_N$ domain corresponds to the eighth amino acid residue N-terminally to the β-strand located at the beginning (N-term) of the $H_C$ domain of BoNT/A, and, wherein the N-terminal amino acid residue of the $H_C$ domain corresponds to the seventh amino acid residue N-terminally to the β-strand located at the beginning (N-term) of the $H_C$ domain of BoNT/B.

A BoNT/AB chimera may comprise an $LH_N$ domain from BoNT/A covalently linked to a $H_C$ domain from BoNT/B, wherein the C-terminal amino acid residue of the $LH_N$ domain corresponds to the C-terminal amino acid residue of the α-helix located at the end (C-term) of $LH_N$ domain of BONT/A, and, wherein the N-terminal amino acid residue of the $H_C$ domain corresponds to the amino acid residue immediately C-terminal to the C-terminal amino acid residue of the α-helix located at the end (C-term) of $LH_N$ domain of BoNT/B.

The rationale of the design process of the BoNT/AB chimera was to try to ensure that the secondary structure was not compromised and thereby minimise any changes to the tertiary structure and to the function of each domain. Without wishing to be bound by theory, it is hypothesized that by not disrupting the four central amino acid residues of the $3_{10}$ helix in the BoNT/AB chimera ensures an optimal conformation for the chimeric neurotoxin, thereby allowing for the chimeric neurotoxin to exert its functions to their full capacity.

The $LH_N$ domain from BoNT/A may correspond to amino acid residues 1 to 872 of SEQ ID NO: 62, or a polypeptide sequence having at least 70% sequence identity thereto. The $LH_N$ domain from BoNT/A may correspond to amino acid residues 1 to 872 of SEQ ID NO: 62, or a polypeptide sequence having at least 80%, 90% or 95% sequence identity thereto. Preferably, the $LH_N$ domain from BoNT/A corresponds to amino acid residues 1 to 872 of SEQ ID NO: 62.

The $H_C$ domain from BoNT/B may correspond to amino acid residues 860 to 1291 of SEQ ID NO: 52, or a polypeptide sequence having at least 70% sequence identity thereto. The $H_C$ domain from BoNT/B may correspond to amino acid residues 860 to 1291 of SEQ ID NO: 52, or a polypeptide sequence having at least 80%, 90% or 95% sequence identity thereto. Preferably, the $H_C$ domain from BoNT/B corresponds to amino acid residues 860 to 1291 of SEQ ID NO: 52.

Preferably, the BoNT/AB chimera comprises a BoNT/A $LH_N$ domain and a BoNT/B $H_C$ domain. More preferably, the $LH_N$ domain corresponds to amino acid residues 1 to 872 of BoNT/A (SEQ ID NO: 62) and the $H_C$ domain corresponds to amino acid residues 860 to 1291 of BoNT/B (SEQ ID NO: 52).

Preferably, a BoNT/B $H_C$ domain further comprises at least one amino acid residue substitution, addition or deletion in the $H_{CC}$ subdomain which has the effect of increasing the binding affinity of BoNT/B neurotoxin for human Syt II as compared to the natural BoNT/B sequence. Suitable amino acid residue substitution, addition or deletion in the BoNT/B $H_{CC}$ subdomain have been disclosed in WO 2013/180799 and in WO 2016/154534 (both herein incorporated by reference).

Suitable amino acid residue substitution, addition or deletion in the BoNT/B $H_{CC}$ subdomain include substitution mutations selected from the group consisting of: V1118M; Y1183M; E1191M; E11911; E1191Q; E1191T; S1199Y; S1199F; S1199L; S1201V; E1191C, E1191V, E1191L, E1191Y, S1199W, S1199E, S1199H, W1178Y, W1178Q, W1178A, W1178S, Y1183C, Y1183P and combinations thereof.

Suitable amino acid residue substitution, addition or deletion in the BoNT/B $H_{CC}$ subdomain further include combinations of two substitution mutations selected from the group consisting of: E1191M and S1199L, E1191M and S1199Y, E1191M and S1199F, E1191Q and S1199L, E1191Q and S1199Y, E1191Q and S1199F, E1191M and S1199W, E1191M and W1178Q, E1191C and S1199W, E1191C and S1199Y, E1191C and W1178Q, E1191Q and S1199W, E1191V and S1199W, E1191V and S1199Y, or E1191V and W1178Q.

Suitable amino acid residue substitution, addition or deletion in the BoNT/B $H_{CC}$ subdomain also include a combination of three substitution mutations which are E1191M, S1199W and W1178Q.

Preferably, the suitable amino acid residue substitution, addition or deletion in the BoNT/B $H_{CC}$ subdomain includes a combination of two substitution mutations which are E1191M and S1199Y.

The modification may be a modification when compared to unmodified BoNT/B shown as SEQ ID NO: 52, wherein the amino acid residue numbering is determined by alignment with SEQ ID NO: 52. As the presence of a methionine residue at position 1 of SEQ ID NO: 52 is optional, the skilled person will take the presence/absence of the methionine residue into account when determining amino acid residue numbering. For example, where SEQ ID NO: 52 includes a methionine, the position numbering will be as defined above (e.g. E1191 will be E1191 of SEQ ID NO: 52). Alternatively, where the methionine is absent from SEQ ID NO: 52 the amino acid residue numbering should be modified by −1 (e.g. E1191 will be E1190 of SEQ ID NO: 52). Similar considerations apply when the methionine at position 1 of the other polypeptide sequences described herein is present/absent, and the skilled person will readily determine the correct amino acid residue numbering using techniques routine in the art.

Thus, in one aspect, the invention provides a clostridial neurotoxin for use in treating a brain disorder by promoting a neuroimmune response in a subject, wherein the clostridial neurotoxin comprises a polypeptide sequence having at least 70% sequence identity to SEQ ID NO: 63 or 64 (preferably wherein the clostridial neurotoxin comprises a polypeptide sequence having at least 70% sequence identity to SEQ ID NO: 63).

In a related aspect, there is provided a method for treating a brain disorder in a subject by promoting neuroimmune activity, the method comprising administering a clostridial neurotoxin to the subject, wherein the clostridial neurotoxin comprises a polypeptide sequence having at least 70% sequence identity to SEQ ID NO: 63 or 64 (preferably wherein the clostridial neurotoxin comprises a polypeptide sequence having at least 70% sequence identity to SEQ ID NO: 63).

In a further related aspect, there is provided use of a clostridial neurotoxin in the manufacture of a medicament for to treating a brain disorder in a subject by promoting a neuroimmune response, wherein the clostridial neurotoxin comprises a clostridial neurotoxin sequence having at least 70% sequence identity to SEQ ID NO: 63 or 64 (preferably wherein the clostridial neurotoxin comprises a polypeptide sequence having at least 70% sequence identity to SEQ ID NO: 63).

In one aspect the invention provides a clostridial neurotoxin for use in treating a brain disorder in a subject, wherein the clostridial neurotoxin comprises a polypeptide sequence having at least 70% sequence identity to SEQ ID NO: 63 or 64 (preferably wherein the clostridial neurotoxin comprises a polypeptide sequence having at least 70% sequence identity to SEQ ID NO: 63).

In a related aspect, there is provided a method for treating a brain disorder in a subject, the method comprising administering a clostridial neurotoxin to the subject, wherein the clostridial neurotoxin comprises a polypeptide sequence having at least 70% sequence identity to SEQ ID NO: 63 or 64 (preferably wherein the clostridial neurotoxin comprises a polypeptide sequence having at least 70% sequence identity to SEQ ID NO: 63).

In a further related aspect, there is provided use of a clostridial neurotoxin in the manufacture of a medicament for treating a brain disorder in a subject, wherein the clostridial neurotoxin comprises a polypeptide sequence having at least 70% sequence identity to SEQ ID NO: 63 or 64 (preferably wherein the clostridial neurotoxin comprises a polypeptide sequence having at least 70% sequence identity to SEQ ID NO: 63).

In one embodiment a clostridial neurotoxin for use according to the invention comprises a polypeptide sequence having at least 80%, 90%, 95% or 98% sequence identity to SEQ ID NO: 63 or 64. Preferably, a clostridial neurotoxin for use according to the invention comprises (more preferably consists of) a polypeptide sequence shown as SEQ ID NO: 63 or 64.

For example, a clostridial neurotoxin for use according to the invention may comprise a polypeptide sequence having at least 80%, 90%, 95% or 98% sequence identity to SEQ ID NO: 64. A clostridial neurotoxin may comprises (more preferably consist of) a polypeptide sequence shown as SEQ ID NO: 64.

In a preferred embodiment, a clostridial neurotoxin for use according to the invention may comprise a polypeptide sequence having at least 80%, 90%, 95% or 98% sequence identity to SEQ ID NO: 64. For example, a particularly suitable clostridial neurotoxin may comprises (more preferably consist of) a polypeptide sequence shown as SEQ ID NO: 63.

Preferably, the clostridial neurotoxin comprising a polypeptide sequence having at least 70% sequence identity to SEQ ID NO: 63 comprises a catalytically-inactive L-chain, such as SEQ ID NO: 64.

A chimeric and/or hybrid clostridial neurotoxin for use in the present invention may comprise a portion of a BoNT/A polypeptide and a portion of a BoNT/B polypeptide, an example of which includes the polypeptide described herein as SEQ ID NO: 44.

Suitable chimeric clostridial neurotoxins may include BoNT/FA. Indeed, in a particularly preferred embodiment, a clostridial neurotoxin (e.g. chimeric clostridial neurotoxin) of the invention may comprise BoNT/FA or a fragment thereof. Catalytically inactive forms of BoNT/FA are described herein as SEQ ID NO: 26 and 34. Suitable fragments of BoNT/FA are also described herein as SEQ ID NOs: 28, 30, and 32.

The term "clostridial neurotoxin" may also embrace newly discovered botulinum neurotoxin protein family members expressed by non-clostridial microorganisms, such as the *Enterococcus* encoded toxin which has closest sequence identity to BoNT/X, the Weissella *oryzae* encoded toxin called BoNT/Wo (NCBI Ref Seq: WP_027699549.1), which cleaves VAMP2 at W89-W90, the *Enterococcus faecium* encoded toxin (GenBank: OTO2244.1), which cleaves VAMP2 and SNAP25, and the *Chryseobacterium pipero* encoded toxin (NCBI Ref.Seq: WP_034687872.1).

The clostridial neurotoxin of the present invention may lack a functional $H_C$ domain of a clostridial neurotoxin and also lack any functionally equivalent exogenous ligand Targeting Moiety (TM).

Thus, in a particularly preferred embodiment, a clostridial neurotoxin of the invention is not a re-targeted clostridial neurotoxin. In a re-targeted clostridial neurotoxin, the clostridial neurotoxin is modified to include an exogenous ligand known as a Targeting Moiety (TM). The TM is selected to provide binding specificity for a desired target cell, and as part of the re-targeting process the native binding portion of the clostridial neurotoxin (e.g. the $H_C$ domain, or the $H_{CC}$ domain) may be removed. Re-targeting technology is described, for example, in: EP-B-0689459; WO 1994/021300; EP-B-0939818; U.S. Pat. Nos. 6,461,617; 7,192,596; WO 1998/007864; EP-B-0826051; U.S. Pat. Nos. 5,989,545; 6,395,513; 6,962,703; WO 1996/033273; EP-B-0996468; U.S. Pat. No. 7,052,702; WO 1999/017806; EP-B-1107794; U.S. Pat. No. 6,632,440; WO 2000/010598; WO 2001/21213; WO 2006/059093; WO 2000/62814; WO 2000/04926; WO 1993/15766; WO 2000/61192; and WO 1999/58571; all of which are hereby incorporated by reference in their entirety.

As discussed above, (full-length) clostridial neurotoxins are formed from two polypeptide chains, the heavy chain (H-chain), which has a molecular mass of approximately 100 kDa, and the light chain (L-chain), which has a molecular mass of approximately 50 kDa. The H-chain comprises a C-terminal targeting component (receptor binding domain or $H_C$ domain) and an N-terminal translocation component ($H_N$ domain).

A clostridial neurotoxin may be selected from BoNT/A, BoNT/B, BoNT/C, BoNT/D, BONT/E, BONT/F, BONT/G, BONT/X, and TeNT (tetanus neurotoxin). Preferably, a clostridial neurotoxin is a botulinum neurotoxin, such as a botulinum neurotoxin selected from BoNT/A, BoNT/B, BoNT/C, BONT/D, BONT/E, BONT/F, BoNT/G, and BoNT/X.

In one embodiment the clostridial neurotoxin may be BoNT/A. A reference BoNT/A sequence is shown as SEQ ID NO: 51. In another embodiment the clostridial neurotoxin may be BoNT/B. A reference BoNT/B sequence is shown as SEQ ID NO: 52. In another embodiment the clostridial neurotoxin may be BoNT/C. A reference BoNT/C sequence is shown as SEQ ID NO: 53. In another embodiment the clostridial neurotoxin may be BoNT/D. A reference BoNT/D sequence is shown as SEQ ID NO: 54. In another embodiment the clostridial neurotoxin may be BoNT/E. A reference BoNT/E sequence is shown as SEQ ID NO: 55. In another embodiment the clostridial neurotoxin may be BoNT/F. A reference BoNT/F sequence is shown as SEQ ID NO: 56. In another embodiment the clostridial neurotoxin may be BoNT/G. A reference BoNT/G sequence is shown as SEQ ID NO: 57. In another embodiment the clostridial neurotoxin may be TeNT. A reference TeNT sequence is shown as SEQ ID NO: 58. In another embodiment the clostridial neurotoxin may be BoNT/X. A reference BoNT/X sequence is shown as SEQ ID NO: 59.

In one embodiment a clostridial neurotoxin of the invention comprises a fragment of a BoNT/A or a fragment of a BoNT/F. In another embodiment, the clostridial neurotoxin of the invention comprises a catalytically inactive L-chain of BoNT/A or BoNT/F. For example, the clostridial neurotoxin of the invention may comprise a catalytically inactive L-chain of BoNT/A.

In embodiments where a clostridial neurotoxin described herein has a tag for purification (e.g. a His-tag) and/or a linker, said tag and/or linker are optional. Suitable full-length clostridial neurotoxins are described herein.

In one embodiment a clostridial neurotoxin of the invention may comprise a polypeptide sequence having at least 70% sequence identity to any one of SEQ ID NOs: 2, 10, 12, 14, 16, 18, 26, 34, 51, 52, 53, 54, 55, 56, 57, 58, 59, 61, 62, 63, 64 or 65, preferably with the proviso that a clostridial neurotoxin L-chain of said clostridial neurotoxin is catalytically inactive. In one embodiment a clostridial neurotoxin of the invention may comprise a polypeptide sequence having at least 80%, 90%, 95% or 98% sequence identity to any one of SEQ ID NOs: 2, 10, 12, 14, 16, 18, 26, 34, 51, 52, 53, 54, 55, 56, 57, 58, 59, 61, 62, 63, 64 or 65, preferably with the proviso that a clostridial neurotoxin L-chain of said clostridial neurotoxin is catalytically inactive. Preferably, a clostridial neurotoxin of the invention may comprise a polypeptide sequence comprising any one of SEQ ID NOs: 2, 10, 12, 14, 16, 18, 26, 34, 51, 52, 53, 54, 55, 56, 57, 58, 59, 61, 62, 63, 64 or 65, preferably with the proviso that a clostridial neurotoxin L-chain of said clostridial neurotoxin is catalytically inactive.

In one embodiment a clostridial neurotoxin of the invention may be one encoded by a nucleotide sequence having at least 70% sequence identity to any one of SEQ ID NOs: 1, 9, 11, 13, 15, 17, 25, 33, or 60, preferably with the proviso that the clostridial neurotoxin L-chain of said clostridial neurotoxin is catalytically inactive. In one embodiment a clostridial neurotoxin of the invention is one encoded by a nucleotide sequence having at least 80%, 90%, 95% or 98% sequence identity to any one of SEQ ID NOs: 1, 9, 11, 13, 15, 17, 25, 33, or 60, preferably with the proviso that the clostridial neurotoxin L-chain of said clostridial neurotoxin is catalytically inactive. Preferably, a clostridial neurotoxin of the invention is one encoded by a nucleotide sequence comprising any one of SEQ ID NOs: 1, 9, 11, 13, 15, 17, 25, 33, or 60, preferably with the proviso that the clostridial neurotoxin L-chain of said clostridial neurotoxin is catalytically inactive.

In one embodiment a clostridial neurotoxin of the invention may comprise a polypeptide sequence having at least 70% sequence identity to any one of SEQ ID NOs: 2, 10, 12, 14, 16, 18, 26, 34, 64 or 65, preferably with the proviso that the clostridial neurotoxin L-chain of said clostridial neurotoxin is catalytically inactive. In one embodiment a clostridial neurotoxin of the invention comprises a polypeptide sequence having at least 80%, 90%, 95% or 98% sequence identity to any one of SEQ ID NOs: 2, 10, 12, 14, 16, 18, 26, 34, 64 or 65, preferably with the proviso that the clostridial neurotoxin L-chain of said clostridial neurotoxin is catalytically inactive. Preferably, a clostridial neurotoxin of the invention comprises any one of SEQ ID NOs: 2, 10, 12, 14, 16, 18, 26, 34, 64 or 65, preferably with the proviso that the clostridial neurotoxin L-chain of said clostridial neurotoxin is catalytically inactive.

In one embodiment a clostridial neurotoxin of the invention is a full-length clostridial neurotoxin selected from BoNT/A, BoNT/B, BoNT/C, BONT/D, BONT/E, BONT/F, BONT/G, BONT/X, and TeNT.

In one embodiment a clostridial neurotoxin of the invention is a full-length clostridial neurotoxin selected from BoNT/B, BoNT/C, BONT/D, BONT/E, BONT/F, BONT/G, BONT/X, and TeNT.

In one embodiment a clostridial neurotoxin of the invention may comprise a polypeptide sequence having at least 70% sequence identity to any one of SEQ ID NOs: 51-59, 61 or 63. In one embodiment a clostridial neurotoxin of the invention may comprise a polypeptide sequence having at least 80%, 90%, 95% or 98% sequence identity to any one of SEQ ID NOs: 51-59, 61 or 63. In one embodiment a clostridial neurotoxin of the invention may comprise a polypeptide sequence having at least 99% or 99.9% sequence identity to any one of SEQ ID NOs: 51-59, 61 or 63. Preferably, a clostridial neurotoxin of the invention may comprise (more preferably consist of) a polypeptide sequence comprising any one of SEQ ID NOs: 51-59, 61 or 63.

In one embodiment a clostridial neurotoxin of the invention may comprise a polypeptide sequence having at least 70% sequence identity to any one of SEQ ID NOs: 52-59, 61 or 63. In one embodiment a clostridial neurotoxin of the invention may comprise a polypeptide sequence having at least 80%, 90%, 95% or 98% sequence identity to any one of SEQ ID NOs: 52-59, 61 or 63. In one embodiment a clostridial neurotoxin of the invention may comprise a polypeptide sequence having at least 99% or 99.9% sequence identity to any one of SEQ ID NOs: 52-59, 61 or 63. Preferably, a clostridial neurotoxin of the invention may comprise (more preferably consist of) a polypeptide sequence comprising any one of SEQ ID NOs: 52-59, 61 or 63.

In one embodiment a clostridial neurotoxin of the invention is not a full-length catalytically active clostridial neurotoxin, e.g. is not full-length catalytically active BoNT/A.

The clostridial neurotoxin of the present invention may comprise (or consist of) a fragment of a clostridial neurotoxin, e.g. a fragment of any full-length clostridial neurotoxin described herein.

In one embodiment a clostridial neurotoxin of the invention may comprise a fragment of a polypeptide sequence having at least 70% sequence identity to any one of SEQ ID NOs: 2, 10, 12, 14, 16, 18, 26, 34, 51, 52, 53, 54, 55, 56, 57, 58, 59, 61, 62, 63, 64 or 65. In one embodiment a clostridial neurotoxin of the invention may comprise a fragment of a polypeptide sequence having at least 80%, 90%, 95% or 98% sequence identity to any one of SEQ ID NOs: 2, 10, 12, 14, 16, 18, 26, 34, 51, 52, 53, 54, 55, 56, 57, 58, 59, 61, 62, 63, 64 or 65. Preferably, a clostridial neurotoxin of the invention may comprise a fragment of a polypeptide sequence comprising any one of SEQ ID NOs: 2, 10, 12, 14, 16, 18, 26, 34, 51, 52, 53, 54, 55, 56, 57, 58, 59, 61, 62, 63, 64 or 65.

In one embodiment a clostridial neurotoxin of the invention comprises (or consists of) a clostridial neurotoxin L-chain or fragment thereof. A fragment of a clostridial neurotoxin L-chain may have ≤400, ≤350, ≤300, ≤250, ≤200, ≤150, ≤100 or ≤50 amino acid residues of a clostridial neurotoxin L-chain. In one embodiment, a fragment of a clostridial neurotoxin L-chain has at least 20, 30, 40, 50, 60, 70, 80, 90, 100, 120, 150 or 200 amino acid residues of a clostridial neurotoxin L-chain. For example, a fragment of a clostridial neurotoxin L-chain may have 20-400, 50-300 or 100-200 amino acid residues of a clostridial neurotoxin L-chain.

Examples of L-chain reference sequences include:

Botulinum type A neurotoxin: amino acid residues 1-448
Botulinum type B neurotoxin: amino acid residues 1-440
Botulinum type C1 neurotoxin: amino acid residues 1-441
Botulinum type D neurotoxin: amino acid residues 1-445
Botulinum type E neurotoxin: amino acid residues 1-422
Botulinum type F neurotoxin: amino acid residues 1-439
Botulinum type G neurotoxin: amino acid residues 1-441
Tetanus neurotoxin: amino acid residues 1-457

For recently-identified BoNT/X, the L-chain has been reported as corresponding to amino acids 1-439 thereof, with the L-chain boundary potentially varying by approximately 25 amino acids (e.g. 1-414 or 1-464).

The above-identified reference sequences should be considered a guide, as slight variations may occur according to sub-serotypes. By way of example, US 2007/0166332 (hereby incorporated by reference in its entirety) cites slightly different clostridial sequences:

Botulinum type A neurotoxin: amino acid residues M1-K448
Botulinum type B neurotoxin: amino acid residues M1-K441
Botulinum type C1 neurotoxin: amino acid residues M1-K449
Botulinum type D neurotoxin: amino acid residues M1-R445
Botulinum type E neurotoxin: amino acid residues M1-R422
Botulinum type F neurotoxin: amino acid residues M1-K439
Botulinum type G neurotoxin: amino acid residues M1-K446
Tetanus neurotoxin: amino acid residues M1-A457

Suitable clostridial neurotoxin L-chains are described herein.

A clostridial neurotoxin L-chain may comprise a polypeptide sequence having at least 70% sequence identity to any one of SEQ ID NOs: 6, 24, 32 or 40 or a fragment thereof. In one embodiment a clostridial neurotoxin L-chain comprises a polypeptide sequence having at least 80%, 90%, 95% or 98% sequence identity to any one of SEQ ID NOs: 6, 24, 32 or 40 or a fragment thereof. Preferably, a clostridial neurotoxin L-chain comprises (more preferably consists of) a polypeptide sequence comprising any one of SEQ ID NOs: 6, 24, 32 or 40 or a fragment thereof.

A clostridial neurotoxin L-chain may be one encoded by a nucleotide sequence having at least 70% sequence identity to any one of SEQ ID NOs: 5, 23, 31 or 39 or a fragment thereof. In one embodiment a clostridial neurotoxin L-chain is one encoded by a nucleotide sequence having at least 80%, 90%, 95% or 98% sequence identity to any one of SEQ ID NOs: 5, 23, 31 or 39 or a fragment thereof. Preferably, a clostridial neurotoxin L-chain is one encoded by a nucleotide sequence comprising any one of SEQ ID NOs: 5, 23, 31 or 39 or a fragment thereof.

In one embodiment a clostridial neurotoxin of the invention comprises (or consists of) a fragment of a clostridial neurotoxin H-chain. A fragment of a clostridial neurotoxin H-chain may have ≤800, ≤700, ≤600, ≤500, ≤400, ≤350, ≤300, ≤250, ≤200, ≤150, ≤100 or ≤50 amino acid residues of a clostridial neurotoxin H-chain. In one embodiment, a fragment of a clostridial neurotoxin H-chain has at least 20, 30, 40, 50, 60, 70, 80, 90, 100, 120, 150 or 200 amino acid residues of a clostridial neurotoxin H-chain. For example, a fragment of a clostridial neurotoxin H-chain may have 20-800, 30-600, 40-400, 50-300 or 100-200 amino acid residues of a clostridial neurotoxin H-chain.

A clostridial neurotoxin H-chain comprises two structural/functional domains: the translocation domain ($H_N$) and receptor binding domain ($H_C$).

In one embodiment a clostridial neurotoxin of the invention comprises (or consists of) a clostridial neurotoxin translocation domain or a fragment thereof. A fragment of a clostridial neurotoxin translocation domain may have ≤400, ≤350, ≤300, ≤250, ≤200, ≤150, ≤100 or ≤50 amino acid residues of a clostridial neurotoxin translocation domain. In one embodiment, a fragment of a clostridial neurotoxin translocation domain has at least 20, 30, 40, 50, 60, 70, 80, 90, 100, 120, 150 or 200 amino acid residues of a clostridial neurotoxin translocation domain. For example, a fragment of a clostridial neurotoxin translocation domain may have 20-400, 50-300 or 100-200 amino acid residues of a clostridial neurotoxin translocation domain.

The translocation domain is a fragment of the H-chain of a clostridial neurotoxin approximately equivalent to the amino-terminal half of the H-chain, or the domain corresponding to that fragment in the intact H-chain. In one embodiment the $H_C$ function of the H-chain may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, in some embodiments the H-chain may be incapable of binding to the Binding Site on a target cell to which native clostridial neurotoxin (i.e. holotoxin) binds.

Examples of suitable (reference) Translocation Domains include:

Botulinum type A neurotoxin-amino acid residues (449-871)
Botulinum type B neurotoxin-amino acid residues (441-858)
Botulinum type C neurotoxin-amino acid residues (442-866)
Botulinum type D neurotoxin-amino acid residues (446-862)
Botulinum type E neurotoxin-amino acid residues (423-845)
Botulinum type F neurotoxin-amino acid residues (440-864)
Botulinum type G neurotoxin-amino acid residues (442-863)
Tetanus neurotoxin-amino acid residues (458-879)

The above-identified reference sequence should be considered a guide as slight variations may occur according to sub-serotypes. By way of example, US 2007/0166332 (hereby incorporated by reference thereto) cites slightly different clostridial sequences:

Botulinum type A neurotoxin-amino acid residues (A449-K871)
Botulinum type B neurotoxin-amino acid residues (A442-S858)
Botulinum type C neurotoxin-amino acid residues (T450-N866)

Botulinum type D neurotoxin-amino acid residues (D446-N862)

Botulinum type E neurotoxin-amino acid residues (K423-K845)

Botulinum type F neurotoxin-amino acid residues (A440-K864)

Botulinum type G neurotoxin-amino acid residues (S447-S863)

Tetanus neurotoxin-amino acid residues (S458-V879)

In the context of the present invention, a variety of clostridial neurotoxin $H_N$ regions comprising a translocation domain can be useful in aspects of the present invention. In one embodiment these active fragments can facilitate the release of a non-cytotoxic protease (e.g. a clostridial L-chain) from intracellular vesicles into the cytoplasm of the target cell and thus participate in executing the overall cellular mechanism whereby a clostridial neurotoxin proteolytically cleaves a substrate. The $H_N$ regions from the heavy chains of clostridial neurotoxins are approximately 410-430 amino acids in length and comprise a translocation domain. Research has shown that the entire length of a $H_N$ region from a clostridial neurotoxin heavy chain is not necessary for the translocating activity of the translocation domain. Thus, aspects of this embodiment can include clostridial neurotoxin $H_N$ regions comprising a translocation domain having a length of, for example, at least 350 amino acids, at least 375 amino acids, at least 400 amino acids and at least 425 amino acids. Other aspects of this embodiment can include clostridial neurotoxin $H_N$ regions comprising a translocation domain having a length of, for example, at most 350 amino acids, at most 375 amino acids, at most 400 amino acids and at most 425 amino acids.

For further details on the genetic basis of toxin production in *Clostridium botulinum* and *C. tetani*, see Henderson et al (1997) in *The Clostridia: Molecular Biology and Pathogenesis, Academic press.*

The term $H_N$ embraces naturally-occurring neurotoxin $H_N$ portions, and modified $H_N$ portions having amino acid sequences that do not occur in nature and/or synthetic amino acid residues. In one embodiment said modified $H_N$ portions still demonstrate the above-mentioned translocation function.

In a preferred embodiment a clostridial neurotoxin of the invention comprises (or consists of) a clostridial neurotoxin receptor binding domain ($H_C$) or a fragment thereof. A fragment of a clostridial neurotoxin receptor binding domain ($H_C$) may have ≤350, ≤300, ≤250, ≤200, ≤150, ≤100 or ≤50 amino acid residues of a clostridial neurotoxin receptor binding domain ($H_C$). In one embodiment, a fragment of a clostridial neurotoxin receptor binding domain ($H_C$) has at least 20, 30, 40, 50, 60, 70, 80, 90, 100, 120, 150 or 200 amino acid residues of a clostridial neurotoxin receptor binding domain ($H_C$). For example, a fragment of a clostridial neurotoxin receptor binding domain ($H_C$) may have 20-350, 50-300 or 100-200 amino acid residues of a clostridial neurotoxin receptor binding domain ($H_C$).

Examples of clostridial neurotoxin receptor binding domain ($H_C$) reference sequences include:

BONT/A-N872-L1296

BONT/B-E859-E1291

BONT/C1-N867-E1291

BONT/D-S863-E1276

BONT/E-R846-K1252

BONT/F-K865-E1274

BONT/G-N864-E1297

TeNT-1880-D1315

For recently-identified BoNT/X, the $H_C$ domain has been reported as corresponding to amino acids 893-1306 thereof, with the domain boundary potentially varying by approximately 25 amino acids (e.g. 868-1306 or 918-1306).

A clostridial neurotoxin H-chain may further comprise a translocation facilitating domain. Said domain facilitates delivery of the L-chain into the cytosol of the target cell and are described, for example, in WO 08/008803 and WO 08/008805, each of which is herein incorporated by reference thereto.

By way of example, a translocation facilitating domain may comprise a clostridial neurotoxin $H_{CN}$ domain or a fragment or variant thereof. In more detail, a clostridial neurotoxin $H_{CN}$ translocation facilitating domain may have a length of at least 200 amino acids, at least 225 amino acids, at least 250 amino acids, at least 275 amino acids. In this regard, a clostridial neurotoxin $H_{CN}$ translocation facilitating domain preferably has a length of at most 200 amino acids, at most 225 amino acids, at most 250 amino acids, or at most 275 amino acids. Specific (reference) examples include:

Botulinum type A neurotoxin-amino acid residues (872-1110)

Botulinum type B neurotoxin-amino acid residues (859-1097)

Botulinum type C neurotoxin-amino acid residues (867-1111)

Botulinum type D neurotoxin-amino acid residues (863-1098)

Botulinum type E neurotoxin-amino acid residues (846-1085)

Botulinum type F neurotoxin-amino acid residues (865-1105)

Botulinum type G neurotoxin-amino acid residues (864-1105)

Tetanus neurotoxin-amino acid residues (880-1127)

The above sequence positions may vary a little according to serotype/sub-type, and further examples of suitable (reference) clostridial neurotoxin $H_{CN}$ domains include:

Botulinum type A neurotoxin-amino acid residues (874-1110)

Botulinum type B neurotoxin-amino acid residues (861-1097)

Botulinum type C neurotoxin-amino acid residues (869-1111)

Botulinum type D neurotoxin-amino acid residues (865-1098)

Botulinum type E neurotoxin-amino acid residues (848-1085)

Botulinum type F neurotoxin-amino acid residues (867-1105)

Botulinum type G neurotoxin-amino acid residues (866-1105)

Tetanus neurotoxin-amino acid residues (882-1127)

Suitable clostridial neurotoxin $H_C$ domains are described herein.

A clostridial neurotoxin $H_C$ domain may comprise a polypeptide sequence having at least 70% sequence identity to any one of SEQ ID NOs: 8, 22, 30, 38, 42, 44, 46, 48 or 50 or a fragment thereof. In one embodiment a clostridial neurotoxin $H_C$ domain comprises a polypeptide sequence having at least 80%, 90%, 95% or 98% sequence identity to any one of SEQ ID NOs: 8, 22, 30, 38, 42, 44, 46, 48 or 50 or a fragment thereof. Preferably, a clostridial neurotoxin $H_C$ domain comprises (more preferably consists of) a polypeptide sequence comprising any one of SEQ ID NOs: 8, 22, 30, 38, 42, 44, 46, 48 or 50 or a fragment thereof.

A clostridial neurotoxin $H_C$ domain may be one encoded by a nucleotide sequence having at least 70% sequence identity to any one of SEQ ID NOs: 7, 21, 29, 37, 41, 43, 45, 47 or 49 or a fragment thereof. In one embodiment a clostridial neurotoxin $H_C$ domain is one encoded by a nucleotide sequence having at least 80%, 90%, 95% or 98% sequence identity to any one of SEQ ID NOs: 7, 21, 29, 37, 41, 43, 45, 47 or 49 or a fragment thereof. Preferably, a clostridial neurotoxin $H_C$ domain is one encoded by a nucleotide sequence comprising any one of SEQ ID NOs: 7, 21, 29, 37, 41, 43, 45, 47 or 49 or a fragment thereof.

In one embodiment a clostridial neurotoxin $H_C$ domain for use in the invention is a variant BoNT/A $H_C$ domain. Said variant BoNT/A $H_C$ domain may comprise a modification of one or more amino acids residues selected from Y1117, F1252, H1253, and L1278. For example, a variant BoNT/A $H_C$ domain may comprise one or more (preferably two or more) of the following modifications Y1117V, F1252Y, H1253K, and L1278F or L1278H.

In one embodiment a variant BoNT/A $H_C$ domain comprises the following modifications: Y1117V and H1253K; or Y1117V, F1252Y, H1253K, and L1278F; or Y1117V, F1252Y, H1253K, and L1278H.

Preferably, a variant BoNT/A $H_C$ domain comprises the following modifications: Y1117V and H1253K; or Y1117V, F1252Y, H1253K, and L1278H.

The modification may be a modification when compared to unmodified BoNT/A shown as SEQ ID NO: 62, wherein the amino acid residue numbering is determined by alignment with SEQ ID NO:

62. As the presence of a methionine residue at position 1 of SEQ ID NO: 62 is optional, the skilled person will take the presence/absence of the methionine residue into account when determining amino acid residue numbering. For example, where SEQ ID NO: 62 includes a methionine, the position numbering will be as defined above (e.g. Y1117 will align against Y1117 of SEQ ID NO: 62). Alternatively, where the methionine is absent from SEQ ID NO: 62 the amino acid residue numbering should be modified by −1 (e.g. Y1117 will align against Y1116 of SEQ ID NO: 52). Similar considerations apply when the methionine at position 1 of the other polypeptide sequences described herein is present/absent, and the skilled person will readily determine the correct amino acid residue numbering using techniques routine in the art.

A variant BoNT/A $H_C$ domain may comprise a polypeptide sequence having at least 70% sequence identity to any one of SEQ ID NOs: 46, 48 or 50 or a fragment thereof with the proviso that the variant BoNT/A $H_C$ domain comprises a modification as described above. In one embodiment a variant BoNT/A $H_C$ domain comprises a polypeptide sequence having at least 80%, 90%, 95% or 98% sequence identity to any one of SEQ ID NOs: 46, 48 or 50 or a fragment thereof with the proviso that the variant BoNT/A $H_C$ domain comprises a modification as described above. In one embodiment a variant BoNT/A $H_C$ domain comprises a polypeptide sequence having at least 99% or 99.9% sequence identity to any one of SEQ ID NOs: 46, 48 or 50 or a fragment thereof with the proviso that the variant BoNT/A $H_C$ domain comprises a modification as described above. Preferably, a variant BoNT/A $H_C$ domain comprises (more preferably consists of) a polypeptide sequence comprising any one of SEQ ID NOs: 46, 48 or 50 or a fragment thereof.

A variant BoNT/A $H_C$ domain may comprise a polypeptide sequence having at least 70% sequence identity to any one of SEQ ID NOs: 46 or 50 or a fragment thereof with the proviso that the variant BONT/A $H_C$ domain comprises a modification as described above. In one embodiment a variant BoNT/A $H_C$ domain comprises a polypeptide sequence having at least 80%, 90%, 95% or 98% sequence identity to any one of SEQ ID NOs: 46 or 50 or a fragment thereof with the proviso that the variant BoNT/A $H_C$ domain comprises a modification as described above. In one embodiment a variant BoNT/A $H_C$ domain comprises a polypeptide sequence having at least 99% or 99.9% sequence identity to any one of SEQ ID NOs: 46 or 50 or a fragment thereof with the proviso that the variant BoNT/A $H_C$ domain comprises a modification as described above. Preferably, a variant BoNT/A $H_C$ domain comprises (more preferably consists of) a polypeptide sequence comprising any one of SEQ ID NOs: 46 or 50 or a fragment thereof.

A variant BoNT/A $H_C$ domain may be one encoded by a nucleotide sequence having at least 70% sequence identity to any one of SEQ ID NOs: 45, 47 or 49 or a fragment thereof with the proviso that the variant BoNT/A $H_C$ domain comprises a modification as described above. In one embodiment a variant BoNT/A $H_C$ domain be one encoded by a nucleotide sequence having at least 80%, 90%, 95% or 98% sequence identity to any one of SEQ ID NOs: 45, 47 or 49 or a fragment thereof with the proviso that the variant BoNT/A $H_C$ domain comprises a modification as described above. In one embodiment a variant BoNT/A $H_C$ domain be one encoded by a nucleotide sequence having at least 99% or 99.9% sequence identity to any one of SEQ ID NOS: 45, 47 or 49 or a fragment thereof with the proviso that the variant BoNT/A $H_C$ domain comprises a modification as described above. Preferably, a variant BoNT/A $H_C$ domain be one encoded by any one of SEQ ID NOs: 45, 47 or 49 or a fragment thereof.

A variant BoNT/A $H_C$ domain may be one encoded by a nucleotide sequence having at least 70% sequence identity to any one of SEQ ID NOs: 45 or 49 or a fragment thereof with the proviso that the variant BoNT/A $H_C$ domain comprises a modification as described above. In one embodiment a variant BoNT/A $H_C$ domain be one encoded by a nucleotide sequence having at least 80%, 90%, 95% or 98% sequence identity to any one of SEQ ID NOs: 45 or 49 or a fragment thereof with the proviso that the variant BoNT/A $H_C$ domain comprises a modification as described above. In one embodiment a variant BoNT/A $H_C$ domain be one encoded by a nucleotide sequence having at least 99% or 99.9% sequence identity to any one of SEQ ID NOs: 45 or 49 or a fragment thereof with the proviso that the variant BoNT/A $H_C$ domain comprises a modification as described above. Preferably, a variant BoNT/A $H_C$ domain be one encoded by any one of SEQ ID NOs: 45 or 49 or a fragment thereof.

Any of the above-described facilitating domains may be combined with any of the previously described translocation domain peptides that are suitable for use in the present invention. Thus, by way of example, a non-clostridial facilitating domain may be combined with non-clostridial translocation domain peptide or with clostridial translocation domain peptide. Alternatively, a clostridial neurotoxin $H_{CN}$ translocation facilitating domain may be combined with a non-clostridial translocation domain peptide. Alternatively, a clostridial neurotoxin $H_{CN}$ facilitating domain may be combined with a clostridial translocation domain peptide, examples of which include:

Botulinum type A neurotoxin-amino acid residues (449-1110)

Botulinum type B neurotoxin-amino acid residues (442-1097)

Botulinum type C neurotoxin-amino acid residues (450-1111)

Botulinum type D neurotoxin-amino acid residues (446-1098)

Botulinum type E neurotoxin-amino acid residues (423-1085)

Botulinum type F neurotoxin-amino acid residues (440-1105)

Botulinum type G neurotoxin-amino acid residues (447-1105)

Tetanus neurotoxin-amino acid residues (458-1127)

In some embodiments the clostridial neurotoxins of the present invention may lack a functional $H_C$ domain of a clostridial neurotoxin. In one embodiment, the clostridial neurotoxins preferably lack the last 50 C-terminal amino acids of a clostridial neurotoxin holotoxin. In another embodiment, the clostridial neurotoxins preferably lack the last 100, preferably the last 150, more preferably the last 200, particularly preferably the last 250, and most preferably the last 300 C-terminal amino acid residues of a clostridial neurotoxin holotoxin. Alternatively, the $H_C$ binding activity may be negated/reduced by mutagenesis—by way of example, referring to BoNT/A for convenience, modification of one or two amino acid residue mutations (W1266 to L and Y1267 to F) in the ganglioside binding pocket causes the $H_C$ region to lose its receptor binding function. Analogous mutations may be made to non-serotype A clostridial peptide components, e.g. a construct based on botulinum B with mutations (W1262 to L and Y1263 to F) or botulinum E (W1224 to L and Y1225 to F). Other mutations to the active site achieve the same ablation of $H_C$ receptor binding activity, e.g. Y1267S in botulinum type A toxin and the corresponding highly conserved residue in the other clostridial neurotoxins. Details of this and other mutations are described in Rummel et al (2004) (Molecular Microbiol. 51:631-634), which is hereby incorporated by reference thereto.

The $H_C$ peptide of a native clostridial neurotoxin comprises approximately 400-440 amino acid residues, and consists of two functionally distinct domains of approximately 25 kDa each, namely the N-terminal region (commonly referred to as the $H_{CN}$ peptide or domain) and the C-terminal region (commonly referred to as the $H_{CC}$ peptide or domain). This fact is confirmed by the following publications, each of which is herein incorporated in its entirety by reference thereto: Umland TC (1997) Nat. Struct. Biol. 4:788-792; Herreros J (2000) Biochem. J. 347:199-204; Halpern J (1993) J. Biol. Chem. 268:15, pp. 11188-11192; Rummel A (2007) PNAS 104:359-364; Lacey DB (1998) Nat. Struct. Biol. 5:898-902; Knapp (1998) Am. Cryst. Assoc. Abstract Papers 25:90; Swaminathan and Eswaramoorthy (2000) Nat. Struct. Biol. 7:1751-1759; and Rummel A (2004) Mol. Microbiol. 51 (3), 631-643. Moreover, it has been well documented that the C-terminal region ($H_{CC}$), which constitutes the C-terminal 160-200 amino acid residues, is responsible for binding of a clostridial neurotoxin to its natural cell receptors, namely to nerve terminals at the neuromuscular junction—this fact is also confirmed by the above publications. Thus, reference throughout this specification to a clostridial heavy-chain lacking a functional heavy chain $H_C$ peptide (or domain) such that the heavy-chain is incapable of binding to cell surface receptors to which a native clostridial neurotoxin binds means that the clostridial heavy-chain simply lacks a functional $H_{CC}$ peptide. In other words, the $H_{CC}$ peptide region may be either partially or wholly deleted, or otherwise modified (e.g. through conventional chemical or proteolytic treatment) to reduce its native binding ability for nerve terminals at the neuromuscular junction.

Thus, in one embodiment, a clostridial neurotoxin $H_N$ peptide of the present invention lacks part of a C-terminal peptide portion ($H_{CC}$) of a clostridial neurotoxin and thus lacks the $H_C$ binding function of native clostridial neurotoxin. By way of example, in one embodiment, the C-terminally extended clostridial $H_N$ peptide lacks the C-terminal 40 amino acid residues, or the C-terminal 60 amino acid residues, or the C-terminal 80 amino acid residues, or the C-terminal 100 amino acid residues, or the C-terminal 120 amino acid residues, or the C-terminal 140 amino acid residues, or the C-terminal 150 amino acid residues, or the C-terminal 160 amino acid residues of a clostridial neurotoxin heavy-chain. In another embodiment, the clostridial $H_N$ peptide of the present invention lacks the entire C-terminal peptide portion ($H_{CC}$) of a clostridial neurotoxin and thus lacks the $H_C$ binding function of native clostridial neurotoxin. By way of example, in one embodiment, the clostridial $H_N$ peptide lacks the C-terminal 165 amino acid residues, or the C-terminal 170 amino acid residues, or the C-terminal 175 amino acid residues, or the C-terminal 180 amino acid residues, or the C-terminal 185 amino acid residues, or the C-terminal 190 amino acid residues, or the C-terminal 195 amino acid residues of a clostridial neurotoxin heavy-chain. By way of further example, the clostridial $H_N$ peptide of the present invention lacks a clostridial $H_{CC}$ reference sequence selected from the group consisting of:

Botulinum type A neurotoxin-amino acid residues (Y1111-L1296)

Botulinum type B neurotoxin-amino acid residues (Y1098-E1291)

Botulinum type C neurotoxin-amino acid residues (Y1112-E1291)

Botulinum type D neurotoxin-amino acid residues (Y1099-E1276)

Botulinum type E neurotoxin-amino acid residues (Y1086-K1252)

Botulinum type F neurotoxin-amino acid residues (Y1106-E1274)

Botulinum type G neurotoxin-amino acid residues (Y1106-E1297)

Tetanus neurotoxin-amino acid residues (Y1128-D1315).

The above-identified reference sequences should be considered a guide as slight variations may occur according to sub-serotypes.

In a preferred embodiment a clostridial neurotoxin of the invention comprises (or consists of) a clostridial neurotoxin L-chain or fragment thereof and a fragment of a clostridial neurotoxin H-chain. For example, a clostridial neurotoxin may comprise (or consist of) a clostridial neurotoxin L-chain or fragment thereof and a clostridial neurotoxin translocation domain ($H_N$). Preferably, the clostridial neurotoxin does not further comprise a clostridial neurotoxin receptor binding domain ($H_C$) or at least the C-terminal portion of a clostridial neurotoxin receptor binding domain ($H_{CC}$). Thus, in one embodiment a clostridial neurotoxin of the present invention lacks a C-terminal portion of a clostridial neurotoxin receptor binding domain ($H_{CC}$). Advantageously, such clostridial neurotoxins lack the endogenous clostridial neurotoxin receptor binding capabilities and thus exhibit fewer off-target effects in a subject administered said clostridial neurotoxin.

In one embodiment a clostridial neurotoxin of the invention consists essentially of a clostridial neurotoxin L-chain or fragment thereof and/or a fragment of a clostridial neurotoxin H-chain. The term "consists essentially of" as used in this context means that the clostridial neurotoxin does not further comprise one or more amino acid residues that confer additional functionality to the clostridial neurotoxin, e.g. when administered to a subject. In other words, a clostridial neurotoxin that "consists essentially of" a clostridial neurotoxin L-chain or fragment thereof and/or a fragment of a clostridial neurotoxin H-chain may further comprise one or more amino acid residues (to those of the clostridial neurotoxin L-chain or fragment thereof and/or fragment of a clostridial neurotoxin H-chain) but said one or more further amino acid residues do not confer additional functionality to the clostridial neurotoxin, e.g. when administered to a subject. Additional functionality may include enzymatic activity, binding activity and/or any physiological activity whatsoever.

In one embodiment a clostridial neurotoxin may comprise non-clostridial neurotoxin sequences in addition to any clostridial neurotoxin sequences. The non-clostridial neurotoxin sequences preferably do not disrupt the ability of a clostridial neurotoxin of the invention to promote a neuro-immune response. Preferably, the non-clostridial neurotoxin sequence is not one having catalytic activity, e.g. enzymatic activity. Preferably, the non-clostridial sequence is not one that binds to a cellular receptor. In other words, it is most preferred that the non-clostridial sequence is not a ligand for a cellular receptor. A cellular receptor may be a proteinaceous cellular receptor, such as an integral membrane protein. Examples of cellular receptors can be found in the IUPHAR Guide to Pharmacology Database, version 2019. Non-clostridial neurotoxin sequences may include tags to aid in purification, such as His-tags. It is preferred that any clostridial neurotoxin sequences comprised in said clostridial neurotoxin consist of a clostridial neurotoxin L-chain or fragment thereof and/or a fragment of a clostridial neurotoxin H-chain. In one embodiment, the clostridial neurotoxin sequence comprised in said clostridial neurotoxin may consist of a clostridial neurotoxin L-chain. In one embodiment, the clostridial neurotoxin sequence comprised in said clostridial neurotoxin may consist of a clostridial neurotoxin translocation domain. In one embodiment, the clostridial neurotoxin sequence comprised in said clostridial neurotoxin may consist of a clostridial neurotoxin receptor binding domain. In one embodiment, the clostridial neurotoxin sequence comprised in said clostridial neurotoxin may consist of a clostridial neurotoxin L-chain and a clostridial neurotoxin translocation domain.

Suitable clostridial neurotoxins comprising (or consisting of) a clostridial neurotoxin L-chain and translocation domain are described herein.

A clostridial neurotoxin comprising (or consisting of) a clostridial neurotoxin L-chain and translocation domain may comprise a polypeptide sequence having at least 70% sequence identity to any one of SEQ ID NOs: 4, 20, 28 or 36 or a fragment thereof. In one a clostridial neurotoxin comprising (or consisting of) a clostridial neurotoxin L-chain and translocation domain comprises a polypeptide sequence having at least 80%, 90%, 95% or 98% sequence identity to any one of SEQ ID NOs: 4, 20, 28 or 36 or a fragment thereof. Preferably, a clostridial neurotoxin comprising (or consisting of) a clostridial neurotoxin L-chain and translocation domain comprises (more preferably consists of) a polypeptide sequence comprising any one of SEQ ID NOs: 4, 20, 28 or 36 or a fragment thereof.

A clostridial neurotoxin comprising (or consisting of) a clostridial neurotoxin L-chain and translocation domain may be one encoded by a nucleotide sequence having at least 70% sequence identity to any one of SEQ ID NOs: 3, 19, 27 or 35 or a fragment thereof. In one embodiment a clostridial neurotoxin comprising (or consisting of) a clostridial neurotoxin L-chain and translocation domain is one encoded by a nucleotide sequence having at least 80%, 90%, 95% or 98% sequence identity to any one of SEQ ID NOs: 3, 19, 27 or 35 or a fragment thereof. Preferably, a clostridial neurotoxin comprising (or consisting of) a clostridial neurotoxin L-chain and translocation domain is one encoded by a nucleotide sequence comprising any one of SEQ ID NOs: 3, 19, 27 or 35 or a fragment thereof.

The clostridial neurotoxin of the present invention may be free from the complexing proteins that are present in a naturally occurring clostridial neurotoxin complex.

The clostridial neurotoxins of the present invention can be produced using recombinant nucleic acid technologies. Thus, in one embodiment, a clostridial neurotoxin (as described above) is a recombinant clostridial neurotoxin.

In one embodiment a clostridial neurotoxin of the invention comprises a clostridial neurotoxin L-chain. It is preferred that the L-chain is catalytically inactive.

Active clostridial neurotoxin L-chain has non-cytotoxic protease activity. Specifically, active clostridial neurotoxin L-chain has endopeptidase activity and is capable of cleaving a protein of the exocytic fusion apparatus in a target cell. A protein of the exocytic fusion apparatus is preferably a SNARE protein, such as SNAP-25, synaptobrevin/VAMP, or syntaxin.

The term "catalytically inactive" as used herein in respect of a clostridial neurotoxin L-chain means that said L-chain exhibits substantially no non-cytotoxic protease activity, preferably the term "catalytically inactive" as used herein in respect of a clostridial neurotoxin L-chain means that said L-chain exhibits no non-cytotoxic protease activity. In one embodiment, a catalytically inactive clostridial neurotoxin L-chain is one that does not cleave a protein of the exocytic fusion apparatus in a target cell. The term "substantially no non-cytotoxic protease activity" means that the clostridial neurotoxin L-chain has less than 5% of the non-cytotoxic protease activity of a catalytically active clostridial neurotoxin L-chain, for example less than 2%, 1% or preferably less than 0.1% of the non-cytotoxic protease activity of a catalytically active clostridial neurotoxin L-chain. Non-cytotoxic protease activity can be determined in vitro by incubating a test clostridial neurotoxin L-chain with a SNARE protein and comparing the amount of SNARE protein cleaved by the test clostridial neurotoxin L-chain when compared to the amount of SNARE protein cleaved by a catalytically active clostridial neurotoxin L-chain under the same conditions. Routine techniques, such as SDS-PAGE and Western blotting can be used to quantify the amount of SNARE protein cleaved. Suitable in vitro assays are described in WO 2019/145577 A1, which is incorporated herein by reference.

Cell-based and in vivo assays may also be used to determine if a clostridial neurotoxin comprising an L-chain and a functional cell binding and translocation domain has non-cytotoxic protease activity. Assays such as the Digit Abduction Score (DAS), the dorsal root ganglia (DRG) assay, spinal cord neuron (SCN) assay, and mouse phrenic nerve hemidiaphragm (PNHD) assay are routine in the art. A suitable assay for determining non-cytotoxic protease activity may be one described in Donald et al (2018), Pharmacol Res Perspect, e00446, 1-14, which is incorporated herein by reference.

A catalytically inactive L-chain may have one or more mutations that inactivate said catalytic activity. For example, a catalytically inactive BoNT/A L-chain may comprise a mutation of an active site residue, such as His223, Glu224, His227, Glu262, and/or Tyr366. The position numbering corresponds to the amino acid positions of SEQ ID NO: 62 and can be determined by aligning a polypeptide with SEQ ID NO: 62. As the presence of a methionine residue at position 1 of SEQ ID NO: 62 is optional, the skilled person will take the presence/absence of the methionine residue into account when determining amino acid residue numbering. For example, where SEQ ID NO: 62 includes a methionine, the position numbering will be as defined above (e.g. His223 will be His223 of SEQ ID NO: 62). Alternatively, where the methionine is absent from SEQ ID NO: 62 the amino acid residue numbering should be modified by −1 (e.g. His223 will be His222 of SEQ ID NO: 62). Similar considerations apply when the methionine at position 1 of the other polypeptide sequences described herein is present/absent, and the skilled person will readily determine the correct amino acid residue numbering using techniques routine in the art.

In a particularly preferred embodiment, a clostridial neurotoxin of the invention may comprise a modified BoNT/A or fragment thereof (preferably a BoNT/A $H_C$ domain or fragment thereof). The modified BoNT/A or fragment thereof may be one that comprises a modification at one or more amino acid residue(s) selected from: ASN 886, ASN 905, GLN 915, ASN 918, GLU 920, ASN 930, ASN 954, SER 955, GLN 991, GLU 992, GLN 995, ASN 1006, ASN 1025, ASN 1026, ASN 1032, ASN 1043, ASN 1046, ASN 1052, ASP 1058, HIS 1064, ASN 1080, GLU 1081, GLU 1083, ASP 1086, ASN 1188, ASP 1213, GLY 1215, ASN 1216, GLN 1229, ASN 1242, ASN 1243, SER 1274, and THR 1277. Such a modified BoNT/A or fragment thereof may demonstrate a reduction in, or absence of, side effects compared to the use of known BoNT/A. The increased tissue retention properties of the modified BoNT/A of the invention may also provide increased potency and/or duration of action and can allow for reduced dosages to be used compared to known clostridial toxin therapeutics (or increased dosages without any additional adverse effects), thus providing further advantages.

The modification may be a modification when compared to unmodified BoNT/A shown as SEQ ID NO: 62, wherein the amino acid residue numbering is determined by alignment with SEQ ID NO: 62. As the presence of a methionine residue at position 1 of SEQ ID NO: 62 (as well as the SEQ ID NOs corresponding to modified BoNT/A polypeptides or fragments thereof described herein) is optional, the skilled person will take the presence/absence of the methionine residue into account when determining amino acid residue numbering. For example, where SEQ ID NO: 62 includes a methionine, the position numbering will be as defined above (e.g. ASN 886 will be ASN 886 of SEQ ID NO: 62). Alternatively, where the methionine is absent from SEQ ID NO: 62 the amino acid residue numbering should be modified by −1 (e.g. ASN 886 will be ASN 885 of SEQ ID NO: 62). Similar considerations apply when the methionine at position 1 of the other polypeptide sequences described herein is present/absent, and the skilled person will readily determine the correct amino acid residue numbering using techniques routine in the art.

The amino acid residue(s) indicated for modification above are surface exposed amino acid residue(s).

A modified BoNT/A or fragment thereof may comprise a modification at one or more amino acid residue(s) selected from: ASN 886, ASN 930, ASN 954, SER 955, GLN 991, ASN 1025, ASN 1026, ASN 1052, ASN 1188, ASP 1213, GLY 1215, ASN 1216, GLN 1229, ASN 1242, ASN 1243, SER 1274 and THR 1277.

The term "one or more amino acid residue(s)" when used in the context of modified BoNT/A or fragment thereof preferably means at least 2, 3, 4, 5, 6 or 7 of the indicated amino acid residue(s). Thus, a modified BoNT/A may comprise at least 2, 3, 4, 5, 6 or 7 (preferably 7) modifications at the indicated amino acid residue(s). A modified BoNT/A or fragment thereof may comprise 1-30, 3-20, or 5-10 amino acid modifications. More preferably, the term "one or more amino acid residue(s)" when used in the context of modified BoNT/A or fragment thereof means all of the indicated amino acid residue(s).

Preferably, beyond the one or more amino acid modification(s) at the indicated amino acid residue(s), the modified BoNT/A or fragment thereof does not contain any further amino acid modifications when compared to SEQ ID NO: 62.

The modification may be selected from:

i. substitution of an acidic surface exposed amino acid residue with a basic amino acid residue;
ii. substitution of an acidic surface exposed amino acid residue with an uncharged amino acid residue;
iii. substitution of an uncharged surface exposed amino acid residue with a basic amino acid residue;
iv. insertion of a basic amino acid residue; and
V. deletion of an acidic surface exposed amino acid residue.

A modification as indicated above results in a modified BoNT/A or fragment thereof that has an increased positive surface charge and increased isoelectric point when compared to the corresponding unmodified BoNT/A or fragment thereof.

The isoelectric point (pI) is a specific property of a given protein. As is well known in the art, proteins are made from a specific sequence of amino acids (also referred to when in a protein as amino acid residues). Each amino acid of the standard set of twenty has a different side chain (or R group), meaning that each amino acid residue in a protein displays different chemical properties such as charge and hydrophobicity. These properties may be influenced by the surrounding chemical environment, such as the temperature and pH. The overall chemical characteristics of a protein will depend on the sum of these various factors.

Certain amino acid residues (detailed below) possess ionisable side chains that may display an electric charge depending on the surrounding pH. Whether such a side chain is charged or not at a given pH depends on the pKa of the relevant ionisable moiety, wherein pKa is the negative logarithm of the acid dissociation constant (Ka) for a specified proton from a conjugate base.

For example, acidic residues such as aspartic acid and glutamic acid have side chain carboxylic acid groups with pKa values of approximately 4.1 (precise pKa values may depend on temperature, ionic strength and the microenvironment of the ionisable group). Thus, these side chains exhibit a negative charge at a pH of 7.4 (often referred to as "physiological pH"). At low pH values, these side chains will become protonated and lose their charge.

Conversely, basic residues such as lysine and arginine have nitrogen-containing side chain groups with pKa values of approximately 10-12. These side chains therefore exhibit a positive charge at a pH of 7.4. These side chains will become de-protonated and lose their charge at high pH values.

The overall (net) charge of a protein molecule therefore depends on the number of acidic and basic residues present in the protein (and their degree of surface exposure) and on the surrounding pH. Changing the surrounding pH changes the overall charge on the protein. Accordingly, for every protein there is a given pH at which the number of positive and negative charges is equal and the protein displays no overall net charge. This point is known as the isoelectric point (pI). The isoelectric point is a standard concept in protein biochemistry with which the skilled person would be familiar.

The isoelectric point (pI) is therefore defined as the pH value at which a protein displays a net charge of zero. An increase in pI means that a higher pH value is required for the protein to display a net charge of zero. Thus, an increase in pI represents an increase in the net positive charge of a protein at a given pH. Conversely, a decrease in pI means that a lower pH value is required for the protein to display a net charge of zero. Thus, a decrease in pI represents a decrease in the net positive charge of a protein at a given pH.

Methods of determining the pI of a protein are known in the art and would be familiar to a skilled person. By way of example, the pI of a protein can be calculated from the average pKa values of each amino acid present in the protein ("calculated pI"). Such calculations can be performed using computer programs known in the art, such as the Compute pI/MW Tool from ExPASy, which is the preferred method for calculating pI in accordance with the present invention. Comparisons of pI values between different molecules should be made using the same calculation technique/program.

Where appropriate, the calculated pI of a protein can be confirmed experimentally using the technique of isoelectric focusing ("observed pI"). This technique uses electrophoresis to separate proteins according to their pI. Isoelectric focusing is typically performed using a gel that has an immobilised pH gradient. When an electric field is applied, the protein migrates through the pH gradient until it reaches the pH at which it has zero net charge, this point being the pI of the protein. Results provided by isoelectric focusing are typically relatively low-resolution in nature, and thus the present inventors believe that results provided by calculated pI (as described above) are more appropriate to use.

Throughout the present specification, "pI" means "calculated pI" unless otherwise stated.

The pI of a protein may be increased or decreased by altering the number of basic and/or acidic groups displayed on its surface. This can be achieved by modifying one or more amino acids of the protein. For example, an increase in pI may be provided by reducing the number of acidic residues, or by increasing the number of basic residues.

A modified BoNT/A or fragment thereof of the invention may have a pI value that is at least 0.2, 0.4, 0.5 or 1 pI units higher than that of an unmodified BoNT/A (e.g. SEQ ID NO: 62) or fragment thereof. Preferably, a modified BoNT/A or fragment thereof may have a pI of at least 6.6, e.g. at least 6.8.

The properties of the 20 standard amino acids are indicated in the table below:

| Amino Acid | | | Side Chain |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

At a pH of 7.4, the side chains of aspartic acid (pKa 3.1) and glutamic acid (pKa 4.1) have a negative charge, while the side chains of arginine (pKa 12.5) and lysine (pKa 10.8) have a positive charge. Aspartic acid and glutamic acid are referred to as acidic amino acid residues. Arginine and lysine are referred to as basic amino acid residues.

The following amino acids are considered uncharged, polar (meaning they can participate in hydrogen bonding) amino acids: asparagine, glutamine, histidine, serine, threonine, tyrosine, cysteine, methionine, and tryptophan.

The following amino acids are considered uncharged, hydrophobic amino acids: alanine, valine, leucine, isoleucine, phenylalanine, proline, and glycine.

In an amino acid insertion, an additional amino acid residue (one that is not normally present) is incorporated into the BoNT/A polypeptide sequence or fragment thereof, thus increasing the total number of amino acid residues in said sequence. In an amino acid deletion, an amino acid residue is removed from the clostridial toxin amino acid sequence, thus reducing the total number of amino acid residues in said sequence.

Preferably, the modification is a substitution, which advantageously maintains the same number of amino acid residues in the modified BoNT/A or fragment thereof. In an amino acid substitution, an amino acid residue that forms part of the BoNT/A polypeptide sequence or fragment thereof is replaced with a different amino acid residue. The replacement amino acid residue may be one of the 20 standard amino acids, as described above. Alternatively, the replacement amino acid in an amino acid substitution may be a non-standard amino acid (an amino acid that is not part of the standard set of 20 described above). By way of example, the replacement amino acid may be a basic non-standard amino acid, e.g. L-Ornithine, L-2-amino-3-guanidinopropionic acid, or D-isomers of Lysine, Arginine and Ornithine). Methods for introducing non-standard amino acids into proteins are known in the art and include recombinant protein synthesis using *E. coli* auxotrophic expression hosts.

In one embodiment, the substitution is selected from: substitution of an acidic amino acid residue with a basic amino acid residue, substitution of an acidic amino acid residue with an uncharged amino acid residue, and substitution of an uncharged amino acid residue with a basic amino acid residue. In one embodiment, wherein the substitution is a substitution of an acidic amino acid residue with an uncharged amino acid residue, the acidic amino acid residue is replaced with its corresponding uncharged amide amino acid residue (i.e. aspartic acid is replaced with asparagine, and glutamic acid is replaced with glutamine).

Preferably, the basic amino acid residue is a lysine residue or an arginine residue. In other words, the substitution is substitution with lysine or arginine. Most preferably, the modification is substitution with lysine.

Preferably, a modified BoNT/A or fragment thereof for use in the invention comprises between 4 and 40 amino acid modifications located in the clostridial toxin Hcn domain. Said modified BoNT/A or fragment thereof preferably also has pI of at least 6.6. Said modified BoNT/A preferably comprises modifications of at least 4 amino acids selected from: ASN 886, ASN 930, ASN 954, SER 955, GLN 991, ASN 1025, ASN 1026, and ASN 1052, wherein said modification comprises substitution of the amino acids with a lysine residue or an arginine residue. For example, said modified BoNT/A or fragment thereof may comprise modifications of at least 5 amino acids selected from: ASN 886, ASN 930, ASN 954, SER 955, GLN 991, ASN 1025, ASN 1026, ASN 1052, and GLN 1229, wherein said modification comprises substitution of the amino acids with a lysine residue or an arginine residue.

Methods for modifying proteins by substitution, insertion or deletion of amino acid residues are known in the art. By way of example, amino acid modifications may be introduced by modification of a DNA sequence encoding a polypeptide (e.g. encoding unmodified BoNT/A or a fragment thereof). This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively, a modified gene sequence can be chemically synthesised.

In one embodiment a clostridial neurotoxin for use according to the invention comprises a polypeptide sequence having at least 80%, 90%, 95% or 98% sequence identity to SEQ ID NO: 42. Preferably, a clostridial neurotoxin for use according to the invention comprises a polypeptide sequence shown as SEQ ID NO: 42.

In one embodiment a clostridial neurotoxin for use according to the invention comprises a polypeptide sequence that is encoded by a nucleotide sequence having at least 80%, 90%, 95% or 98% sequence identity to SEQ ID NO: 41. Preferably, a clostridial neurotoxin for use according to the invention comprises a polypeptide sequence that is encoded by a nucleotide sequence shown as SEQ ID NO: 41.

In one embodiment a clostridial neurotoxin for use according to the invention (e.g. comprising SEQ ID NO: 42 or encoded by SEQ ID NO: 41) may be a portion of a polypeptide having at least 70% sequence identity to SEQ ID NO: 61 or 65. Thus, in one embodiment a clostridial neurotoxin for use according to the invention may comprise a polypeptide sequence having at least 80%, 90%, 95% or 98% sequence identity to SEQ ID NO: 61 or 65. Preferably, a clostridial neurotoxin for use according to the invention may comprise (more preferably consist of) SEQ ID NO: 61 or 65. In one embodiment the clostridial neurotoxin comprises a catalytically-inactive L-chain (e.g. as per SEQ ID NO: 65).

In one embodiment a clostridial neurotoxin for use according to the invention (e.g. comprising SEQ ID NO: 42 or encoded by SEQ ID NO: 41) may be encoded by a nucleotide sequence having at least 70% sequence identity to SEQ ID NO: 60. Thus, in one embodiment a clostridial neurotoxin for use according to the invention may be encoded by a nucleotide sequence having at least 80%, 90%, 95% or 98% sequence identity to SEQ ID NO: 60. Preferably, a clostridial neurotoxin for use according to the invention may be encoded by a nucleotide sequence comprising (more preferably consisting of) SEQ ID NO: 60. In one embodiment the clostridial neurotoxin comprises a catalytically-inactive L-chain.

SEQ ID NO: 42 is an example of a modified BoNT/A fragment and SEQ ID NOs: 61 and 65 are examples of modified BoNT/A polypeptides that are catalytically active and inactive, respectively. Such modified BoNT/A polypeptides and fragments are particularly preferred for use in the present invention. The polypeptides shown as SEQ ID NO: 42, 61 and 62 have a number of amino acid modifications (e.g. substitutions) when compared to wild-type BoNT/A, which increase the isoelectric point of the polypeptide. Without wishing to be bound by theory, it is believed that the increased net positive charge promotes electrostatic interactions between the polypeptide and anionic extracellular components, thereby promoting binding between the polypeptide and cell surface thus increasing retention at a site of administration and/or duration of action. Thus, it is envisaged that neuroimmune response-promotion properties of SEQ ID NO: 42, 61 and 65 will be improved compared to equivalent polypeptides lacking said modifications.

For the catalytically active modified BoNT/A polypeptides described above (e.g. SEQ ID NO: 61), one way in which these advantageous properties (which represent an increase in the therapeutic index) may be defined is in terms of the Safety Ratio of the modified BoNT/A. In this regard, undesired effects of a clostridial neurotoxin (caused by diffusion of the toxin away from the site of administration) can be assessed experimentally by measuring percentage bodyweight loss in a relevant animal model (e.g. a mouse, where loss of bodyweight is detected within seven days of administration). Conversely, desired on-target effects of a clostridial neurotoxin can be assessed experimentally by Digital Abduction Score (DAS) assay, a measurement of muscle paralysis. The DAS assay may be performed by injection of 20 μl of clostridial neurotoxin, formulated in Gelatin Phosphate Buffer, into the mouse gastrocnemius/soleus complex, followed by assessment of Digital Abduction Score using the method of Aoki (Aoki KR, Toxicon 39:1815-1820; 2001). In the DAS assay, mice are suspended briefly by the tail in order to elicit a characteristic startle response in which the mouse extends its hind limbs and abducts its hind digits. Following clostridial neurotoxin injection, the varying degrees of digit abduction are scored on a five-point scale (0=normal to 4=maximal reduction in digit abduction and leg extension).

The Safety Ratio of a clostridial neurotoxin may then be expressed as the ratio between the amount of toxin required for a 10% drop in a bodyweight (measured at peak effect within the first seven days after dosing in a mouse) and the amount of toxin required for a DAS score of 2. High Safety Ratio scores are therefore desired and indicate a toxin that is able to effectively paralyse a target muscle with little undesired off-target effects. A catalytically active modified BoNT/A of the present invention may have a Safety Ratio that is higher than the Safety Ratio of an equivalent unmodified (native) botulinum toxin (e.g. SEQ ID NO: 62).

Thus, in one embodiment, a catalytically active modified BoNT/A of the present invention has a Safety Ratio of at least 8 (for example, at least 8, 9, 10, 15, 20, 25, 30, 35, 40, 45 or 50), wherein Safety Ratio is calculated as: dose of toxin required for-10% bodyweight change (pg/mouse) divided by DAS $ED_{50}$ (pg/mouse) [$ED_{50}$=dose required to produce a DAS score of 2].

In one embodiment, a catalytically active modified BoNT/A of the present invention has a Safety Ratio of at least 10. In one embodiment, a modified BoNT/A or fragment thereof of the present invention has a Safety Ratio of at least 15.

Clostridial neurotoxins comprising at least 70% sequence identity to SEQ ID NO: 61 are described in WO 2015/004461 A1, which is incorporated herein by reference in its entirety.

In one embodiment a clostridial neurotoxin comprising a polypeptide sequence having at least 70% sequence identity to SEQ ID NO: 42, 61 or 65 and/or comprising a polypeptide sequence that is encoded by a nucleotide sequence having at least 70% sequence identity to SEQ ID NO: 41 or 60 comprises a substitution at one or more (preferably two or more, three or more, four or more, five or more or six or more, more preferably at all) of positions 930, 955, 991, 1026, 1052, 1229, and 886. The position numbering corresponds to the positions of SEQ ID NO: 62 and can be determined by aligning the polypeptide sequence with SEQ ID NO: 62 (unmodified/wild-type BoNT/A). As the presence of a methionine residue at position 1 of SEQ ID NO: 62 is optional, the skilled person will take the presence/absence of the methionine residue into account when determining amino acid residue numbering. For example, where SEQ ID NO: 62 includes a methionine, the position numbering will be as defined above (e.g. position 886 will be ASN 886 of SEQ ID NO: 62). Alternatively, where the methionine is absent from SEQ ID NO: 62 the amino acid residue numbering should be modified by −1 (e.g. position 886 will be ASN 885 of SEQ ID NO: 62). Similar considerations apply when the methionine at position 1 of the other polypeptide sequences described herein is present/absent, and the skilled person will readily determine the correct amino acid residue numbering using techniques routine in the art.

Preferably, the clostridial neurotoxin comprising a polypeptide sequence having at least 70% sequence identity to SEQ ID NO: 42, 61 or 65 and/or comprising a polypeptide sequence that is encoded by a nucleotide sequence having at least 70% sequence identity to SEQ ID NO: 41 or 60 comprises lysine or arginine (more preferably lysine) at one or more of positions 930, 955, 991, 1026, 1052, 1229, and 886. In one embodiment, the clostridial neurotoxin comprises lysine or arginine (more preferably lysine) at least two, three, four, five, six or all of positions 930, 955, 991, 1026, 1052, 1229, and 886. Most preferably, the clostridial neurotoxin comprises lysine or arginine (more preferably lysine) at all of positions 930, 955, 991, 1026, 1052, 1229, and 886.

Embodiments related to the various therapeutic uses of the invention are intended to be applied equally to methods of treatment, polypeptides of the invention, and vice versa.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264 (4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics: 1428-1435 (2004).

Thus, percent sequence identity is determined by conventional methods. See, for example, Altschul et al., Bull. Math. Bio. 48:603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |

-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\begin{array}{c}[\text{length of the longer sequence plus the}\\ \text{number of gaps introduced into the longer}\\ \text{sequence in order to align the two sequences}]\end{array}} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine, lysine, histidine
Acidic: glutamic acid, aspartic acid
Polar: glutamine, asparagine
Hydrophobic: leucine, isoleucine, valine
Aromatic: phenylalanine, tryptophan, tyrosine
Small: glycine, alanine, serine, threonine, methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244:1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such agents and reference to "the clostridial neurotoxin" includes reference to one or more clostridial neurotoxin and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

SEQUENCE LISTING

Figure 1:
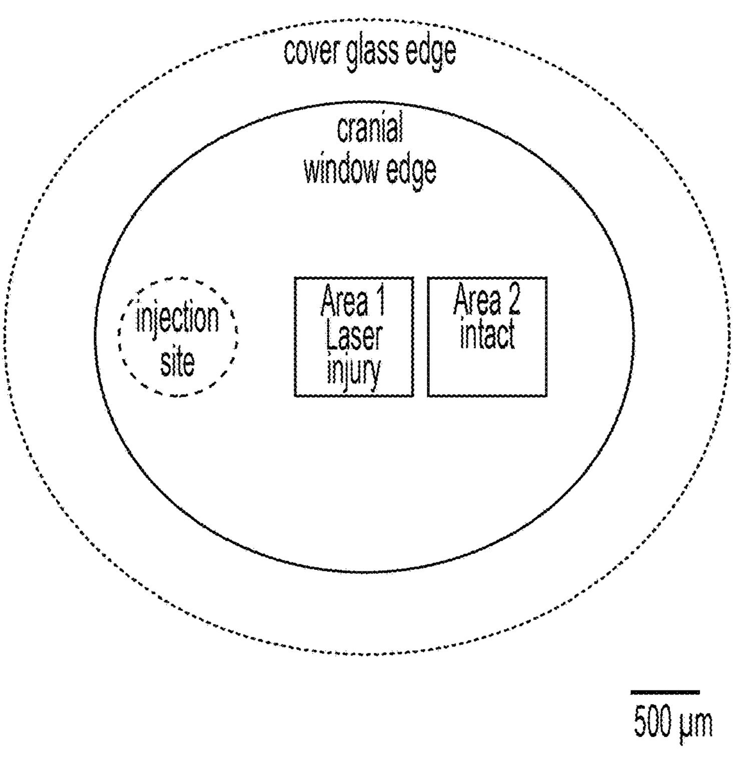
FIG. 1. Schematic diagram of imaging areas' location in the study.

Where an initial Met amino acid residue or a corresponding initial codon is indicated in any of the following SEQ ID NOs, said residue/codon is optional.

SEQ ID NO: 1—Nucleotide Sequence of Recombinant Catalytically Inactive BoNT/A (rBoNT/A (0))

SEQ ID NO: 2—Polypeptide Sequence of rBoNT/A (0)

SEQ ID NO: 3—Nucleotide Sequence of $rLH_N$/A (light-chain plus translocation domain only).

SEQ ID NO: 4—Polypeptide Sequence of $rLH_N$/A

SEQ ID NO: 5—Nucleotide Sequence of rL/A (light-chain only)

SEQ ID NO: 6—Polypeptide Sequence of rL/A

SEQ ID NO: 7—Nucleotide Sequence of $rH_C$/A

SEQ ID NO: 8—Polypeptide Sequence of $rH_C$/A

SEQ ID NO: 9—Nucleotide Sequence of rBoNT/B (0)

SEQ ID NO: 10—Polypeptide Sequence of rBoNT/B (0)

SEQ ID NO: 11—Nucleotide Sequence of rBoNT/C(0)

SEQ ID NO: 12—Polypeptide Sequence of rBoNT/C(0)

SEQ ID NO: 13—Nucleotide Sequence of rBoNT/E (0)

SEQ ID NO: 14—Polypeptide Sequence of rBoNT/E (0)

SEQ ID NO: 15—Nucleotide Sequence of rBoNT/F (0)

SEQ ID NO: 16—Polypeptide Sequence of rBoNT/F (0)

SEQ ID NO: 17—Nucleotide Sequence of rBoNT/A (0) (His-tagged)

SEQ ID NO: 18—Polypeptide Sequence of rBoNT/A (0) (His-tagged)

SEQ ID NO: 19—Nucleotide Sequence of $rLH_N$/A (His-tagged)

SEQ ID NO: 20—Polypeptide Sequence of $rLH_N$/A (His-tagged)

SEQ ID NO: 21—Nucleotide Sequence of $rH_C$/A (His-tagged)

SEQ ID NO: 22—Polypeptide Sequence of $rH_C$/A (His-tagged)

SEQ ID NO: 23—Nucleotide Sequence of rLC/A (His-tagged)

SEQ ID NO: 24—Polypeptide Sequence of rLC/A (His-tagged)

SEQ ID NO: 25—Nucleotide Sequence of rBoNT/FA (0) (His-tagged)

SEQ ID NO: 26—Polypeptide Sequence of rBoNT/FA (0) (His-tagged)

SEQ ID NO: 27—Nucleotide Sequence of $rLH_N$/FA (His-tagged)

SEQ ID NO: 28—Polypeptide Sequence of $rLH_N$/FA (His-tagged)

SEQ ID NO: 29—Nucleotide Sequence of $rH_C$/FA (His-tagged)

SEQ ID NO: 30—Polypeptide Sequence of $rH_C$/FA (His-tagged)

SEQ ID NO: 31—Nucleotide Sequence of rLC/FA (His-tagged)

SEQ ID NO: 32—Polypeptide Sequence of rLC/FA (His-tagged)

SEQ ID NO: 33—Nucleotide Sequence of rBoNT/F (0) (His-tagged)

SEQ ID NO: 34—Polypeptide Sequence of rBoNT/F (0) (His-tagged)

SEQ ID NO: 35—Nucleotide Sequence of $rL_H$N/F (His-tagged)

SEQ ID NO: 36—Polypeptide Sequence of $rLH_N$/F (His-tagged)

SEQ ID NO: 37—Nucleotide Sequence of $rH_C$/F (His-tagged)

SEQ ID NO: 38—Polypeptide Sequence of $rH_C$/F (His-tagged)

SEQ ID NO: 39—Nucleotide Sequence of rLC/F (His-tagged)

SEQ ID NO: 40—Polypeptide Sequence of rLC/F (His-tagged)

SEQ ID NO: 41—Nucleotide Sequence of Cationic $rH_C$/A (His-tagged)

SEQ ID NO: 42—Polypeptide Sequence of Cationic $rH_C$/A (His-tagged)

SEQ ID NO: 43—Nucleotide Sequence of $rH_C$/AB (His-tagged)

SEQ ID NO: 44—Polypeptide Sequence of $rH_C$/AB (His-tagged)

SEQ ID NO: 45—Nucleotide Sequence of $rH_C$/A Variant Y1117V H1253K (His-tagged)

SEQ ID NO: 46—Polypeptide Sequence of $rH_C$/A Variant Y1117V H1253K (His-tagged)

SEQ ID NO: 47—Nucleotide Sequence of $rH_C$/A Variant Y1117V F1252Y H1253K L1278F (His-tagged)

SEQ ID NO: 48—Polypeptide Sequence of $rH_C$/A Variant Y1117V F1252Y H1253K L1278F (His-tagged)

SEQ ID NO: 49—Nucleotide Sequence of $rH_C$/A Variant Y1117V F1252Y H1253K L1278H (His-tagged)

SEQ ID NO: 50—Polypeptide Sequence of $rH_C$/A Variant Y1117V F1252Y H1253K L1278H (His-tagged)

SEQ ID NO: 51—Polypeptide Sequence of BoNT/A—UniProt P10845

SEQ ID NO: 52—Polypeptide Sequence of BoNT/B—UniProt P10844

SEQ ID NO: 53—Polypeptide Sequence of BoNT/C—UniProt P18640

SEQ ID NO: 54—Polypeptide Sequence of BoNT/D—UniProt P19321

SEQ ID NO: 55—Polypeptide Sequence of BoNT/E—UniProt Q00496

SEQ ID NO: 56—Polypeptide Sequence of BoNT/F—UniProt A7GBG3

SEQ ID NO: 57—Polypeptide Sequence of BoNT/G—UniProt Q60393

SEQ ID NO: 58—Polypeptide Sequence of TeNT—UniProt P04958

SEQ ID NO: 59—Polypeptide Sequence of BoNT/X

SEQ ID NO: 60—Nucleotide Sequence of mrBoNT/A

SEQ ID NO: 61—Polypeptide Sequence of mrBoNT/A

SEQ ID NO: 62—Polypeptide Sequence of Unmodified BoNT/A1

SEQ ID NO: 63—Polypeptide Sequence of mrBoNT/AB

SEQ ID NO: 64—Polypeptide Sequence of mrBoNT/AB (0)

SEQ ID NO: 65—Polypeptide Sequence of mrBoNT/A (0)

```
Nucleotide Sequence of rBoNT/A(0)
                                                              SEQ ID NO: 1
ATGCCATTCGTCAACAAGCAATTCAACTACAAAGACCCAGTCAACGGCGTCGACATCGCATACATCAAGATTCCG

AACGCCGGTCAAATGCAGCCGGTTAAGGCTTTTAAGATCCACAACAAGATTTGGGTTATCCCGGAGCGTGACACC

TTCACGAACCCGGAAGAAGGCGATCTGAACCCGCCACCGGAAGCGAAGCAAGTCCCTGTCAGCTACTACGATTCG

ACGTACCTGAGCACGGATAACGAAAAAGATAACTACCTGAAAGGTGTGACCAAGCTGTTCGAACGTATCTACAGC
```

-continued

ACGGATCTGGGTCGCATGCTGCTGACTAGCATTGTTCGCGGTATCCCGTTCTGGGGTGGTAGCACGATTGACACC

GAACTGAAGGTTATCGACACTAACTGCATTAACGTTATTCAACCGGATGGTAGCTATCGTAGCGAAGAGCTGAAT

CTGGTCATCATTGGCCCGAGCGCAGACATTATCCAATTCGAGTGCAAGAGCTTTGGTCACGAGGTTCTGAATCTG

ACCCGCAATGGCTATGGTAGCACCCAGTACATTCGTTTTTCGCCGGATTTTACCTTCGGCTTTGAAGAGAGCCTG

GAGGTTGATACCAATCCGTTGCTGGGTGCGGGCAAATTCGCTACCGATCCGGCTGTCACGCTGGCCCATCAACTG

ATCtACGCAGGCCACCGCCTGTACGGCATTGCCATCAACCCAAACCGTGTGTTCAAGGTTAATACGAATGCATAC

TACGAGATGAGCGGCCTGGAAGTCAGCTTCGAAGAACTGCGCACCTTCGGTGGCCATGACGCTAAATTCATTGAC

AGCTTGCAAGAGAATGAGTTCCGTCTGTACTACTATAACAAATTCAAAGACATTGCAAGCACGTTGAACAAGGCC

AAAAGCATCGTTGGTACTACCGCGTCGTTGCAGTATATGAAGAATGTGTTTAAAGAGAAGTACCTGCTGTCCGAG

GATACCTCCGGCAAGTTTAGCGTTGATAAGCTGAAGTTTGACAAACTGTACAAGATGCTGACCGAGATTTACACC

GAGGACAACTTTGTGAAATTCTTCAAAGTGTTGAATCGTAAAACCTATCTGAATTTTGACAAAGCGGTTTTCAAG

ATTAACATCGTGCCGAAGGTGAACTACACCATCTATGACGGTTTTAACCTGCGTAACACCAACCTGGCGGCGAAC

TTTAACGGTCAGAATACGGAAATCAACAACATGAATTTCACGAAGTTGAAGAACTTCACGGGTCTGTTCGAGTTC

TATAAGCTGCTGTGCGTGCGCGGTATCATCACCAGCAAAACCAAAAGCCTGGACAAAGGCTACAACAAGGCGCTG

AATGACCTGTGCATTAAGGTAAACAATTGGGATCTGTTCTTTTCGCCATCCGAAGATAATTTTACCAACGACCTG

AACAAGGGTGAAGAAATCACCAGCGATACGAATATTGAAGCAGCGGAAGAGAATATCAGCCTGGATCTGATCCAG

CAGTACTATCTGACCTTTAACTTCGACAATGAACCGGAGAACATTAGCATTGAGAATCTGAGCAGCGACATTATC

GGTCAGCTGGAACTGATGCCGAATATCGAACGTTTCCCGAACGGCAAAAAGTACGAGCTGGACAAGTACACTATG

TTCCATTACCTGCGTGCACAGGAGTTTGAACACGGTAAAAGCCGTATCGCGCTGACCAACAGCGTTAACGAGGCC

CTGCTGAACCCGAGCCGTGTCTATACCTTCTTCAGCAGCGACTATGTTAAGAAAGTGAACAAAGCCACTGAGGCC

GCGATGTTCCTGGGCTGGGTGGAACAGCTGGTATATGACTTCACGGACGAGACGAGCGAAGTGAGCACTACCGAC

AAAATTGCTGATATTACCATCATTATCCCGTATATTGGTCCGGCACTGAACATTGGCAACATGCTGTACAAAGAC

GATTTTGTGGGTGCCCTGATCTTCTCCGGTGCCGTGATTCTGCTGGAGTTCATTCCGGAGATTGCGATCCCGGTG

TTGGGTACCTTCGCGCTGGTGTCCTACATCGCGAATAAGGTTCTGACGGTTCAGACCATCGATAACGCGCTGTCG

AAACGTAATGAAAAAATGGGACGAGGTTTACAAATACATTGTTACGAATTGGCTGGCGAAAGTCAATACCCAGATC

GACCTGATCCGTAAGAAAATGAAAGAGGCGCTGGAGAATCAGGCGGAGGCCACCAAAGCAATTATCAACTACCAA

TACAACCAGTACACGGAAGAAGAGAAGAATAACATTAACTTCAATATCGATGATTTGAGCAGCAAGCTGAATGAA

TCTATCAACAAAGCGATGATCAATATCAACAAGTTTTTGAATCAGTGTAGCGTTTCGTACCTGATGAATAGCATG

ATTCCGTATGGCGTCAAACGTCTGGAGGACTTCGACGCCAGCCTGAAAGATGCGTTGCTGAAATACATTTACGAC

AATCGTGGTACGCTGATTGGCCAAGTTGACCGCTTGAAAGACAAAGTTAACAATACCCTGAGCACCGACATCCCA

TTTCAACTGAGCAAGTATGTTGATAATCAACGTCTGTTGAGCACTTTCACCGAGTATATCAAAAACATCATCAAT

ACTAGCATTCTGAACCTGCGTTACGAGAGCAATCATCTGATTGATCTGAGCCGTTATGCAAGCAAGATCAACATC

GGTAGCAAGGTCAATTTTGACCCGATCGATAAGAACCAGATCCAGCTGTTTAATCTGGAATCGAGCAAAATTGAG

GTTATCCTGAAAAACGCCATTGTCTACAACTCCATGTACGAGAATTTCTCCACCAGCTTCTGGATTCGCATCCCG

AAATACTTCAACAGCATTAGCCTGAACAACGAGTATACTATCATCAACTGTATGGAGAACAACAGCGGTTGGAAG

GTGTCTCTGAACTATGGTGAGATCATTTGGACCTTGCAGGACACCCAAGAGATCAAGCAGCGCGTCGTGTTCAAG

TACTCTCAAATGATCAACATTTCCGATTACATTAATCGTTGGATCTTCGTGACCATTACGAATAACCGTCTGAAT

AACAGCAAGATTTACATCAATGGTCGCTTGATCGATCAGAAACCGATTAGCAACCTGGGTAATATCCACGCAAGC

AACAACATTATGTTCAAATTGGACGGTTGCCGCGATACCCATCGTTATATCTGGATCAAGTATTTCAACCTGTTT

GATAAAGAACTGAATGAGAAGGAGATCAAAGATTTGTATGACAACCAATCTAACAGCGGCATTTTGAAGGACTTC

-continued

TGGGGCGATTATCTGCAATACGATAAGCCGTACTATATGCTGAACCTGTATGATCCGAACAAATATGTGGATGTC

AATAATGTGGGTATTCGTGGTTACATGTATTTGAAGGGTCCGCGTGGCAGCGTTATGACGACCAACATTTACCTG

AACTCTAGCCTGTACCGTGGTACGAAATTCATCATTAAGAAATATGCCAGCGGCAACAAAGATAACATTGTGCGT

AATAACGATCGTGTCTACATCAACGTGGTCGTGAAGAATAAAGAGTACCGTCTGGCGACCAACGCTTCGCAGGCG

GGTGTTGAGAAAATTCTGAGCGCGTTGGAGATCCCTGATGTCGGTAATCTGAGCCAAGTCGTGGTTATGAAGAGC

AAGAACGACCAGGGTATCACTAACAAGTGCAAGATGAACCTGCAAGACAACAATGGTAACGACATCGGCTTTATT

GGTTTCCACCAGTTCAACAATATTGCTAAACTGGTAGCGAGCAATTGGTACAATCGTCAGATTGAGCGCAGCAGC

CGTACTTTGGGCTGTAGCTGGGAGTTTATCCCGGTCGATGATGGTTGGGGCGAACGTCCGCTG

Polypeptide Sequence of rBoNT/A(0)

SEQ ID NO: 2

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHQL

IYAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTFTEYIKNIINTSILNLRYESNHLIDLSRYASKINI

GSKVNFDPIDKNQIQLFNLESSKIEVILKNAIVYNSMYENFSTSFWIRIPKYENSISLNNEYTIINCMENNSGWK

VSLNYGEIIWTLQDTQEIKQRVVFKYSQMINISDYINRWIFVTITNNRLNNSKIYINGRLIDQKPISNLGNIHAS

NNIMFKLDGCRDTHRYIWIKYFNLFDKELNEKEIKDLYDNQSNSGILKDFWGDYLQYDKPYYMLNLYDPNKYVDV

NNVGIRGYMYLKGPRGSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQFNNIAKLVASNWYNRQIERSS

RTLGCSWEFIPVDDGWGERPL

Nucleotide Sequence of $rLH_N/A$

SEQ ID NO: 3 atggagttcgttaacaaacagttcaactataaagacccagttaacggtgttgacattgcttacatcaaaatcccg aacgctggccagatgcagccggtaaaggcattcaaaatccacaacaaaatctgggttatcccggaacgtgatacc tttactaacccggaagaaggtgacctgaacccgccaccggaagcgaaacaggtgccggtatcttactatgactcc acctacctgtctaccgataacgaaaaggacaactacctgaaaggtgttactaaactgttcgagcgtatttactcc accgacctgggccgtatgctgctgactagcatcgttcgcggtatcccgttctggggcggttctaccatcgatacc gaactgaaagtaatcgacactaactgcatcaacgttattcagccggacggttcctatcgttccgaagaactgaac ctggtgatcatcggcccgtctgctgatatcatccagttcgagtgtaagagctttggtcacgaagttctgaacctc acccgtaacggctacggttccactcagtacatccgtttctctccggacttcaccttcggttttgaagaatccctg gaagtagacacgaacccactgctgggcgctggtaaattcgcaactgatcctgcggttaccctggctcacgaactg attcatgcaggccaccgcctgtacggtatcgccatcaatccgaaccgtgtcttcaaagttaacaccaacgcgtat tacgagatgtccggtctggaagttagcttcgaagaactgcgtacttttggcggtcacgacgctaaattcatcgac tctctgcaagaaaacgagttccgtctgtactactataacaagttcaaagatatcgcatccaccctgaacaaagcg aaatccatcgtgggtaccactgcttctctccagtacatgaagaacgtttttaagaaaaatacctgctcagcgaa gacacctccggcaaattctctgtagacaagttgaaattcgataaactttacaaaatgctgactgaaatttacacc gaagacaacttcgttaagttctttaaagttctgaaccgcaaaacctatctgaacttcgacaaggcagtattcaaa atcaacatcgtgccgaaagttaactacactatctacgatggtttcaacctgcgtaacaccaacctggctgctaat tttaacggccagaacacggaaatcaacaacatgaacttcacaaaactgaaaaacttcactggtctgttcgagttt tacaagctgctgtgcGTCGACGGCATCATTACCTCCAAAACTAAATCTGACGATGACGATAAAAACAAAGCGCTG AACCTGCAGtgtatcaaggttaacaactgggatttattcttcagcccgagtgaagacaacttcaccaacgacctg aacaaaggtgaagaaatcacctcagatactaacatcgaagcagccgaagaaaacatctcgctggacctgatccag cagtactacctgacctttaatttcgacaacgagccggaaaacatttctatcgaaaacctgagctctgatatcatc ggccagctggaactgatgccgaacatcgaacgtttcccaaacggtaaaaagtacgagctggacaaatataccatg ttccactacctgcgcgcgcaggaatttgaacacggcaaatcccgtatcgcactgactaactccgttaacgaagct ctgctcaacccgtcccgtgtatacaccttcttctctagcgactacgtgaaaaaggtcaacaaagcgactgaagct gcaatgttcttgggttgggttgaacagcttgtttatgattttaccgacgagacgtccgaagtatctactaccgac aaaattgcggatatcactatcatcatcccgtacatcggtccggctctgaacattggcaacatgctgtacaaagac gacttcgttggcgcactgatcttctccggtgcggtgatcctgctggagttcatcccggaaatcgccatcccggta ctgggcacctttgctctggtttcttacattgcaaacaaggttctgactgtacaaaccatcgacaacgcgctgagc aaacgtaacgaaaaatgggatgaagtttacaaatatatcgtgaccaactggctggctaaggttaatactcagatc gacctcatccgcaaaaaaatgaaagaagcactggaaaaccaggcggaagctaccaaggcaatcattaactaccag tacaaccagtacaccgaggaagaaaaaaacaacatcaacttcaacatcgacgatctgtcctctaaactgaacgaa tccatcaacaaagctatgatcaacatcaacaagttcctgaaccagtgctctgtaagctatctgatgaactccatg atcccgtacggtgttaaacgtctggaggacttcgatgcgtctctgaaagacgccctgctgaaatacatttacgac aaccgtggcactctgatcggtcaggttgatcgtctgaaggacaaagtgaacaataccttatcgaccgacatccct tttcagctcagtaaatatgtcgataaccaacgccttttgtccactctagaagcaCACCATCATCACcaccatcac catcaccat Polypeptide Sequence of $rLH_N$/A

SEQ ID NO: 4

MEFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTINKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVDGIITSKTKSDDDDKNKAL

NLQCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTLEAHHHHHHHHHH

Nucleotide Sequence of rL/A

SEQ ID NO: 5

ATGCCATTCGTCAACAAGCAATTCAACTACAAAGACCCAGTCAACGGCGTCGACATCGCATACATCAAGATTCCG

AACGCCGGTCAAATGCAGCCGGTTAAGGCTTTTAAGATCCACAACAAGATTTGGGTTATCCCGGAGCGTGACACC

TTCACGAACCCGGAAGAAGGCGATCTGAACCCGCCACCGGAAGCGAAGCAAGTCCCTGTCAGCTACTACGATTCG

-continued

ACGTACCTGAGCACGGATAACGAAAAAGATAACTACCTGAAAGGTGTGACCAAGCTGTTCGAACGTATCTACAGC

ACGGATCTGGGTCGCATGCTGCTGACTAGCATTGTTCGCGGTATCCCGTTCTGGGGTGGTAGCACGATTGACACC

GAACTGAAGGTTATCGACACTAACTGCATTAACGTTATTCAACCGGATGGTAGCTATCGTAGCGAAGAGCTGAAT

CTGGTCATCATTGGCCCGAGCGCAGACATTATCCAATTCGAGTGCAAGAGCTTTGGTCACGAGGTTCTGAATCTG

ACCCGCAATGGCTATGGTAGCACCCAGTACATTCGTTTTTCGCCGGATTTTACCTTCGGCTTTGAAGAGAGCCTG

GAGGTTGATACCAATCCGTTGCTGGGTGCGGGCAAATTCGCTACCGATCCGGCTGTCACGCTGGCCCATGAACTG

ATCCACGCAGGCCACCGCCTGTACGGCATTGCCATCAACCCAAACCGTGTGTTCAAGGTTAATACGAATGCATAC

TACGAGATGAGCGGCCTGGAAGTCAGCTTCGAAGAACTGCGCACCTTCGGTGGCCATGACGCTAAATTCATTGAC

AGCTTGCAAGAGAATGAGTTCCGTCTGTACTACTATAACAAATTCAAAGACATTGCAAGCACGTTGAACAAGGCC

AAAAGCATCGTTGGTACTACCGCGTCGTTGCAGTATATGAAGAATGTGTTTAAAGAGAAGTACCTGCTGTCCGAG

GATACCTCCGGCAAGTTTAGCGTTGATAAGCTGAAGTTTGACAAACTGTACAAGATGCTGACCGAGATTTACACC

GAGGACAACTTTGTGAAATTCTTCAAAGTGTTGAATCGTAAAACCTATCTGAATTTTGACAAAGCGGTTTTCAAG

ATTAACATCGTGCCGAAGGTGAACTACACCATCTATGACGGTTTTAACCTGCGTAACACCAACCTGGCGGCGAAC

TTTAACGGTCAGAATACGGAAATCAACAACATGAATTTCACGAAGTTGAAGAACTTCACGGGTCTGTTCGAGTTC

TATAAGCTGCTGGgtctagaagcaCACCATCATCACcaccatcaccatcaccat

Polypeptide Sequence of rL/A

SEQ ID NO: 6

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLGLEAHHHHHHHHHH

Nucleotide Sequence of $rH_C/A$

SEQ ID NO: 7

ATGCATCATCACCATCACCACAAAAACATCATCAATACTAGCATTCTGAACCTGCGTTACGAGAGCAATCATCTG

ATTGATCTGAGCCGTTATGCAAGCAAGATCAACATCGGTAGCAAGGTCAATTTTGACCCGATCGATAAGAACCAG

ATCCAGCTGTTTAATCTGGAATCGAGCAAAATTGAGGTTATCCTGAAAAACGCCATTGTCTACAACTCCATGTAC

GAGAATTTCTCCACCAGCTTCTGGATTCGCATCCCGAAATACTTCAACAGCATTAGCCTGAACAACGAGTATACT

ATCATCAACTGTATGGAGAACAACAGCGGTTGGAAGGTGTCTCTGAACTATGGTGAGATCATTTGGACCTTGCAG

GACACCCAAGAGATCAAGCAGCGCGTCGTGTTCAAGTACTCTCAAATGATCAACATTTCCGATTACATTAATCGT

TGGATCTTCGTGACCATTACGAATAACCGTCTGAATAACAGCAAGATTTACATCAATGGTCGCTTGATCGATCAG

AAACCGATTAGCAACCTGGGTAATATCCACGCAAGCAACAACATTATGTTCAAATTGGACGGTTGCCGCGATACC

CATCGTTATATCTGGATCAAGTATTTCAACCTGTTTGATAAAGAACTGAATGAGAAGGAGATCAAAGATTTGTAT

GACAACCAATCTAACAGCGGCATTTTGAAGGACTTCTGGGGCGATTATCTGCAATACGATAAGCCGTACTATATG

CTGAACCTGTATGATCCGAACAAATATGTGGATGTCAATAATGTGGGTATTCGTGGTTACATGTATTTGAAGGGT

CCGCGTGGCAGCGTTATGACGACCAACATTTACCTGAACTCTAGCCTGTACCGTGGTACGAAATTCATCATTAAG

AAATATGCCAGCGGCAACAAAGATAACATTGTGCGTAATAACGATCGTGTCTACATCAACGTGGTCGTGAAGAAT

AAAGAGTACCGTCTGGCGACCAACGCTTCGCAGGCGGGTGTTGAGAAAATTCTGAGCGCGTTGGAGATCCCTGAT

GTCGGTAATCTGAGCCAAGTCGTGGTTATGAAGAGCAAGAACGACCAGGGTATCACTAACAAGTGCAAGATGAAC

CTGCAAGACAACAATGGTAACGACATCGGCTTTATTGGTTTCCACCAGTTCAACAATATTGCTAAACTGGTAGCG

AGCAATTGGTACAATCGTCAGATTGAGCGCAGCAGCCGTACTTTGGGCTGTAGCTGGGAGTTTATCCCGGTCGAT

GATGGTTGGGGCGAACGTCCGCTG

-continued

Polypeptide Sequence of $rH_C$/A

SEQ ID NO: 8

MHHHHHHKNIINTSILNLRYESNHLIDLSRYASKINIGSKVNFDPIDKNQIQLENLESSKIEVILKNAIVYNSMY

ENFSTSFWIRIPKYENSISLNNEYTIINCMENNSGWKVSLNYGEIIWTLQDTQEIKQRVVFKYSQMINISDYINR

WIFVTITNNRLNNSKIYINGRLIDQKPISNLGNIHASNNIMFKLDGCRDTHRYIWIKYFNLEDKELNEKEIKDLY

DNQSNSGILKDFWGDYLQYDKPYYMLNLYDPNKYVDVNNVGIRGYMYLKGPRGSVMTTNIYLNSSLYRGTKFIIK

KYASGNKDNIVRNNDRVYINVVVKNKEYRLATNASQAGVEKILSALEIPDVGNLSQVVVMKSKNDQGITNKCKMN

LQDNNGNDIGFIGFHQFNNIAKLVASNWYNRQIERSSRTLGCSWEFIPVDDGWGERPL

Nucleotide Sequence of rBoNT/B(0)

SEQ ID NO: 9

ATGCCGGTGACGATTAACAACTTCAACTACAACGACCCGATTGACAACAACAACATTATCATGATGGAACCGCCG

TTTGCACGCGGCACGGGCCGTTATTACAAAGCGTTTAAAATCACCGATCGTATTTGGATTATCCCGGAACGCTAC

ACGTTTGGTTATAAACCGGAAGACTTCAACAAAAGCTCTGGCATCTTCAACCGTGATGTTTGCGAATACTACGAT

CCGGACTACCTGAACACCAACGATAAGAAAAACATTTTTCTGCAAACGATGATCAAACTGTTCAATCGCATTAAA

AGCAAACCGCTGGGTGAAAAACTGCTGGAAATGATTATCAATGGCATTCCGTATCTGGGTGATCGTCGCGTGCCG

CTGGAAGAATTTAACACCAATATCGCGAGTGTTACGGTCAACAAACTGATTTCCAATCCGGGTGAAGTCGAACGT

AAAAAAGGCATCTTCGCCAACCTGATCATCTTCGGCCCGGGTCCGGTGCTGAACGAAAATGAAACCATTGATATC

GGTATTCAGAACCATTTTGCCTCACGCGAAGGCTTCGGCGGTATTATGCAAATGAAATTTTGCCCGGAATATGTG

TCGGTTTTCAACAATGTTCAGGAAAACAAAGGTGCAAGCATCTTTAATCGTCGCGGCTATTTCTCTGATCCGGCT

CTGATCCTGATGCACCAACTGATTtATGTGCTGCACGGCCTGTATGGTATCAAAGTGGATGACCTGCCGATCGTT

CCGAACGAGAAAAAATTTTTCATGCAGAGCACCGACGCAATTCAAGCTGAAGAACTGTATACGTTTGGCGGTCAG

GACCCGTCTATTATCACCCCGAGCACCGACAAAAGCATCTACGATAAAGTGCTGCAAAACTTTCGTGGCATTGTT

GACCGCCTGAATAAAGTCCTGGTGTGTATCTCTGATCCGAACATCAACATCAACATCTACAAAAACAAATTCAAA

GACAAATACAAATTCGTTGAAGATTCTGAAGGCAAATATAGTATTGACGTCGAATCCTTTGATAAACTGTACAAA

AGTCTGATGTTCGGTTTCACCGAAACGAACATCGCGGAAAACTACAAAATCAAAACCCGCGCCTCCTATTTCAGC

GACTCTCTGCCGCCGGTTAAAATCAAAAATCTGCTGGATAACGAAATTTATACGATCGAAGAAGGTTTCAACATC

AGCGATAAAGACATGGAAAAAGAATACCGTGGCCAGAATAAAGCAATCAACAAACAGGCGTATGAAGAAATTAGT

AAAGAACATCTGGCGGTCTACAAAATTCAGATGTGCAAATCCGTGAAAGCCCCGGGTATTTGTATCGATGTTGAC

AATGAAGACCTGTTTTTCATCGCCGATAAAAACAGTTTTTCCGATGACCTGTCAAAAAATGAACGCATCGAATAC

AACACCCAATCGAACTACATCGAAAACGATTTCCCGATCAACGAACTGATTCTGGATACGGACCTGATTAGTAAA

ATCGAACTGCCGTCAGAAAACACCGAATCGCTGACGGACTTTAATGTTGATGTCCCGGTGTATGAAAAACAGCCG

GCAATTAAGAAAATTTTTACCGATGAAAACACGATCTTCCAGTACCTGTACAGCCAAACCTTTCCGCTGGACATT

CGCGATATCTCTCTGACGAGTTCCTTTGATGACGCACTGCTGTTCAGCAACAAAGTGTACTCCTTTTTCTCAATG

GATTACATCAAAACCGCTAACAAAGTGGTTGAAGCGGGCCTGTTTGCCGGTTGGGTGAAACAGATCGTTAACGAT

TTCGTCATCGAAGCCAACAAAAGTAACACGATGGATAAAATTGCTGATATCTCCCTGATTGTCCCGTATATTGGC

CTGGCACTGAATGTGGGTAACGAAACGGCGAAAGGCAATTTTGAAAACGCCTTCGAAATTGCAGGCGCTTCAATC

CTGCTGGAATTTATTCCGGAACTGCTGATCCCGGTCGTGGGTGCGTTCCTGCTGGAATCTTACATCGACAACAAA

AACAAAATCATCAAAACCATTGATAACGCGCTGACGAAACGTAACGAAAAATGGTCAGATATGTACGGCCTGATT

GTTGCCCAGTGGCTGAGCACCGTCAACACGCAATTTTACACCATCAAAGAAGGTATGTACAAAGCGCTGAATTAT

CAGGCGCAAGCCCTGGAAGAAATCATCAAATACCGCTACAACATCTACAGCGAAAAAGAAAAATCTAACATCAAC

ATCGACTTTAATGATATCAACAGCAAACTGAACGAAGGTATCAACCAGGCAATCGATAACATCAACAACTTCATC

AACGGCTGCTCAGTGTCGTATCTGATGAAGAAAATGATCCCGCTGGCTGTTGAAAAACTGCTGGATTTTGACAAC

-continued

ACCCTGAAGAAAAACCTGCTGAACTACATCGATGAAAACAAACTGTACCTGATCGGCTCAGCCGAATACGAAAAA

TCGAAAGTGAACAAATACCTGAAAACCATCATGCCGTTTGACCTGAGTATTTACACCAACGATACGATCCTGATC

GAAATGTTCAACAAATACAACTCCGAAATTCTGAACAATATTATCCTGAACCTGCGTTACAAAGACAACAATCTG

ATCGATCTGAGCGGCTATGGTGCAAAAGTTGAAGTCTACGACGGTGTCGAACTGAACGATAAAAACCAGTTCAAA

CTGACCTCATCGGCTAACTCAAAAATTCGTGTGACGCAGAACCAAAACATCATCTTCAACTCGGTCTTTCTGGAC

TTCAGCGTGTCTTTCTGGATTCGCATCCCGAAATATAAAAATGATGGCATCCAGAACTACATCCATAACGAATAC

ACCATCATCAACTGTATGAAAAACAACAGTGGTTGGAAAATTTCCATCCGTGGCAACCGCATTATCTGGACCCTG

ATTGATATCAATGGTAAAACGAAAAGCGTGTTTTTCGAATACAACATCCGTGAAGATATCTCTGAATACATCAAT

CGCTGGTTTTTCGTGACCATTACGAACAATCTGAACAATGCGAAAATCTATATCAACGGCAAACTGGAAAGTAAT

ACCGACATCAAAGATATTCGTGAAGTTATCGCCAACGGTGAAATCATCTTCAAACTGGATGGCGACATCGATCGC

ACCCAGTTCATTTGGATGAAATACTTCTCCATCTTCAACACGGAACTGAGTCAGTCCAATATCGAAGAACGCTAC

AAAATCCAATCATACTCGGAATACCTGAAAGATTTCTGGGGTAACCCGCTGATGTACAACAAAGAATACTACATG

TTCAACGCGGGCAACAAAAACTCATACATCAAACTGAAAAAAGATTCGCCGGTGGGTGAAATCCTGACCCGTAGC

AAATACAACCAGAACTCTAAATACATCAACTATCGCGATCTGTACATTGGCGAAAAATTTATTATCCGTCGCAAA

AGCAACTCTCAGAGTATTAATGATGACATCGTGCGTAAAGAAGACTACATCTATCTGGATTTCTTTAATCTGAAC

CAAGAATGGCGCGTTTATACCTACAAATACTTCAAAAAAGAAGAAGAGAAACTGTTCCTGGCCCCGATTAGCGAC

AGCGATGAATTTTACAACACCATCCAGATCAAAGAATACGATGAACAGCCGACGTATAGTTGCCAACTGCTGTTC

AAAAAAGACGAAGAATCCACCGATGAAATTGGCCTGATTGGTATCCACCGTTTCTATGAAAGCGGTATCGTTTTC

GAAGAATACAAAGATTACTTCTGTATCTCTAAATGGTATCTGAAAGAAGTCAAACGCAAACCGTACAACCTGAAA

CTGGGCTGCAACTGGCAATTTATCCCGAAAGACGAAGGCTGGACCGAA

Polypeptide Sequence of rBoNT/B(0)

SEQ ID NO: 10

MPVTINNENYNDPIDNNNIIMMEPPFARGTGRYYKAFKITDRIWIIPERYTFGYKPEDENKSSGIFNRDVCEYYD

PDYLNTNDKKNIFLQTMIKLFNRIKSKPLGEKLLEMIINGIPYLGDRRVPLEEFNTNIASVTVNKLISNPGEVER

KKGIFANLIIFGPGPVLNENETIDIGIQNHFASREGFGGIMQMKFCPEYVSVENNVQENKGASIFNRRGYFSDPA

LILMHQLIYVLHGLYGIKVDDLPIVPNEKKFFMQSTDAIQAEELYTFGGQDPSIITPSTDKSIYDKVLQNFRGIV

DRLNKVLVCISDPNININIYKNKFKDKYKFVEDSEGKYSIDVESFDKLYKSLMFGFTETNIAENYKIKTRASYFS

DSLPPVKIKNLLDNEIYTIEEGFNISDKDMEKEYRGQNKAINKQAYEEISKEHLAVYKIQMCKSVKAPGICIDVD

NEDLFFIADKNSESDDLSKNERIEYNTQSNYIENDFPINELILDTDLISKIELPSENTESLTDFNVDVPVYEKQP

AIKKIFTDENTIFQYLYSQTFPLDIRDISLTSSFDDALLESNKVYSFFSMDYIKTANKVVEAGLFAGWVKQIVND

FVIEANKSNTMDKIADISLIVPYIGLALNVGNETAKGNFENAFEIAGASILLEFIPELLIPVVGAFLLESYIDNK

NKIIKTIDNALTKRNEKWSDMYGLIVAQWLSTVNTQFYTIKEGMYKALNYQAQALEEIIKYRYNIYSEKEKSNIN

IDENDINSKLNEGINQAIDNINNFINGCSVSYLMKKMIPLAVEKLLDFDNTLKKNLLNYIDENKLYLIGSAEYEK

SKVNKYLKTIMPFDLSIYTNDTILIEMFNKYNSEILNNIILNLRYKDNNLIDLSGYGAKVEVYDGVELNDKNQFK

LTSSANSKIRVTQNQNIIFNSVFLDESVSFWIRIPKYKNDGIQNYIHNEYTIINCMKNNSGWKISIRGNRIIWTL

IDINGKTKSVFFEYNIREDISEYINRWFFVTITNNLNNAKIYINGKLESNTDIKDIREVIANGEIIFKLDGDIDR

TQFIWMKYFSIFNTELSQSNIEERYKIQSYSEYLKDFWGNPLMYNKEYYMFNAGNKNSYIKLKKDSPVGEILTRS

KYNQNSKYINYRDLYIGEKFIIRRKSNSQSINDDIVRKEDYIYLDFFNLNQEWRVYTYKYFKKEEEKLFLAPISD

SDEFYNTIQIKEYDEQPTYSCQLLFKKDEESTDEIGLIGIHRFYESGIVFEEYKDYFCISKWYLKEVKRKPYNLK

LGCNWQFIPKDEGWTE

-continued

Nucleotide Sequence of rBoNT/C(0)

SEQ ID NO: 11

ATGCCGATCACGATTAATAATTTCAACTATAGCGATCCGGTGGACAATAAGAATATTCTGTATCTGGATACTCAT

CTGAATACGCTGGCTAACGAACCGGAGAAAGCGTTCCGCATCACAGGCAACATCTGGGTTATTCCCGATCGCTTT

TCACGCAACAGCAACCCTAATCTGAACAAACCTCCTCGTGTCACCAGTCCTAAATCCGGTTATTACGACCCAAAC

TATCTGAGTACGGATAGCGATAAAGATCCCTTTCTGAAAGAGATCATTAAGCTGTTCAAACGCATTAACTCTCGC

GAAATTGGGGAAGAGCTGATCTATCGGCTTTCGACAGATATCCCGTTCCCAGGTAACAATAATACCCCGATTAAT

ACTTTCGACTTTGATGTTGATTTCAATTCTGTGGATGTGAAAACGCGTCAAGGCAATAATTGGGTGAAAACTGGT

AGCATTAACCCGAGTGTAATTATCACAGGTCCCCGTGAGAACATCATCGACCCGGAAACCTCTACCTTCAAGCTG

ACGAACAACACGTTTGCTGCACAGGAAGGGTTTGGTGCCCTGTCAATCATTTCCATCTCACCGCGTTTCATGTTA

ACCTACTCCAATGCCACAAATGATGTTGGCGAAGGACGTTTTAGCAAATCAGAATTTTGCATGGACCCAATTCTC

ATTCTGATGggCacGCTGAACaATGCGATGCACAACTTGTATGGCATTGCTATTCCAAACGATCAAACCATTAGC

TCCGTTACCAGTAATATCTTCTATAGCCAGTATAATGTCAAATTGGAGTATGCCGAAATTTACGCCTTTGGAGGC

CCGACCATTGACCTGATTCCGAAATCTGCACGCAAATACTTCGAAGAAAAGGCGTTAGATTACTATCGCAGCATC

GCGAAACGCCTGAACTCGATTACCACGGCCAATCCGTCGTCGTTCAACAAATACATTGGTGAATATAAACAGAAA

CTGATTCGCAAATATCGGTTTGTCGTAGAAAGCTCTGGTGAAGTGACTGTAAACCGCAACAAATTTGTCGAACTC

TACAACGAGTTGACCCAAATCTTTACCGAGTTTAACTACGCAAAGATCTATAACGTACAGAACCGCAAGATTTAT

CTTAGCAATGTATACACACCGGTTACTGCGAACATCTTAGACGACAATGTGTATGATATTCAGAATGGCTTTAAC

ATCCCGAAATCAAATCTGAACGTTCTGTTTATGGGCCAGAACCTGAGTCGTAATCCAGCACTGCGTAAAGTGAAC

CCGGAAAATATGCTCTACTTGTTTACCAAATTTTGCCACAAAGCGATTGATGGCCGCTCTCTCTATAACAAAACG

CTGGATTGTCGTGAGTTACTTGTGAAGAACACTGATTTACCGTTCATTGGGGATATCTCCGACGTGAAAACCGAT

ATCTTCCTGCGCAAAGACATTAATGAAGAAACGGAAGTCATCTATTACCCCGACAATGTGAGCGTTGATCAGGTC

ATTTTATCGAAGAACACCTCCGAACATGGTCAGTTGGATTTGCTGTACCCTAGCATTGACTCGGAGAGTGAAATC

CTTCCGGGCGAAAATCAAGTGTTTTACGACAACCGTACCCAAAATGTTGATTATTTGAATTCTTATTACTACCTG

GAATCTCAGAAATTGAGCGACAATGTGGAAGATTTCACGTTCACACGCTCCATTGAGGAAGCGCTGGATAATAGC

GCGAAAGTGTATACGTATTTCCCTACCTTGGCGAATAAAGTAAATGCTGGTGTCCAGGGAGGCTTATTTCTGATG

TGGGCGAATGATGTGGTAGAAGATTTTACGACCAATATTTTGCGTAAGGACACCTTAGATAAAATTAGCGATGTT

AGCGCCATCATCCCCTATATTGGCCCAGCACTGAATATCTCGAACTCTGTGCGTCGCGGAAACTTCACCGAAGCA

TTTGCGGTGACCGGGGTTACTATTCTGTTGGAAGCCTTTCCGGAGTTTACTATTCCGGCGCTGGGTGCGTTTGTG

ATTTATTCGAAAGTACAAGAACGCAATGAAATTATCAAAACCATCGATAATTGCCTGGAACAACGCATTAAACGC

TGGAAGGATTCTTATGAATGGATGATGGGCACCTGGTTATCCCGTATTATCACACAGTTTAACAACATCTCGTAT

CAGATGTACGATTCACTGAACTACCAAGCAGGGGCGATCAAAGCCAAGATCGACTTAGAATACAAGAAATATTCA

GGTAGCGATAAAGAGAATATTAAAAGCCAGGTTGAAAACCTGAAGAACTCTCTGGATGTCAAAATTTCAGAGGCT

ATGAACAACATTAACAAATTTATCCGCGAATGTAGCGTCACGTATCTGTTTAAAAACATGCTCCCGAAAGTGATT

GATGAGCTCAACGAGTTTGATCGCAACACAAAGGCCAAACTGATTAACCTGATTGATAGTCACAATATTATTTTA

GTCGGTGAAGTTGACAAGCTGAAGGCTAAGGTCAATAACAGCTTTCAGAACACTATTCCGTTTAATATTTTCTCC

TATACGAACAATAGTCTGCTGAAAGACATTATCAACGAATACTTCAACAATATTAATGACAGCAAAATTCTGAGC

CTGCAGAATCGTAAGAATACGCTGGTAGATACCAGTGGATATAATGCGGAAGTCTCAGAAGAGGGTGATGTACAG

CTGAACCCGATCTTTCCGTTCGACTTTAAACTGGGGTCTAGTGGTGAAGATCGCGGTAAAGTGATCGTTACCCAA

AACGAGAACATTGTGTATAACAGCATGTACGAGAGTTTCTCAATTTCTTTCTGGATTCGCATCAATAAATGGGTT

TCTAATTTGCCTGGCTATACCATCATTGATAGCGTCAAAAACAACTCGGGCTGGTCGATTGGCATTATTAGCAAC

-continued

TTTCTGGTGTTTACCCTGAAACAGAATGAGGATTCGGAACAGAGCATTAACTTCTCCTACGACATCAGCAACAAT

GCACCAGGGTATAACAAATGGTTCTTCGTAACGGTGACGAACAATATGATGGGCAATATGAAAATCTACATTAAC

GGGAAACTTATCGACACCATTAAAGTGAAAGAGCTTACTGGGATCAATTTTAGTAAAACCATTACCTTTGAGATC

AACAAAATTCCGGACACGGGTCTGATTACCTCCGATTCGGATAATATCAATATGTGGATTCGCGACTTTTATATC

TTCGCCAAAGAACTTGATGGCAAAGATATCAACATTTTGTTTAATTCCCTGCAGTATACCAATGTCGTTAAGGAC

TATTGGGGCAATGATCTCCGCTACAATAAAGAATACTACATGGTTAACATCGACTATCTCAATCGCTACATGTAT

GCTAACTCGCGTCAAATTGTGTTTAACACACGTCGTAACAACAACGATTTTAACGAAGGTTATAAAATCATTATC

AAACGGATCCGCGGCAATACGAACGATACTCGTGTTCGTGGCGGTGACATTCTGTATTTCGACATGACGATTAAT

AATAAAGCGTACAATCTGTTCATGAAGAACGAAACCATGTACGCCGATAACCATTCCACTGAAGATATCTACGCA

ATCGGACTTCGCGAACAGACCAAAGACATTAACGACAACATCATCTTTCAGATTCAACCGATGAATAATACCTAC

TACTATGCCTCCCAGATCTTCAAAAGTAATTTCAACGGCGAAAACATTTCAGGCATTTGCTCAATCGGCACTTAT

CGGTTCCGGTTAGGTGGTGATTGGTATCGTCACAACTACCTTGTTCCCACAGTGAAACAAGGCAACTATGCATCG

CTCTTAGAAAGCACATCTACGCATTGGGGTTTTGTGCCAGTCAGTGAA

Polypeptide Sequence of rBoNT/C(0)

SEQ ID NO: 12

MPITINNFNYSDPVDNKNILYLDTHLNTLANEPEKAFRITGNIWVIPDRFSRNSNPNLNKPPRVTSPKSGYYDPN

YLSTDSDKDPFLKEIIKLFKRINSREIGEELIYRLSTDIPFPGNNNTPINTFDFDVDFNSVDVKTRQGNNWVKTG

SINPSVIITGPRENIIDPETSTFKLTNNTFAAQEGFGALSIISISPRFMLTYSNATNDVGEGRFSKSEFCMDPIL

ILMGTLNNAMHNLYGIAIPNDQTISSVTSNIFYSQYNVKLEYAEIYAFGGPTIDLIPKSARKYFEEKALDYYRSI

AKRLNSITTANPSSENKYIGEYKQKLIRKYRFVVESSGEVTVNRNKEVELYNELTQIFTEFNYAKIYNVQNRKIY

LSNVYTPVTANILDDNVYDIQNGFNIPKSNLNVLFMGQNLSRNPALRKVNPENMLYLFTKFCHKAIDGRSLYNKT

LDCRELLVKNTDLPFIGDISDVKTDIFLRKDINEETEVIYYPDNVSVDQVILSKNTSEHGQLDLLYPSIDSESEI

LPGENQVFYDNRTQNVDYLNSYYYLESQKLSDNVEDFTFTRSIEEALDNSAKVYTYFPTLANKVNAGVQGGLFLM

WANDVVEDFTTNILRKDTLDKISDVSAIIPYIGPALNISNSVRRGNFTEAFAVTGVTILLEAFPEFTIPALGAFV

IYSKVQERNEIIKTIDNCLEQRIKRWKDSYEWMMGTWLSRIITQFNNISYQMYDSLNYQAGAIKAKIDLEYKKYS

GSDKENIKSQVENLKNSLDVKISEAMNNINKFIRECSVTYLFKNMLPKVIDELNEFDRNTKAKLINLIDSHNIIL

VGEVDKLKAKVNNSFQNTIPFNIFSYTNNSLLKDIINEYFNNINDSKILSLQNRKNTLVDTSGYNAEVSEEGDVQ

LNPIFPFDFKLGSSGEDRGKVIVTQNENIVYNSMYESFSISFWIRINKWVSNLPGYTIIDSVKNNSGWSIGIISN

FLVFTLKQNEDSEQSINFSYDISNNAPGYNKWFFVTVTNNMMGNMKIYINGKLIDTIKVKELTGINFSKTITFEI

NKIPDTGLITSDSDNINMWIRDFYIFAKELDGKDINILFNSLQYTNVVKDYWGNDLRYNKEYYMVNIDYLNRYMY

ANSRQIVENTRRNNNDFNEGYKIIIKRIRGNTNDTRVRGGDILYFDMTINNKAYNLFMKNETMYADNHSTEDIYA

IGLREQTKDINDNIIFQIQPMNNTYYYASQIFKSNENGENISGICSIGTYRFRLGGDWYRHNYLVPTVKQGNYAS

LLESTSTHWGFVPVSE

Nucleotide Sequence of rBoNT/E(0)

SEQ ID NO: 13 atgccgaaaatcaactctttcaactacaacgacccggttaacgaccgtaccatcctgtatatcaaaccgggtggt tgccaggagttctacaaatctttcaacatcatgaaaaacatctggatcatcccggaacgtaacgttatcggtacc accccgcaggacttccacccgccgacctctctgaaaaacggtgactcttcttactacgacccgaactacctccag tctgacgaagaaaaagaccgtttcctgaaaatcgttaccaaaatcttcaaccgtatcaacaacaacctgtctggt ggtatcctgctggaagaactgtctaaagctaacccgtacctgggtaacgacaacaccccggacaaccagttccac atcggtgacgcttctgctgttgaaatcaaattctctaacggttctcaggacatcctgctgccgaacgttatcatc atgggtgctgaaccggacctgttcgaaaccaactcttctaacatctctctgcgtaacaactacatgccgtctaac cacggtttcggttctatcgctatcgttaccttctctccggaatactctttccgtttcaacgacaacagcatgaac -continued

```
gagttcatccaggacccggctctgaccctgatgcaccaactgatctactctctgcacggtctgtacggtgctaaa
ggtatcaccaccaaatacaccatcacccagaaacagaacccgctgatcaccaacatccgtggtaccaacatcgaa
gagttcctgaccttcggtggtaccgacctgaacatcatcacctctgctcagtctaacgacatctacaccaacctg
ctggctgactacaaaaaaatcgcttctaaactgtctaaagttcaggtttctaacccgctgctgaacccgtacaaa
gacgttttcgaagctaaatacggtctggacaaagacgcttctggtatctactctgttaacatcaacaaattcaac
gacatcttcaaaaaactgtactctttcaccgagttcgacctggcgaccaaattccaggttaaatgccgtcagacc
tacatcggtcagtacaaatacttcaaactgtctaacctgctgaacgactctatctacaacatctctgaaggttac
aacatcaacaacctgaaagttaacttccgtggtcagaacgctaacctgaacccgcgtatcatcaccccgatcacc
ggtcgtggtctggttaaaaaaatcatccgtttctgcAAGAATATTGTAAGCGTTAAAGGAATAAGAAAAAGTATC
tgcatcgaaatcaacaacggtgaactgttcttcgttgcttctgaaaactcttacaacgacgacaacatcaacacc
ccgaaagaaatcgacgacaccgttacctctaacaacaactacgaaaacgacctggaccaggttatcctgaacttc
aactctgaatctgctccgggtctgtctgacgaaaaactgaacctgaccatccagaacgacgcttacatcccgaaa
tacgactctaacggtacctctgacatcgaacagcacgacgttaacgaactgaacgttttcttctacctggacgct
cagaaagttccggaaggtgaaaacaacgttaacctgacctcttctatcgacaccgctctgctggaacagccgaaa
atctacaccttcttctcttctgagttcatcaacaacgttaacaaaccggttcaggctgctctgttcgtttcttgg
attcagcaggttctggttgacttcaccaccgaagctaaccagaaatctaccgttgacaaaatcgctgacatctct
atcgttgttccgtacatcggtctggctctgaacatcggtaacgaagctcagaaaggtaacttcaaagacgctctg
gaactgctgggtgctggtatcctgctggagttcgaaccggaactgctgatcccgaccatcctggttttcaccatc
aaatctttcctgggttcttctgacaacaaaaacaaagttatcaaagctatcaacaacgctctgaaagaacgtgac
gaaaaatggaaagaagtttactctttcatcgtttctaactggatgaccaaaatcaacacccagttcaacaaacgt
aaagaacagatgtaccaggctctccagaaccaggttaacgctatcaaaaccatcatcgaatctaaatacaactct
tacaccctggaagaaaaaaacgaactgaccaacaaatacgacatcaaacagatcgaaaacgaactgaaccagaaa
gtttctatcgctatgaacaacatcgaccgtttcctgaccgaatcttctatctcttacctgatgaaactcatcaac
gaagttaaaatcaacaaactgcgtgaatacgacgaaaacgttaaaacctacctgctgaactacatcatccagcac
ggttctatcctgggtgaatctcagcaggaactgaactctatggttaccgacaccctgaacaactctatcccgttc
aaactgtcttcttacaccgacgacaaaatcctGATCTCTTACTTCAACAAATTCTTTAAAcgcATTAAGAGTTCA
TCGGTTctgaatATGCGGTACAAAAATGATAAAtatGTCGATACTTCTGGATATgatAGCAATATCAACATTAAC
GGCGACGTGTATAAATATccgACAAATAAAAACCAGTTTGGGATATATAACGACAAGctgTCGGAGGTCAATatt
TCTCAAAACGACtatATCattTACGATAATaaaTATAAAAACTTTAGCATTAGTtttTGGGTTcgtATACCTAAT
tatGACAATaaaattGTAAATGTGAATAACGAGTATACCATTATAAACTGTATGcgcGACAATAACAGTGGTTGG
AAGGTATCGctgAACCATAATGAGATTATCTGGACCctgcagGATAATgcaGGTATAAACCAGAAACTGGCTTTT
AACTATGGAAACGCAAATGGGATCTCAGATTACATTaataaaTGGatttttGTTaccATTACGAACGATcgcTTA
GGCGACTCAAAACTTTATATTAATggcAATctgATAGATCAGAAATCAATCTTAAATTTGGGCAATATTCATGTC
TCTgatAACATCTTGTTCAAGATCGTTAATTGCAGTTACACTcgtTATATTGGCATTCGTTACTTTAATATCTTC
gataaaGAActgGACGAGACGGAAATCcagACTCTGTATTCAAACGAGCCCAATACTAATATATTGAAAGATTTT
TGGGGTAACTATCTTTTATATGATAAAGAATACTATCTCCTGaatGTATTGAAGCCAAACAATTTCATAGATAGA
CGCAAGGATAGCACATTAAGTATCAACAATATCAGATCTACTATActgttaGCAAATCGCCTcTACTCCggtATT
AAAGTGAAGATTcagCGGGTTAATAACTCCAGTACCAATGATAATCTGGTCCGTAAGAACGATCAGGTATACATC
aatTTCGTCGCGAGCAAAACTcatCTCTTCCCGCTTTACGCCgatACAGCTACGACAAACAAGGAAAAAACCATA
AAAATTTCCAGCTCCGGAAACAGATTCAATCAAGTAGTTGTAATGAACTCTGTGGGTaatAATTGTACGATGAAC
```

-continued

TTTaagAATAACAATGGGAACAATattGGACTTTTGGGCTTcAAAGCCGACACAGTGGTGGCGTCCACCTGGTAT

TACACGcacATGcggGACCATACGAATTCGAACGGTTGCTTCTGGAACTTTATCTCGGAAgaaCACGGGTGGCAA

GAAAAA

Polypeptide Sequence of rBoNT/E(0)

SEQ ID NO: 14

MPKINSFNYNDPVNDRTILYIKPGGCQEFYKSFNIMKNIWIIPERNVIGTTPQDFHPPTSLKNGDSSYYDPNYLQ

SDEEKDRFLKIVTKIFNRINNNLSGGILLEELSKANPYLGNDNTPDNQFHIGDASAVEIKFSNGSQDILLPNVII

MGAEPDLFETNSSNISLRNNYMPSNHGFGSIAIVTFSPEYSFRENDNSMNEFIQDPALTLMHQLIYSLHGLYGAK

GITTKYTITQKQNPLITNIRGTNIEEFLTFGGTDLNIITSAQSNDIYTNLLADYKKIASKLSKVQVSNPLLNPYK

DVFEAKYGLDKDASGIYSVNINKENDIFKKLYSFTEFDLATKFQVKCRQTYIGQYKYFKLSNLLNDSIYNISEGY

NINNLKVNFRGQNANLNPRIITPITGRGLVKKIIRFCKNIVSVKGIRKSICIEINNGELFFVASENSYNDDNINT

PKEIDDTVTSNNNYENDLDQVILNENSESAPGLSDEKLNLTIQNDAYIPKYDSNGTSDIEQHDVNELNVFFYLDA

QKVPEGENNVNLTSSIDTALLEQPKIYTFFSSEFINNVNKPVQAALFVSWIQQVLVDETTEANQKSTVDKIADIS

IVVPYIGLALNIGNEAQKGNEKDALELLGAGILLEFEPELLIPTILVFTIKSFLGSSDNKNKVIKAINNALKERD

EKWKEVYSFIVSNWMTKINTQFNKRKEQMYQALQNQVNAIKTIIESKYNSYTLEEKNELTNKYDIKQIENELNQK

VSIAMNNIDRELTESSISYLMKLINEVKINKLREYDENVKTYLLNYIIQHGSILGESQQELNSMVTDTLNNSIPF

KLSSYTDDKILISYFNKFFKRIKSSSVLNMRYKNDKYVDTSGYDSNININGDVYKYPTNKNQFGIYNDKLSEVNI

SQNDYIIYDNKYKNFSISFWVRIPNYDNKIVNVNNEYTIINCMRDNNSGWKVSLNHNEIIWTLQDNAGINQKLAF

NYGNANGISDYINKWIFVTITNDRLGDSKLYINGNLIDQKSILNLGNIHVSDNILFKIVNCSYTRYIGIRYFNIF

DKELDETEIQTLYSNEPNTNILKDFWGNYLLYDKEYYLLNVLKPNNFIDRRKDSTLSINNIRSTILLANRLYSGI

KVKIQRVNNSSTNDNLVRKNDQVYINFVASKTHLFPLYADTATTNKEKTIKISSSGNRFNQVVVMNSVGNNCTMN

FKNNNGNNIGLLGFKADTVVASTWYYTHMRDHTNSNGCFWNFISEEHGWQEK

Nucleotide Sequence of rBoNT/F(0)

SEQ ID NO: 15

ATGCCGGTGGTCATCAACAGCTTCAACTACAACGACCCAGTAAACGACGACACGATCCTGTATATGCAAATCCCG

TATGAAGAGAAGAGCAAGAAGTACTATAAGGCCTTTGAAATCATGCGCAATGTGTGGATTATTCCGGAGCGTAAT

ACGATTGGTACTGACCCAAGCGACTTCGATCCACCTGCGTCTTTGGAAAACGGCTCGTCCGCATATTACGACCCG

AATTACCTGACCACCGATGCGGAGAAAGATCGTTATTTGAAAACCACCATCAAGCTGTTCAAACGCATTAACAGC

AATCCGGCAGGTGAGGTCCTGCTGCAAGAGATTAGCTACGCAAAGCCTTATCTGGGTAATGAGCATACGCCTATT

AACGAGTTTCACCCGGTTACCCGCACTACCAGCGTTAACATCAAGTCCTCGACCAACGTGAAGTCTAGCATTATC

CTGAACCTGCTGGTTCTGGGTGCCGGTCCGGACATCTTCGAAAACTCTAGCTACCCGGTGCGTAAACTGATGGAT

AGCGGCGGTGTTTATGACCCGAGCAATGACGGTTTTGGCAGCATCAATATCGTGACGTTTAGCCCGGAGTACGAG

TACACCTTCAATGATATCAGCGGTGGTTACAATTCTTCTACCGAGAGCTTCATCGCCGACCCGGCGATCAGCCTG

GCACACCAACTGATCTATGCATTGCATGGCTTGTACGGTGCCCGTGGTGTGACGTATAAAGAGACTATCAAGGTT

AAGCAGGCACCTCTGATGATTGCGGAAAAGCCGATTCGCCTGGAAGAGTTCCTGACCTTCGGCGGTCAAGATTTG

AACATCATTACCTCGGCCATGAAAGAGAAAATCTATAACAATTTGCTGGCCAACTATGAAAAGATTGCAACGCGC

TTGTCTCGTGTTAACTCCGCTCCGCCGGAATACGACATTAATGAGTACAAAGACTACTTTCAATGGAAATATGGC

CTGGACAAAAATGCGGATGGTTCTTATACCGTGAATGAAAACAAATTCAATGAAATCTACAAGAAACTGTACAGC

TTCACCGAAATCGATCTGGCGAACAAGTTCAAAGTCAAATGTCGTAATACCTACTTCATCAAATATGGCTTCCTG

AAAGTCCCGAACCTGCTGGACGATGACATCTATACCGTCAGCGAAGGCTTCAACATCGGCAATCTGGCCGTGAAT

AATCGTGGTCAGAACATCAAACTGAATCCGAAAATCATTGACTCCATCCCAGACAAGGGCCTGGTTGAGAAAATC

GTGAAGTTCTGCAAAAGCGTTATTCCGCGTAAAGGTACGAAAGCACCGCCTCGCCTGTGCATTCGCGTTAACAAC

CGTGAGTTGTTCTTTGTGGCATCTGAAAGCAGCTACAACGAGAACGACATCAACACCCCTAAAGAAATTGATGAT

-continued

ACCACGAACCTGAATAACAATTATCGCAACAATCTGGACGAGGTGATCCTGGATTACAATTCGGAAACCATTCCG
CAAATTAGCAATCAGACGCTGAACACCCTGGTTCAGGACGATAGCTACGTTCCGCGTTACGACTCCAATGGTACT
AGCGAGATTGAAGAACACAACGTAGTGGACTTGAACGTTTTCTTTTATCTGCACGCCCAGAAGGTTCCGGAGGGC
GAAACCAATATTAGCCTGACCAGCTCGATCGACACCGCGCTGTCTGAGGAGAGCCAAGTCTACACCTTTTTCAGC
AGCGAGTTTATCAACACTATTAACAAGCCAGTTCATGCTGCATTGTTTATCTCTTGGATTAACCAGGTGATTCGC
GACTTTACGACGGAGGCGACCCAGAAGTCTACCTTCGACAAAATTGCAGACATCTCCCTGGTCGTCCCATACGTC
GGCCTGGCGTTGAATATTGGCAATGAAGTTCAAAAAGAGAACTTCAAAGAAGCGTTCGAGCTGCTGGGTGCAGGC
ATCCTGCTGGAGTTCGTGCCGGAACTGTTGATCCCGACCATCCTGGTGTTCACCATTAAGAGCTTCATTGGATCC
TCCGAGAATAAGAACAAGATCATCAAGGCGATCAATAACAGCCTGATGGAGCGTGAAACGAAGTGGAAAGAAATC
TATAGCTGGATTGTTAGCAATTGGCTGACTCGTATTAACACGCAATTCAACAAGCGTAAAGAGCAAATGTACCAA
GCCCTGCAAAACCAAGTTGACGCCATCAAAACGGTAATTGAATACAAGTACAACAATTACACGAGCGATGAGCGC
AACCGCCTGGAAAGCGAATACAACATCAACAACATTCGCGAAGAATTGAACAAGAAAGTGAGCCTGGCGATGGAG
AACATTGAGCGTTTTATCACCGAAAGCAGCATCTTTTACCTGATGAAATTGATTAATGAGGCGAAAGTCTCGAAA
CTGCGTGAGTACGACGAAGGTGTGAAAGAGTATCTGCTGGATTACATTAGCGAGCACCGTAGCATCTTGGGTAAC
TCGGTTCAGGAGCTGAACGATCTGGTGACCTCTACCCTGAACAATAGCATCCCGTTCGAACTGAGCAGCTATACC
AATGACAAGATTCTGATTCTGTATTTCAATAAACTGTATAAGAAGATCAAGGATAACAGCATTCTGGATATGCGT
TACGAAAACAATAAGTTTATCGACATTTCTGGTTACGGCAGCAACATTTCCATCAATGGCGATGTCTACATCTAC
AGCACCAATCGCAACCAGTTCGGCATCTACTCTAGCAAACCGAGCGAAGTTAACATCGCACAGAACAATGATATT
ATTTATAACGGTCGTTATCAAAACTTCTCTATCAGCTTTTGGGTCCGTATCCCGAAGTACTTCAATAAAGTCAAT
CTGAATAATGAATACACGATCATCGACTGCATTCGCAATAACAACAGCGGTTGGAAAATCAGCCTGAATTACAAC
AAAATTATTTGGACCCTGCAAGATACGGCGGGTAACAATCAGAAACTGGTGTTTAACTACACGCAAATGATCAGC
ATTTCTGACTATATCAACAAGTGGATCTTTGTTACCATCACCAATAATCGTCTGGGCAATAGCCGTATTTACATC
AACGGTAACCTGATTGATGAGAAAAGCATCAGCAACCTGGGCGATATTCACGTCAGCGACAACATTCTGTTCAAA
ATTGTTGGTTGTAACGATACCCGTTACGTCGGCATCCGTTATTTCAAGGTTTTCGATACGGAGCTGGGTAAAACG
GAAATCGAAACGTTGTACTCCGATGAACCAGATCCGAGCATTCTGAAGGACTTTTGGGGTAACTACTTGCTGTAC
AATAAACGTTACTATCTGCTGAATCTGTTGCGCACCGACAAGAGCATTACCCAAAACAGCAATTTCCTGAACATT
AATCAGCAACGCGGCGTATACCAAAAACCGAACATCTTCAGCAATACGCGCCTGTATACTGGTGTTGAAGTGATC
ATTCGTAAGAACGGTAGCACCGACATTAGCAACACGGACAATTTCGTCCGTAAGAATGACCTGGCGTACATTAAC
GTCGTGGACCGTGATGTCGAGTATCGTCTGTACGCAGACATCAGCATTGCGAAACCGGAAAAGATTATCAAGCTG
ATCCGTACCAGCAACAGCAACAACAGCCTGGGTCAGATCATTGTGATGGACAGCATTGGTAATAACTGCACGATG
AACTTCCAGAACAACAATGGTGGTAATATCGGTCTGCTGGGTTTTCACAGCAATAATCTGGTTGCTTCCAGCTGG
TACTACAATAACATTCGTAAAAACACGTCTAGCAATGGTTGTTTTTGGAGCTTTATCAGCAAAGAGCACGGCTGG
CAAGAAAAT

Polypeptide Sequence of rBoNT/F(0)

SEQ ID NO: 16

MPVVINSFNYNDPVNDDTILYMQIPYEEKSKKYYKAFEIMRNVWIIPERNTIGTDPSDFDPPASLENGSSAYYDP
NYLTTDAEKDRYLKTTIKLFKRINSNPAGEVLLQEISYAKPYLGNEHTPINEFHPVTRTTSVNIKSSTNVKSSII
LNLLVLGAGPDIFENSSYPVRKLMDSGGVYDPSNDGFGSINIVTFSPEYEYTENDISGGYNSSTESFIADPAISL
AHQLIYALHGLYGARGVTYKETIKVKQAPLMIAEKPIRLEEFLTFGGQDLNIITSAMKEKIYNNLLANYEKIATR
LSRVNSAPPEYDINEYKDYFQWKYGLDKNADGSYTVNENKFNEIYKKLYSFTEIDLANKFKVKCRNTYFIKYGFL
KVPNLLDDDIYTVSEGFNIGNLAVNNRGQNIKLNPKIIDSIPDKGLVEKIVKFCKSVIPRKGTKAPPRLCIRVNN

-continued

RELFFVASESSYNENDINTPKEIDDTTNLNNNYRNNLDEVILDYNSETIPQISNQTLNTLVQDDSYVPRYDSNGT

SEIEEHNVVDLNVFFYLHAQKVPEGETNISLTSSIDTALSEESQVYTFFSSEFINTINKPVHAALFISWINQVIR

DFTTEATQKSTEDKIADISLVVPYVGLALNIGNEVQKENFKEAFELLGAGILLEFVPELLIPTILVFTIKSFIGS

SENKNKIIKAINNSLMERETKWKEIYSWIVSNWLTRINTQFNKRKEQMYQALQNQVDAIKTVIEYKYNNYTSDER

NRLESEYNINNIREELNKKVSLAMENIERFITESSIFYLMKLINEAKVSKLREYDEGVKEYLLDYISEHRSILGN

SVQELNDLVTSTLNNSIPFELSSYTNDKILILYENKLYKKIKDNSILDMRYENNKFIDISGYGSNISINGDVYIY

STNRNQFGIYSSKPSEVNIAQNNDIIYNGRYQNFSISFWVRIPKYFNKVNLNNEYTIIDCIRNNNSGWKISLNYN

KIIWTLQDTAGNNQKLVFNYTQMISISDYINKWIFVTITNNRLGNSRIYINGNLIDEKSISNLGDIHVSDNILFK

IVGCNDTRYVGIRYFKVFDTELGKTEIETLYSDEPDPSILKDFWGNYLLYNKRYYLLNLLRTDKSITQNSNFLNI

NQQRGVYQKPNIFSNTRLYTGVEVIIRKNGSTDISNTDNFVRKNDLAYINVVDRDVEYRLYADISIAKPEKIIKL

IRTSNSNNSLGQIIVMDSIGNNCTMNFQNNNGGNIGLLGFHSNNLVASSWYYNNIRKNTSSNGCFWSFISKEHGW

QEN

Nucleotide Sequence of rBoNT/A(0) (His-tagged)

SEQ ID NO: 17

ATGCCGTTTGTGAACAAGCAGTTCAACTATAAAGATCCGGTTAATGGTGTGGATATCGCCTATATCAAAATTCCG

AATGCAGGTCAGATGCAGCCGGTTAAAGCCTTTAAAATCCATAACAAAATTTGGGTGATTCCGGAACGTGATACC

TTTACCAATCCGGAAGAAGGTGATCTGAATCCGCCTCCGGAAGCAAAACAGGTTCCGGTTAGCTATTATGATAGC

ACCTATCTGAGCACCGATAACGAGAAAGATAACTATCTGAAAGGTGTGACCAAACTGTTTGAACGCATTTATAGT

ACCGATCTGGGTCGTATGCTGCTGACCAGCATTGTTCGTGGTATTCCGTTTTGGGGGGTAGCACCATTGATACC

GAACTGAAAGTTATTGACACCAACTGCATTAATGTGATTCAGCCGGATGGTAGCTATCGTAGCGAAGAACTGAAT

CTGGTTATTATTGGTCCGAGCGCAGATATCATTCAGTTTGAATGTAAAAGCTTTGGCCACGAAGTTCTGAATCTG

ACCCGTAATGGTTATGGTAGTACCCAGTATATTCGTTTCAGTCCGGATTTTACCTTTGGCTTTGAAGAAAGCCTG

GAAGTTGATACAAATCCGCTGTTAGGTGCAGGTAAATTTGCAACCGATCCGGCAGTTACCCTGGCACACCAGCTG

ATTTATGCCGGTCATCGTCTGTATGGTATTGCCATTAATCCGAATCGTGTGTTCAAAGTGAATACCAACGCCTAT

TATGAAATGAGCGGTCTGGAAGTGAGTTTTGAAGAACTGCGTACCTTTGGTGGTCATGATGCCAAATTTATCGAT

AGCCTGCAAGAAAATGAATTTCGCCTGTACTACTATAACAAATTCAAGGATATTGCGAGCACCCTGAATAAAGCC

AAAAGCATTGTTGGCACCACCGCAAGCCTGCAGTATATGAAAAATGTGTTTAAAGAAAAATATCTGCTGAGCGAA

GATACCAGCGGTAAATTTAGCGTTGACAAACTGAAATTCGATAAACTGTACAAGATGCTGACCGAGATTTATACC

GAAGATAACTTCGTGAAGTTTTTCAAAGTGCTGAACCGCAAAACCTACCTGAACTTTGATAAAGCCGTGTTCAAA

ATCAACATCGTGCCGAAAGTGAACTATACCATCTATGATGGTTTTAACCTGCGCAATACCAATCTGGCAGCAAAC

TTTAATGGTCAGAACACCGAAATCAACAACATGAACTTTACCAAACTGAAGAACTTCACCGGTCTGTTCGAATTT

TACAAACTGCTGTGTGTTCGTGGCATTATTACCAGCAAAACCAAAAGTCTGGATAAAGGCTACAATAAAGCCCTG

AATGATCTGTGCATTAAGGTGAATAATTGGGACCTGTTTTTTAGCCCGAGCGAGGATAATTTCACCAACGATCTG

AACAAAGGCGAAGAAATTACCAGCGATACCAATATTGAAGCAGCCGAAGAAAACATTAGCCTGGATCTGATTCAG

CAGTATTATCTGACCTTCAACTTCGATAATGAGCCGGAAAATATCAGCATTGAAAACCTGAGCAGCGATATTATT

GGCCAGCTGGAACTGATGCCGAATATTGAACGTTTTCCGAACGGCAAAAAATACGAGCTGGATAAATACACCATG

TTCCATTATCTGCGTGCCCAAGAATTTGAACATGGTAAAAGCCGTATTGCACTGACCAATAGCGTTAATGAAGCA

CTGCTGAACCCGAGCCGTGTTTATACCTTTTTTAGCAGCGATTACGTGAAAAAGGTTAACAAAGCAACCGAAGCA

GCCATGTTTTTAGGTTGGGTTGAACAGCTGGTTTATGATTTCACCGATGAAACCAGCGAAGTTAGCACCACCGAT

AAAATTGCAGATATTACCATCATCATCCCGTATATCGGTCCGGCACTGAATATTGGCAATATGCTGTATAAAGAC

GATTTTGTGGGTGCCCTGATTTTTAGCGGTGCAGTTATTCTGCTGGAATTTATTCCGGAAATTGCCATTCCGGTT

CTGGGCACCTTTGCACTGGTGAGCTATATTGCAAATAAAGTTCTGACCGTGCAGACCATCGATAATGCACTGAGC

-continued

AAACGTAACGAAAAATGGGATGAAGTGTACAAGTATATCGTGACCAATTGGCTGGCAAAAGTTAACACCCAGATT

GACCTGATTCGCAAGAAGATGAAAGAAGCACTGGAAAATCAGGCAGAAGCAACCAAAGCCATTATCAACTATCAG

TATAACCAGTACACCGAAGAAGAGAAAAATAACATCAACTTCAACATCGACGATCTGTCCAGCAAACTGAACGAA

AGCATCAACAAAGCCATGATTAACATTAACAAATTTCTGAACCAGTGCAGCGTGAGCTATCTGATGAATAGCATG

ATTCCGTATGGTGTGAAACGTCTGGAAGATTTTGATGCAAGCCTGAAAGATGCCCTGCTGAAATATATCTATGAT

AATCGTGGCACCCTGATTGGTCAGGTTGATCGTCTGAAAGATAAAGTGAACAACACCCTGAGTACCGATATTCCT

TTTCAGCTGAGCAAATATGTGGATAATCAGCGTCTGCTGTCAACCTTTACCGAATACATTAAGAACATCATCAAC

ACCAGCATTCTGAACCTGCGTTATGAAAGCAATCATCTGATTGATCTGAGCCGTTATGCCAGCAAAATCAATATA

GGCAGCAAGGTTAACTTCGACCCGATTGACAAAAATCAGATACAGCTGTTTAATCTGGAAAGCAGCAAAATTGAG

GTGATCCTGAAAAACGCCATTGTGTATAATAGCATGTACGAGAATTTCTCGACCAGCTTTTGGATTCGTATCCCG

AAATACTTTAATAGCATCAGCCTGAACAACGAGTACACCATTATTAACTGCATGGAAAACAATAGCGGCTGGAAA

GTTAGCCTGAATTATGGCGAAATTATCTGGACCCTGCAGGATACCCAAGAAATCAAACAGCGTGTGGTTTTCAAA

TACAGCCAGATGATTAATATCAGCGACTATATCAACCGCTGGATTTTTGTGACCATTACCAATAATCGCCTGAAT

AACAGCAAGATCTATATTAACGGTCGTCTGATTGACCAGAAACCGATTAGTAATCTGGGTAATATTCATGCGAGC

AACAACATCATGTTTAAACTGGATGGTTGTCGTGATACCCATCGTTATATTTGGATCAAGTACTTCAACCTGTTC

GATAAAGAGTTGAACGAAAAAGAAATTAAAGACCTGTATGATAACCAGAGCAACAGCGGTATTCTGAAGGATTTT

TGGGGAGATTATCTGCAGTATGACAAACCGTATTATATGCTGAATCTGTACGACCCGAATAAATACGTGGATGTG

AATAATGTTGGCATCCGTGGTTATATGTACCTGAAAGGTCCGCGTGGTAGCGTTATGACCACAAACATTTATCTG

AATAGCAGCCTGTATCGCGGAACCAAATTCATCATTAAAAAGTATGCCAGCGGCAACAAGGATAATATTGTGCGT

AATAATGATCGCGTGTACATTAACGTTGTGGTGAAGAATAAAGAATATCGCCTGGCAACCAATGCAAGCCAGGCA

GGCGTTGAAAAAATTCTGAGTGCCCTGGAAATTCCGGATGTTGGTAATCTGAGCCAGGTTGTTGTGATGAAAAGC

AAAAATGATCAGGGCATCACCAACAAGTGCAAAATGAATCTGCAGGACAATAACGGCAACGATATTGGTTTTATT

GGCTTCCACCAGTTCAACAATATTGCGAAACTGGTTGCAAGCAATTGGTATAATCGTCAGATTGAACGTAGCAGT

CGTACCCTGGGTTGTAGCTGGGAATTTATCCCTGTGGATGATGGTTGGGGTGAACGTCCGCTGGAAAACCTGTAT

TTTCAAGGTGCAAGTCATCATCACCATCACCACCATCATTAA

Polypeptide Sequence of rBoNT/A(0) (His-tagged)

SEQ ID NO: 18

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHQL

IYAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTFTEYIKNIINTSILNLRYESNHLIDLSRYASKINI

GSKVNFDPIDKNQIQLENLESSKIEVILKNAIVYNSMYENFSTSFWIRIPKYENSISLNNEYTIINCMENNSGWK

VSLNYGEIIWTLQDTQEIKQRVVFKYSQMINISDYINRWIFVTITNNRLNNSKIYINGRLIDQKPISNLGNIHAS

-continued

NNIMFKLDGCRDTHRYIWIKYFNLFDKELNEKEIKDLYDNQSNSGILKDFWGDYLQYDKPYYMLNLYDPNKYVDV

NNVGIRGYMYLKGPRGSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQENNIAKLVASNWYNRQIERSS

RTLGCSWEFIPVDDGWGERPLENLYFQGASHHHHHHHH

Nucleotide Sequence of $rLH_N$/A (His-tagged)

SEQ ID NO: 19

ATGCCGTTTGTGAACAAGCAGTTCAACTATAAAGATCCGGTTAATGGTGTGGATATCGCCTATATCAAAATTCCG

AATGCAGGTCAGATGCAGCCGGTTAAAGCCTTTAAAATCCATAACAAAATTTGGGTGATTCCGGAACGTGATACC

TTTACCAATCCGGAAGAAGGTGATCTGAATCCGCCTCCGGAAGCAAAACAGGTTCCGGTTAGCTATTATGATAGC

ACCTATCTGAGCACCGATAACGAGAAAGATAACTATCTGAAAGGTGTGACCAAACTGTTTGAACGCATTTATAGT

ACCGATCTGGGTCGTATGCTGCTGACCAGCATTGTTCGTGGTATTCCGTTTTGGGGTGGTAGCACCATTGATACC

GAACTGAAAGTTATTGACACCAACTGCATTAATGTGATTCAGCCGGATGGTAGCTATCGTAGCGAAGAACTGAAT

CTGGTTATTATTGGTCCGAGCGCAGATATCATTCAGTTTGAATGTAAATCCTTTGGCCACGAAGTTCTGAATCTG

ACCCGTAATGGTTATGGTAGTACCCAGTATATTCGTTTCAGTCCGGATTTTACCTTTGGCTTTGAAGAAAGCCTG

GAAGTTGATACAAATCCGCTGTTAGGTGCAGGTAAATTTGCAACCGATCCGGCAGTTACCCTGGCACATGAACTG

ATTCATGCCGGTCATCGTCTGTATGGTATTGCAATTAATCCGAACCGTGTGTTCAAAGTGAATACCAACGCATAT

TATGAAATGAGCGGTCTGGAAGTGTCATTTGAAGAACTGCGTACCTTTGGTGGTCATGATGCCAAATTTATCGAT

AGCCTGCAAGAAAATGAATTTCGCCTGTACTACTATAACAAATTCAAGGATATTGCGAGCACCCTGAATAAAGCC

AAAAGCATTGTTGGCACCACCGCAAGCCTGCAGTATATGAAAAATGTGTTTAAAGAAAAATATCTGCTGAGCGAA

GATACCAGCGGTAAATTTAGCGTTGACAAACTGAAATTCGATAAACTGTACAAGATGCTGACCGAGATTTATACC

GAAGATAACTTCGTGAAGTTTTTCAAAGTGCTGAACCGCAAAACCTACCTGAACTTTGATAAAGCCGTGTTCAAA

ATCAACATCGTGCCGAAAGTGAACTATACCATCTATGATGGTTTTAACCTGCGCAATACCAATCTGGCAGCAAAC

TTTAATGGTCAGAACACCGAAATCAACAACATGAACTTTACCAAACTGAAGAACTTCACCGGTCTGTTCGAATTT

TACAAACTGCTGTGTGTTCGTGGCATTATTACCAGCAAAACCAAAAGTCTGGATAAAGGCTACAATAAAGCCCTG

AATGATCTGTGCATTAAGGTGAATAATTGGGACCTGTTTTTTAGCCCGAGCGAGGATAATTTCACCAACGATCTG

AACAAAGGCGAAGAAATTACCAGCGATACCAATATTGAAGCAGCCGAAGAAAACATTAGCCTGGATCTGATTCAG

CAGTATTATCTGACCTTCAACTTCGATAATGAGCCGGAAAATATCAGCATTGAAAACCTGAGCAGCGATATTATT

GGCCAGCTGGAACTGATGCCGAATATTGAACGTTTTCCGAACGGCAAAAAATACGAGCTGGATAAATACACCATG

TTCCATTATCTGCGTGCCCAAGAATTTGAACATGGTAAAAGCCGTATTGCACTGACCAATAGCGTTAATGAAGCA

CTGCTGAACCCGAGCCGTGTTTATACCTTTTTTAGCAGCGATTACGTGAAAAAGGTTAACAAAGCAACCGAAGCA

GCCATGTTTTTAGGTTGGGTTGAACAGCTGGTTTATGATTTCACCGATGAAACCAGCGAAGTTAGCACCACCGAT

AAAATTGCAGATATTACCATCATCATCCCGTATATCGGTCCGGCACTGAATATTGGCAATATGCTGTATAAAGAC

GATTTTGTGGGTGCCCTGATTTTTAGCGGTGCAGTTATTCTGCTGGAATTTATTCCGGAAATTGCCATTCCGGTT

CTGGGCACCTTTGCACTGGTGAGCTATATTGCAAATAAAGTTCTGACCGTGCAGACCATCGATAATGCACTGAGC

AAACGTAACGAAAAATGGGATGAAGTGTACAAGTATATCGTGACCAATTGGCTGGCAAAAGTTAACACCCAGATT

GACCTGATTCGCAAGAAGATGAAAGAAGCACTGGAAAATCAGGCAGAAGCAACCAAAGCCATTATCAACTATCAG

TATAACCAGTACACCGAAGAAGAGAAAAATAACATCAACTTCAACATCGACGATCTGTCCAGCAAACTGAACGAA

AGCATCAACAAAGCCATGATTAACATTAACAAATTTCTGAACCAGTGCAGCGTGAGCTATCTGATGAATAGCATG

ATTCCGTATGGTGTGAAACGTCTGGAAGATTTTGATGCAAGCCTGAAAGATGCCCTGCTGAAATATATCTATGAT

AATCGTGGCACCCTGATTGGTCAGGTTGATCGTCTGAAAGATAAAGTGAACAACACCCTGAGTACCGATATTCCT

TTTCAGCTGAGCAAATATGTGGATAATCAGCGTCTGCTGTCAACCGAAAATCTGTATTTCCAGGGTGCAAGTCAT

CATCACCATCACCACCATCATTAA

-continued

Polypeptide Sequence of $rLH_N/A$ (His-tagged)

SEQ ID NO: 20

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTENLYFQGASHHHHHHHH

Nucleotide Sequence of $rH_C/A$ (His-tagged)

SEQ ID NO: 21

ATGCATCATCACCATCACCACGAAAATCTATACTTCCAAGGAAAAAACATCATCAATACTAGCATTCTGAACCTG

CGTTACGAGAGCAATCATCTGATTGATCTGAGCCGTTATGCAAGCAAGATCAACATCGGTAGCAAGGTCAATTTT

GACCCGATCGATAAGAACCAGATCCAGCTGTTTAATCTGGAATCGAGCAAAATTGAGGTTATCCTGAAAAACGCC

ATTGTCTACAACTCCATGTACGAGAATTTCTCCACCAGCTTCTGGATTCGCATCCCGAAATACTTCAACAGCATT

AGCCTGAACAACGAGTATACTATCATCAACTGTATGGAGAACAACAGCGGTTGGAAGGTGTCTCTGAACTATGGT

GAGATCATTTGGACCTTGCAGGACACCCAAGAGATCAAGCAGCGCGTCGTGTTCAAGTACTCTCAAATGATCAAC

ATTTCCGATTACATTAATCGTTGGATCTTCGTGACCATTACGAATAACCGTCTGAATAACAGCAAGATTTACATC

AATGGTCGCTTGATCGATCAGAAACCGATTAGCAACCTGGGTAATATCCACGCAAGCAACAACATTATGTTCAAA

TTGGACGGTTGCCGCGATACCCATCGTTATATCTGGATCAAGTATTTCAACCTGTTTGATAAAGAACTGAATGAG

AAGGAGATCAAAGATTTGTATGACAACCAATCTAACAGCGGCATTTTGAAGGACTTCTGGGGCGATTATCTGCAA

TACGATAAGCCGTACTATATGCTGAACCTGTATGATCCGAACAAATATGTGGATGTCAATAATGTGGGTATTCGT

GGTTACATGTATTTGAAGGGTCCGCGTGGCAGCGTTATGACGACCAACATTTACCTGAACTCTAGCCTGTACCGT

GGTACGAAATTCATCATTAAGAAATATGCCAGCGGCAACAAAGATAACATTGTGCGTAATAACGATCGTGTCTAC

ATCAACGTGGTCGTGAAGAATAAAGAGTACCGTCTGGCGACCAACGCTTCGCAGGCGGGTGTTGAGAAAATTCTG

AGCGCGTTGGAGATCCCTGATGTCGGTAATCTGAGCCAAGTCGTGGTTATGAAGAGCAAGAACGACCAGGGTATC

ACTAACAAGTGCAAGATGAACCTGCAAGACAACAATGGTAACGACATCGGCTTTATTGGTTTCCACCAGTTCAAC

AATATTGCTAAACTGGTAGCGAGCAATTGGTACAATCGTCAGATTGAGCGCAGCAGCCGTACTTTGGGCTGTAGC

TGGGAGTTTATCCCGGTCGATGATGGTTGGGGCGAACGTCCGCTGTAA

Polypeptide Sequence of $rH_C/A$ (His-tagged)

SEQ ID NO: 22

MHHHHHHENLYFQGKNIINTSILNLRYESNHLIDLSRYASKINIGSKVNFDPIDKNQIQLENLESSKIEVILKNA

IVYNSMYENFSTSFWIRIPKYFNSISLNNEYTIINCMENNSGWKVSLNYGEIIWTLQDTQEIKQRVVFKYSQMIN

ISDYINRWIFVTITNNRLNNSKIYINGRLIDQKPISNLGNIHASNNIMFKLDGCRDTHRYIWIKYFNLEDKELNE

KEIKDLYDNQSNSGILKDFWGDYLQYDKPYYMLNLYDPNKYVDVNNVGIRGYMYLKGPRGSVMTTNIYLNSSLYR

GTKFIIKKYASGNKDNIVRNNDRVYINVVVKNKEYRLATNASQAGVEKILSALEIPDVGNLSQVVVMKSKNDQGI

TNKCKMNLQDNNGNDIGFIGFHQFNNIAKLVASNWYNRQIERSSRTLGCSWEFIPVDDGWGERPL

-continued

Nucleotide Sequence of rLC/A (His-tagged)

SEQ ID NO: 23

ATGCCGTTTGTGAACAAGCAGTTCAACTATAAAGATCCGGTTAATGGTGTGGATATCGCCTATATCAAAATTCCG

AATGCAGGTCAGATGCAGCCGGTTAAAGCCTTTAAAATCCATAACAAAATTTGGGTGATTCCGGAACGTGATACC

TTTACCAATCCGGAAGAAGGTGATCTGAATCCGCCTCCGGAAGCAAAACAGGTTCCGGTTAGCTATTATGATAGC

ACCTATCTGAGCACCGATAACGAGAAAGATAACTATCTGAAAGGTGTGACCAAACTGTTTGAACGCATTTATAGT

ACCGATCTGGGTCGTATGCTGCTGACCAGCATTGTTCGTGGTATTCCGTTTTGGGGTGGTAGCACCATTGATACC

GAACTGAAAGTTATTGACACCAACTGCATTAATGTGATTCAGCCGGATGGTAGCTATCGTAGCGAAGAACTGAAT

CTGGTTATTATTGGTCCGAGCGCAGATATCATTCAGTTTGAATGTAAATCCTTTGGCCACGAAGTTCTGAATCTG

ACCCGTAATGGTTATGGTAGTACCCAGTATATTCGTTTCAGTCCGGATTTTACCTTTGGCTTTGAAGAAAGCCTG

GAAGTTGATACAAATCCGCTGTTAGGTGCAGGTAAATTTGCAACCGATCCGGCAGTTACCCTGGCACATGAACTG

ATTCATGCCGGTCATCGTCTGTATGGTATTGCAATTAATCCGAACCGTGTGTTCAAAGTGAATACCAACGCATAT

TATGAAATGAGCGGTCTGGAAGTGTCATTTGAAGAACTGCGTACCTTTGGTGGTCATGATGCCAAATTTATCGAT

AGCCTGCAAGAAAATGAATTTCGCCTGTACTACTATAACAAATTCAAGGATATTGCGAGCACCCTGAATAAAGCC

AAAAGCATTGTTGGCACCACCGCAAGCCTGCAGTATATGAAAAATGTGTTTAAAGAAAAATATCTGCTGAGCGAA

GATACCAGCGGTAAATTTAGCGTTGACAAACTGAAATTCGATAAACTGTACAAGATGCTGACCGAGATTTATACC

GAAGATAACTTCGTGAAGTTTTTCAAAGTGCTGAACCGCAAAACCTACCTGAACTTTGATAAAGCCGTGTTCAAA

ATCAACATCGTGCCGAAAGTGAACTATACCATCTATGATGGTTTTAACCTGCGCAATACCAATCTGGCAGCAAAC

TTTAATGGTCAGAACACCGAAATCAACAACATGAACTTTACCAAACTGAAGAACTTCACCGGTCTGTTTGAAGAG

AATCTGTATTTCCAGGGTGCAAGTCATCATCACCATCACCACCATCATTAA

Polypeptide Sequence of rLC/A (His-tagged)

SEQ ID NO: 24

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEENLYFQGASHHHHHHHH

Nucleotide Sequence of rBoNT/FA(0) (His-tagged)

SEQ ID NO: 25

ATGCCGGTTGTGATTAACAGCTTCAATTATGATGATCCGGTGAACGATAACACCATCATTTATATCCGTCCGCCT

TATTATGAAACCAGCAACACCTATTTCAAAGCCTTCCAGATTATGGATAACGTGTGGATTATTCCGGAACGTTAT

CGTCTGGGTATTGATCCGAGCCTGTTTAATCCGCCTGTTAGCCTGAAAGCAGGTAGTGATGGTTATTTTGATCCG

AATTATCTGAGCACCAACACCGAGAAAAACAAATACCTGCAGATTATGATCAAGCTGTTCAAACGCATTAATAGC

AAACCGGCAGGTCAGATTCTGCTGGAAGAAATCAAAAATGCAATTCCGTATCTGGGCAACAGCTATACCCAAGAA

GAACAGTTTACCACCAATAATCGTACCGTGAGCTTTAATGTTAAACTGGCCAATGGTAATATCGTTCAGCAGATG

GCAAATCTGATTATTTGGGGTCCGGGTCCTGATCTGACCACAAATAAAACCGGTGGTATCATCTATAGCCCGTAT

CAGAGCATGGAAGCAACCCCGTATAAAGATGGTTTTGGTAGCATTATGACCGTGGAATTTAGTCCGGAATATGCA

ACCGCCTTTAACGATATTTCAATTGCAAGCCATAGTCCGTCGCTGTTTATCAAAGATCCGGCACTGATTCTGATG

CACCAGCTGATTTATGTTCTGCATGGTCTGTATGGCACCTATATCACCGAATACAAAATTACCCCGAATGTGGTT

CAGAGCTATATGAAAGTTACCAAACCGATTACCAGCGCAGAATTTCTGACCTTTGGTGGTCGTGATCGCAATATT

GTTCCGCAGAGCATTCAGAGCCAGCTGTATAACAAAGTTCTGAGCGATTATAAACGTATTGCCAGCCGTCTGAAT

AAAGTTAATACCGCAACCGCACTGATCAACATCGATGAATTCAAAAACCTGTACGAGTGGAAATACCAGTTTGCC

-continued

```
AAAGATAGCAATGGTGTGTATAGCGTGGATCTGAACAAATTTGAGCAGCTGTACAAAAAAATCTATAGCTTCACC

GAATTCAACCTGGCCTATGAGTTTAAAATCAAAACCCGTCTGGGTTATCTGGCCGAAAATTTTGGTCCGTTTTAT

CTGCCGAATCTGCTGGATGATAGCATTTATACCGAAGTGGATGGTTTTAACATTGGTGCACTGAGCATTAACTAT

CAGGGTCAGAATATTGGCAGCGATATCAACAGCATCAAAAAACTGCAAGGTCAGGGTGTTGTTAGCCGTGTTGTT

CGTCTGTGTAGCAATAGCAATACCAAAAACAGCCTGTGCATTACCGTTAATAATCGCGACCTGTTTTTTATCGCA

AGCCAAGAAAGCTATGGCGAGAATACCATTAACACCTATAAAGAGATTGACGATACCACCACACTGGATCCGAGC

TTTGAAGATATTCTGGATAAAGTGATCCTGAACTTCAACGAACAGGTTATTCCGCAGATGCCGAATCGTAATGTT

AGCACCGATATTCAGAAAGACAACTACATCCCGAAATACGATTATAACCGCACCGACATTATCGATAGCTATGAA

GTTGGTCGCAACTACAACACCTTTTTCTATCTGAATGCCCAGAAATTTAGCCCGAACGAAAGCAATATTACCCTG

ACCAGCAGCTTTGATACAGGTCTGTTAGAAGGTAGCAAAGTGTATACCTTTTTCAGCAGCGATTTCATTAACAAC

ATCAACAAACCGGTTCAGGCCCTGCTGTTTATTGAATGGGTTAAACAGGTGATTCGCGATTTTACCACCGAAGCA

ACCAAAACCTCAACCGTTGATAAACTGAAAGATATTAGCCTGGTGGTGCCGTATATTGGTCTGGCACTGAATATT

GGTGATGAGATCTACAAACAGCATTTTGCAGAAGCAGTTGAACTGGTTGGTGCAGGTCTGCTGCTGGAATTTTCA

CCGGAATTTCTTATTCCGACGCTGCTGATTTTTACCATCAAAGGTTATCTGACCGGTAGCATTCGCGATAAAGAC

AAAATCATTAAAACCCTGGATAACGCCCTGAATGTTCGTGATCAGAAATGGAAAGAACTGTATCGTTGGGTTGTT

AGCAAATGGCTGACCACCATTAATACGCAGTTCAACAAACGCAAAGAACAAATGTACAAAGCCCTGAAAAATCAG

GCCACCGCCATTAAAAAGATCATCGAGAACAAATATAACAACTATACCACCGATGAAAAAAGCAAGATCGATAGC

AGCTATAACATCAACGAAATTGAACGCACCCTGAACGAAAAAATCAATCTGGCCATGAAAAACATCGAGCAGTTT

ATTACCGAAAGCAGCATTGCCTATCTGATCAATATCATCAACAACGAAACGATCCAGAAACTGAAAAGCTATGAT

GACCTGGTTCGTCGTTATCTGCTGGGTTATATTCGTAATCATAGCAGCATTCTGGGCAATAGCGTTGAAGAACTG

AATTCCAAAGTGAACAACCATCTGGATAATGGCATTCCGTTTGAACTGAGCAGTTATACCAATGATAGCCTGCTG

ATCCGCTACTTCAATAAAAACTATGGCGAACTGAAGTACAACTGCATTCTGAACATCAAATATGAGATGGATCGT

GACAAACTGGTTGATAGCAGCGGTTATCGTAGCCGTATCAATATTGGTACAGGCGTCAAATTTAGCGAGATCGAT

AAAAATCAAGTGCAGCTGAGCAATCTGGAATCCAGCAAAATTGAAGTCATTCTGAATAACGGCGTCATCTATAAC

AGCATGTATGAAAACTTTTCGACCAGCTTTTGGATTCGCATTCCGAAATACTTTCGCAACATCAATAACGAGTAC

AAGATCATCAGCTGTATGCAGAATAATAGCGGTTGGGAAGTGAGCCTGAATTTTAGCAATATGAACTCGAAAATC

ATCTGGACCCTGCAGGATACCGAAGGTATCAAAAAAACCGTTGTGTTTCAGTACACCCAGAACATTAACATTAGC

GACTATATCAACCGCTGGATCTTTGTGACCATTACAAATAATCGTCTGAGCAACAGCAAAATCTACATTAATGGT

CGCCTGATCAACGAAGAAAGCATTAGCGATCTGGGTAATATCCATGCCAGCAACAACATTATGTTTAAACTGGAT

GGTTGCCGTGATCCGCATCGTTATATCTGGATTAAATACTTTAACCTGTTTGACAAAGAGCTGAACAAGAAAGAA

ATTAAAGATCTGTACGACAACCAGAGCAATAGCGGTATTCTGAAAGATTTCTGGGGTGATTATCTGCAGTATGAC

AAACCGTATTATATGCTGAATCTGTATGACCCGAATAAGTATCTGGATGTGAATAATGTTGGCATCCGTGGCTAT

ATGTATCTGAAAGGTCCGCGTGGTCGTATTGTGACCACCAACATTTATCTGAATAGCACCCTGTATATGGGCACC

AAATTCATCATTAAGAAATATGCCAGCGGCAACAAAGATAACATTGTGCGTAATAATGATCGCGTGTATATTAAC

GTGGTGGTGAAGAATAAAGAATATCGCCTGGCAACCAATGCAAGCCAGGCAGGCGTTGAAAAAATTCTGAGCGCA

GTTGAAATCCCGGATGTTGGTAATCTGAGCCAGGTTGTTGTGATGAAAAGCGAAAATGATCAGGGCATTCGCAAC

AAGTGTAAAATGAATCTGCAAGACAATAACGGCAACGATATTGGCTTTATCGGCTTTCACCAGTTTAATAACATT

GCAAAACTGGTGGCCAGCAACTGGTATAACCGTCAGATTGGTAAAGCAAGCCGTACCTTTGGTTGTAGCTGGGAA

TTTATCCCGGTTGATGATGGTTGGGGTGAAAGCAGCCTGGAAAATCTGTATTTCCAGGGTGCCAGTCATCATCAC

CACCATCACCATCACTGA
```

-continued

Polypeptide Sequence of rBoNT/FA(0) (His-tagged)

SEQ ID NO: 26

MPVVINSFNYDDPVNDNTIIYIRPPYYETSNTYFKAFQIMDNVWIIPERYRIGIDPSLENPPVSLKAGSDGYFDP

NYLSTNTEKNKYLQIMIKLFKRINSKPAGQILLEEIKNAIPYLGNSYTQEEQFTTNNRTVSFNVKLANGNIVQQM

ANLIIWGPGPDLTTNKTGGIIYSPYQSMEATPYKDGFGSIMTVEFSPEYATAFNDISIASHSPSLFIKDPALILM

HQLIYVLHGLYGTYITEYKITPNVVQSYMKVTKPITSAEFLTFGGRDRNIVPQSIQSQLYNKVLSDYKRIASRLN

KVNTATALINIDEFKNLYEWKYQFAKDSNGVYSVDLNKFEQLYKKIYSFTEFNLAYEFKIKTRLGYLAENFGPFY

LPNLLDDSIYTEVDGENIGALSINYQGQNIGSDINSIKKLQGQGVVSRVVRLCSNSNTKNSLCITVNNRDLFFIA

SQESYGENTINTYKEIDDTTTLDPSFEDILDKVILNFNEQVIPQMPNRNVSTDIQKDNYIPKYDYNRTDIIDSYE

VGRNYNTFFYLNAQKFSPNESNITLTSSFDTGLLEGSKVYTFFSSDFINNINKPVQALLFIEWVKQVIRDETTEA

TKTSTVDKLKDISLVVPYIGLALNIGDEIYKQHFAEAVELVGAGLLLEFSPEFLIPTLLIFTIKGYLTGSIRDKD

KIIKTLDNALNVRDQKWKELYRWVVSKWLTTINTQFNKRKEQMYKALKNQATAIKKIIENKYNNYTTDEKSKIDS

SYNINEIERTLNEKINLAMKNIEQFITESSIAYLINIINNETIQKLKSYDDLVRRYLLGYIRNHSSILGNSVEEL

NSKVNNHLDNGIPFELSSYTNDSLLIRYFNKNYGELKYNCILNIKYEMDRDKLVDSSGYRSRINIGTGVKFSEID

KNQVQLSNLESSKIEVILNNGVIYNSMYENFSTSFWIRIPKYFRNINNEYKIISCMQNNSGWEVSLNFSNMNSKI

IWTLQDTEGIKKTVVFQYTQNINISDYINRWIFVTITNNRLSNSKIYINGRLINEESISDLGNIHASNNIMFKLD

GCRDPHRYIWIKYFNLFDKELNKKEIKDLYDNQSNSGILKDFWGDYLQYDKPYYMLNLYDPNKYLDVNNVGIRGY

MYLKGPRGRIVTTNIYLNSTLYMGTKFIIKKYASGNKDNIVRNNDRVYINVVVKNKEYRLATNASQAGVEKILSA

VEIPDVGNLSQVVVMKSENDQGIRNKCKMNLQDNNGNDIGFIGFHQFNNIAKLVASNWYNRQIGKASRTFGCSWE

FIPVDDGWGESSLENLYFQGASHHHHHHHH

Nucleotide Sequence of rLH$_N$/FA (His-tagged)

SEQ ID NO: 27

ATGCCGGTTGTGATTAACAGCTTCAATTATGATGATCCGGTGAACGATAACACCATCATTTATATCCGTCCGCCT

TATTATGAAACCAGCAACACCTATTTCAAAGCCTTCCAGATTATGGATAACGTGTGGATTATTCCGGAACGTTAT

CGTCTGGGTATTGATCCGAGCCTGTTTAATCCGCCTGTTAGCCTGAAAGCAGGTAGTGATGGTTATTTTGATCCG

AATTATCTGAGCACCAACACCGAGAAAAACAAATACCTGCAGATTATGATCAAGCTGTTCAAACGCATTAATAGC

AAACCGGCAGGTCAGATTCTGCTGGAAGAAATCAAAAATGCAATTCCGTATCTGGGCAACAGCTATACCCAAGAA

GAACAGTTTACCACCAATAATCGTACCGTGAGCTTTAATGTTAAACTGGCCAATGGTAATATCGTTCAGCAGATG

GCAAATCTGATTATTTGGGGTCCGGGTCCTGATCTGACCACAAATAAAACCGGTGGTATCATCTATAGCCCGTAT

CAGAGCATGGAAGCAACCCCGTATAAAGATGGTTTTGGTAGCATTATGACCGTGGAATTTAGTCCGGAATATGCA

ACCGCCTTTAACGATATTTCAATTGCAAGCCATAGTCCGTCGCTGTTTATCAAAGATCCGGCACTGATTCTGATG

CATGAACTGATTCATGTTCTGCATGGTCTGTATGGCACCTATATTACCGAATACAAAATTACCCCGAATGTGGTG

CAGAGCTATATGAAAGTTACCAAACCGATTACCAGCGCAGAATTTCTGACCTTTGGTGGTCGTGATCGCAATATT

GTTCCGCAGAGCATTCAGAGCCAGCTGTATAACAAAGTTCTGAGCGATTATAAACGTATTGCCAGCCGTCTGAAT

AAAGTTAATACCGCAACCGCACTGATCAACATCGATGAATTCAAAAACCTGTACGAGTGGAAATACCAGTTTGCC

AAAGATAGCAATGGTGTGTATAGCGTGGATCTGAACAAATTTGAGCAGCTGTACAAAAAAATCTATAGCTTCACC

GAATTCAACCTGGCCTATGAGTTTAAAATCAAAACCCGTCTGGGTTATCTGGCCGAAAATTTTGGTCCGTTTTAT

CTGCCGAATCTGCTGGATGATAGCATTTATACCGAAGTGGATGGTTTTAACATTGGTGCACTGAGCATTAACTAT

CAGGGTCAGAATATTGGCAGCGATATCAACAGCATCAAAAAACTGCAAGGTCAGGGTGTTGTTAGCCGTGTTGTT

CGTCTGTGTAGCAATAGCAATACCAAAAACAGCCTGTGCATTACCGTTAATAATCGCGACCTGTTTTTTATCGCA

AGCCAAGAAAGCTATGGCGAGAATACCATTAACACCTATAAAGAGATTGACGATACCACCACACTGGATCCGAGC

TTTGAAGATATTCTGGATAAAGTGATCCTGAACTTCAACGAACAGGTTATTCCGCAGATGCCGAATCGTAATGTT

-continued

AGCACCGATATTCAGAAAGACAACTACATCCCGAAATACGATTATAACCGCACCGACATTATCGATAGCTATGAA

GTTGGTCGCAACTACAACACCTTTTTCTATCTGAATGCCCAGAAATTTAGCCCGAACGAAAGCAATATTACCCTG

ACCAGCAGCTTTGATACAGGTCTGTTAGAAGGTAGCAAAGTGTATACCTTTTTCAGCAGCGATTTCATTAACAAC

ATCAACAAACCGGTTCAGGCCCTGCTGTTTATTGAATGGGTTAAACAGGTGATTCGCGATTTTACCACCGAAGCA

ACCAAAACCTCAACCGTTGATAAACTGAAAGATATTAGCCTGGTGGTGCCGTATATTGGTCTGGCACTGAATATT

GGTGATGAGATCTACAAACAGCATTTTGCAGAAGCAGTTGAACTGGTTGGTGCAGGTCTGCTGCTGGAATTTTCA

CCGGAATTTCTTATTCCGACGCTGCTGATTTTTACCATCAAAGGTTATCTGACCGGTAGCATTCGCGATAAAGAC

AAAATCATTAAAACCCTGGATAACGCCCTGAATGTTCGTGATCAGAAATGGAAAGAACTGTATCGTTGGGTTGTT

AGCAAATGGCTGACCACCATTAATACGCAGTTCAACAAACGCAAAGAACAAATGTACAAAGCCCTGAAAAATCAG

GCCACCGCCATTAAAAAGATCATCGAGAACAAATATAACAACTATACCACCGATGAAAAAAGCAAGATCGATAGC

AGCTATAACATCAACGAAATTGAACGCACCCTGAACGAAAAAATCAATCTGGCCATGAAAAACATCGAGCAGTTT

ATTACAGAAAGCAGCATTGCCTACCTGATCAATATCATCAACAACGAAACCATTCAGAAACTGAAAAGCTATGAT

GACCTGGTTCGTCGTTATCTGCTGGGTTATATTCGTAATCATAGCAGCATTCTGGGCAATAGCGTTGAAGAACTG

AATTCCAAAGTGAACAACCATCTGGATAATGGCATTCCGTTTGAACTGAGCAGTTATACCAATGATAGCCTGCTG

ATCCGCTACTTCAATAAAAACTATGGCGAAGAGAACCTGTATTTCCAGGGTGCCAGTCATCATCACCACCATCAC

CATCACTGA

Polypeptide Sequence of rLH$_N$/FA (His-tagged)

SEQ ID NO: 28

MPVVINSFNYDDPVNDNTIIYIRPPYYETSNTYFKAFQIMDNVWIIPERYRLGIDPSLENPPVSLKAGSDGYFDP

NYLSTNTEKNKYLQIMIKLFKRINSKPAGQILLEEIKNAIPYLGNSYTQEEQFTTNNRTVSFNVKLANGNIVQQM

ANLIIWGPGPDLTTNKTGGIIYSPYQSMEATPYKDGFGSIMTVEFSPEYATAFNDISIASHSPSLFIKDPALILM

HELIHVLHGLYGTYITEYKITPNVVQSYMKVTKPITSAEFLTFGGRDRNIVPQSIQSQLYNKVLSDYKRIASRLN

KVNTATALINIDEFKNLYEWKYQFAKDSNGVYSVDLNKFEQLYKKIYSFTEFNLAYEFKIKTRLGYLAENFGPFY

LPNLLDDSIYTEVDGENIGALSINYQGQNIGSDINSIKKLQGQGVVSRVVRLCSNSNTKNSLCITVNNRDLFFIA

SQESYGENTINTYKEIDDTTTLDPSFEDILDKVILNFNEQVIPQMPNRNVSTDIQKDNYIPKYDYNRTDIIDSYE

VGRNYNTFFYLNAQKESPNESNITLTSSFDTGLLEGSKVYTFFSSDFINNINKPVQALLFIEWVKQVIRDETTEA

TKTSTVDKLKDISLVVPYIGLALNIGDEIYKQHFAEAVELVGAGLLLEFSPEFLIPTLLIFTIKGYLTGSIRDKD

KIIKTLDNALNVRDQKWKELYRWVVSKWLTTINTQFNKRKEQMYKALKNQATAIKKIIENKYNNYTTDEKSKIDS

SYNINEIERTLNEKINLAMKNIEQFITESSIAYLINIINNETIQKLKSYDDLVRRYLLGYIRNHSSILGNSVEEL

NSKVNNHLDNGIPFELSSYTNDSLLIRYFNKNYGEENLYFQGASHHHHHHHH

Nucleotide Sequence of rH$_C$/FA (His-tagged)

SEQ ID NO: 29

ATGCTGAAGTATAACTGCATCCTGAACATCAAATATGAGATGGATCGTGATAAACTGGTTGATAGCAGCGGTTAT

CGTAGCCGTATCAATATTGGCACCGGTGTGAAATTTAGCGAGATCGATAAAAATCAGGTGCAGCTGAGCAATCTG

GAAAGCAGCAAAATTGAAGTGATTCTGAATAACGGCGTGATCTACAATAGCATGTATGAAAACTTTTCGACCAGC

TTCTGGATTCGCATTCCGAAATACTTTCGCAACATCAACAACGAGTACAAGATTATCAGCTGTATGCAGAATAAT

AGCGGTTGGGAAGTTAGCCTGAATTTCAGCAATATGAACAGCAAAATCATTTGGACCCTGCAGGATACCGAAGGT

ATCAAAAAAACCGTTGTGTTTCAGTACACCCAGAACATTAACATCAGCGATTACATTAACCGCTGGATCTTTGTG

ACCATTACCAATAATCGTCTGAGCAACAGCAAGATCTATATTAACGGTCGCCTGATTAACGAAGAGAGCATTAGC

GATCTGGGTAATATTCATGCCAGCAACAACATCATGTTTAAACTGGATGGTTGTCGTGATCCGCATCGTTATATT

TGGATCAAATACTTCAACCTGTTTGATAAAGAACTGAACAAAAAAGAAATCAAAGACCTGTATGATAACCAGAGC

AATAGCGGCATTCTGAAAGATTTTTGGGGTGATTATCTGCAGTATGACAAACCGTATTACATGCTGAATCTGTAC

GATCCGAACAAATATCTGGATGTGAATAATGTGGGTATCCGTGGCTATATGTATCTGAAAGGTCCGCGTGGTCGT

-continued

ATTGTTACCACCAACATTTATCTGAATAGCACCCTGTATATGGGCACCAAATTCATCATTAAAAAGTATGCCAGC

GGCAACAAAGATAACATTGTGCGTAATAATGATCGCGTGTATATCAATGTGGTGGTGAAGAATAAAGAATATCGT

CTGGCCACCAATGCAAGCCAGGCAGGCGTTGAAAAAATTCTGAGCGCAGTTGAAATTCCGGATGTTGGTAATCTG

AGCCAGGTTGTTGTTATGAAAAGCGAAAATGATCAGGGCATTCGCAACAAATGCAAAATGAATCTGCAGGACAAT

AACGGCAACGATATTGGTTTTATTGGCTTCCACCAGTTCAACAACATTGCAAAACTGGTGGCGAGCAATTGGTAT

AATCGTCAGATTGGTAAAGCAAGCCGTACCTTTGGTTGTAGCTGGGAATTTATTCCGGTTGATGATGGTTGGGGT

GAAAGCAGCCTGGAAAATCTGTATTTTCAGGGTGCAAGTCATCATCACCACCATCACCATCATTAA

Polypeptide Sequence of $rH_C$/FA (His-tagged)

SEQ ID NO: 30

MLKYNCILNIKYEMDRDKLVDSSGYRSRINIGTGVKFSEIDKNQVQLSNLESSKIEVILNNGVIYNSMYENESTS

FWIRIPKYFRNINNEYKIISCMQNNSGWEVSLNFSNMNSKIIWTLQDTEGIKKTVVFQYTQNINISDYINRWIFV

TITNNRLSNSKIYINGRLINEESISDLGNIHASNNIMFKLDGCRDPHRYIWIKYFNLFDKELNKKEIKDLYDNQS

NSGILKDFWGDYLQYDKPYYMLNLYDPNKYLDVNNVGIRGYMYLKGPRGRIVTTNIYLNSTLYMGTKFIIKKYAS

GNKDNIVRNNDRVYINVVVKNKEYRLATNASQAGVEKILSAVEIPDVGNLSQVVVMKSENDQGIRNKCKMNLQDN

NGNDIGFIGFHQFNNIAKLVASNWYNRQIGKASRTFGCSWEFIPVDDGWGESSLENLYFQGASHHHHHHHH

Nucleotide Sequence of rLC/FA (His-tagged)

SEQ ID NO: 31

ATGCCGGTTGTGATTAACAGCTTCAATTATGATGATCCGGTGAACGATAACACCATCATTTATATCCGTCCGCCT

TATTATGAAACCAGCAACACCTATTTCAAAGCCTTCCAGATTATGGATAACGTGTGGATTATTCCGGAACGTTAT

CGTCTGGGTATTGATCCGAGCCTGTTTAATCCGCCTGTTAGCCTGAAAGCAGGTAGTGATGGTTATTTTGATCCG

AATTATCTGAGCACCAACACCGAGAAAAACAAATACCTGCAGATTATGATCAAGCTGTTCAAACGCATTAATAGC

AAACCGGCAGGTCAGATTCTGCTGGAAGAAATCAAAAATGCAATTCCGTATCTGGGCAACAGCTATACCCAAGAA

GAACAGTTTACCACCAATAATCGTACCGTGAGCTTTAATGTTAAACTGGCCAATGGTAATATCGTTCAGCAGATG

GCAAATCTGATTATTTGGGGTCCGGGTCCTGATCTGACCACAAATAAAACCGGTGGTATCATCTATAGCCCGTAT

CAGAGCATGGAAGCAACCCCGTATAAAGATGGTTTTGGTAGCATTATGACCGTGGAATTTAGTCCGGAATATGCA

ACCGCCTTTAACGATATTTCAATTGCAAGCCATAGTCCGTCGCTGTTTATCAAAGATCCGGCACTGATTCTGATG

CATGAACTGATTCATGTTCTGCATGGTCTGTATGGCACCTATATTACCGAATACAAAATTACCCCGAATGTGGTG

CAGAGCTATATGAAAGTTACCAAACCGATTACCAGCGCAGAATTTCTGACCTTTGGTGGTCGTGATCGCAATATT

GTTCCGCAGAGCATTCAGAGCCAGCTGTATAACAAAGTTCTGAGCGATTATAAACGTATTGCCAGCCGTCTGAAT

AAAGTTAATACCGCAACCGCACTGATCAACATCGATGAATTCAAAAACCTGTACGAGTGGAAATACCAGTTTGCC

AAAGATAGCAATGGTGTGTATAGCGTGGATCTGAACAAATTTGAGCAGCTGTACAAAAAAATCTATAGCTTCACC

GAATTCAACCTGGCCTATGAGTTTAAAATCAAAACCCGTCTGGGTTATCTGGCCGAAAATTTTGGTCCGTTTTAT

CTGCCGAATCTGCTGGATGATAGCATTTATACCGAAGTGGATGGTTTTAACATTGGTGCACTGAGCATTAACTAT

CAGGGTCAGAATATTGGCAGCGATATCAACAGCATCAAAAAACTGCAAGGTCAGGGTGTTGTTAGCCGTGTTGTT

CGTCTGTGTAGCAATAGCGAAAATCTGTATTTTCAGGGTGCCAGTCATCATCACCACCATCACCATCACTGA

Polypeptide Sequence of rLC/FA (His-tagged)

SEQ ID NO: 32

MPVVINSFNYDDPVNDNTIIYIRPPYYETSNTYFKAFQIMDNVWIIPERYRLGIDPSLFNPPVSLKAGSDGYFDP

NYLSTNTEKNKYLQIMIKLFKRINSKPAGQILLEEIKNAIPYLGNSYTQEEQFTTNNRTVSFNVKLANGNIVQQM

ANLIIWGPGPDLTTNKTGGIIYSPYQSMEATPYKDGFGSIMTVEFSPEYATAFNDISIASHSPSLFIKDPALILM

HELIHVLHGLYGTYITEYKITPNVVQSYMKVTKPITSAEFLTFGGRDRNIVPQSIQSQLYNKVLSDYKRIASRLN

KVNTATALINIDEFKNLYEWKYQFAKDSNGVYSVDLNKFEQLYKKIYSFTEFNLAYEFKIKTRLGYLAENFGPFY

LPNLLDDSIYTEVDGFNIGALSINYQGQNIGSDINSIKKLQGQGVVSRVVRLCSNSENLYFQGASHHHHHHHH

-continued

Nucleotide Sequence of rBoNT/F(0) (His-tagged)

SEQ ID NO: 33

ATGCCGGTTGTGATTAACAGCTTCAATTATAACGATCCGGTGAACGATGATACCATCCTGTATATGCAGATTCCG

TATGAAGAGAAAAGCAAAAAGTACTACAAAGCCTTTGAGATCATGCGCAACGTTTGGATTATTCCGGAACGTAAT

ACCATTGGCACCGATCCGAGCGATTTTGATCCGCCTGCAAGCCTGGAAAATGGTAGCAGCGCATATTATGATCCG

AATTATCTGACCACCGATGCCGAAAAAGATCGTTATCTGAAAACCACCATCAAACTGTTCAAACGCATTAATAGC

AATCCGGCAGGCGAAGTTCTGCTGCAAGAAATTAGCTATGCAAAACCGTATCTGGGCAATGAACATACCCCGATT

AATGAATTTCATCCGGTTACACGTACCACGAGCGTTAACATTAAAAGCAGCACCAATGTGAAGTCCAGCATTATT

CTGAATCTGCTGGTTTTAGGTGCAGGTCCGGATATTTTTGAAAATTCAAGCTATCCGGTGCGCAAACTGATGGAT

AGCGGTGGTGTGTATGATCCGTCAAATGATGGTTTTGGCAGCATTAACATTGTGACCTTTAGTCCGGAATATGAA

TACACCTTCAACGATATTAGCGGTGGCTATAATAGCAGCACCGAAAGTTTTATTGCAGATCCGGCAATTAGCCTG

GCACACCAGCTGATTTATGCACTGCATGGTCTGTATGGTGCACGTGGTGTTACCTATAAAGAAACCATTAAAGTT

AAACAGGCACCGCTGATGATTGCGGAAAAACCGATTCGTCTGGAAGAATTTCTGACCTTTGGTGGTCAGGATCTG

AACATTATTACCAGCGCAATGAAAGAGAAAATCTATAATAACCTGCTGGCCAACTATGAGAAAATTGCAACCCGT

CTGAGCCGTGTTAATAGCGCACCTCCTGAATATGATATCAACGAGTATAAAGACTATTTTCAGTGGAAATACGGC

CTGGATAAAAATGCAGATGGTAGCTATACCGTGAACGAGAACAAATTTAACGAGATCTACAAAAAACTGTATAGC

TTCACCGAAATCGATCTGGCCAACAAATTCAAAGTGAAATGCCGCAACACCTACTTCATCAAATATGGCTTTCTG

AAAGTTCCGAACCTGCTTGATGATGATATCTATACCGTTAGCGAAGGCTTTAACATTGGTAATCTGGCCGTTAAT

AATCGCGGTCAGAACATTAAACTGAACCCGAAAATTATCGATAGCATCCCGGATAAAGGCCTGGTTGAAAAAATT

GTGAAATTCTGCAAAAGCGTGATTCCGCGTAAAGGCACCAAAGCACCGCCTCGTCTGTGTATTCGTGTGAATAAT

CGTGAACTGTTTTTTGTTGCAAGCGAGAGCAGCTATAACGAGAATGATATTAACACCCCGAAAGAGATTGACGAT

ACCACCAATCTGAATAACAACTATCGCAACAATCTGGATGAAGTGATCCTGGATTATAACAGCGAAACCATTCCG

CAGATTAGCAATCAGACCCTGAATACCCTGGTTCAGGATGATAGCTATGTTCCGCGTTATGATAGCAATGGCACC

AGCGAAATTGAAGAACATAATGTGGTTGATCTGAACGTGTTCTTTTATCTGCATGCACAGAAAGTGCCGGAAGGT

GAAACCAATATTAGCCTGACCAGCAGCATTGATACCGCACTGAGCGAAGAAAGCCAGGTTTATACCTTTTTTAGC

AGCGAATTCATCAACACCATTAACAAACCGGTTCATGCAGCACTGTTTATTAGCTGGATTAATCAGGTGATTCGC

GATTTTACCACCGAAGCAACCCAGAAAAGCACCTTTGATAAAATTGCCGATATTAGTCTGGTGGTGCCGTATGTT

GGTCTGGCACTGAATATTGGTAATGAAGTGCAGAAAGAGAACTTTAAAGAAGCCTTCGAACTGTTAGGTGCCGGT

ATTCTGCTGGAATTTGTGCCGGAACTGCTGATTCCGACCATTCTGGTTTTTACCATTAAGAGCTTTATTGGCAGC

AGCGAGAACAAGAACAAAATCATTAAAGCCATCAACAACAGCCTGATGGAACGCGAAACCAAATGGAAAGAAATT

TACAGCTGGATTGTGAGCAATTGGCTGACCCGTATCAATACCCAGTTTAACAAACGCAAAGAACAAATGTATCAG

GCCCTGCAGAATCAGGTTGATGCAATTAAAACCGTGATCGAATACAAATACAACAACTATACCAGCGACGAACGT

AATCGCCTGGAAAGCGAATACAACATTAATAACATTCGCGAAGAACTGAACAAAAAAGTGAGCCTGGCAATGGAA

AACATCGAACGTTTTATTACCGAAAGCAGCATCTTCTACCTGATGAAACTGATTAACGAAGCCAAAGTTAGCAAA

CTGCGCGAATATGATGAAGGCGTTAAAGAATATCTGCTGGACTATATTAGCGAACATCGTAGCATTCTGGGTAAT

AGCGTTCAAGAGCTGAATGATCTGGTTACCAGCACACTGAATAATAGCATTCCGTTTGAACTGAGCAGCTACACC

AACGATAAAATCCTGATCCTGTACTTCAACAAACTGTACAAGAAGATCAAGGACAACAGCATACTGGATATGCGC

TATGAAAACAACAAGTTCATTGATATCAGCGGCTATGGTAGCAACATTAGCATTAATGGTGATGTGTATATCTAC

AGCACCAACCGCAATCAGTTTGGTATTTATAGCAGCAAACCGAGCGAAGTTAATATTGCGCAGAATAACGATATC

ATCTACAACGGTCGCTATCAGAACTTTAGCATTAGCTTTTGGGTTCGCATTCCGAAATACTTTAACAAGGTGAAC

CTGAACAACGAGTACACCATTATTGATTGCATTCGCAATAATAACAGCGGCTGGAAAATCAGCCTGAACTATAAC

AAAATTATCTGGACCCTGCAGGATACCGCAGGTAATAATCAGAAACTGGTGTTTAACTACACCCAGATGATTAGC

-continued

ATCAGCGACTATATCAACAAATGGATCTTTGTGACCATTACCAACAATCGTCTGGGTAACAGCCGCATTTATATC

AATGGCAATCTGATCGACGAAAAAAGCATTTCAAATCTGGGCGATATTCACGTGAGCGATAACATTCTGTTCAAA

ATTGTTGGCTGCAACGATACCCGTTATGTTGGTATTCGTTACTTCAAAGTGTTTGATACGGAACTGGGCAAAACG

GAAATTGAAACCCTGTATAGTGATGAACCGGATCCGAGCATTCTGAAAGATTTTTGGGGTAATTATCTGCTGTAC

AACAAACGCTACTATCTGCTGAACCTGCTGCGTACCGATAAAAGCATTACACAGAATAGCAACTTTCTGAACATC

AATCAGCAGCGTGGTGTTTATCAGAAACCGAACATTTTTAGCAACACCCGTCTGTATACCGGTGTGGAAGTTATT

ATTCGTAAAAACGGTAGCACCGATATCAGCAACACCGATAACTTTGTGCGTAAAAATGACCTGGCCTATATTAAC

GTTGTTGATCGTGATGTTGAGTATCGTCTGTATGCGGATATTAGCATTGCCAAACCGGAAAAGATTATCAAACTG

ATCCGTACCAGCAACAGCAATAATTCACTGGGTCAGATTATCGTGATGGACAGCATTGGTAACAATTGCACCATG

AATTTCCAGAACAATAACGGTGGTAATATTGGCCTGCTGGGCTTTCATAGCAATAATCTGGTTGCAAGCAGCTGG

TATTACAACAACATCCGTAAAAATACCAGCAGTAATGGTTGCTTTTGGAGCTTTATCAGTAAAGAACATGGCTGG

CAAGAAAACGAGAACCTGTATTTTCAGGGTGCAAGTCATCATCACCATCACCACCATCATTAA

Polypeptide Sequence of rBoNT/F(0) (His-tagged)

SEQ ID NO: 34

MPVVINSFNYNDPVNDDTILYMQIPYEEKSKKYYKAFEIMRNVWIIPERNTIGTDPSDFDPPASLENGSSAYYDP

NYLTTDAEKDRYLKTTIKLFKRINSNPAGEVLLQEISYAKPYLGNEHTPINEFHPVTRTTSVNIKSSTNVKSSII

LNLLVLGAGPDIFENSSYPVRKLMDSGGVYDPSNDGFGSINIVTFSPEYEYTENDISGGYNSSTESFIADPAISL

AHQLIYALHGLYGARGVTYKETIKVKQAPLMIAEKPIRLEEFLTFGGQDLNIITSAMKEKIYNNLLANYEKIATR

LSRVNSAPPEYDINEYKDYFQWKYGLDKNADGSYTVNENKFNEIYKKLYSFTEIDLANKFKVKCRNTYFIKYGEL

KVPNLLDDDIYTVSEGENIGNLAVNNRGQNIKLNPKIIDSIPDKGLVEKIVKFCKSVIPRKGTKAPPRLCIRVNN

RELFFVASESSYNENDINTPKEIDDTTNLNNNYRNNLDEVILDYNSETIPQISNQTLNTLVQDDSYVPRYDSNGT

SEIEEHNVVDLNVFFYLHAQKVPEGETNISLTSSIDTALSEESQVYTFFSSEFINTINKPVHAALFISWINQVIR

DFTTEATQKSTEDKIADISLVVPYVGLALNIGNEVQKENFKEAFELLGAGILLEFVPELLIPTILVFTIKSFIGS

SENKNKIIKAINNSLMERETKWKEIYSWIVSNWLTRINTQFNKRKEQMYQALQNQVDAIKTVIEYKYNNYTSDER

NRLESEYNINNIREELNKKVSLAMENIERFITESSIFYLMKLINEAKVSKLREYDEGVKEYLLDYISEHRSILGN

SVQELNDLVTSTLNNSIPFELSSYTNDKILILYFNKLYKKIKDNSILDMRYENNKFIDISGYGSNISINGDVYIY

STNRNQFGIYSSKPSEVNIAQNNDIIYNGRYQNFSISFWVRIPKYFNKVNLNNEYTIIDCIRNNNSGWKISLNYN

KIIWTLQDTAGNNQKLVENYTQMISISDYINKWIFVTITNNRLGNSRIYINGNLIDEKSISNLGDIHVSDNILFK

IVGCNDTRYVGIRYFKVFDTELGKTEIETLYSDEPDPSILKDFWGNYLLYNKRYYLLNLLRTDKSITQNSNFLNI

NQQRGVYQKPNIFSNTRLYTGVEVIIRKNGSTDISNTDNFVRKNDLAYINVVDRDVEYRLYADISIAKPEKIIKL

IRTSNSNNSLGQIIVMDSIGNNCTMNFQNNNGGNIGLLGFHSNNLVASSWYYNNIRKNTSSNGCFWSFISKEHGW

QENENLYFQGASHHHHHHHH

Nucleotide Sequence of $rL_HN/F$ (His-tagged)

SEQ ID NO: 35

ATGCCGGTTGTGATTAACAGCTTCAATTATAACGATCCGGTGAACGATGATACCATCCTGTATATGCAGATTCCG

TATGAAGAGAAAAGCAAAAAGTACTACAAAGCCTTTGAGATCATGCGCAACGTTTGGATTATTCCGGAACGTAAT

ACCATTGGCACCGATCCGAGCGATTTTGATCCGCCTGCAAGCCTGGAAAATGGTAGCAGCGCATATTATGATCCG

AATTATCTGACCACCGATGCCGAAAAAGATCGTTATCTGAAAACCACCATCAAACTGTTCAAACGCATTAATAGC

AATCCGGCAGGCGAAGTTCTGCTGCAAGAAATTAGCTATGCAAAACCGTATCTGGGCAATGAACATACCCCGATT

AATGAATTTCATCCGGTTACACGTACCACGAGCGTTAACATTAAAAGCAGCACCAATGTGAAGTCCAGCATTATT

CTGAATCTGCTGGTTTTAGGTGCAGGTCCGGATATTTTTGAAAATTCAAGCTATCCGGTGCGCAAACTGATGGAT

AGCGGTGGTGTGTATGATCCGTCAAATGATGGTTTTGGCAGCATTAACATTGTGACCTTTAGTCCGGAATATGAA

-continued

TACACCTTCAACGATATTAGCGGTGGCTATAATAGCAGCACCGAAAGTTTTATTGCAGATCCGGCAATTAGCCTG

GCACATGAACTGATTCATGCACTGCATGGTCTGTATGGTGCACGTGGTGTTACCTATAAAGAAACCATTAAAGTT

AAACAGGCACCGCTGATGATTGCGGAAAAACCGATTCGTCTGGAAGAATTTCTGACCTTTGGTGGTCAGGATCTG

AACATTATTACCAGCGCAATGAAAGAGAAAATCTATAATAACCTGCTGGCCAACTATGAGAAAATTGCAACCCGT

CTGAGCCGTGTTAATAGCGCACCTCCTGAATATGATATCAACGAGTATAAAGACTATTTTCAGTGGAAATACGGC

CTGGATAAAAATGCAGATGGTAGCTATACCGTGAACGAGAACAAATTTAACGAGATCTACAAAAAACTGTATAGC

TTCACCGAAATCGATCTGGCCAACAAATTCAAAGTGAAATGCCGCAACACCTACTTCATCAAATATGGCTTTCTG

AAAGTTCCGAACCTGCTTGATGATGATATCTATACCGTTAGCGAAGGCTTTAACATTGGTAATCTGGCCGTTAAT

AATCGCGGTCAGAACATTAAACTGAACCCGAAAATTATCGATAGCATCCCGGATAAAGGCCTGGTTGAAAAAATT

GTGAAATTCTGCAAAAGCGTGATTCCGCGTAAAGGCACCAAAGCACCGCCTCGTCTGTGTATTCGTGTGAATAAT

CGTGAACTGTTTTTTGTTGCAAGCGAGAGCAGCTATAACGAGAATGATATTAACACCCCGAAAGAGATTGACGAT

ACCACCAATCTGAATAACAACTATCGCAACAATCTGGATGAAGTGATCCTGGATTATAACAGCGAAACCATTCCG

CAGATTAGCAATCAGACCCTGAATACCCTGGTTCAGGATGATAGCTATGTTCCGCGTTATGATAGCAATGGCACC

AGCGAAATTGAAGAACATAATGTGGTTGATCTGAACGTGTTCTTTTATCTGCATGCACAGAAAGTGCCGGAAGGT

GAAACCAATATTAGCCTGACCAGCAGCATTGATACCGCACTGAGCGAAGAAAGCCAGGTTTATACCTTTTTTAGC

AGCGAATTCATCAACACCATTAACAAACCGGTTCATGCAGCACTGTTTATTAGCTGGATTAATCAGGTGATTCGC

GATTTTACCACCGAAGCAACCCAGAAAAGCACCTTTGATAAAATTGCCGATATTAGTCTGGTGGTGCCGTATGTT

GGTCTGGCACTGAATATTGGTAATGAAGTGCAGAAAGAGAACTTTAAAGAAGCCTTCGAACTGTTAGGTGCCGGT

ATTCTGCTGGAATTTGTGCCGGAACTGCTGATTCCGACCATTCTGGTTTTTACCATTAAGAGCTTTATTGGCAGC

AGCGAGAACAAGAACAAAATCATTAAAGCCATCAACAACAGCCTGATGGAACGCGAAACCAAATGGAAAGAAATT

TACAGCTGGATTGTGAGCAATTGGCTGACCCGTATCAATACCCAGTTTAACAAACGCAAAGAACAAATGTATCAG

GCCCTGCAGAATCAGGTTGATGCAATTAAAACCGTGATCGAATACAAATACAACAACTATACCAGCGACGAACGT

AATCGCCTGGAAAGCGAATACAACATTAATAACATTCGCGAAGAACTGAACAAAAAAGTGAGCCTGGCAATGGAA

AACATCGAACGTTTTATTACCGAAAGCAGCATCTTCTACCTGATGAAACTGATTAACGAAGCCAAAGTTAGCAAA

CTGCGCGAATATGATGAAGGCGTTAAAGAATATCTGCTGGACTATATTAGCGAACATCGTAGCATTCTGGGTAAT

AGCGTTCAAGAGCTGAATGATCTGGTTACCAGCACACTGAATAATAGCATTCCGTTTGAACTGAGCAGCTACACC

AACGATAAAATCCTGATCCTGTACTTCAACAAACTGTACAAGAAAGAAAACCTGTATTTTCAGGGTGCAAGCCAT

CATCACCACCATCACCATCATTAA

Polypeptide Sequence of $rL_H$N/F (His-tagged)

SEQ ID NO: 36

MPVVINSFNYNDPVNDDTILYMQIPYEEKSKKYYKAFEIMRNVWIIPERNTIGTDPSDFDPPASLENGSSAYYDP

NYLTTDAEKDRYLKTTIKLFKRINSNPAGEVLLQEISYAKPYLGNEHTPINEFHPVTRTTSVNIKSSTNVKSSII

LNLLVLGAGPDIFENSSYPVRKLMDSGGVYDPSNDGFGSINIVTFSPEYEYTENDISGGYNSSTESFIADPAISL

AHELIHALHGLYGARGVTYKETIKVKQAPLMIAEKPIRLEEFLTFGGQDLNIITSAMKEKIYNNLLANYEKIATR

LSRVNSAPPEYDINEYKDYFQWKYGLDKNADGSYTVNENKFNEIYKKLYSFTEIDLANKFKVKCRNTYFIKYGFL

KVPNLLDDDIYTVSEGENIGNLAVNNRGQNIKLNPKIIDSIPDKGLVEKIVKFCKSVIPRKGTKAPPRLCIRVNN

RELFFVASESSYNENDINTPKEIDDTTNLNNNYRNNLDEVILDYNSETIPQISNQTLNTLVQDDSYVPRYDSNGT

SEIEEHNVVDLNVFFYLHAQKVPEGETNISLTSSIDTALSEESQVYTFFSSEFINTINKPVHAALFISWINQVIR

DETTEATQKSTFDKIADISLVVPYVGLALNIGNEVQKENFKEAFELLGAGILLEFVPELLIPTILVFTIKSFIGS

SENKNKIIKAINNSLMERETKWKEIYSWIVSNWLTRINTQFNKRKEQMYQALQNQVDAIKTVIEYKYNNYTSDER

NRLESEYNINNIREELNKKVSLAMENIERFITESSIFYLMKLINEAKVSKLREYDEGVKEYLLDYISEHRSILGN

SVQELNDLVTSTLNNSIPFELSSYTNDKILILYFNKLYKKENLYFQGASHHHHHHHH

-continued

Nucleotide Sequence of $rH_C$/F (His-tagged)

SEQ ID NO: 37

ATGATCAAGGATAACAGCATTCTGGATATGCGCTATGAGAACAACAAATTCATTGATATTAGCGGCTATGGCAGC

AACATTAGCATTAATGGTGATGTGTATATCTACAGCACCAACCGTAATCAGTTTGGCATTTATAGCAGCAAACCG

AGCGAAGTTAATATTGCCCAGAACAACGATATCATCTATAACGGTCGCTATCAGAACTTCAGCATTAGCTTTTGG

GTTCGCATTCCGAAATACTTCAATAAGGTGAACCTGAACAACGAGTATACCATCATTGATTGCATTCGCAATAAT

AACAGCGGCTGGAAAATTAGCCTGAACTACAACAAAATTATCTGGACCCTGCAGGATACCGCAGGTAATAATCAG

AAACTGGTGTTTAACTACACCCAGATGATTAGCATCAGCGACTATATCAACAAATGGATCTTTGTGACCATTACC

AATAATCGCCTGGGTAATAGCCGCATTTATATCAATGGTAACCTGATCGATGAGAAAAGCATTAGCAATCTGGGT

GATATTCATGTGAGCGATAACATCCTGTTTAAAATCGTGGGTTGTAACGATACCCGTTATGTTGGTATTCGCTAC

TTCAAAGTGTTTGATACCGAACTGGGTAAAACCGAAATTGAAACCCTGTATAGTGATGAACCGGATCCGAGCATT

CTGAAAGATTTTTGGGGTAATTATCTGCTGTACAACAAACGCTACTATCTGCTGAATCTGCTGCGTACCGATAAA

TCAATTACCCAGAATAGCAACTTCCTGAACATTAATCAGCAGCGTGGTGTTTATCAGAAACCGAACATTTTTAGC

AACACCCGTCTGTATACCGGTGTGGAAGTTATTATTCGTAAAAATGGCAGCACCGATATCAGCAACACCGATAAC

TTTGTTCGCAAAAATGATCTGGCGTATATCAACGTTGTTGATCGTGATGTTGAATATCGTCTGTATGCCGATATT

AGCATTGCCAAACCGGAAAAAATCATCAAACTGATCCGTACCAGCAACAGCAATAATTCACTGGGTCAGATTATT

GTGATGGATAGCATTGGTAATAACTGCACCATGAACTTTCAGAACAATAACGGTGGTAATATTGGTCTGCTGGGC

TTTCATAGTAATAATCTGGTTGCAAGCAGCTGGTATTATAACAACATCCGTAAAAATACCAGCAGCAATGGTTGC

TTTTGGAGCTTTATTAGCAAAGAACATGGCTGGCAAGAAAACGAGAATCTGTATTTTCAGGGTGCAAGTCATCAT

CACCACCATCACCATCATTAA

Polypeptide Sequence of $rH_C$/F (His-tagged)

SEQ ID NO: 38

MIKDNSILDMRYENNKFIDISGYGSNISINGDVYIYSTNRNQFGIYSSKPSEVNIAQNNDIIYNGRYQNFSISFW

VRIPKYFNKVNLNNEYTIIDCIRNNNSGWKISLNYNKIIWTLQDTAGNNQKLVFNYTQMISISDYINKWIFVTIT

NNRLGNSRIYINGNLIDEKSISNLGDIHVSDNILFKIVGCNDTRYVGIRYFKVEDTELGKTEIETLYSDEPDPSI

LKDFWGNYLLYNKRYYLLNLLRTDKSITQNSNFLNINQQRGVYQKPNIFSNTRLYTGVEVIIRKNGSTDISNTDN

FVRKNDLAYINVVDRDVEYRLYADISIAKPEKIIKLIRTSNSNNSLGQIIVMDSIGNNCTMNFQNNNGGNIGLLG

FHSNNLVASSWYYNNIRKNTSSNGCFWSFISKEHGWQENENLYFQGASHHHHHHHH

Nucleotide Sequence of rLC/F (His-tagged)

SEQ ID NO: 39

ATGCCGGTTGTGATTAACAGCTTCAATTATAACGATCCGGTGAACGATGATACCATCCTGTATATGCAGATTCCG

TATGAAGAGAAAAGCAAAAAGTACTACAAAGCCTTTGAGATCATGCGCAACGTTTGGATTATTCCGGAACGTAAT

ACCATTGGCACCGATCCGAGCGATTTTGATCCGCCTGCAAGCCTGGAAAATGGTAGCAGCGCATATTATGATCCG

AATTATCTGACCACCGATGCCGAAAAAGATCGTTATCTGAAAACCACCATCAAACTGTTCAAACGCATTAATAGC

AATCCGGCAGGCGAAGTTCTGCTGCAAGAAATTAGCTATGCAAAACCGTATCTGGGCAATGAACATACCCCGATT

AATGAATTTCATCCGGTTACACGTACCACGAGCGTTAACATTAAAAGCAGCACCAATGTGAAGTCCAGCATTATT

CTGAATCTGCTGGTTTTAGGTGCAGGTCCGGATATTTTTGAAAATTCAAGCTATCCGGTGCGCAAACTGATGGAT

AGCGGTGGTGTGTATGATCCGTCAAATGATGGTTTTGGCAGCATTAACATTGTGACCTTTAGTCCGGAATATGAA

TACACCTTCAACGATATTAGCGGTGGCTATAATAGCAGCACCGAAAGTTTTATTGCAGATCCGGCAATTAGCCTG

GCACATGAACTGATTCATGCACTGCATGGTCTGTATGGTGCACGTGGTGTTACCTATAAAGAAACCATTAAAGTT

AAACAGGCACCGCTGATGATTGCGGAAAAACCGATTCGTCTGGAAGAATTTCTGACCTTTGGTGGTCAGGATCTG

AACATTATTACCAGCGCAATGAAAGAGAAAATCTATAATAACCTGCTGGCCAACTATGAGAAAATTGCAACCCGT

CTGAGCCGTGTTAATAGCGCACCTCCTGAATATGATATCAACGAGTATAAAGACTATTTTCAGTGGAAATACGGC

-continued

CTGGATAAAAATGCAGATGGTAGCTATACCGTGAACGAGAACAAATTTAACGAGATCTACAAAAAACTGTATAGC

TTCACCGAAATCGATCTGGCCAACAAATTCAAAGTGAAATGCCGCAACACCTACTTCATCAAATATGGCTTTCTG

AAAGTTCCGAACCTGCTTGATGATGATATCTATACCGTTAGCGAAGGCTTTAACATTGGTAATCTGGCCGTTAAT

AATCGCGGTCAGAACATTAAACTGAACCCGAAAATTATCGATAGCATCCCGGATAAAGGCCTGGTTGAAAAAATT

GTGAAATTCTGCAAAAGCGAGAACCTGTATTTTCAGGGTGCAAGTCATCATCACCATCACCACCATCATTAA

Polypeptide Sequence of rLC/F (His-tagged)

SEQ ID NO: 40

MPVVINSFNYNDPVNDDTILYMQIPYEEKSKKYYKAFEIMRNVWIIPERNTIGTDPSDFDPPASLENGSSAYYDP

NYLTTDAEKDRYLKTTIKLFKRINSNPAGEVLLQEISYAKPYLGNEHTPINEFHPVTRTTSVNIKSSTNVKSSII

LNLLVLGAGPDIFENSSYPVRKLMDSGGVYDPSNDGFGSINIVTFSPEYEYTENDISGGYNSSTESFIADPAISL

AHELIHALHGLYGARGVTYKETIKVKQAPLMIAEKPIRLEEFLTFGGQDLNIITSAMKEKIYNNLLANYEKIATR

LSRVNSAPPEYDINEYKDYFQWKYGLDKNADGSYTVNENKFNEIYKKLYSFTEIDLANKFKVKCRNTYFIKYGEL

KVPNLLDDDIYTVSEGENIGNLAVNNRGQNIKLNPKIIDSIPDKGLVEKIVKFCKSENLYFQGASHHHHHHHH

Nucleotide Sequence of Cationic $rH_C$/A (His-tagged)

SEQ ID NO: 41

ATGATCATCAACACCAGCATTCTGAACCTGCGTTATGAAAGCAAACATCTGATTGATCTGAGCCGTTATGCCAGC

AAAATCAATATAGGCAGCAAGGTTAACTTCGACCCGATTGACAAAAATCAGATACAGCTGTTTAATCTGGAAAGC

AGCAAAATTGAGGTGATCCTGAAAAAAGCGATCGTGTATAATAGCATGTACGAGAATTTTTCGACCAGCTTTTGG

ATTCGCATCCCGAAATACTTTAACAAGATTAGCCTGAACAACGAGTATACCATCATTAACTGCATGGAAAACAAT

AGCGGTTGGAAAGTCAGCCTGAATTATGGCGAAATTATCTGGACCCTGCAGGATACCAAAGAAATCAAACAGCGT

GTGGTGTTCAAATACAGCCAGATGATTAATATCAGCGACTATATCAACCGCTGGATTTTTGTGACCATTACCAAT

AATCGGCTGAACAAGAGCAAGATCTATATTAACGGTCGTCTGATTGACCAGAAACCGATTAGTAATCTGGGTAAT

ATTCATGCGAGCAACAAAATCATGTTTAAACTGGATGGTTGCCGTGATACCCATCGTTATATTTGGATCAAATAC

TTCAACCTGTTCGATAAAGAGTTGAACGAAAAAGAAATTAAAGACCTGTACGATAACCAGAGCAATAGCGGCATA

CTGAAAGATTTTTGGGGAGATTATCTGCAGTATGACAAACCGTATTATATGCTGAATCTGTACGACCCGAATAAA

TACGTGGATGTTAATAATGTGGGCATCCGTGGTTATATGTACCTGAAAGGTCCGCGTGGTAGCGTTATGACCACA

AACATTTATCTGAATAGCAGCCTGTATCGCGGAACCAAATTCATCATTAAAAAGTATGCCAGCGGCAACAAGGAT

AATATTGTGCGTAATAATGATCGCGTGTACATTAACGTTGTGGTGAAGAATAAAGAATATCGCCTGGCAACCAAT

GCAAGCCAGGCAGGCGTTGAAAAAATTCTGAGTGCCCTGGAAATTCCGGATGTTGGTAATCTGAGCCAGGTTGTT

GTGATGAAAAGCAAAAACGATAAAGGCATCACCAACAAATGCAAGATGAATCTGCAGGACAATAACGGCAATGAT

ATTGGCTTCATTGGCTTTCACCAGTTTAACAACATTGCAAAACTGGTTGCGAGCAATTGGTATAATCGTCAGATT

GAACGTAGCAGTCGTACCCTGGGTTGTAGCTGGGAATTTATCCCTGTGGATGATGGTTGGGGTGAACGTCCGCTG

AAGCTTGCGGCCGCACTCGAGCACCACCACCACCACCACTGA

Polypeptide Sequence of Cationic $rH_C$/A (His-tagged)

SEQ ID NO: 42

MIINTSILNLRYESKHLIDLSRYASKINIGSKVNFDPIDKNQIQLFNLESSKIEVILKKAIVYNSMYENFSTSFW

IRIPKYFNKISLNNEYTIINCMENNSGWKVSLNYGEIIWTLQDTKEIKQRVVFKYSQMINISDYINRWIFVTITN

NRLNKSKIYINGRLIDQKPISNLGNIHASNKIMFKLDGCRDTHRYIWIKYENLEDKELNEKEIKDLYDNQSNSGI

LKDFWGDYLQYDKPYYMLNLYDPNKYVDVNNVGIRGYMYLKGPRGSVMTTNIYLNSSLYRGTKFIIKKYASGNKD

NIVRNNDRVYINVVVKNKEYRLATNASQAGVEKILSALEIPDVGNLSQVVVMKSKNDKGITNKCKMNLQDNNGND

IGFIGFHQFNNIAKLVASNWYNRQIERSSRTLGCSWEFIPVDDGWGERPLKLAAALEHHHHHH

Nucleotide Sequence of $rH_C$/AB (His-tagged)

SEQ ID NO: 43

ATGATTCTGAACAATATTATCCTGAACCTGCGTTACAAAGACAACAATCTGATCGATCTGAGCGGCTATGGTGCA

AAAGTTGAAGTCTACGACGGTGTCGAACTGAACGATAAAAACCAGTTCAAACTGACCTCATCGGCTAACTCAAAA

-continued

ATTCGTGTGACGCAGAACCAAAACATCATCTTCAACTCGGTCTTTCTGGACTTCAGCGTGTCTTTCTGGATTCGC

ATCCCGAAATATAAAAATGATGGCATCCAGAACTACATCCATAACGAATACACCATCATCAACTGTATGAAAAAC

AACAGTGGTTGGAAAATTTCCATCCGTGGCAACCGCATTATCTGGACCCTGATTGATATCAATGGTAAAACGAAA

AGCGTGTTTTTCGAATACAACATCCGTGAAGATATCTCTGAATACATCAATCGCTGGTTTTTCGTGACCATTACG

AACAATCTGAACAATGCGAAAATCTATATCAACGGCAAACTGGAAAGTAATACCGACATCAAAGATATTCGTGAA

GTTATCGCCAACGGTGAAATCATCTTCAAACTGGATGGCGACATCGATCGCACCCAGTTCATTTGGATGAAATAC

TTCTCCATCTTCAACACGGAACTGAGTCAGTCCAATATCGAAGAACGCTACAAAATCCAATCATACTCGGAATAC

CTGAAAGATTTCTGGGGTAACCCGCTGATGTACAACAAAGAATACTACATGTTCAACGCGGGCAACAAAAACTCA

TACATCAAACTGAAAAAAGATTCGCCGGTGGGTGAAATCCTGACCCGTAGCAAATACAACCAGAACTCTAAATAC

ATCAACTATCGCGATCTGTACATTGGCGAAAAATTTATTATCCGTCGCAAAAGCAACTCTCAGAGTATTAATGAT

GACATCGTGCGTAAAGAAGACTACATCTATCTGGATTTCTTTAATCTGAACCAAGAATGGCGCGTTTATACCTAC

AAATACTTCAAAAAAGAAGAAATGAAACTGTTCCTGGCCCCGATTTACGACAGCGATGAATTTTACAACACCATC

CAGATCAAAGAATACGATGAACAGCCGACGTATAGTTGCCAACTGCTGTTCAAAAAAGACGAAGAATCCACCGAT

GAAATTGGCCTGATTGGTATCCACCGTTTCTATGAAAGCGGTATCGTTTTCGAAGAATACAAAGATTACTTCTGT

ATCTCTAAATGGTATCTGAAAGAAGTCAAACGCAAACCGTACAACCTGAAACTGGGCTGCAACTGGCAATTTATC

CCGAAAGACGAAGGCTGGACCGAAAAGCTTGCGGCCGCACTCGAGCACCACCACCACCACCACTGA

Polypeptide Sequence of $rH_C$/AB (His-tagged)

SEQ ID NO: 44

MILNNIILNLRYKDNNLIDLSGYGAKVEVYDGVELNDKNQFKLTSSANSKIRVTQNQNIIFNSVFLDFSVSFWIR

IPKYKNDGIQNYIHNEYTIINCMKNNSGWKISIRGNRIIWTLIDINGKTKSVFFEYNIREDISEYINRWFFVTIT

NNLNNAKIYINGKLESNTDIKDIREVIANGEIIFKLDGDIDRTQFIWMKYFSIFNTELSQSNIEERYKIQSYSEY

LKDFWGNPLMYNKEYYMFNAGNKNSYIKLKKDSPVGEILTRSKYNQNSKYINYRDLYIGEKFIIRRKSNSQSIND

DIVRKEDYIYLDFFNLNQEWRVYTYKYFKKEEMKLFLAPIYDSDEFYNTIQIKEYDEQPTYSCQLLFKKDEESTD

EIGLIGIHRFYESGIVFEEYKDYFCISKWYLKEVKRKPYNLKLGCNWQFIPKDEGWTEKLAAALEHHHHHH

Nucleotide Sequence of $rH_C$/A Variant Y1117V H1253K (His-tagged)

SEQ ID NO: 45

ATGATCATCAATACTAGCATTCTGAACCTGCGTTACGAGAGCAATCATCTGATTGATCTGAGCCGTTATGCAAGC

AAGATCAACATCGGTAGCAAGGTCAATTTTGACCCGATCGATAAGAACCAGATCCAGCTGTTTAATCTGGAATCG

AGCAAAATTGAGGTTATCCTGAAAAACGCCATTGTCTACAACTCCATGTACGAGAATTTCTCCACCAGCTTCTGG

ATTCGCATCCCGAAATACTTCAACAGCATTAGCCTGAACAACGAGTATACTATCATCAACTGTATGGAGAACAAC

AGCGGTTGGAAGGTGTCTCTGAACTATGGTGAGATCATTTGGACCTTGCAGGACACCCAAGAGATCAAGCAGCGC

GTCGTGTTCAAGTACTCTCAAATGATCAACATTTCCGATTACATTAATCGTTGGATCTTCGTGACCATTACGAAT

AACCGTCTGAATAACAGCAAGATTTACATCAATGGTCGCTTGATCGATCAGAAACCGATTAGCAACCTGGGTAAT

ATCCACGCAAGCAACAACATTATGTTCAAATTGGACGGTTGCCGCGATACCCATCGTTATATCTGGATCAAGTAT

TTCAACCTGTTTGATAAAGAACTGAATGAGAAGGAGATCAAAGATTTGTATGACAACCAATCTAACAGCGGCATT

TTGAAGGACTTCTGGGGCGATTATCTGCAATACGATAAGCCGTACTATATGCTGAACCTGgtTGATCCGAACAAA

TATGTGGATGTCAATAATGTGGGTATTCGTGGTTACATGTATTTGAAGGGTCCGCGTGGCAGCGTTATGACGACC

AACATTTACCTGAACTCTAGCCTGTACCGTGGTACGAAATTCATCATTAAGAAATATGCCAGCGGCAACAAAGAT

AACATTGTGCGTAATAACGATCGTGTCTACATCAACGTGGTCGTGAAGAATAAAGAGTACCGTCTGGCGACCAAC

GCTTCGCAGGCGGGTGTTGAGAAAATTCTGAGCGCGTTGGAGATCCCTGATGTCGGTAATCTGAGCCAAGTCGTG

GTTATGAAGAGCAAGAACGACCAGGGTATCACTAACAAGTGCAAGATGAACCTGCAAGACAACAATGGTAACGAC

ATCGGCTTTATTGGTTTCaAaCAGTTCAACAATATTGCTAAACTGGTAGCGAGCAATTGGTACAATCGTCAGATT

-continued

GAGCGCAGCAGCCGTACTTTGGGCTGTAGCTGGGAGTTTATCCCGGTCGATGATGGTTGGGGCGAACGTCCGCTG

CACCATCACCATCACCATCACCATCACCATT

Polypeptide Sequence of $rH_C$/A Variant Y1117V H1253K (His-tagged)

SEQ ID NO: 46

MIINTSILNLRYESNHLIDLSRYASKINIGSKVNFDPIDKNQIQLENLESSKIEVILKNAIVYNSMYENFSTSFW

IRIPKYFNSISLNNEYTIINCMENNSGWKVSLNYGEIIWTLQDTQEIKQRVVFKYSQMINISDYINRWIFVTITN

NRLNNSKIYINGRLIDQKPISNLGNIHASNNIMFKLDGCRDTHRYIWIKYFNLFDKELNEKEIKDLYDNQSNSGI

LKDFWGDYLQYDKPYYMLNLVDPNKYVDVNNVGIRGYMYLKGPRGSVMTTNIYLNSSLYRGTKFIIKKYASGNKD

NIVRNNDRVYINVVVKNKEYRLATNASQAGVEKILSALEIPDVGNLSQVVVMKSKNDQGITNKCKMNLQDNNGND

IGFIGFKQFNNIAKLVASNWYNRQIERSSRTLGCSWEFIPVDDGWGERPLHHHHHHHHHH

Nucleotide Sequence of $rH_C$/A Variant Y1117V F1252Y H1253K L1278F (His-tagged)

SEQ ID NO: 47

ATGATCATCAATACTAGCATTCTGAACCTGCGTTACGAGAGCAATCATCTGATTGATCTGAGCCGTTATGCAAGC

AAGATCAACATCGGTAGCAAGGTCAATTTTGACCCGATCGATAAGAACCAGATCCAGCTGTTTAATCTGGAATCG

AGCAAAATTGAGGTTATCCTGAAAAACGCCATTGTCTACAACTCCATGTACGAGAATTTCTCCACCAGCTTCTGG

ATTCGCATCCCGAAATACTTCAACAGCATTAGCCTGAACAACGAGTATACTATCATCAACTGTATGGAGAACAAC

AGCGGTTGGAAGGTGTCTCTGAACTATGGTGAGATCATTTGGACCTTGCAGGACACCCAAGAGATCAAGCAGCGC

GTCGTGTTCAAGTACTCTCAAATGATCAACATTTCCGATTACATTAATCGTTGGATCTTCGTGACCATTACGAAT

AACCGTCTGAATAACAGCAAGATTTACATCAATGGTCGCTTGATCGATCAGAAACCGATTAGCAACCTGGGTAAT

ATCCACGCAAGCAACAACATTATGTTCAAATTGGACGGTTGCCGCGATACCCATCGTTATATCTGGATCAAGTAT

TTCAACCTGTTTGATAAAGAACTGAATGAGAAGGAGATCAAAGATTTGTATGACAACCAATCTAACAGCGGCATT

TTGAAGGACTTCTGGGGCGATTATCTGCAATACGATAAGCCGTACTATATGCTGAACCTGgtTGATCCGAACAAA

TATGTGGATGTCAATAATGTGGGTATTCGTGGTTACATGTATTTGAAGGGTCCGCGTGGCAGCGTTATGACGACC

AACATTTACCTGAACTCTAGCCTGTACCGTGGTACGAAATTCATCATTAAGAAATATGCCAGCGGCAACAAAGAT

AACATTGTGCGTAATAACGATCGTGTCTACATCAACGTGGTCGTGAAGAATAAAGAGTACCGTCTGGCGACCAAC

GCTTCGCAGGCGGGTGTTGAGAAAATTCTGAGCGCGTTGGAGATCCCTGATGTCGGTAATCTGAGCCAAGTCGTG

GTTATGAAGAGCAAGAACGACCAGGGTATCACTAACAAGTGCAAGATGAACCTGCAAGACAACAATGGTAACGAC

ATCGGCTTTATTGGTTaCaAaCAGTTCAACAATATTGCTAAACTGGTAGCGAGCAATTGGTACAATCGTCAGATT

GAGCGCAGCAGCCGTACTTTtGGCTGTAGCTGGGAGTTTATCCCGGTCGATGATGGTTGGGGCGAACGTCCGCTG

CACCATCACCATCACCATCACCATCACCATTAA

Polypeptide Sequence of $rH_C$/A Variant Y1117V F1252Y H1253K L1278F (His-tagged)

SEQ ID NO: 48

MIINTSILNLRYESNHLIDLSRYASKINIGSKVNFDPIDKNQIQLENLESSKIEVILKNAIVYNSMYENFSTSFW

IRIPKYFNSISLNNEYTIINCMENNSGWKVSLNYGEIIWTLQDTQEIKQRVVFKYSQMINISDYINRWIFVTITN

NRLNNSKIYINGRLIDQKPISNLGNIHASNNIMFKLDGCRDTHRYIWIKYFNLFDKELNEKEIKDLYDNQSNSGI

LKDFWGDYLQYDKPYYMLNLVDPNKYVDVNNVGIRGYMYLKGPRGSVMTTNIYLNSSLYRGTKFIIKKYASGNKD

NIVRNNDRVYINVVVKNKEYRLATNASQAGVEKILSALEIPDVGNLSQVVVMKSKNDQGITNKCKMNLQDNNGND

IGFIGYKQFNNIAKLVASNWYNRQIERSSRTFGCSWEFIPVDDGWGERPLHHHHHHHHHH

Nucleotide Sequence of $rH_C$/A Variant Y1117V F1252Y H1253K L1278H (His-tagged)

SEQ ID NO: 49

ATGATCATCAATACTAGCATTCTGAACCTGCGTTACGAGAGCAATCATCTGATTGATCTGAGCCGTTATGCAAGC

AAGATCAACATCGGTAGCAAGGTCAATTTTGACCCGATCGATAAGAACCAGATCCAGCTGTTTAATCTGGAATCG

AGCAAAATTGAGGTTATCCTGAAAAACGCCATTGTCTACAACTCCATGTACGAGAATTTCTCCACCAGCTTCTGG

-continued

ATTCGCATCCCGAAATACTTCAACAGCATTAGCCTGAACAACGAGTATACTATCATCAACTGTATGGAGAACAAC

AGCGGTTGGAAGGTGTCTCTGAACTATGGTGAGATCATTTGGACCTTGCAGGACACCCAAGAGATCAAGCAGCGC

GTCGTGTTCAAGTACTCTCAAATGATCAACATTTCCGATTACATTAATCGTTGGATCTTCGTGACCATTACGAAT

AACCGTCTGAATAACAGCAAGATTTACATCAATGGTCGCTTGATCGATCAGAAACCGATTAGCAACCTGGGTAAT

ATCCACGCAAGCAACAACATTATGTTCAAATTGGACGGTTGCCGCGATACCCATCGTTATATCTGGATCAAGTAT

TTCAACCTGTTTGATAAAGAACTGAATGAGAAGGAGATCAAAGATTTGTATGACAACCAATCTAACAGCGGCATT

TTGAAGGACTTCTGGGGCGATTATCTGCAATACGATAAGCCGTACTATATGCTGAACCTGgtTGATCCGAACAAA

TATGTGGATGTCAATAATGTGGGTATTCGTGGTTACATGTATTTGAAGGGTCCGCGTGGCAGCGTTATGACGACC

AACATTTACCTGAACTCTAGCCTGTACCGTGGTACGAAATTCATCATTAAGAAATATGCCAGCGGCAACAAAGAT

AACATTGTGCGTAATAACGATCGTGTCTACATCAACGTGGTCGTGAAGAATAAAGAGTACCGTCTGGCGACCAAC

GCTTCGCAGGCGGGTGTTGAGAAAATTCTGAGCGCGTTGGAGATCCCTGATGTCGGTAATCTGAGCCAAGTCGTG

GTTATGAAGAGCAAGAACGACCAGGGTATCACTAACAAGTGCAAGATGAACCTGCAAGACAACAATGGTAACGAC

ATCGGCTTTATTGGTTaCaAaCAGTTCAACAATATTGCTAAACTGGTAGCGAGCAATTGGTACAATCGTCAGATT

GAGCGCAGCAGCCGTACTcatGGCTGTAGCTGGGAGTTTATCCCGGTCGATGATGGTTGGGGCGAACGTCCGCTG

CACCATCACCATCACCAT

Polypeptide Sequence of r$H_C$/A Variant Y1117V F1252Y H1253K L1278H (His-tagged)

SEQ ID NO: 50

MIINTSILNLRYESNHLIDLSRYASKINIGSKVNFDPIDKNQIQLENLESSKIEVILKNAIVYNSMYENFSTSFW

IRIPKYFNSISLNNEYTIINCMENNSGWKVSLNYGEIIWTLQDTQEIKQRVVFKYSQMINISDYINRWIFVTITN

NRLNNSKIYINGRLIDQKPISNLGNIHASNNIMFKLDGCRDTHRYIWIKYFNLFDKELNEKEIKDLYDNQSNSGI

LKDFWGDYLQYDKPYYMLNLVDPNKYVDVNNVGIRGYMYLKGPRGSVMTTNIYLNSSLYRGTKFIIKKYASGNKD

NIVRNNDRVYINVVVKNKEYRLATNASQAGVEKILSALEIPDVGNLSQVVVMKSKNDQGITNKCKMNLQDNNGND

IGFIGYKQFNNIAKLVASNWYNRQIERSSRTHGCSWEFIPVDDGWGERPLHHHHHH

Polypeptide Sequence of BoNT/A-UniProt P10845

SEQ ID NO: 51

MPFVNKQFNYKDPVNGVDIAYIKIPNVGQMQPVKAFKIHNKIWVIPERDTFTNPEEGDLN

PPPEAKQVPVSYYDSTYLSTDNEKDNYLKGVTKLFERIYSTDLGRMLLTSIVRGIPFWGG

STIDTELKVIDTNCINVIQPDGSYRSEELNLVIIGPSADIIQFECKSFGHEVLNLTRNGY

GSTQYIRESPDFTFGFEESLEVDTNPLLGAGKFATDPAVTLAHELIHAGHRLYGIAINPN

RVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKEDKLYKMLTEIYTEDNFVKFFKV

LNRKTYLNFDKAVFKINIVPKVNYTIYDGENLRNTNLAANFNGQNTEINNMNFTKLKNFT

GLFEFYKLLCVRGIITSKTKSLDKGYNKALNDLCIKVNNWDLFFSPSEDNETNDLNKGEE

ITSDTNIEAAEENISLDLIQQYYLTENEDNEPENISIENLSSDIIGQLELMPNIEREPNG

KKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIESG

AVILLEFIPEIAIPVLGTFALVSYIANKVLTVQTIDNALSKRNEKWDEVYKYIVTNWLAK

VNTQIDLIRKKMKEALENQAEATKAIINYQYNQYTEEEKNNINFNIDDLSSKLNESINKA

MININKFLNQCSVSYLMNSMIPYGVKRLEDEDASLKDALLKYIYDNRGTLIGQVDRLKDK

VNNTLSTDIPFQLSKYVDNQRLLSTFTEYIKNIINTSILNLRYESNHLIDLSRYASKINI

GSKVNFDPIDKNQIQLENLESSKIEVILKNAIVYNSMYENFSTSFWIRIPKYENSISLNN

EYTIINCMENNSGWKVSLNYGEIIWTLQDTQEIKQRVVFKYSQMINISDYINRWIFVTIT

-continued

NNRLNNSKIYINGRLIDQKPISNLGNIHASNNIMFKLDGCRDTHRYIWIKYENLEDKELN

EKEIKDLYDNQSNSGILKDFWGDYLQYDKPYYMLNLYDPNKYVDVNNVGIRGYMYLKGPR

GSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQENNIAK

LVASNWYNRQIERSSRTLGCSWEFIPVDDGWGERPL

Polypeptide Sequence of BoNT/B-UniProt P10844

SEQ ID NO: 52

MPVTINNENYNDPIDNNNIIMMEPPFARGTGRYYKAFKITDRIWIIPERYTFGYKPEDEN

KSSGIFNRDVCEYYDPDYLNTNDKKNIFLQTMIKLENRIKSKPLGEKLLEMIINGIPYLG

DRRVPLEEFNTNIASVTVNKLISNPGEVERKKGIFANLIIFGPGPVLNENETIDIGIQNH

FASREGFGGIMQMKFCPEYVSVENNVQENKGASIFNRRGYFSDPALILMHELIHVLHGLY

GIKVDDLPIVPNEKKFFMQSTDAIQAEELYTFGGQDPSIITPSTDKSIYDKVLQNERGIV

DRLNKVLVCISDPNININIYKNKFKDKYKFVEDSEGKYSIDVESEDKLYKSLMFGFTETN

IAENYKIKTRASYFSDSLPPVKIKNLLDNEIYTIEEGENISDKDMEKEYRGQNKAINKQA

YEEISKEHLAVYKIQMCKSVKAPGICIDVDNEDLFFIADKNSESDDLSKNERIEYNTQSN

YIENDFPINELILDTDLISKIELPSENTESLTDFNVDVPVYEKQPAIKKIFTDENTIFQY

LYSQTFPLDIRDISLTSSEDDALLFSNKVYSFFSMDYIKTANKVVEAGLFAGWVKQIVND

FVIEANKSNTMDKIADISLIVPYIGLALNVGNETAKGNFENAFEIAGASILLEFIPELLI

PVVGAFLLESYIDNKNKIIKTIDNALTKRNEKWSDMYGLIVAQWLSTVNTQFYTIKEGMY

KALNYQAQALEEIIKYRYNIYSEKEKSNINIDENDINSKLNEGINQAIDNINNFINGCSV

SYLMKKMIPLAVEKLLDEDNTLKKNLLNYIDENKLYLIGSAEYEKSKVNKYLKTIMPEDL

SIYTNDTILIEMENKYNSEILNNIILNLRYKDNNLIDLSGYGAKVEVYDGVELNDKNQFK

LTSSANSKIRVTQNQNIIFNSVELDFSVSFWIRIPKYKNDGIQNYIHNEYTIINCMKNNS

GWKISIRGNRIIWTLIDINGKTKSVFFEYNIREDISEYINRWFFVTITNNLNNAKIYING

KLESNTDIKDIREVIANGEIIFKLDGDIDRTQFIWMKYFSIENTELSQSNIEERYKIQSY

SEYLKDFWGNPLMYNKEYYMENAGNKNSYIKLKKDSPVGEILTRSKYNQNSKYINYRDLY

IGEKFIIRRKSNSQSINDDIVRKEDYIYLDFFNLNQEWRVYTYKYFKKEEEKLFLAPISD

SDEFYNTIQIKEYDEQPTYSCQLLFKKDEESTDEIGLIGIHRFYESGIVFEEYKDYFCIS

KWYLKEVKRKPYNLKLGCNWQFIPKDEGWTE

Polypeptide Sequence of BoNT/C-UniProt P18640

SEQ ID NO: 53

MPITINNENYSDPVDNKNILYLDTHLNTLANEPEKAFRITGNIWVIPDRFSRNSNPNLNK

PPRVTSPKSGYYDPNYLSTDSDKDPFLKEIIKLFKRINSREIGEELIYRLSTDIPFPGNN

NTPINTFDFDVDENSVDVKTRQGNNWVKTGSINPSVIITGPRENIIDPETSTEKLINNTE

AAQEGFGALSIISISPREMLTYSNATNDVGEGRFSKSEFCMDPILILMHELNHAMHNLYG

IAIPNDQTISSVTSNIFYSQYNVKLEYAEIYAFGGPTIDLIPKSARKYFEEKALDYYRSI

AKRLNSITTANPSSENKYIGEYKQKLIRKYRFVVESSGEVTVNRNKEVELYNELTQIFTE

FNYAKIYNVQNRKIYLSNVYTPVTANILDDNVYDIQNGFNIPKSNLNVLFMGQNLSRNPA

LRKVNPENMLYLFTKFCHKAIDGRSLYNKTLDCRELLVKNTDLPFIGDISDVKTDIFLRK

DINEETEVIYYPDNVSVDQVILSKNTSEHGQLDLLYPSIDSESEILPGENQVFYDNRTQN

VDYLNSYYYLESQKLSDNVEDFTFTRSIEEALDNSAKVYTYFPTLANKVNAGVQGGLFLM

WANDVVEDFTTNILRKDTLDKISDVSAIIPYIGPALNISNSVRRGNFTEAFAVTGVTILL

EAFPEFTIPALGAFVIYSKVQERNEIIKTIDNCLEQRIKRWKDSYEWMMGTWLSRIITQF

-continued

NNISYQMYDSLNYQAGAIKAKIDLEYKKYSGSDKENIKSQVENLKNSLDVKISEAMNNIN
KFIRECSVTYLFKNMLPKVIDELNEFDRNTKAKLINLIDSHNIILVGEVDKLKAKVNNSF
QNTIPFNIFSYTNNSLLKDIINEYENNINDSKILSLQNRKNTLVDTSGYNAEVSEEGDVQ
LNPIFPFDFKLGSSGEDRGKVIVTQNENIVYNSMYESFSISEWIRINKWVSNLPGYTIID
SVKNNSGWSIGIISNFLVFTLKQNEDSEQSINESYDISNNAPGYNKWFFVTVTNNMMGNM
KIYINGKLIDTIKVKELTGINFSKTITFEINKIPDTGLITSDSDNINMWIRDFYIFAKEL
DGKDINILENSLQYTNVVKDYWGNDLRYNKEYYMVNIDYLNRYMYANSRQIVENTRRNNN
DENEGYKIIIKRIRGNTNDTRVRGGDILYFDMTINNKAYNLFMKNETMYADNHSTEDIYA
IGLREQTKDINDNIIFQIQPMNNTYYYASQIFKSNENGENISGICSIGTYRFRLGGDWYR
HNYLVPTVKQGNYASLLESTSTHWGFVPVSE

Polypeptide Sequence of BoNT/D-UniProt P19321

SEQ ID NO: 54

MTWPVKDFNYSDPVNDNDILYLRIPQNKLITTPVKAFMITQNIWVIPERFSSDTNPSLSK
PPRPTSKYQSYYDPSYLSTDEQKDTFLKGIIKLFKRINERDIGKKLINYLVVGSPEMGDS
STPEDTFDFTRHTTNIAVEKFENGSWKVTNIITPSVLIFGPLPNILDYTASLTLQGQQSN
PSFEGFGTLSILKVAPEFLLTESDVTSNQSSAVLGKSIFCMDPVIALMHELTHSLHQLYG
INIPSDKRIRPQVSEGFFSQDGPNVQFEELYTFGGLDVEIIPQIERSQLREKALGHYKDI
AKRLNNINKTIPSSWISNIDKYKKIFSEKYNFDKDNTGNFVVNIDKENSLYSDLTNVMSE
VVYSSQYNVKNRTHYFSRHYLPVFANILDDNIYTIRDGENLINKGENIENSGQNIERNPA
LQKLSSESVVDLFTKVCLRLTKNSRDDSTCIKVKNNRLPYVADKDSISQEIFENKIITDE
TNVQNYSDKFSLDESILDGQVPINPEIVDPLLPNVNMEPLNLPGEEIVFYDDITKYVDYL
NSYYYLESQKLSNNVENITLTTSVEEALGYSNKIYTFLPSLAEKVNKGVQAGLELNWANE
VVEDETTNIMKKDTLDKISDVSVIIPYIGPALNIGNSALRGNENQAFATAGVAFLLEGEP
EFTIPALGVFTFYSSIQEREKIIKTIENCLEQRVKRWKDSYQWMVSNWLSRITTQFNHIN
YQMYDSLSYQADAIKAKIDLEYKKYSGSDKENIKSQVENLKNSLDVKISEAMNNINKFIR
ECSVTYLFKNMLPKVIDELNKEDLRTKTELINLIDSHNIILVGEVDRLKAKVNESFENTM
PFNIFSYTNNSLLKDIINEYENSINDSKILSLQNKKNALVDTSGYNAEVRVGDNVQLNTI
YTNDFKLSSSGDKIIVNLNNNILYSAIYENSSVSFWIKISKDLINSHNEYTIINSIEQNS
GWKLCIRNGNIEWILQDVNRKYKSLIFDYSESLSHTGYTNKWFFVTITNNIMGYMKLYIN
GELKQSQKIEDLDEVKLDKTIVFGIDENIDENQMLWIRDENIFSKELSNEDINIVYEGQI
LRNVIKDYWGNPLKEDTEYYIINDNYIDRYIAPESNVLVLVQYPDRSKLYTGNPITIKSV
SDKNPYSRILNGDNIILHMLYNSRKYMIIRDTDTIYATQGGECSQNCVYALKLQSNLGNY
GIGIFSIKNIVSKNKYCSQIFSSFRENTMLLADIYKPWRFSFKNAYTPVAVTNYETKLLS
TSSFWKFISRDPGWVE

Polypeptide Sequence of BoNT/E-UniProt Q00496

SEQ ID NO: 55

MPKINSFNYNDPVNDRTILYIKPGGCQEFYKSENIMKNIWIIPERNVIGTTPQDFHPPTS
LKNGDSSYYDPNYLQSDEEKDRFLKIVTKIFNRINNNLSGGILLEELSKANPYLGNDNTP
DNQFHIGDASAVEIKFSNGSQDILLPNVIIMGAEPDLFETNSSNISLRNNYMPSNHRFGS
IAIVTESPEYSFRENDNCMNEFIQDPALTLMHELIHSLHGLYGAKGITTKYTITQKQNPL
ITNIRGTNIEEFLTFGGTDLNIITSAQSNDIYTNLLADYKKIASKLSKVQVSNPLLNPYK
DVFEAKYGLDKDASGIYSVNINKENDIFKKLYSFTEFDLRTKFQVKCRQTYIGQYKYFKL

-continued

SNLLNDSIYNISEGYNINNLKVNFRGQNANLNPRIITPITGRGLVKKIIRFCKNIVSVKG
IRKSICIEINNGELFFVASENSYNDDNINTPKEIDDTVTSNNNYENDLDQVILNENSESA
PGLSDEKLNLTIQNDAYIPKYDSNGTSDIEQHDVNELNVFFYLDAQKVPEGENNVNLTSS
IDTALLEQPKIYTFFSSEFINNVNKPVQAALFVSWIQQVLVDETTEANQKSTVDKIADIS
IVVPYIGLALNIGNEAQKGNEKDALELLGAGILLEFEPELLIPTILVFTIKSFLGSSDNK
NKVIKAINNALKERDEKWKEVYSFIVSNWMTKINTQFNKRKEQMYQALQNQVNAIKTIIE
SKYNSYTLEEKNELTNKYDIKQIENELNQKVSIAMNNIDRELTESSISYLMKIINEVKIN
KLREYDENVKTYLLNYIIQHGSILGESQQELNSMVTDTLNNSIPFKLSSYTDDKILISYF
NKFFKRIKSSSVLNMRYKNDKYVDTSGYDSNININGDVYKYPTNKNQFGIYNDKLSEVNI
SQNDYIIYDNKYKNFSISFWVRIPNYDNKIVNVNNEYTIINCMRDNNSGWKVSLNHNEII
WTFEDNRGINQKLAFNYGNANGISDYINKWIFVTITNDRLGDSKLYINGNLIDQKSILNL
GNIHVSDNILFKIVNCSYTRYIGIRYENIFDKELDETEIQTLYSNEPNTNILKDEWGNYL
LYDKEYYLLNVLKPNNFIDRRKDSTLSINNIRSTILLANRLYSGIKVKIQRVNNSSTNDN
LVRKNDQVYINFVASKTHLFPLYADTATTNKEKTIKISSSGNRFNQVVVMNSVGNCTMNF
KNNNGNNIGLLGFKADTVVASTWYYTHMRDHTNSNGCFWNFISEEHGWQEK

Polypeptide Sequence of BoNT/F-UniProt A7GBG3

SEQ ID NO: 56

MPVVINSFNYNDPVNDDTILYMQIPYEEKSKKYYKAFEIMRNVWIIPERNTIGTDPSDED
PPASLENGSSAYYDPNYLTTDAEKDRYLKTTIKLFKRINSNPAGEVLLQEISYAKPYLGN
EHTPINEFHPVTRTTSVNIKSSTNVKSSIILNLLVLGAGPDIFENSSYPVRKLMDSGGVY
DPSNDGFGSINIVTFSPEYEYTENDISGGYNSSTESFIADPAISLAHELIHALHGLYGAR
GVTYKETIKVKQAPLMIAEKPIRLEEFLTFGGQDLNIITSAMKEKIYNNLLANYEKIATR
LSRVNSAPPEYDINEYKDYFQWKYGLDKNADGSYTVNENKFNEIYKKLYSFTEIDLANKF
KVKCRNTYFIKYGFLKVPNLLDDDIYTVSEGFNIGNLAVNNRGQNIKLNPKIIDSIPDKG
LVEKIVKFCKSVIPRKGTKAPPRLCIRVNNRELFFVASESSYNENDINTPKEIDDTTNLN
NNYRNNLDEVILDYNSETIPQISNQTLNTLVQDDSYVPRYDSNGTSEIEEHNVVDLNVFF
YLHAQKVPEGETNISLTSSIDTALSEESQVYTFFSSEFINTINKPVHAALFISWINQVIR
DFTTEATQKSTFDKIADISLVVPYVGLALNIGNEVQKENFKEAFELLGAGILLEFVPELL
IPTILVFTIKSFIGSSENKNKIIKAINNSLMERETKWKEIYSWIVSNWLTRINTQFNKRK
EQMYQALQNQVDAIKTVIEYKYNNYTSDERNRLESEYNINNIREELNKKVSLAMENIERF
ITESSIFYLMKLINEAKVSKLREYDEGVKEYLLDYISEHRSILGNSVQELNDLVTSTLNN
SIPFELSSYTNDKILILYENKLYKKIKDNSILDMRYENNKFIDISGYGSNISINGDVYIY
STNRNQFGIYSSKPSEVNIAQNNDIIYNGRYQNFSISFWVRIPKYFNKVNLNNEYTIIDC
IRNNNSGWKISLNYNKIIWTLQDTAGNNQKLVFNYTQMISISDYINKWIFVTITNNRLGN
SRIYINGNLIDEKSISNLGDIHVSDNILFKIVGCNDTRYVGIRYFKVFDTELGKTEIETL
YSDEPDPSILKDFWGNYLLYNKRYYLLNLLRTDKSITQNSNFLNINQQRGVYQKPNIFSN
TRLYTGVEVIIRKNGSTDISNTDNFVRKNDLAYINVVDRDVEYRLYADISIAKPEKIIKL
IRTSNSNNSLGQIIVMDSIGNNCTMNFQNNNGGNIGLLGFHSNNLVASSWYYNNIRKNTS
SNGCFWSFISKEHGWQEN

Polypeptide Sequence of BoNT/G-UniProt Q60393

SEQ ID NO: 57

MPVNIKXFNYNDPINNDDIIMMEPENDPGPGTYYKAFRIIDRIWIVPERFTYGFQPDQEN
ASTGVFSKDVYEYYDPTYLKTDAEKDKFLKTMIKLFNRINSKPSGQRLLDMIVDAIPYLG

-continued

NASTPPDKFAANVANVSINKKIIQPGAEDQIKGLMTNLIIFGPGPVLSDNFTDSMIMNGH

SPISEGFGARMMIRFCPSCLNVENNVQENKDTSIFSRRAYFADPALTLMHELIHVLHGLY

GIKISNLPITPNTKEFFMQHSDPVQAEELYTFGGHDPSVISPSTDMNIYNKALQNFQDIA

NRLNIVSSAQGSGIDISLYKQIYKNKYDFVEDPNGKYSVDKDKFDKLYKALMFGFTETNL

AGEYGIKTRYSYFSEYLPPIKTEKLLDNTIYTQNEGENIASKNLKTEFNGQNKAVNKEAY

EEISLEHLVIYRIAMCKPVMYKNTGKSEQCIIVNNEDLFFIANKDSFSKDLAKAETIAYN

TQNNTIENNESIDQLILDNDLSSGIDLPNENTEPFTNEDDIDIPVYIKQSALKKIFVDGD

SLFEYLHAQTFPSNIENLQLTNSLNDALRNNNKVYTFFSTNLVEKANTVVGASLFVNWVK

GVIDDFTSESTQKSTIDKVSDVSIIIPYIGPALNVGNETAKENFKNAFEIGGAAILMEFI

PELIVPIVGFFTLESYVGNKGHIIMTISNALKKRDQKWTDMYGLIVSQWLSTVNTQFYTI

KERMYNALNNQSQAIEKIIEDQYNRYSEEDKMNINIDENDIDFKLNQSINLAINNIDDFI

NQCSISYLMNRMIPLAVKKLKDFDDNLKRDLLEYIDTNELYLLDEVNILKSKVNRHLKDS

IPFDLSLYTKDTILIQVENNYISNISSNAILSLSYRGGRLIDSSGYGATMNVGSDVIEND

IGNGQFKLNNSENSNITAHQSKFVVYDSMFDNESINFWVRTPKYNNNDIQTYLQNEYTII

SCIKNDSGWKVSIKGNRIIWTLIDVNAKSKSIFFEYSIKDNISDYINKWFSITITNDRLG

NANIYINGSLKKSEKILNLDRINSSNDIDEKLINCTDTTKFVWIKDENIFGRELNATEVS

SLYWIQSSTNTLKDFWGNPLRYDTQYYLFNQGMQNIYIKYFSKASMGETAPRTNENNAAI

NYQNLYLGLRFIIKKASNSRNINNDNIVREGDYIYLNIDNISDESYRVYVLVNSKEIQTQ

LFLAPINDDPTFYDVLQIKKYYEKTTYNCQILCEKDTKTFGLFGIGKFVKDYGYVWDTYD

NYFCISQWYLRRISENINKLRLGCNWQFIPVDEGWTE

Polypeptide Sequence of TeNT-UniProt P04958

SEQ ID NO: 58

MPITINNFRYSDPVNNDTIIMMEPPYCKGLDIYYKAFKITDRIWIVPERYEFGTKPEDEN

PPSSLIEGASEYYDPNYLRTDSDKDRFLQTMVKLFNRIKNNVAGEALLDKIINAIPYLGN

SYSLLDKFDTNSNSVSFNLLEQDPSGATTKSAMLTNLIIFGPGPVLNKNEVRGIVLRVDN

KNYFPCRDGFGSIMQMAFCPEYVPTFDNVIENITSLTIGKSKYFQDPALLLMHELIHVLH

GLYGMQVSSHEIIPSKQEIYMQHTYPISAEELFTFGGQDANLISIDIKNDLYEKTLNDYK

AIANKLSQVTSCNDPNIDIDSYKQIYQQKYQFDKDSNGQYIVNEDKFQILYNSIMYGFTE

IELGKKFNIKTRLSYFSMNHDPVKIPNLLDDTIYNDTEGFNIESKDLKSEYKGQNMRVNT

NAFRNVDGSGLVSKLIGLCKKIIPPTNIRENLYNRTASLTDLGGELCIKIKNEDLTFIAE

KNSFSEEPFQDEIVSYNTKNKPLNFNYSLDKIIVDYNLQSKITLPNDRTTPVTKGIPYAP

EYKSNAASTIEIHNIDDNTIYQYLYAQKSPTTLQRITMTNSVDDALINSTKIYSYFPSVI

SKVNQGAQGILFLQWVRDIIDDFTNESSQKTTIDKISDVSTIVPYIGPALNIVKQGYEGN

FIGALETTGVVLLLEYIPEITLPVIAALSIAESSTQKEKIIKTIDNFLEKRYEKWIEVYK

LVKAKWLGTVNTQFQKRSYQMYRSLEYQVDAIKKIIDYEYKIYSGPDKEQIADEINNLKN

KLEEKANKAMININIFMRESSRSFLVNQMINEAKKQLLEFDTQSKNILMQYIKANSKFIG

ITELKKLESKINKVFSTPIPFSYSKNLDCWVDNEEDIDVILKKSTILNLDINNDIISDIS

GENSSVITYPDAQLVPGINGKAIHLVNNESSEVIVHKAMDIEYNDMENNFTVSFWLRVPK

VSASHLEQYGTNEYSIISSMKKHSLSIGSGWSVSLKGNNLIWTLKDSAGEVRQITERDLP

DKFNAYLANKWVFITITNDRLSSANLYINGVLMGSAEITGLGAIREDNNITLKLDRCNNN

NQYVSIDKFRIFCKALNPKEIEKLYTSYLSITFLRDFWGNPLRYDTEYYLIPVASSSKDV

QLKNITDYMYLTNAPSYTNGKLNIYYRRLYNGLKFIIKRYTPNNEIDSFVKSGDFIKLYV

SYNNNEHIVGYPKDGNAFNNLDRILRVGYNAPGIPLYKKMEAVKLRDLKTYSVQLKLYDD

KNASLGLVGTHNGQIGNDPNRDILIASNWYFNHLKDKILGCDWYFVPTDEGWIND

Polypeptide Sequence of BoNT/X

SEQ ID NO: 59

MKLEINKENYNDPIDGINVITMRPPRHSDKINKGKGPFKAFQVIKNIWIVPERYNETNNT

NDLNIPSEPIMEADAIYNPNYLNTPSEKDEFLQGVIKVLERIKSKPEGEKLLELISSSIP

LPLVSNGALTLSDNETIAYQENNNIVSNLQANLVIYGPGPDIANNATYGLYSTPISNGEG

TLSEVSFSPFYLKPFDESYGNYRSLVNIVNKFVKREFAPDPASTLMHELVHVTHNLYGIS

NRNFYYNEDTGKIETSRQQNSLIFEELLTEGGIDSKAISSLIIKKIIETAKNNYTTLISE

RLNTVTVENDLLKYIKNKIPVQGRLGNFKLDTAEFEKKLNTILFVLNESNLAQRFSILVR

KHYLKERPIDPIYVNILDDNSYSTLEGENISSQGSNDFQGQLLESSYFEKIESNALRAFI

KICPRNGLLYNAIYRNSKNYLNNIDLEDKKTTSKTNVSYPCSLLNGCIEVENKDLFLISN

KDSLNDINLSEEKIKPETTVFFKDKLPPQDITLSNYDFTEANSIPSISQQNILERNEELY

EPIRNSLFEIKTIYVDKLTTFHFLEAQNIDESIDSSKIRVELTDSVDEALSNPNKVYSPF

KNMSNTINSIETGITSTYIFYQWLRSIVKDESDETGKIDVIDKSSDTLAIVPYIGPLLNI

GNDIRHGDFVGAIELAGITALLEYVPEFTIPILVGLEVIGGELAREQVEAIVNNALDKRD

QKWAEVYNITKAQWWGTIHLQINTRLAHTYKALSRQANAIKMNMEFQLANYKGNIDDKAK

IKNAISETEILLNKSVEQAMKNTEKFMIKLSNSYLTKEMIPKVQDNLKNEDLETKKTLDK

FIKEKEDILGTNLSSSLRRKVSIRLNKNIAFDINDIPESEFDDLINQYKNEIEDYEVLNL

GAEDGKIKDLSGTTSDINIGSDIELADGRENKAIKIKGSENSTIKIAMNKYLRFSATDNE

SISFWIKHPKPTNLLNNGIEYTLVENFNQRGWKISIQDSKLIWYLRDHNNSIKIVTPDYI

AFNGWNLITITNNRSKGSIVYVNGSKIEEKDISSIWNTEVDDPIIFRLKNNRDTQAFTLL

DQFSIYRKELNQNEVVKLYNYYENSNYIRDIWGNPLQYNKKYYLQTQDKPGKGLIREYWS

SFGYDYVILSDSKTITFPNNIRYGALYNGSKVLIKNSKKLDGLVRNKDFIQLEIDGYNMG

ISADRFNEDTNYIGTTYGTTHDLTTDFEIIQRQEKYRNYCQLKTPYNIFHKSGLMSTETS

KPTFHDYRDWVYSSAWYFQNYENLNLRKHTKTNWYFIPKDEGWDED

Nucleotide Sequence of mrBoNT/A

SEQ ID NO: 60

ATGCCATTCGTCAACAAGCAATTCAACTACAAAGACCCAGTCAACGGCGTCGACATCGCATACATCAAGATTCCG

AACGCCGGTCAAATGCAGCCGGTTAAGGCTTTTAAGATCCACAACAAGATTTGGGTTATCCCGGAGCGTGACACC

TTCACGAACCCGGAAGAAGGCGATCTGAACCCGCCACCGGAAGCGAAGCAAGTCCCTGTCAGCTACTACGATTCG

ACGTACCTGAGCACGGATAACGAAAAAGATAACTACCTGAAAGGTGTGACCAAGCTGTTCGAACGTATCTACAGC

ACGGATCTGGGTCGCATGCTGCTGACTAGCATTGTTCGCGGTATCCCGTTCTGGGGTGGTAGCACGATTGACACC

GAACTGAAGGTTATCGACACTAACTGCATTAACGTTATTCAACCGGATGGTAGCTATCGTAGCGAAGAGCTGAAT

CTGGTCATCATTGGCCCGAGCGCAGACATTATCCAATTCGAGTGCAAGAGCTTTGGTCACGAGGTTCTGAATCTG

ACCCGCAATGGCTATGGTAGCACCCAGTACATTCGTTTTTCGCCGGATTTTACCTTCGGCTTTGAAGAGAGCCTG

GAGGTTGATACCAATCCGTTGCTGGGTGCGGGCAAATTCGCTACCGATCCGGCTGTCACGCTGGCCCATGAACTG

ATCCACGCAGGCCACCGCCTGTACGGCATTGCCATCAACCCAAACCGTGTGTTCAAGGTTAATACGAATGCATAC

TACGAGATGAGCGGCCTGGAAGTCAGCTTCGAAGAACTGCGCACCTTCGGTGGCCATGACGCTAAATTCATTGAC

AGCTTGCAAGAGAATGAGTTCCGTCTGTACTACTATAACAAATTCAAAGACATTGCAAGCACGTTGAACAAGGCC

AAAAGCATCGTTGGTACTACCGCGTCGTTGCAGTATATGAAGAATGTGTTTAAAGAGAAGTACCTGCTGTCCGAG

GATACCTCCGGCAAGTTTAGCGTTGATAAGCTGAAGTTTGACAAACTGTACAAGATGCTGACCGAGATTTACACC

-continued

GAGGACAACTTTGTGAAATTCTTCAAAGTGTTGAATCGTAAAACCTATCTGAATTTTGACAAAGCGGTTTTCAAG

ATTAACATCGTGCCGAAGGTGAACTACACCATCTATGACGGTTTTAACCTGCGTAACACCAACCTGGCGGCGAAC

TTTAACGGTCAGAATACGGAAATCAACAACATGAATTTCACGAAGTTGAAGAACTTCACGGGTCTGTTCGAGTTC

TATAAGCTGCTGTGCGTGCGCGGTATCATCACCAGCAAAACCAAAAGCCTGGACAAAGGCTACAACAAGGCGCTG

AATGACCTGTGCATTAAGGTAAACAATTGGGATCTGTTCTTTTCGCCATCCGAAGATAATTTTACCAACGACCTG

AACAAGGGTGAAGAAATCACCAGCGATACGAATATTGAAGCAGCGGAAGAGAATATCAGCCTGGATCTGATCCAG

CAGTACTATCTGACCTTTAACTTCGACAATGAACCGGAGAACATTAGCATTGAGAATCTGAGCAGCGACATTATC

GGTCAGCTGGAACTGATGCCGAATATCGAACGTTTCCCGAACGGCAAAAAGTACGAGCTGGACAAGTACACTATG

TTCCATTACCTGCGTGCACAGGAGTTTGAACACGGTAAAAGCCGTATCGCGCTGACCAACAGCGTTAACGAGGCC

CTGCTGAACCCGAGCCGTGTCTATACCTTCTTCAGCAGCGACTATGTTAAGAAAGTGAACAAAGCCACTGAGGCC

GCGATGTTCCTGGGCTGGGTGGAACAGCTGGTATATGACTTCACGGACGAGACGAGCGAAGTGAGCACTACCGAC

AAAATTGCTGATATTACCATCATTATCCCGTATATTGGTCCGGCACTGAACATTGGCAACATGCTGTACAAAGAC

GATTTTGTGGGTGCCCTGATCTTCTCCGGTGCCGTGATTCTGCTGGAGTTCATTCCGGAGATTGCGATCCCGGTG

TTGGGTACCTTCGCGCTGGTGTCCTACATCGCGAATAAGGTTCTGACGGTTCAGACCATCGATAACGCGCTGTCG

AAACGTAATGAAAAATGGGACGAGGTTTACAAATACATTGTTACGAATTGGCTGGCGAAAGTCAATACCCAGATC

GACCTGATCCGTAAGAAAATGAAAGAGGCGCTGGAGAATCAGGCGGAGGCCACCAAAGCAATTATCAACTACCAA

TACAACCAGTACACGGAAGAAGAGAAGAATAACATTAACTTCAATATCGATGATTTGAGCAGCAAGCTGAATGAA

TCTATCAACAAAGCGATGATCAATATCAACAAGTTTTTGAATCAGTGTAGCGTTTCGTACCTGATGAATAGCATG

ATTCCGTATGGCGTCAAACGTCTGGAGGACTTCGACGCCAGCCTGAAAGATGCGTTGCTGAAATACATTTACGAC

AATCGTGGTACGCTGATTGGCCAAGTTGACCGCTTGAAAGACAAAGTTAACAATACCCTGAGCACCGACATCCCA

TTTCAACTGAGCAAGTATGTTGATAATCAACGTCTGTTGAGCACTTTCACCGAGTATATCAAAAACATCATCAAT

ACTAGCATTCTGAACCTGCGTTACGAGAGCAAGCATCTGATTGATCTGAGCCGTTATGCTAGCAAGATCAACATC

GGTAGCAAGGTCAATTTTGACCCGATCGATAAGAACCAGATCCAGCTGTTTAATCTGGAATCGAGCAAAATTGAG

GTTATCCTGAAAAAGGCCATTGTCTACAACTCCATGTACGAGAATTTCTCCACCAGCTTCTGGATTCGCATCCCG

AAATACTTCAACAAGATTAGCCTGAACAACGAGTATACTATCATCAACTGTATGGAGAACAACAGCGGTTGGAAG

GTGTCTCTGAACTATGGTGAGATCATTTGGACCTTGCAGGACACCAAAGAGATCAAGCAGCGCGTCGTGTTCAAG

TACTCTCAAATGATCAACATTTCCGATTACATTAATCGTTGGATCTTCGTGACCATTACGAATAACCGTCTGAAT

AAGAGCAAGATTTACATCAATGGTCGCTTGATCGATCAGAAACCGATTAGCAACCTGGGTAATATCCACGCAAGC

AACAAGATTATGTTCAAATTGGACGGTTGCCGCGATACCCATCGTTATATCTGGATCAAGTATTTCAACCTGTTT

GATAAAGAACTGAATGAGAAGGAGATCAAAGATTTGTATGACAACCAATCTAACAGCGGCATTTTGAAGGACTTC

TGGGGCGATTATCTGCAATACGATAAGCCGTACTATATGCTGAACCTGTATGATCCGAACAAATATGTGGATGTC

AATAATGTGGGTATTCGTGGTTACATGTATTTGAAGGGTCCGCGTGGCAGCGTTATGACGACCAACATTTACCTG

AACTCTAGCCTGTACCGTGGTACGAAATTCATCATTAAGAAATATGCCAGCGGCAACAAAGATAACATTGTGCGT

AATAACGATCGTGTCTACATCAACGTGGTCGTGAAGAATAAAGAGTACCGTCTGGCGACCAACGCTTCGCAGGCG

GGTGTTGAGAAAATTCTGAGCGCGTTGGAGATCCCTGATGTCGGTAATCTGAGCCAAGTCGTGGTTATGAAGAGC

AAGAACGACAAGGGTATCACTAACAAGTGCAAGATGAACCTGCAAGACAACAATGGTAACGACATCGGCTTTATT

GGTTTCCACCAGTTCAACAATATTGCTAAACTGGTAGCGAGCAATTGGTACAATCGTCAGATTGAGCGCAGCAGC

CGTACTTTGGGCTGTAGCTGGGAGTTTATCCCGGTCGATGATGGTTGGGGCGAACGTCCGCTG

-continued

Polypeptide Sequence of mrBoNT/A

SEQ ID NO: 61

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNEDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKELNQCSVSYLMNSMIPYGVKRLEDFDASLKDALLKYIYD

NRGTLIGQVDRLKDKVNNTLSTDIPFQLSKYVDNQRLLSTFTEYIKNIINTSILNLRYESKHLIDLSRYASKINI

GSKVNFDPIDKNQIQLENLESSKIEVILKKAIVYNSMYENFSTSFWIRIPKYFNKISLNNEYTIINCMENNSGWK

VSLNYGEIIWTLQDTKEIKQRVVFKYSQMINISDYINRWIFVTITNNRLNKSKIYINGRLIDQKPISNLGNIHAS

NKIMFKLDGCRDTHRYIWIKYFNLEDKELNEKEIKDLYDNQSNSGILKDFWGDYLQYDKPYYMLNLYDPNKYVDV

NNVGIRGYMYLKGPRGSVMTTNIYLNSSLYRGTKFIIKKYASGNKDNIVRNNDRVYINVVVKNKEYRLATNASQA

GVEKILSALEIPDVGNLSQVVVMKSKNDKGITNKCKMNLQDNNGNDIGFIGFHQENNIAKLVASNWYNRQIERSS

RTLGCSWEFIPVDDGWGERPL

Polypeptide Sequence of Unmodified BoNT/A1

SEQ ID NO: 62

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTFTEYIKNIINTSILNLRYESNHLIDLSRYASKINI

GSKVNFDPIDKNQIQLFNLESSKIEVILKNAIVYNSMYENFSTSFWIRIPKYENSISLNNEYTIINCMENNSGWK

VSLNYGEIIWTLQDTQEIKQRVVFKYSQMINISDYINRWIFVTITNNRLNNSKIYINGRLIDQKPISNLGNIHAS

NNIMFKLDGCRDTHRYIWIKYFNLFDKELNEKEIKDLYDNQSNSGILKDFWGDYLQYDKPYYMLNLYDPNKYVDV

NNVGIRGYMYLKGPRGSVMTTNIYLNSSLYRGTKFIIKKYASGNKDNIVRNNDRVYINVVVKNKEYRLATNASQA

GVEKILSALEIPDVGNLSQVVVMKSKNDQGITNKCKMNLQDNNGNDIGFIGFHQFNNIAKLVASNWYNRQIERSS

RTLGCSWEFIPVDDGWGERPL

-continued

Polypeptide Sequence of mrBoNT/AB

SEQ ID NO: 63

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHEL

IHAGHRLYGIAINPNRVFKVNTNAYYEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYTEDNFVKFFKVLNRKTYLNEDKAVFK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTFTEYIKNILNNIILNLRYKDNNLIDLSGYGAKVEV

YDGVELNDKNQFKLTSSANSKIRVTQNQNIIFNSVFLDFSVSFWIRIPKYKNDGIQNYIHNEYTIINCMKNNSGW

KISIRGNRIIWTLIDINGKTKSVFFEYNIREDISEYINRWFFVTITNNLNNAKIYINGKLESNTDIKDIREVIAN

GEIIFKLDGDIDRTQFIWMKYFSIFNTELSQSNIEERYKIQSYSEYLKDFWGNPLMYNKEYYMFNAGNKNSYIKL

KKDSPVGEILTRSKYNQNSKYINYRDLYIGEKFIIRRKSNSQSINDDIVRKEDYIYLDFFNLNQEWRVYTYKYFK

KEEMKLFLAPIYDSDEFYNTIQIKEYDEQPTYSCQLLFKKDEESTDEIGLIGIHRFYESGIVFEEYKDYFCISKW

YLKEVKRKPYNLKLGCNWQFIPKDEGWTE

Polypeptide Sequence of mrBoNT/AB(0)

SEQ ID NO: 64

MPFVNKQFNYKDPVNGVDIAYIKIPNAGQMQPVKAFKIHNKIWVIPERDTFTNPEEGDLNPPPEAKQVPVSYYDS

TYLSTDNEKDNYLKGVTKLFERIYSTDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESLEVDTNPLLGAGKFATDPAVTLAHQL

IYAGHRLYGIAINPNRVFKVNTNAYYEMSGLEVSFEELRTFGGHDAKFIDSLQENEFRLYYYNKFKDIASTINKA

KSIVGTTASLQYMKNVFKEKYLLSEDTSGKFSVDKLKFDKLYKMLTEIYTEDNFVKFFKVLNRKTYLNFDKAVEK

INIVPKVNYTIYDGFNLRNTNLAANFNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQQYYLTFNFDNEPENISIENLSSDII

GQLELMPNIERFPNGKKYELDKYTMFHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKDDFVGALIFSGAVILLEFIPEIAIPV

LGTFALVSYIANKVLTVQTIDNALSKRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSMIPYGVKRLEDFDASLKDALLKYIYD

NRGTLIGQVDRLKDKVNNTLSTDIPFQLSKYVDNQRLLSTFTEYIKNILNNIILNLRYKDNNLIDLSGYGAKVEV

YDGVELNDKNQFKLTSSANSKIRVTQNQNIIFNSVFLDFSVSFWIRIPKYKNDGIQNYIHNEYTIINCMKNNSGW

KISIRGNRIIWTLIDINGKTKSVFFEYNIREDISEYINRWFFVTITNNLNNAKIYINGKLESNTDIKDIREVIAN

GEIIFKLDGDIDRTQFIWMKYFSIFNTELSQSNIEERYKIQSYSEYLKDFWGNPLMYNKEYYMFNAGNKNSYIKL

KKDSPVGEILTRSKYNQNSKYINYRDLYIGEKFIIRRKSNSQSINDDIVRKEDYIYLDFFNLNQEWRVYTYKYFK

KEEMKLFLAPIYDSDEFYNTIQIKEYDEQPTYSCQLLFKKDEESTDEIGLIGIHRFYESGIVFEEYKDYFCISKW

YLKEVKRKPYNLKLGCNWQFIPKDEGWTE

-continued

Polypeptide Sequence of mrBoNT/A(0)

SEQ ID NO: 65

```
MPFVNKQFNYKDPVNGVDIAYIKIPNAGQMQPVKAFKIHNKIWVIPERDT

FTNPEEGDLNPPPEAKQVPVSYYDSTYLSTDNEKDNYLKGVTKLFERIYS

TDLGRMLLTSIVRGIPFWGGSTIDTELKVIDTNCINVIQPDGSYRSEELN

LVIIGPSADIIQFECKSFGHEVLNLTRNGYGSTQYIRFSPDFTFGFEESL

EVDTNPLLGAGKFATDPAVTLAHQLIYAGHRLYGIAINPNRVFKVNTNAY

YEMSGLEVSFEELRTFGGHDAKFIDSLQENEFRLYYYNKFKDIASTLNKA

KSIVGTTASLQYMKNVFKEKYLLSEDTSGKFSVDKLKFDKLYKMLTEIYT

EDNFVKFFKVLNRKTYLNFDKAVFKINIVPKVNYTIYDGENLRNTNLAAN

FNGQNTEINNMNFTKLKNFTGLFEFYKLLCVRGIITSKTKSLDKGYNKAL

NDLCIKVNNWDLFFSPSEDNFTNDLNKGEEITSDTNIEAAEENISLDLIQ

QYYLTFNFDNEPENISIENLSSDIIGQLELMPNIERFPNGKKYELDKYTM

FHYLRAQEFEHGKSRIALTNSVNEALLNPSRVYTFFSSDYVKKVNKATEA

AMFLGWVEQLVYDFTDETSEVSTTDKIADITIIIPYIGPALNIGNMLYKD

DFVGALIFSGAVILLEFIPEIAIPVLGTFALVSYIANKVLTVQTIDNALS

KRNEKWDEVYKYIVTNWLAKVNTQIDLIRKKMKEALENQAEATKAIINYQ

YNQYTEEEKNNINFNIDDLSSKLNESINKAMININKFLNQCSVSYLMNSM

IPYGVKRLEDFDASLKDALLKYIYDNRGTLIGQVDRLKDKVNNTLSTDIP

FQLSKYVDNQRLLSTFTEYIKNIINTSILNLRYESKHLIDLSRYASKINI

GSKVNFDPIDKNQIQLFNLESSKIEVILKKAIVYNSMYENFSTSFWIRIP

KYFNKISLNNEYTIINCMENNSGWKVSLNYGEIIWTLQDTKEIKQRVVFK

YSQMINISDYINRWIFVTITNNRLNKSKIYINGRLIDQKPISNLGNIHAS

NKIMFKLDGCRDTHRYIWIKYFNLFDKELNEKEIKDLYDNQSNSGILKDF

WGDYLQYDKPYYMLNLYDPNKYVDVNNVGIRGYMYLKGPRGSVMTTNIYL

NSSLYRGTKFIIKKYASGNKDNIVRNNDRVYINVVVKNKEYRLATNASQA

GVEKILSALEIPDVGNLSQVVVMKSKNDKGITNKCKMNLQDNNGNDIGFI

GFHQFNNIAKLVASNWYNRQIERSSRTLGCSWEFIPVDDGWGERPL
```

EXAMPLES

Materials and Methods

Animals

Six wild-type (WT) mice were used in the pilot study; 24 CX3CR1-GFP mice (breeding pairs purchased from the JAX Laboratory, USA) were used for the main study; 12 mice were used in the imaging study. Mice were aged 3-5 months at the starting of imaging. For imaging experiments, mice were fitted with a cranial window with access port to allow for imaging and neurotoxin injection (more details below).

CX3CR1-GFP mice are described elsewhere, see Nimmerjahn et al. (Science. 2005 May 27;308 (5726): 1314-8), incorporated herein by reference.

Botulinum Neurotoxin (BoNT) and Control Injection

BoNT/A was used, namely Dysport (abobotulinum toxin A (aboBoNT-A)), dissolved in 2 μL saline. In control experiments, Vehicle only (2 μL saline) solutions were used.

Intracortically-administered Dysport was well tolerated: 3 WT mice (pilot study) were administered with 0.5 U/animal of Dysport (dissolved in 2 μL of saline) and 3 WT mice with Vehicle solution and observed for clinical signs and measured their body weight for 2 days. No clinical signs or behavioural changes associated with neurotoxic effects, and no significant difference in the weight between the treatment groups, thus the dose of 0.5 U/animal was approved for the main study.

For the main study, 0.5 U of Dysport (dissolved in 2 μL saline) or Vehicle (2 μL saline) solutions were injected (during the first imaging session) through a silicone access port (of the cranial window) into the somatosensory cortex of the mouse. Solution was injected at the rate of 2 nL/second.

Experimental Set-Up

Thirty days before Dysport injection (Day −30), the mice were fitted with a cranial window with access port (thirty days were allowed to elapse before further experimentation, to provide time for brain/neuroimmune response activity and behaviour to normalise following instalment of the cranial window). In the course of the study, animals were imaged at several timepoints. On Day 0 (Day of the cortical injection of either Dysport or Vehicle) imaging was done just before the laser injury as well at 6-, 18-, 30-and 42-minutes post-injury. In addition, imaging was done on Day 1 (24 hours post injection/23.5 hours post laser injury) and at Day 2 (48 hours post-injection/47.5 hours post laser injury). On the injection day (Day 0), baseline imaging (imaging session #1) was conducted immediately before injection. Imaging session #2 was conducted one day after injection (Day 1). Imaging session #3 was conducted two days after injection (Day 2).

Craniotomy and Instalment of the Glass Plates

For implantation of a cranial window with access port (the implantation replacing a piece of the skull to allow imaging of and access to the brain), mice were anesthetized with ketamine/xylazine. The cranial window was inserted over the somatosensory cortex at the following coordinates: AP −1.8, ML −2.0 from Bregma. Dental drill (HP4-917, Foredom) was used to remove a round-shaped (d=4 mm) piece of skull, and the hole in the bone was covered with a round cover glass (d=5 mm; #72296-05, Electron Microscopy Sciences). Before implantation of the cover glass, a small eccentrically located hole was drilled in the glass and filled with silicone (Sylgard 184) to create an access port for intracortical injections in chronic cranial windows. Head-plate was placed over the cover glass and fixed with dental cement (Rapid Repair; Dentsply) mixed with cyanoacrylate glue (Loctite 401; Henkel) to a skull surface.

Image Acquisition Setup

Illumination: 900 nm, femtosecond laser Mai-Tai Broad Band DeepSee.

Emission filter: Channel 2—band pass 468-552 nm for the enhanced-Green Fluorescent Protein (EGFP) fluorescence.

Stacks of 60 images were collected with the vertical step of 2 μm (total imaged depth of stacks: 120 μm) in at least two imaging areas. Each imaging area covered 500×500 $\mu m^2$ of space in xy coordinates.

To induce laser injury in Area 1 (see FIG. 1 for schematic diagram of imaging areas' location), micrometre-size region of interest (ROI) was selected in the focal plane at the depth of 25-35 micrometres from the cortical surface and the infrared laser at 100% intensity was applied for 5 seconds during the first hour after intracortical injection. In order to target light (laser) intensity at a particular region of the brain, to provide a distinct focal point of laser-induced injury, two-photon microscopy technology was employed. In rare instances of unsuccessful laser injury induction during the first imaging session, the injury induction was repeated 24 hours later.

Imaging Sessions

In the course of the study, animals were imaged at several timepoints. On Day 0 (Day of the cortical injection of either Dysport or Vehicle) imaging was done just before the laser injury as well at 6-, 18-, 30-and 42-minutes post-injury. In addition, imaging was done on Day 1 (24 hours post injection/23.5 hours post laser injury) and at Day 2 (48 hours post-injection/47.5 hours post laser injury).

Data Processing and Analysis

After acquisition, the image stacks were aligned in Fiji/ImageJ software. Shifts of tissue in x, y and z directions were compensated using plugins in the Fiji software. The aligned image stacks were used for analysis of density, morphology and laser-induced process extension of microglia cells using the set of plugins described below.

For analysis of microglia density and morphology changes "MorphoLibJ" was used: a collection of mathematical morphology methods and plugins for ImageJ, created at INRA-IJPB Modeling and Digital Imaging lab. The image stack with thickness of 40 micrometres was included in data analysis in Area 1 (+20 micrometres from the slice with laser injury location) and in Area 2 (the most superficial 40 micrometres).

The following sequence of steps was implemented in MorphoLibJ plugin:

1) Aligned image stacks were filtered using GreyScale and 3D Morphological filters to enhance the contrast between the cells and surrounding tissue;
2) Automatic Otsu thresholding was applied to all images to create a binary mask of the cells (minimal size threshold 20 pixels, no maximal threshold);
3) "Particle analysis 3D" and "Intensity measurements 3d" plugins were applied to the image stacks to get the numerical results.

Objects number (to calculate density of the cells), total volume and mean volume of the cells, sphericity index of the cells and mean fluorescent intensity of the cells were calculated. For the 3D analysis used in this study, the sphericity index can be defined as the ratio of the squared volume (V) over the cube of the surface area(S):

$$\text{sphericity} = 36\pi\frac{V^2}{S^3}$$

For measurement of microglia process extension toward laser injury, two circles with diameter of 25 (small circle=s.c.) and 50 micrometres (big circle=b.c.) were drawn around the epicentre of the injury site and redistribution of fluorescence from the large circle into the smaller circle was measured. Microglia process extension was calculated using the following equation:

$$\text{Microglia process extension} = \frac{\text{fluorescence } s.c.(tx) - \text{fluorescence } s.c.(t)}{\text{fluorescence } b.c.(t0)}$$

where $tx$ = timepoint $x$, and $t0$ = timepoint 0 (baseline)

Numerical data were then transferred to Microsoft Excel, Microcal Origin and Graphpad Prism software for statistical analysis and plotting of the graphs. For statistical comparisons between the treatment groups, either Student t-test was used (in case of normal data distribution) or Mann-Whitney non-parametric test (in case the data were distributed not normally). For statistical comparisons vs baseline, either paired Student t-test was used (in case of normal data distribution) or Wilcoxon signed ranks test (in case the data were distributed not normally). For test of normality of distribution, the Shapiro-Wilcoxon normality test was used.

Example 1—Clostridial Neurotoxin Induces a Significant Increase in Microglia Density, Decrease in Soma Sphericity and Enhancement of Processes Extension The inventors established a robust, controlled experimental system to investigate the effect of clostridial neurotoxin administration on the activity of the neuroimmune response subsequent to neural tissue damage. The system allows for induction of precise neural damage in the brain, such neural damage representing that caused by brain disorders described herein (e.g. such as neural tissue damage caused by the presence of a brain tumor, or an infection, or nerve death due to oxygen depletion following death).

The system employs transgenic mice in which key immune cells of the neuroimmune response (microglia) specifically express GFP, allowing for time lapse imaging of said immune cells such that their activity in response to neural damage, in either the presence or absence of clostridial neurotoxin administration, can be tracked and analysed. A further advantage of the system (employing advanced light microscopy) is that it can be coupled to a laser to induce the precise area of neuron damage. Full details of the system are provided in the materials and methods section (above).

Two imaging areas were imaged in all animals (see FIG. 1 for illustration): Area 1, closer to the injection site (distance range 600-1000 micrometres from the edge of the Area to the injection site), Area 2 (distance at least 1000 micrometres).

In all analysed mice, a clear expression pattern of GFP was observed consistent with the morphology of microglial cells. Laser injury was introduced in the Area 1 at Day 0, within one hour after intracortical injection of Dysport (see FIGS. 1 and 2). The chronic window with access port was confirmed as a reliable model for repetitive post-injection imaging in the CX3CR1-GFP mouse line. For optimal imaging, a superficial cortical layer was laser-injured and imaged. The laser injury was successfully induced in all 12 mice.

Figure 2:
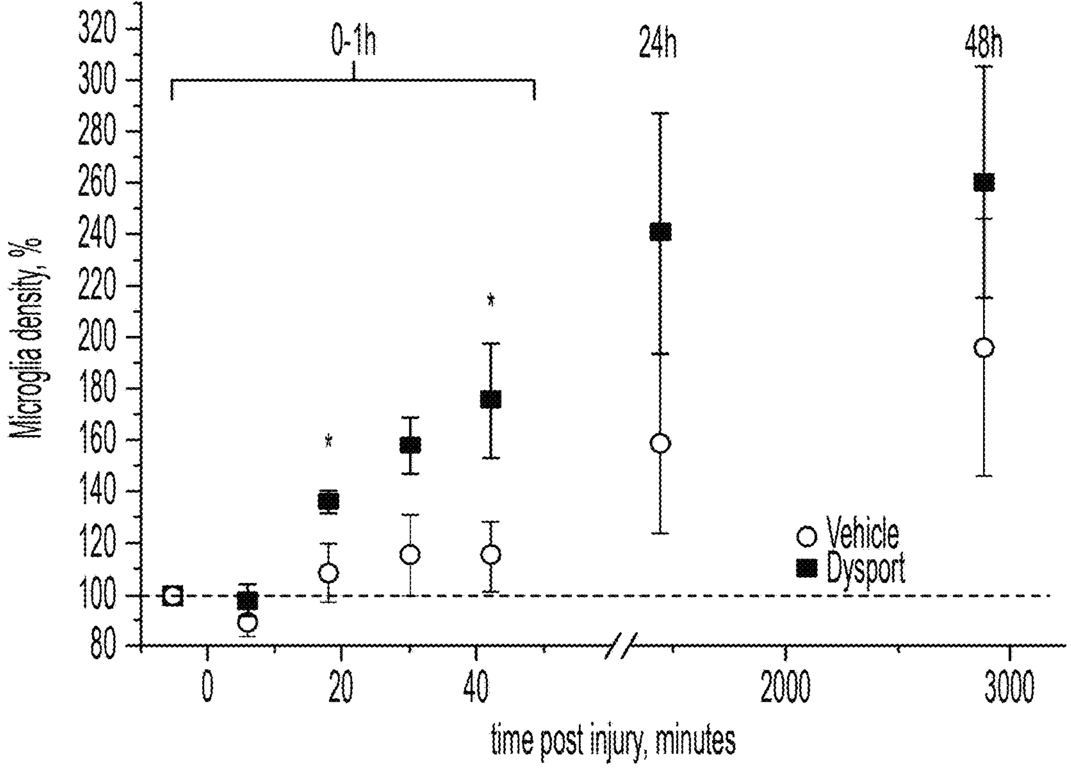
FIG. 2. Graph showing laser injury-induced changes in microglia density in Area 1. In Dysport-treated mice, more microglia migrated towards the lesion site (increasing microglia cell density).
Figure 3:
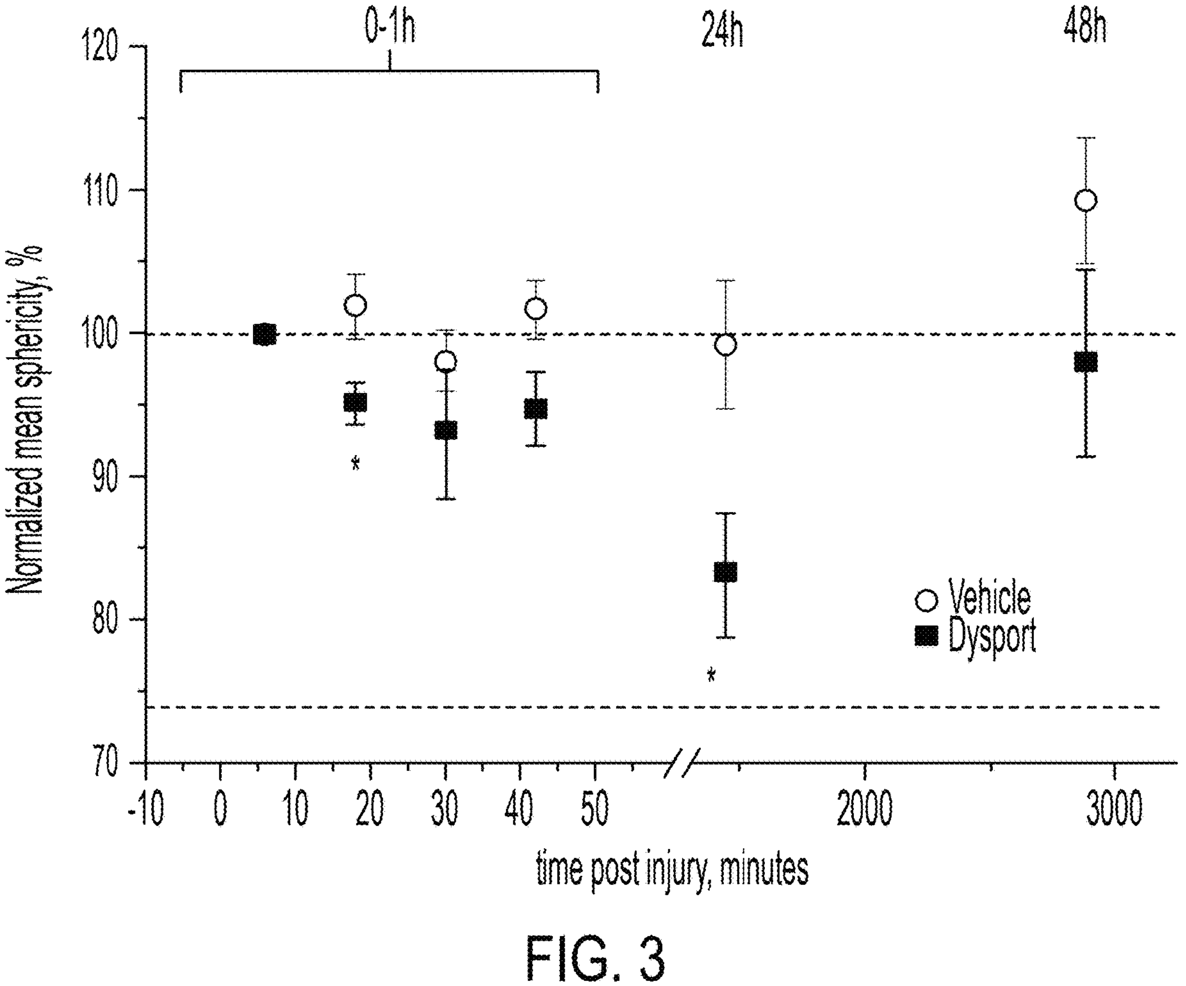
FIG. 3. Graph showing laser-induced activation changes in microglia mean sphericity index in Area 1. Activated microglia have a lower sphericity index (cell soma shape is more elongated).

The laser-injury induced changes in the density and morphology of the microglia in the Area 1 were analysed (see FIGS. 2 and 3 for analysis results). First, a statistically significant increase was observed in the density of microglia after focal laser injury in Dysport-treated mice but not in the Vehicle-treated mice (FIG. 2; $p<0.05$ vs baseline for all timepoints staring from 18 minutes in Dysport group; $p>0.05$ vs baseline for all timepoints in Vehicle group). During the first post-injury hour the difference in the microglia density in the lesion area between the groups reached the level of statistical significance ($p<0.05$ between the treatment groups at 18 and 42 minutes). These observations suggest the increased migration of microglia into the lesion area in Dysport-treated mice during the first post-lesion hour.

Next, the changes in the morphology of the microglia in the lesion-containing Area 1 were analysed to find the signs of microglial activation. For this, three parameters were analysed: mean volume, mean surface area and mean sphericity index (FIG. 3). For the first two parameters the transformation of microglia to activated state is associated with increase in the values (microglia somata swell and become enlarged), while for sphericity index the activation is accompanied by a decrease in the values (more elongated shape).

It was found that both for mean volume and mean surface area, there was a gradual increase in the values after the laser injury, characteristic of more activated microglia shape. Interestingly, the difference between the treatment groups was observed for the mean sphericity of the cells (see FIG. 3). Summarising, these data suggests that Dysport affects the post-lesion change in density and sphericity of microglia but not in the volume and cell surface area. In other words, Dysport may mostly enhance migration of the microglia cells towards the lesion site but not the activation-related morphological changes.

Figure 4:
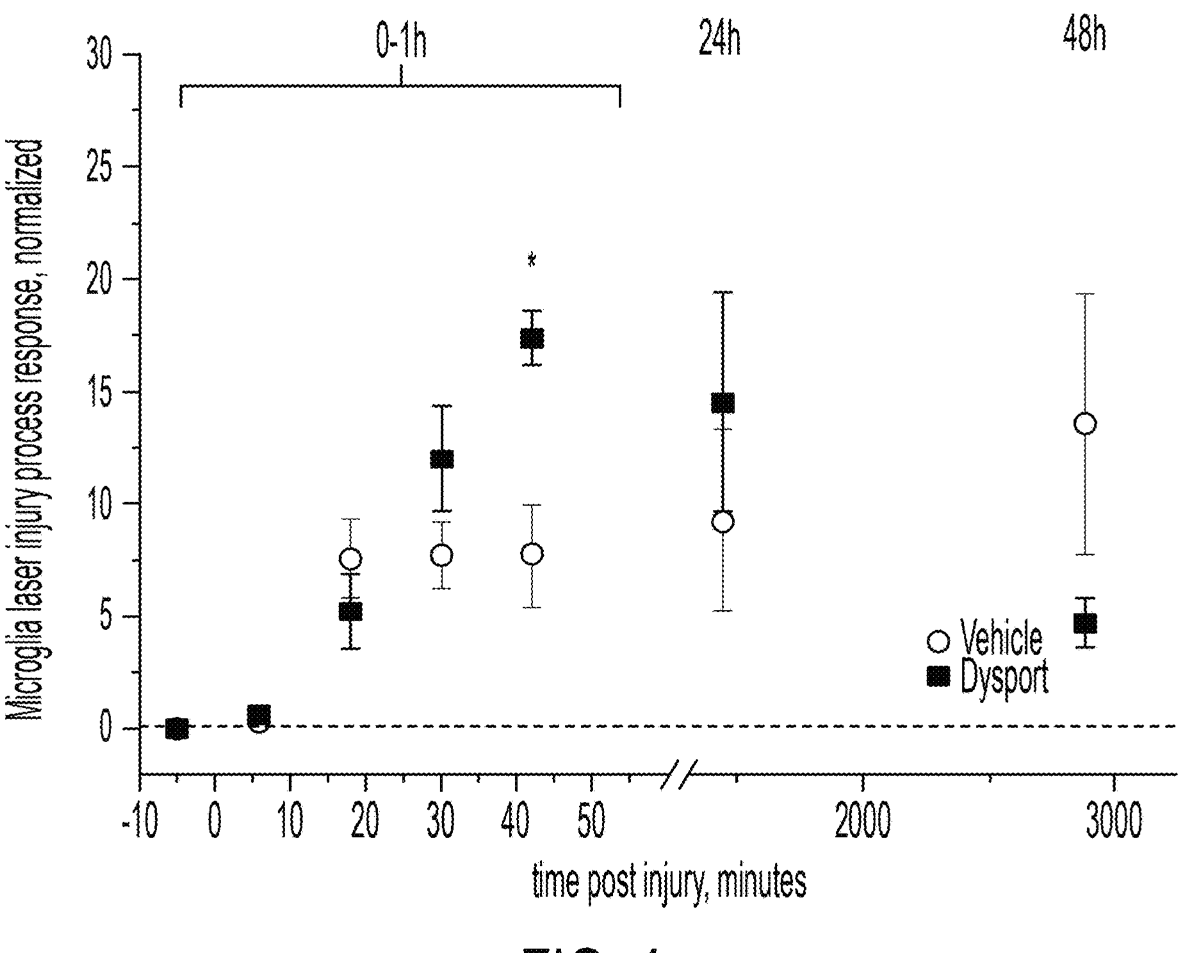
FIG. 4. Graph showing fluorescence change after laser-induced microglia process extension (outliers removed; scar formation in Area 1): microglia response was significantly stronger at 42 minutes in Dysport-treated mice.

Next, the effects of Dysport injection on laser-induced microglia process extension and scar formation was investigated (see FIG. 4). In this analysis, the immediate vicinity (50 μm) of the lesion spot was analysed. A fast brightening of the scar fluorescence was observed which peaked around 40 minutes after laser injury induction (FIG. 4). A single run of Grubb's outlier test was used to remove any outliers. A statistically significant difference (Dysport treated vs Vehicle-only controls) was observed at the timepoint of 42 minutes post-injury induction (FIG. 4, p-value of 0.0303 in Mann-Whitney test). At this timepoint scar fluorescence was stronger in Dysport-treated mice, which is consistent with the notion that Dysport enhances microglial process extension toward the lesion site.

Finally, the density and morphology of microglia in Area 2 was analysed, where laser injury was not induced (e.g. Area 2 providing a control area). Briefly, no statistically significant differences were observed between the treatment groups in terms of density. In this Area 2, imaging took place at 4 timepoints: at Day 0 before and after intracortical injection, at Day 1 (24 hours) and at Day 2 (48 hours). Decline in sphericity index at Area 2 was observed, suggestive of microglia activation and migration away e.g. toward injury at Area 1.

In summary, no significant effects were observed of Dysport injection on microglia in the Area 2 which remained intact in terms of laser injury. This demonstrates that the effect of Dysport occurs responsive to a site of injury.

Summary of Results

Microglia are a major player in regulating neuroprotection and neuronal cell death. Here, the inventor investigated the influence of clostridial neurotoxin administration on injury-induced microglia activation.

Adult, female CX3CR1-GFP heterozygous C57BL/6JCRL mice (n=24) were anesthetized before being implanted with chronic cranial glass windows (equipped with injection access ports) suitable for repeated in vivo two-photon imaging. After 7 days, 15 animals, selected for imaging studies, were anesthetized prior to injection of aboBoNT-A (0.5 U dissolved in 2 μL) or its vehicle (saline) in somatosensory cortex ~1 h before the adjacent area received a μm-size infrared laser irradiation injury to induce microglia activation. Imaging sessions were performed at baseline, after aboBoNT-A injection (before irradiation) and after laser injury at 10-min intervals during the first 40 min and again 24-and 48 h post-injury.

Intracortical injections of aboBoNT-A 0.5 U in mice were safe and did not affect behavior or body weight growth, with no substantially observable effect on microglia before laser injury. After laser injury, aboBoNT-A induced between 15 and 50% increases ($p<0.05$) in microglia density 10-40 min post-injury, a decrease in soma sphericity and enhancement of processes extension, compared with the Vehicle-injected group. The inventor observed no significant differences in microglial density between Vehicle and aboBoNT-A groups in a 'control' area of of the same brain (somatosensory cortex) which was left intact i.e. unaffected by laser injury.

In summary, while microglia morphology and density was not observably changed by aboBoNT-A in the absence of the laser injury, aboBoNT-A significantly enhanced (promoted)

laser injury-induced microglial cell migration and process extension. Thus, aboBoNT-A can be employed to mediate upregulation of microglial activation.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

I claim:

1. A method for increasing microglial cell density in a patient in need thereof, the method comprising administering a clostridial neurotoxin to the patient, wherein the clostridial neurotoxin comprises botulinum neurotoxin A (BoNT/A).

2. The method of claim 1, wherein the clostridial neurotoxin is administered subcutaneously.

3. The method of claim 1, wherein the clostridial neurotoxin is administered by intracranial injection.

4. The method of claim 1, wherein the clostridial neurotoxin is administered at a site of brain tissue damage.

5. The method of claim 1, wherein the clostridial neurotoxin is administered within 4 days before brain tissue damage occurs.

6. The method of claim 1, wherein the clostridial neurotoxin is administered between 1-3 days before brain tissue damage occurs.

7. The method of claim 1, wherein the clostridial neurotoxin is administered within 24 hours following the occurrence of brain tissue damage.

8. The method of claim 1, wherein the clostridial neurotoxin is administered within 2 hours following the occurrence of brain tissue damage.

9. The method of claim 1, wherein the clostridial neurotoxin is administered within 10 minutes following the occurrence of brain tissue damage.

10. The method of claim 4, wherein the brain tissue damage is caused by infectious disease.

11. The method of claim 10, wherein the infectious disease is selected from encephalitis, meningitis, and a brain abscess.

12. The method of claim 1, wherein the clostridial neurotoxin is administered intrathecally or intranasally.

13. The method of claim 1, wherein the clostridial neurotoxin is a chimeric neurotoxin.

14. The method of claim 1, wherein the clostridial neurotoxin is administered in a flat dose of 100 ng.

15. The method of claim 1, wherein the clostridial neurotoxin is an unmodified botulinum A (BoNT/A) neurotoxin.

16. The method of claim 1, wherein the clostridial neurotoxin comprises a $LH_N$ domain corresponding to amino acid residues 1 to 872 of SEQ ID NO: 62.

17. The method of claim 16, wherein the clostridial neurotoxin comprises a $H_C$ domain corresponding to amino acid residues 860 to 1291 of SEQ ID NO: 52.

18. The method of claim 17, wherein the $H_C$ domain comprises an amino acid substitution selected from the group consisting of: V1118M; Y1183M; E1191M; E11911; E1191Q; E1191T; S1199Y; S1199F; S1199L; S1201V; E1191C; E1191V, E1191L; E1191Y; S1199W; S1199E; S1199H; W1178Y; W1178Q; W1178A; W1178S; Y1183C; and Y1183P.

19. The method of claim 17, wherein the $H_C$ domain comprises two amino acid substitutions selected from the group consisting of: E1191M and $1199L; E1191M and $1199Y; E1191M and S1199F; E1191Q and S1199L; E1191Q and S1199Y; E1191Q and S1199F; E1191M and S1199W; E1191M and W1178Q; E1191C and S1199W; E1191C and S1199Y; E1191C and W1178Q; E1191Q and S1199W; E1191V and S1199W; E1191V and $1199Y; and E1191V and W1178Q.

20. The method of claim 1, wherein the clostridial neurotoxin comprises a di-chain form of SEQ ID NO: 44, SEQ ID NO: 63, or SEQ ID NO: 64.

* * * * *

SEQUENCE LISTING

```
<160> NUMBER OF SEQ ID NOS: 76

<210> SEQ ID NO 1
<211> LENGTH: 3888
<212> TYPE: DNA
<213> ORGANISM: Artificial Sequence
<220> FEATURE:
<223> OTHER INFORMATION: Nucleotide Sequence of rBoNT/A(0)

<400> SEQUENCE: 1

atgccattcg tcaacaagca attcaactac aaagacccag tcaacggcgt cgacatcgca     60

tacatcaaga ttccgaacgc cggtcaaatg cagccggtta aggcttttaa gatccacaac    120

aagatttggg ttatcccgga gcgtgacacc ttcacgaacc cggaagaagg cgatctgaac    180

ccgccaccgg aagcgaagca agtccctgtc agctactacg attcgacgta cctgagcacg    240

gataacgaaa aagataacta cctgaaaggt gtgaccaagc tgttcgaacg tatctacagc    300

acggatctgg gtcgcatgct gctgactagc attgttcgcg gtatcccgtt ctggggtggt    360

agcacgattg acaccgaact gaaggttatc gacactaact gcattaacgt tattcaaccg    420

gatggtagct atcgtagcga agagctgaat ctggtcatca ttggcccgag cgcagacatt    480

atccaattcg agtgcaagag ctttggtcac gaggttctga atctgacccg caatggctat    540

ggtagcaccc agtacattcg tttttcgccg gattttacct tcggctttga agagagcctg    600

gaggttgata ccaatccgtt gctgggtgcg ggcaaattcg ctaccgatcc ggctgtcacg    660

ctggcccatc aactgatcta cgcaggccac cgcctgtacg gcattgccat caacccaaac    720

cgtgtgttca aggttaatac gaatgcatac tacgagatga gcggcctgga agtcagcttc    780

gaagaactgc gcaccttcgg tggccatgac gctaaattca ttgacagctt gcaagagaat    840

gagttccgtc tgtactacta taacaaattc aaagacattg caagcacgtt gaacaaggcc    900

aaaagcatcg ttggtactac cgcgtcgttg cagtatatga agaatgtgtt taaagagaag    960

tacctgctgt ccgaggatac ctccggcaag tttagcgttg ataagctgaa gtttgacaaa   1020

ctgtacaaga tgctgaccga gatttacacc gaggacaact ttgtgaaatt cttcaaagtg   1080

ttgaatcgta aaacctatct gaattttgac aaagcggttt tcaagattaa catcgtgccg   1140

aaggtgaact acaccatcta tgacggtttt aacctgcgta acaccaacct ggcggcgaac   1200

tttaacggtc agaatacgga aatcaacaac atgaatttca cgaagttgaa gaacttcacg   1260

ggtctgttcg agttctataa gctgctgtgc gtgcgcggta tcatcaccag caaaaccaaa   1320

agcctggaca aaggctacaa caaggcgctg aatgacctgt gcattaaggt aaacaattgg   1380

gatctgttct tttcgccatc cgaagataat tttaccaacg acctgaacaa gggtgaagaa   1440

atcaccagcg atacgaatat tgaagcagcg gaagagaata tcagcctgga tctgatccag   1500

cagtactatc tgacctttaa cttcgacaat gaaccggaga acattagcat tgagaatctg   1560

agcagcgaca ttatcggtca gctggaactg atgccgaata tcgaacgttt cccgaacggc   1620

aaaaagtacg agctggacaa gtacactatg ttccattacc tgcgtgcaca ggagtttgaa   1680
```

```
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg gcaacatgct gtacaaagac gattttgtgg gtgccctgat cttctccggt   1980
gccgtgattc tgctggagtt cattccggag attgcgatcc cggtgttggg taccttcgcg   2040
ctggtgtcct acatcgcgaa taaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca aagcaattat caactaccaa tacaaccagt acacggaaga agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
gttaacaata ccctgagcac cgacatccca tttcaactga gcaagtatgt tgataatcaa   2580
cgtctgttga gcactttcac cgagtatatc aaaaacatca tcaatactag cattctgaac   2640
ctgcgttacg agagcaatca tctgattgat ctgagccgtt atgcaagcaa gatcaacatc   2700
ggtagcaagg tcaattttga cccgatcgat aagaaccaga tccagctgtt taatctggaa   2760
tcgagcaaaa ttgaggttat cctgaaaaac gccattgtct acaactccat gtacgagaat   2820
ttctccacca gcttctggat tcgcatcccg aaatacttca acagcattag cctgaacaac   2880
gagtatacta tcatcaactg tatggagaac aacagcggtt ggaaggtgtc tctgaactat   2940
ggtgagatca tttggacctt gcaggacacc caagagatca agcagcgcgt cgtgttcaag   3000
tactctcaaa tgatcaacat ttccgattac attaatcgtt ggatcttcgt gaccattacg   3060
aataaccgtc tgaataacag caagatttac atcaatggtc gcttgatcga tcagaaaccg   3120
attagcaacc tgggtaatat ccacgcaagc aacaacatta tgttcaaatt ggacggttgc   3180
cgcgataccc atcgttatat ctggatcaag tatttcaacc tgtttgataa agaactgaat   3240
gagaaggaga tcaaagattt gtatgacaac caatctaaca gcggcatttt gaaggacttc   3300
tggggcgatt atctgcaata cgataagccg tactatatgc tgaacctgta tgatccgaac   3360
aaatatgtgg atgtcaataa tgtgggtatt cgtggttaca tgtatttgaa gggtccgcgt   3420
ggcagcgtta tgacgaccaa catttacctg aactctagcc tgtaccgtgg tacgaaattc   3480
atcattaaga aatatgccag cggcaacaaa gataacattg tgcgtaataa cgatcgtgtc   3540
tacatcaacg tggtcgtgaa gaataaagag taccgtctgg cgaccaacgc ttcgcaggcg   3600
ggtgttgaga aaattctgag cgcgttggag atccctgatg tcggtaatct gagccaagtc   3660
gtggttatga agagcaagaa cgaccagggt atcactaaca agtgcaagat gaacctgcaa   3720
gacaacaatg gtaacgacat cggctttatt ggtttccacc agttcaacaa tattgctaaa   3780
ctggtagcga gcaattggta caatcgtcag attgagcgca gcagccgtac tttgggctgt   3840
agctgggagt ttatcccggt cgatgatggt tggggcgaac gtccgctg                3888
```

<210> SEQ ID NO 2
<211> LENGTH: 1296
<212> TYPE: PRT
<213> ORGANISM: Artificial Sequence
<220> FEATURE:
<223> OTHER INFORMATION: Polypeptide Sequence of rBoNT/A(0)

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400
```

```
Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815
```

```
Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                 1005

Asp Tyr  Ile Asn Arg Trp Ile  Phe Val Thr Ile Thr  Asn Asn Arg
    1010                 1015                 1020

Leu Asn  Asn Ser Lys Ile Tyr  Ile Asn Gly Arg Leu  Ile Asp Gln
    1025                 1030                 1035

Lys Pro  Ile Ser Asn Leu Gly  Asn Ile His Ala Ser  Asn Asn Ile
    1040                 1045                 1050

Met Phe  Lys Leu Asp Gly Cys  Arg Asp Thr His Arg  Tyr Ile Trp
    1055                 1060                 1065

Ile Lys  Tyr Phe Asn Leu Phe  Asp Lys Glu Leu Asn  Glu Lys Glu
    1070                 1075                 1080

Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Gln Gly  Ile Thr Asn
```

```
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290

Arg Pro  Leu
    1295
```

<210> SEQ ID NO 3
<211> LENGTH: 2634
<212> TYPE: DNA
<213> ORGANISM: Artificial Sequence
<220> FEATURE:
<223> OTHER INFORMATION: Nucleotide Sequence of rLHN/A

<400> SEQUENCE: 3

```
atggagttcg ttaacaaaca gttcaactat aaagacccag ttaacggtgt tgacattgct     60

tacatcaaaa tcccgaacgc tggccagatg cagccggtaa aggcattcaa aatccacaac    120

aaaatctggg ttatcccgga acgtgatacc tttactaacc cggaagaagg tgacctgaac    180

ccgccaccgg aagcgaaaca ggtgccggta tcttactatg actccaccta cctgtctacc    240

gataacgaaa aggacaacta cctgaaaggt gttactaaac tgttcgagcg tatttactcc    300

accgacctgg gccgtatgct gctgactagc atcgttcgcg gtatcccgtt ctggggcggt    360

tctaccatcg ataccgaact gaaagtaatc gacactaact gcatcaacgt tattcagccg    420

gacggttcct atcgttccga agaactgaac ctggtgatca tcggcccgtc tgctgatatc    480

atccagttcg agtgtaagag ctttggtcac gaagttctga acctcacccg taacggctac    540

ggttccactc agtacatccg tttctctccg gacttcacct tcggttttga agaatccctg    600

gaagtagaca cgaacccact gctgggcgct ggtaaattcg caactgatcc tgcggttacc    660

ctggctcacg aactgattca tgcaggccac cgcctgtacg gtatcgccat caatccgaac    720

cgtgtcttca aagttaacac caacgcgtat tacgagatgt ccggtctgga agttagcttc    780

gaagaactgc gtacttttgg cggtcacgac gctaaattca tcgactctct gcaagaaaac    840

gagttccgtc tgtactacta taacaagttc aaagatatcg catccaccct gaacaaagcg    900

aaatccatcg tgggtaccac tgcttctctc cagtacatga agaacgtttt taaagaaaaa    960

tacctgctca gcgaagacac ctccggcaaa ttctctgtag acaagttgaa attcgataaa   1020

ctttacaaaa tgctgactga aatttacacc gaagacaact tcgttaagtt ctttaaagtt   1080

ctgaaccgca aaacctatct gaacttcgac aaggcagtat tcaaaatcaa catcgtgccg   1140

aaagttaact acactatcta cgatggtttc aacctgcgta acaccaacct ggctgctaat   1200

tttaacggcc agaacacgga aatcaacaac atgaacttca caaaactgaa aaacttcact   1260

ggtctgttcg agttttacaa gctgctgtgc gtcgacggca tcattacctc caaaactaaa   1320

tctgacgatg acgataaaaa caaagcgctg aacctgcagt gtatcaaggt taacaactgg   1380

gatttattct tcagcccgag tgaagacaac ttcaccaacg acctgaacaa aggtgaagaa   1440

atcacctcag atactaacat cgaagcagcc gaagaaaaca tctcgctgga cctgatccag   1500

cagtactacc tgacctttaa tttcgacaac gagccggaaa acatttctat cgaaaacctg   1560
```

```
agctctgata tcatcggcca gctggaactg atgccgaaca tcgaacgttt cccaaacggt   1620

aaaaagtacg agctggacaa atataccatg ttccactacc tgcgcgcgca ggaatttgaa   1680

cacggcaaat cccgtatcgc actgactaac tccgttaacg aagctctgct caacccgtcc   1740

cgtgtataca ccttcttctc tagcgactac gtgaaaaagg tcaacaaagc gactgaagct   1800

gcaatgttct tgggttgggt tgaacagctt gtttatgatt ttaccgacga gacgtccgaa   1860

gtatctacta ccgacaaaat tgcggatatc actatcatca tcccgtacat cggtccggct   1920

ctgaacattg gcaacatgct gtacaaagac gacttcgttg gcgcactgat cttctccggt   1980

gcggtgatcc tgctggagtt catcccggaa atcgccatcc cggtactggg cacctttgct   2040

ctggtttctt acattgcaaa caaggttctg actgtacaaa ccatcgacaa cgcgctgagc   2100

aaacgtaacg aaaaatggga tgaagtttac aaatatatcg tgaccaactg gctggctaag   2160

gttaatactc agatcgacct catccgcaaa aaaatgaaag aagcactgga aaaccaggcg   2220

gaagctacca aggcaatcat taactaccag tacaaccagt acaccgagga agaaaaaaac   2280

aacatcaact tcaacatcga cgatctgtcc tctaaactga acgaatccat caacaaagct   2340

atgatcaaca tcaacaagtt cctgaaccag tgctctgtaa gctatctgat gaactccatg   2400

atcccgtacg gtgttaaacg tctggaggac ttcgatgcgt ctctgaaaga cgccctgctg   2460

aaatacattt acgacaaccg tggcactctg atcggtcagg ttgatcgtct gaaggacaaa   2520

gtgaacaata ccttatcgac cgacatccct tttcagctca gtaaatatgt cgataaccaa   2580

cgccttttgt ccactctaga agcacaccat catcaccacc atcaccatca ccat         2634
```

<210> SEQ ID NO 4
<211> LENGTH: 878
<212> TYPE: PRT
<213> ORGANISM: Artificial Sequence
<220> FEATURE:
<223> OTHER INFORMATION: Polypeptide Sequence of rLHN/A

<400> SEQUENCE: 4

```
Met Glu Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175
```

```
Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Asn Lys
        435                 440                 445

Ala Leu Asn Leu Gln Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
```

```
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Leu Glu Ala His His His His His His His His His His
865                 870                 875
```

<210> SEQ ID NO 5
<211> LENGTH: 1329
<212> TYPE: DNA
<213> ORGANISM: Artificial Sequence
<220> FEATURE:
<223> OTHER INFORMATION: Nucleotide Sequence of rL/A

<400> SEQUENCE: 5

```
atgccattcg tcaacaagca attcaactac aaagacccag tcaacggcgt cgacatcgca     60

tacatcaaga ttccgaacgc cggtcaaatg cagccggtta aggcttttaa gatccacaac    120

aagatttggg ttatcccgga gcgtgacacc ttcacgaacc cggaagaagg cgatctgaac    180

ccgccaccgg aagcgaagca agtccctgtc agctactacg attcgacgta cctgagcacg    240

gataacgaaa aagataacta cctgaaaggt gtgaccaagc tgttcgaacg tatctacagc    300

acggatctgg gtcgcatgct gctgactagc attgttcgcg gtatcccgtt ctggggtggt    360

agcacgattg acaccgaact gaaggttatc gacactaact gcattaacgt tattcaaccg    420

gatggtagct atcgtagcga agagctgaat ctggtcatca ttggcccgag cgcagacatt    480
```

```
atccaattcg agtgcaagag ctttggtcac gaggttctga atctgacccg caatggctat    540

ggtagcaccc agtacattcg tttttcgccg gattttacct tcggctttga agagagcctg    600

gaggttgata ccaatccgtt gctgggtgcg ggcaaattcg ctaccgatcc ggctgtcacg    660

ctggcccatg aactgatcca cgcaggccac cgcctgtacg gcattgccat caacccaaac    720

cgtgtgttca aggttaatac gaatgcatac tacgagatga gcggcctgga agtcagcttc    780

gaagaactgc gcaccttcgg tggccatgac gctaaattca ttgacagctt gcaagagaat    840

gagttccgtc tgtactacta taacaaattc aaagacattg caagcacgtt gaacaaggcc    900

aaaagcatcg ttggtactac cgcgtcgttg cagtatatga agaatgtgtt taaagagaag    960

tacctgctgt ccgaggatac ctccggcaag tttagcgttg ataagctgaa gtttgacaaa   1020

ctgtacaaga tgctgaccga gatttacacc gaggacaact ttgtgaaatt cttcaaagtg   1080

ttgaatcgta aaacctatct gaattttgac aaagcggttt tcaagattaa catcgtgccg   1140

aaggtgaact acaccatcta tgacggtttt aacctgcgta acaccaacct ggcggcgaac   1200

tttaacggtc agaatacgga aatcaacaac atgaatttca cgaagttgaa gaacttcacg   1260

ggtctgttcg agttctataa gctgctgggt ctagaagcac accatcatca ccaccatcac   1320

catcaccat                                                           1329
```

<210> SEQ ID NO 6
<211> LENGTH: 443
<212> TYPE: PRT
<213> ORGANISM: Artificial Sequence
<220> FEATURE:
<223> OTHER INFORMATION: Polypeptide Sequence of rL/A

<400> SEQUENCE: 6

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205
```

```
Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Gly Leu Glu
            420                 425                 430

Ala His His His His His His His His His His
        435                 440
```

<210> SEQ ID NO 7
<211> LENGTH: 1299
<212> TYPE: DNA
<213> ORGANISM: Artificial Sequence
<220> FEATURE:
<223> OTHER INFORMATION: Nucleotide Sequence of rHC/A

<400> SEQUENCE: 7

```
atgcatcatc accatcacca caaaaacatc atcaatacta gcattctgaa cctgcgttac     60

gagagcaatc atctgattga tctgagccgt tatgcaagca agatcaacat cggtagcaag    120

gtcaattttg acccgatcga taagaaccag atccagctgt ttaatctgga atcgagcaaa    180

attgaggtta tcctgaaaaa cgccattgtc tacaactcca tgtacgagaa tttctccacc    240

agcttctgga ttcgcatccc gaaatacttc aacagcatta gcctgaacaa cgagtatact    300

atcatcaact gtatggagaa caacagcggt tggaaggtgt ctctgaacta tggtgagatc    360

atttggacct tgcaggacac ccaagagatc aagcagcgcg tcgtgttcaa gtactctcaa    420

atgatcaaca tttccgatta cattaatcgt tggatcttcg tgaccattac gaataaccgt    480

ctgaataaca gcaagattta catcaatggt cgcttgatcg atcagaaacc gattagcaac    540

ctgggtaata tccacgcaag caacaacatt atgttcaaat tggacggttg ccgcgatacc    600

catcgttata tctggatcaa gtatttcaac ctgtttgata aagaactgaa tgagaaggag    660

atcaaagatt tgtatgacaa ccaatctaac agcggcattt tgaaggactt ctggggcgat    720
```

```
tatctgcaat acgataagcc gtactatatg ctgaacctgt atgatccgaa caaatatgtg    780

gatgtcaata atgtgggtat tcgtggttac atgtatttga agggtccgcg tggcagcgtt    840

atgacgacca acatttacct gaactctagc ctgtaccgtg gtacgaaatt catcattaag    900

aaatatgcca gcggcaacaa agataacatt gtgcgtaata acgatcgtgt ctacatcaac    960

gtggtcgtga agaataaaga gtaccgtctg gcgaccaacg cttcgcaggc gggtgttgag   1020

aaaattctga gcgcgttgga gatccctgat gtcggtaatc tgagccaagt cgtggttatg   1080

aagagcaaga acgaccaggg tatcactaac aagtgcaaga tgaacctgca agacaacaat   1140

ggtaacgaca tcggctttat tggtttccac cagttcaaca atattgctaa actggtagcg   1200

agcaattggt acaatcgtca gattgagcgc agcagccgta ctttgggctg tagctgggag   1260

tttatcccgg tcgatgatgg ttggggcgaa cgtccgctg                          1299
```

```
<210> SEQ ID NO 8
<211> LENGTH: 433
<212> TYPE: PRT
<213> ORGANISM: Artificial Sequence
<220> FEATURE:
<223> OTHER INFORMATION: Polypeptide Sequence of rHC/A

<400> SEQUENCE: 8

Met His His His His His His Lys Asn Ile Ile Asn Thr Ser Ile Leu
1               5                   10                  15

Asn Leu Arg Tyr Glu Ser Asn His Leu Ile Asp Leu Ser Arg Tyr Ala
            20                  25                  30

Ser Lys Ile Asn Ile Gly Ser Lys Val Asn Phe Asp Pro Ile Asp Lys
        35                  40                  45

Asn Gln Ile Gln Leu Phe Asn Leu Glu Ser Ser Lys Ile Glu Val Ile
    50                  55                  60

Leu Lys Asn Ala Ile Val Tyr Asn Ser Met Tyr Glu Asn Phe Ser Thr
65                  70                  75                  80

Ser Phe Trp Ile Arg Ile Pro Lys Tyr Phe Asn Ser Ile Ser Leu Asn
                85                  90                  95

Asn Glu Tyr Thr Ile Ile Asn Cys Met Glu Asn Asn Ser Gly Trp Lys
            100                 105                 110

Val Ser Leu Asn Tyr Gly Glu Ile Ile Trp Thr Leu Gln Asp Thr Gln
        115                 120                 125

Glu Ile Lys Gln Arg Val Val Phe Lys Tyr Ser Gln Met Ile Asn Ile
    130                 135                 140

Ser Asp Tyr Ile Asn Arg Trp Ile Phe Val Thr Ile Thr Asn Asn Arg
145                 150                 155                 160

Leu Asn Asn Ser Lys Ile Tyr Ile Asn Gly Arg Leu Ile Asp Gln Lys
                165                 170                 175

Pro Ile Ser Asn Leu Gly Asn Ile His Ala Ser Asn Asn Ile Met Phe
            180                 185                 190

Lys Leu Asp Gly Cys Arg Asp Thr His Arg Tyr Ile Trp Ile Lys Tyr
        195                 200                 205

Phe Asn Leu Phe Asp Lys Glu Leu Asn Glu Lys Glu Ile Lys Asp Leu
    210                 215                 220

Tyr Asp Asn Gln Ser Asn Ser Gly Ile Leu Lys Asp Phe Trp Gly Asp
225                 230                 235                 240

Tyr Leu Gln Tyr Asp Lys Pro Tyr Tyr Met Leu Asn Leu Tyr Asp Pro
                245                 250                 255

Asn Lys Tyr Val Asp Val Asn Asn Val Gly Ile Arg Gly Tyr Met Tyr
```

```
            260                 265                 270

Leu Lys Gly Pro Arg Gly Ser Val Met Thr Thr Asn Ile Tyr Leu Asn
        275                 280                 285

Ser Ser Leu Tyr Arg Gly Thr Lys Phe Ile Ile Lys Lys Tyr Ala Ser
    290                 295                 300

Gly Asn Lys Asp Asn Ile Val Arg Asn Asn Asp Arg Val Tyr Ile Asn
305                 310                 315                 320

Val Val Val Lys Asn Lys Glu Tyr Arg Leu Ala Thr Asn Ala Ser Gln
                325                 330                 335

Ala Gly Val Glu Lys Ile Leu Ser Ala Leu Glu Ile Pro Asp Val Gly
            340                 345                 350

Asn Leu Ser Gln Val Val Val Met Lys Ser Lys Asn Asp Gln Gly Ile
        355                 360                 365

Thr Asn Lys Cys Lys Met Asn Leu Gln Asp Asn Asn Gly Asn Asp Ile
    370                 375                 380

Gly Phe Ile Gly Phe His Gln Phe Asn Asn Ile Ala Lys Leu Val Ala
385                 390                 395                 400

Ser Asn Trp Tyr Asn Arg Gln Ile Glu Arg Ser Ser Arg Thr Leu Gly
                405                 410                 415

Cys Ser Trp Glu Phe Ile Pro Val Asp Asp Gly Trp Gly Glu Arg Pro
            420                 425                 430

Leu


<210> SEQ ID NO 9
<211> LENGTH: 3873
<212> TYPE: DNA
<213> ORGANISM: Artificial Sequence
<220> FEATURE:
<223> OTHER INFORMATION: Nucleotide Sequence of rBoNT/B(0)

<400> SEQUENCE: 9

atgccggtga cgattaacaa cttcaactac aacgacccga ttgacaacaa caacattatc     60

atgatggaac cgccgtttgc acgcggcacg ggccgttatt acaaagcgtt taaaatcacc    120

gatcgtattt ggattatccc ggaacgctac acgtttggtt ataaaccgga agacttcaac    180

aaaagctctg gcatcttcaa ccgtgatgtt tgcgaatact acgatccgga ctacctgaac    240

accaacgata agaaaaacat ttttctgcaa acgatgatca aactgttcaa tcgcattaaa    300

agcaaaccgc tgggtgaaaa actgctggaa atgattatca atggcattcc gtatctgggt    360

gatcgtcgcg tgccgctgga agaatttaac accaatatcg cgagtgttac ggtcaacaaa    420

ctgatttcca atccgggtga agtcgaacgt aaaaaaggca tcttcgccaa cctgatcatc    480

ttcggcccgg gtccggtgct gaacgaaaat gaaaccattg atatcggtat tcagaaccat    540

tttgcctcac gcgaaggctt cggcggtatt atgcaaatga aattttgccc ggaatatgtg    600

tcggttttca acaatgttca ggaaaacaaa ggtgcaagca tctttaatcg tcgcggctat    660

ttctctgatc cggctctgat cctgatgcac caactgattt atgtgctgca cggcctgtat    720

ggtatcaaag tggatgacct gccgatcgtt ccgaacgaga aaaaattttt catgcagagc    780

accgacgcaa ttcaagctga agaactgtat acgtttggcg gtcaggaccc gtctattatc    840

accccgagca ccgacaaaag catctacgat aaagtgctgc aaaactttcg tggcattgtt    900

gaccgcctga ataaagtcct ggtgtgtatc tctgatccga acatcaacat caacatctac    960

aaaaacaaat tcaaagacaa atacaaattc gttgaagatt ctgaaggcaa atatagtatt   1020

gacgtcgaat cctttgataa actgtacaaa agtctgatgt tcggtttcac cgaaacgaac   1080
```

```
atcgcggaaa actacaaaat caaaacccgc gcctcctatt tcagcgactc tctgccgccg   1140
gttaaaatca aaaatctgct ggataacgaa atttatacga tcgaagaagg tttcaacatc   1200
agcgataaag acatggaaaa agaataccgt ggccagaata aagcaatcaa caaacaggcg   1260
tatgaagaaa ttagtaaaga acatctggcg gtctacaaaa ttcagatgtg caaatccgtg   1320
aaagccccgg gtatttgtat cgatgttgac aatgaagacc tgtttttcat cgccgataaa   1380
aacagttttt ccgatgacct gtcaaaaaat gaacgcatcg aatacaacac ccaatcgaac   1440
tacatcgaaa acgatttccc gatcaacgaa ctgattctgg atacggacct gattagtaaa   1500
atcgaactgc cgtcagaaaa caccgaatcg ctgacggact ttaatgttga tgtcccggtg   1560
tatgaaaaac agccggcaat taagaaaatt tttaccgatg aaaacacgat cttccagtac   1620
ctgtacagcc aaacctttcc gctggacatt cgcgatatct ctctgacgag ttcctttgat   1680
gacgcactgc tgttcagcaa caaagtgtac tcctttttct caatggatta catcaaaacc   1740
gctaacaaag tggttgaagc gggcctgttt gccggttggg tgaaacagat cgttaacgat   1800
ttcgtcatcg aagccaacaa aagtaacacg atggataaaa ttgctgatat ctccctgatt   1860
gtcccgtata ttggcctggc actgaatgtg ggtaacgaaa cggcgaaagg caattttgaa   1920
aacgccttcg aaattgcagg cgcttcaatc ctgctggaat ttattccgga actgctgatc   1980
ccggtcgtgg gtgcgttcct gctggaatct tacatcgaca acaaaaacaa aatcatcaaa   2040
accattgata acgcgctgac gaaacgtaac gaaaaatggt cagatatgta cggcctgatt   2100
gttgcccagt ggctgagcac cgtcaacacg caattttaca ccatcaaaga aggtatgtac   2160
aaagcgctga attatcaggc gcaagccctg gaagaaatca tcaaataccg ctacaacatc   2220
tacagcgaaa aagaaaaatc taacatcaac atcgacttta atgatatcaa cagcaaactg   2280
aacgaaggta tcaaccaggc aatcgataac atcaacaact tcatcaacgg ctgctcagtg   2340
tcgtatctga tgaagaaaat gatcccgctg gctgttgaaa aactgctgga ttttgacaac   2400
accctgaaga aaaacctgct gaactacatc gatgaaaaca aactgtacct gatcggctca   2460
gccgaatacg aaaaatcgaa agtgaacaaa tacctgaaaa ccatcatgcc gtttgacctg   2520
agtatttaca ccaacgatac gatcctgatc gaaatgttca acaaatacaa ctccgaaatt   2580
ctgaacaata ttatcctgaa cctgcgttac aaagacaaca atctgatcga tctgagcggc   2640
tatggtgcaa aagttgaagt ctacgacggt gtcgaactga acgataaaaa ccagttcaaa   2700
ctgacctcat cggctaactc aaaaattcgt gtgacgcaga accaaaacat catcttcaac   2760
tcggtctttc tggacttcag cgtgtctttc tggattcgca tcccgaaata taaaaatgat   2820
ggcatccaga actacatcca taacgaatac accatcatca actgtatgaa aaacaacagt   2880
ggttggaaaa tttccatccg tggcaaccgc attatctgga ccctgattga tatcaatggt   2940
aaaacgaaaa gcgtgttttt cgaatacaac atccgtgaag atatctctga atacatcaat   3000
cgctggtttt tcgtgaccat tacgaacaat ctgaacaatg cgaaaatcta tatcaacggc   3060
aaactggaaa gtaataccga catcaaagat attcgtgaag ttatcgccaa cggtgaaatc   3120
atcttcaaac tggatggcga catcgatcgc acccagttca tttggatgaa atacttctcc   3180
atcttcaaca cggaactgag tcagtccaat atcgaagaac gctacaaaat ccaatcatac   3240
tcggaatacc tgaaagattt ctggggtaac ccgctgatgt acaacaaaga atactacatg   3300
ttcaacgcgg gcaacaaaaa ctcatacatc aaactgaaaa aagattcgcc ggtgggtgaa   3360
atcctgaccc gtagcaaata caaccagaac tctaaataca tcaactatcg cgatctgtac   3420
```

```
attggcgaaa aatttattat ccgtcgcaaa agcaactctc agagtattaa tgatgacatc   3480

gtgcgtaaag aagactacat ctatctggat ttctttaatc tgaaccaaga atggcgcgtt   3540

tatacctaca aatacttcaa aaaagaagaa gagaaactgt tcctggcccc gattagcgac   3600

agcgatgaat tttacaacac catccagatc aaagaatacg atgaacagcc gacgtatagt   3660

tgccaactgc tgttcaaaaa agacgaagaa tccaccgatg aaattggcct gattggtatc   3720

caccgtttct atgaaagcgg tatcgttttc gaagaataca aagattactt ctgtatctct   3780

aaatggtatc tgaaagaagt caaacgcaaa ccgtacaacc tgaaactggg ctgcaactgg   3840

caatttatcc cgaaagacga aggctggacc gaa                                3873
```

<210> SEQ ID NO 10
<211> LENGTH: 1291
<212> TYPE: PRT
<213> ORGANISM: Artificial Sequence
<220> FEATURE:
<223> OTHER INFORMATION: Polypeptide Sequence of rBoNT/B(0)

<400> SEQUENCE: 10

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Gln Leu Ile Tyr Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285
```

```
Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700
```

```
Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
```

```
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185

Glu Glu  Glu Lys Leu Phe Leu  Ala Pro Ile Ser Asp  Ser Asp Glu
    1190                1195                1200

Phe Tyr  Asn Thr Ile Gln Ile  Lys Glu Tyr Asp Glu  Gln Pro Thr
    1205                1210                1215

Tyr Ser  Cys Gln Leu Leu Phe  Lys Lys Asp Glu Glu  Ser Thr Asp
    1220                1225                1230

Glu Ile  Gly Leu Ile Gly Ile  His Arg Phe Tyr Glu  Ser Gly Ile
    1235                1240                1245

Val Phe  Glu Glu Tyr Lys Asp  Tyr Phe Cys Ile Ser  Lys Trp Tyr
    1250                1255                1260

Leu Lys  Glu Val Lys Arg Lys  Pro Tyr Asn Leu Lys  Leu Gly Cys
    1265                1270                1275

Asn Trp  Gln Phe Ile Pro Lys  Asp Glu Gly Trp Thr  Glu
    1280                1285                1290
```

```
<210> SEQ ID NO 11
<211> LENGTH: 3873
<212> TYPE: DNA
<213> ORGANISM: Artificial Sequence
<220> FEATURE:
<223> OTHER INFORMATION: Nucleotide Sequence of rBoNT/C(0)

<400> SEQUENCE: 11

atgccgatca cgattaataa tttcaactat agcgatccgg tggacaataa gaatattctg     60

tatctggata ctcatctgaa tacgctggct aacgaaccgg agaaagcgtt ccgcatcaca    120

ggcaacatct gggttattcc cgatcgcttt tcacgcaaca gcaaccctaa tctgaacaaa    180

cctcctcgtg tcaccagtcc taaatccggt tattacgacc caaactatct gagtacggat    240

agcgataaag atccctttct gaaagagatc attaagctgt tcaaacgcat taactctcgc    300

gaaattgggg aagagctgat ctatcggctt tcgacagata tcccgttccc aggtaacaat    360

aataccccga ttaatacttt cgactttgat gttgatttca attctgtgga tgtgaaaacg    420

cgtcaaggca ataattgggt gaaaactggt agcattaacc cgagtgtaat tatcacaggt    480

ccccgtgaga acatcatcga cccggaaacc tctaccttca agctgacgaa caacacgttt    540

gctgcacagg aagggtttgg tgccctgtca atcatttcca tctcaccgcg tttcatgtta    600

acctactcca atgccacaaa tgatgttggc gaaggacgtt ttagcaaatc agaattttgc    660

atggacccaa ttctcattct gatgggcacg ctgaacaatg cgatgcacaa cttgtatggc    720

attgctattc caaacgatca aaccattagc tccgttacca gtaatatctt ctatagccag    780

tataatgtca aattggagta tgccgaaatt tacgcctttg gaggcccgac cattgacctg    840

attccgaaat ctgcacgcaa atacttcgaa gaaaaggcgt tagattacta tcgcagcatc    900

gcgaaacgcc tgaactcgat taccacggcc aatccgtcgt cgttcaacaa atacattggt    960

gaatataaac agaaactgat tcgcaaatat cggtttgtcg tagaaagctc tggtgaagtg   1020
```

```
actgtaaacc gcaacaaatt tgtcgaactc tacaacgagt tgacccaaat ctttaccgag   1080
tttaactacg caaagatcta taacgtacag aaccgcaaga tttatcttag caatgtatac   1140
acaccggtta ctgcgaacat cttagacgac aatgtgtatg atattcagaa tggctttaac   1200
atcccgaaat caaatctgaa cgttctgttt atgggccaga acctgagtcg taatccagca   1260
ctgcgtaaag tgaacccgga aaatatgctc tacttgttta ccaaattttg ccacaaagcg   1320
attgatggcc gctctctcta taacaaaacg ctggattgtc gtgagttact tgtgaagaac   1380
actgatttac cgttcattgg ggatatctcc gacgtgaaaa ccgatatctt cctgcgcaaa   1440
gacattaatg aagaaacgga agtcatctat taccccgaca atgtgagcgt tgatcaggtc   1500
attttatcga agaacacctc cgaacatggt cagttggatt tgctgtaccc tagcattgac   1560
tcggagagtg aaatccttcc gggcgaaaat caagtgtttt acgacaaccg tacccaaaat   1620
gttgattatt tgaattctta ttactacctg gaatctcaga aattgagcga caatgtggaa   1680
gatttcacgt tcacacgctc cattgaggaa gcgctggata atagcgcgaa agtgtatacg   1740
tatttcccta ccttggcgaa taaagtaaat gctggtgtcc agggaggctt atttctgatg   1800
tgggcgaatg atgtggtaga agattttacg accaatattt tgcgtaagga caccttagat   1860
aaaattagcg atgttagcgc catcatcccc tatattggcc cagcactgaa tatctcgaac   1920
tctgtgcgtc gcggaaactt caccgaagca tttgcggtga ccggggttac tattctgttg   1980
gaagcctttc cggagtttac tattccggcg ctgggtgcgt ttgtgattta ttcgaaagta   2040
caagaacgca atgaaattat caaaaccatc gataattgcc tggaacaacg cattaaacgc   2100
tggaaggatt cttatgaatg gatgatgggc acctggttat cccgtattat cacacagttt   2160
aacaacatct cgtatcagat gtacgattca ctgaactacc aagcaggggc gatcaaagcc   2220
aagatcgact tagaatacaa gaaatattca ggtagcgata aagagaatat taaaagccag   2280
gttgaaaacc tgaagaactc tctggatgtc aaaatttcag aggctatgaa caacattaac   2340
aaatttatcc gcgaatgtag cgtcacgtat ctgtttaaaa acatgctccc gaaagtgatt   2400
gatgagctca acgagtttga tcgcaacaca aaggccaaac tgattaacct gattgatagt   2460
cacaatatta ttttagtcgg tgaagttgac aagctgaagg ctaaggtcaa taacagcttt   2520
cagaacacta ttccgtttaa tattttctcc tatacgaaca atagtctgct gaaagacatt   2580
atcaacgaat acttcaacaa tattaatgac agcaaaattc tgagcctgca gaatcgtaag   2640
aatacgctgg tagataccag tggatataat gcggaagtct cagaagaggg tgatgtacag   2700
ctgaacccga tctttccgtt cgactttaaa ctggggtcta gtggtgaaga tcgcggtaaa   2760
gtgatcgtta cccaaaacga gaacattgtg tataacagca tgtacgagag tttctcaatt   2820
tctttctgga ttcgcatcaa taaatgggtt tctaatttgc ctggctatac catcattgat   2880
agcgtcaaaa acaactcggg ctggtcgatt ggcattatta gcaactttct ggtgtttacc   2940
ctgaaacaga atgaggattc ggaacagagc attaacttct cctacgacat cagcaacaat   3000
gcaccagggt ataacaaatg gttcttcgta acggtgacga acaatatgat gggcaatatg   3060
aaaatctaca ttaacgggaa acttatcgac accattaaag tgaaagagct tactgggatc   3120
aattttagta aaaccattac ctttgagatc aacaaaattc cggacacggg tctgattacc   3180
tccgattcgg ataatatcaa tatgtggatt cgcgactttt atatcttcgc caaagaactt   3240
gatggcaaag atatcaacat tttgtttaat tccctgcagt ataccaatgt cgttaaggac   3300
tattggggca atgatctccg ctacaataaa gaatactaca tggttaacat cgactatctc   3360
aatcgctaca tgtatgctaa ctcgcgtcaa attgtgttta acacacgtcg taacaacaac   3420
```

```
gattttaacg aaggttataa aatcattatc aaacggatcc gcggcaatac gaacgatact   3480

cgtgttcgtg gcggtgacat tctgtatttc gacatgacga ttaataataa agcgtacaat   3540

ctgttcatga agaacgaaac catgtacgcc gataaccatt ccactgaaga tatctacgca   3600

atcggacttc gcgaacagac caaagacatt aacgacaaca tcatctttca gattcaaccg   3660

atgaataata cctactacta tgcctcccag atcttcaaaa gtaatttcaa cggcgaaaac   3720

atttcaggca tttgctcaat cggcacttat cggttccggt taggtggtga ttggtatcgt   3780

cacaactacc ttgttcccac agtgaaacaa ggcaactatg catcgctctt agaaagcaca   3840

tctacgcatt ggggttttgt gccagtcagt gaa                                 3873
```

<210> SEQ ID NO 12
<211> LENGTH: 1291
<212> TYPE: PRT
<213> ORGANISM: Artificial Sequence
<220> FEATURE:
<223> OTHER INFORMATION: Polypeptide Sequence of rBoNT/C(0)

<400> SEQUENCE: 12

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met Gly Thr Leu Asn Asn Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
```

-continued

```
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700
```

-continued

```
Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn  Ala Pro Gly Tyr Asn  Lys Trp Phe
        995                 1000                1005

Phe Val  Thr Val Thr Asn Asn  Met Met Gly Asn Met  Lys Ile Tyr
    1010                1015                1020

Ile Asn  Gly Lys Leu Ile Asp  Thr Ile Lys Val Lys  Glu Leu Thr
    1025                1030                1035

Gly Ile  Asn Phe Ser Lys Thr  Ile Thr Phe Glu Ile  Asn Lys Ile
    1040                1045                1050

Pro Asp  Thr Gly Leu Ile Thr  Ser Asp Ser Asp Asn  Ile Asn Met
    1055                1060                1065

Trp Ile  Arg Asp Phe Tyr Ile  Phe Ala Lys Glu Leu  Asp Gly Lys
    1070                1075                1080

Asp Ile  Asn Ile Leu Phe Asn  Ser Leu Gln Tyr Thr  Asn Val Val
    1085                1090                1095

Lys Asp  Tyr Trp Gly Asn Asp  Leu Arg Tyr Asn Lys  Glu Tyr Tyr
    1100                1105                1110
```

```
Met Val  Asn Ile Asp Tyr Leu  Asn Arg Tyr Met Tyr  Ala Asn Ser
    1115                 1120                 1125

Arg Gln  Ile Val Phe Asn Thr  Arg Arg Asn Asn Asn  Asp Phe Asn
    1130                 1135                 1140

Glu Gly  Tyr Lys Ile Ile Ile  Lys Arg Ile Arg Gly  Asn Thr Asn
    1145                 1150                 1155

Asp Thr  Arg Val Arg Gly Gly  Asp Ile Leu Tyr Phe  Asp Met Thr
    1160                 1165                 1170

Ile Asn  Asn Lys Ala Tyr Asn  Leu Phe Met Lys Asn  Glu Thr Met
    1175                 1180                 1185

Tyr Ala  Asp Asn His Ser Thr  Glu Asp Ile Tyr Ala  Ile Gly Leu
    1190                 1195                 1200

Arg Glu  Gln Thr Lys Asp Ile  Asn Asp Asn Ile Ile  Phe Gln Ile
    1205                 1210                 1215

Gln Pro  Met Asn Asn Thr Tyr  Tyr Tyr Ala Ser Gln  Ile Phe Lys
    1220                 1225                 1230

Ser Asn  Phe Asn Gly Glu Asn  Ile Ser Gly Ile Cys  Ser Ile Gly
    1235                 1240                 1245

Thr Tyr  Arg Phe Arg Leu Gly  Gly Asp Trp Tyr Arg  His Asn Tyr
    1250                 1255                 1260

Leu Val  Pro Thr Val Lys Gln  Gly Asn Tyr Ala Ser  Leu Leu Glu
    1265                 1270                 1275

Ser Thr  Ser Thr His Trp Gly  Phe Val Pro Val Ser  Glu
    1280                 1285                 1290
```

<210> SEQ ID NO 13
<211> LENGTH: 3756
<212> TYPE: DNA
<213> ORGANISM: Artificial Sequence
<220> FEATURE:
<223> OTHER INFORMATION: Nucleotide Sequence of rBoNT/E(0)

<400> SEQUENCE: 13

```
atgccgaaaa tcaactcttt caactacaac gacccggtta acgaccgtac catcctgtat     60

atcaaaccgg gtggttgcca ggagttctac aaatctttca acatcatgaa aaacatctgg    120

atcatcccgg aacgtaacgt tatcggtacc accccgcagg acttccaccc gccgacctct    180

ctgaaaaacg gtgactcttc ttactacgac ccgaactacc tccagtctga cgaagaaaaa    240

gaccgtttcc tgaaaatcgt taccaaaatc ttcaaccgta tcaacaacaa cctgtctggt    300

ggtatcctgc tggaagaact gtctaaagct aacccgtacc tgggtaacga caacaccccg    360

gacaaccagt tccacatcgg tgacgcttct gctgttgaaa tcaaattctc taacggttct    420

caggacatcc tgctgccgaa cgttatcatc atgggtgctg aaccggacct gttcgaaacc    480

aactcttcta acatctctct gcgtaacaac tacatgccgt ctaaccacgg tttcggttct    540

atcgctatcg ttaccttctc tccggaatac tctttccgtt tcaacgacaa cagcatgaac    600

gagttcatcc aggacccggc tctgaccctg atgcaccaac tgatctactc tctgcacggt    660

ctgtacggtg ctaaaggtat caccaccaaa tacaccatca cccagaaaca gaacccgctg    720

atcaccaaca tccgtggtac caacatcgaa gagttcctga ccttcggtgg taccgacctg    780

aacatcatca cctctgctca gtctaacgac atctacacca acctgctggc tgactacaaa    840

aaaatcgctt ctaaactgtc taaagttcag gtttctaacc cgctgctgaa cccgtacaaa    900

gacgttttcg aagctaaata cggtctggac aaagacgctt ctggtatcta ctctgttaac    960

atcaacaaat tcaacgacat cttcaaaaaa ctgtactctt tcaccgagtt cgacctggcg   1020
```

```
accaaattcc aggttaaatg ccgtcagacc tacatcggtc agtacaaata cttcaaactg   1080
tctaacctgc tgaacgactc tatctacaac atctctgaag gttacaacat caacaacctg   1140
aaagttaact tccgtggtca gaacgctaac ctgaacccgc gtatcatcac cccgatcacc   1200
ggtcgtggtc tggttaaaaa aatcatccgt ttctgcaaga atattgtaag cgttaaagga   1260
ataagaaaaa gtatctgcat cgaaatcaac aacggtgaac tgttcttcgt tgcttctgaa   1320
aactcttaca acgacgacaa catcaacacc ccgaaagaaa tcgacgacac cgttacctct   1380
aacaacaact acgaaaacga cctggaccag gttatcctga acttcaactc tgaatctgct   1440
ccgggtctgt ctgacgaaaa actgaacctg accatccaga acgacgctta catcccgaaa   1500
tacgactcta acggtacctc tgacatcgaa cagcacgacg ttaacgaact gaacgttttc   1560
ttctacctgg acgctcagaa agttccggaa ggtgaaaaca acgttaacct gacctcttct   1620
atcgacaccg ctctgctgga acagccgaaa atctacacct tcttctcttc tgagttcatc   1680
aacaacgtta acaaaccggt tcaggctgct ctgttcgttt cttggattca gcaggttctg   1740
gttgacttca ccaccgaagc taaccagaaa tctaccgttg acaaaatcgc tgacatctct   1800
atcgttgttc cgtacatcgg tctggctctg aacatcggta acgaagctca gaaaggtaac   1860
ttcaaagacg ctctggaact gctgggtgct ggtatcctgc tggagttcga accggaactg   1920
ctgatcccga ccatcctggt tttcaccatc aaatctttcc tgggttcttc tgacaacaaa   1980
aacaaagtta tcaaagctat caacaacgct ctgaaagaac gtgacgaaaa atggaaagaa   2040
gtttactctt tcatcgtttc taactggatg accaaaatca acacccagtt caacaaacgt   2100
aaagaacaga tgtaccaggc tctccagaac caggttaacg ctatcaaaac catcatcgaa   2160
tctaaataca actcttacac cctggaagaa aaaaacgaac tgaccaacaa atacgacatc   2220
aaacagatcg aaaacgaact gaaccagaaa gtttctatcg ctatgaacaa catcgaccgt   2280
ttcctgaccg aatcttctat ctcttacctg atgaaactca tcaacgaagt taaaatcaac   2340
aaactgcgtg aatacgacga aaacgttaaa acctacctgc tgaactacat catccagcac   2400
ggttctatcc tgggtgaatc tcagcaggaa ctgaactcta tggttaccga caccctgaac   2460
aactctatcc cgttcaaact gtcttcttac accgacgaca aaatcctgat ctcttacttc   2520
aacaaattct ttaaacgcat taagagttca tcggttctga atatgcggta caaaaatgat   2580
aaatatgtcg atacttctgg atatgatagc aatatcaaca ttaacggcga cgtgtataaa   2640
tatccgacaa ataaaaacca gtttgggata tataacgaca agctgtcgga ggtcaatatt   2700
tctcaaaacg actatatcat ttacgataat aaatataaaa actttagcat tagtttttgg   2760
gttcgtatac ctaattatga caataaaatt gtaaatgtga ataacgagta taccattata   2820
aactgtatgc gcgacaataa cagtggttgg aaggtatcgc tgaaccataa tgagattatc   2880
tggaccctgc aggataatgc aggtataaac cagaaactgg cttttaacta tggaaacgca   2940
aatgggatct cagattacat taataaatgg atttttgtta ccattacgaa cgatcgctta   3000
ggcgactcaa aactttatat taatggcaat ctgatagatc agaaatcaat cttaaatttg   3060
ggcaatattc atgtctctga taacatcttg ttcaagatcg ttaattgcag ttacactcgt   3120
tatattggca ttcgttactt taatatcttc gataaagaac tggacgagac ggaaatccag   3180
actctgtatt caaacgagcc caatactaat atattgaaag atttttgggg taactatctt   3240
ttatatgata aagaatacta tctcctgaat gtattgaagc caaacaattt catagataga   3300
cgcaaggata gcacattaag tatcaacaat atcagatcta ctatactgtt agcaaatcgc   3360
```

ctctactccg gtattaaagt gaagattcag cgggttaata actccagtac caatgataat 3420
ctggtccgta agaacgatca ggtatacatc aatttcgtcg cgagcaaaac tcatctcttc 3480
ccgctttacg ccgatacagc tacgacaaac aaggaaaaaa ccataaaaat ttccagctcc 3540
ggaaacagat tcaatcaagt agttgtaatg aactctgtgg gtaataattg tacgatgaac 3600
tttaagaata acaatgggaa caatattgga cttttgggct tcaaagccga cacagtggtg 3660
gcgtccacct ggtattacac gcacatgcgg gaccatacga attcgaacgg ttgcttctgg 3720
aactttatct cggaagaaca cgggtggcaa gaaaaa 3756

<210> SEQ ID NO 14
<211> LENGTH: 1252
<212> TYPE: PRT
<213> ORGANISM: Artificial Sequence
<220> FEATURE:
<223> OTHER INFORMATION: Polypeptide Sequence of rBoNT/E(0)

<400> SEQUENCE: 14

Met Pro Lys Ile Asn Ser Phe Asn Tyr Asn Asp Pro Val Asn Asp Arg
1 5 10 15

Thr Ile Leu Tyr Ile Lys Pro Gly Gly Cys Gln Glu Phe Tyr Lys Ser
20 25 30

Phe Asn Ile Met Lys Asn Ile Trp Ile Ile Pro Glu Arg Asn Val Ile
35 40 45

Gly Thr Thr Pro Gln Asp Phe His Pro Pro Thr Ser Leu Lys Asn Gly
50 55 60

Asp Ser Ser Tyr Tyr Asp Pro Asn Tyr Leu Gln Ser Asp Glu Glu Lys
65 70 75 80

Asp Arg Phe Leu Lys Ile Val Thr Lys Ile Phe Asn Arg Ile Asn Asn
85 90 95

Asn Leu Ser Gly Gly Ile Leu Leu Glu Glu Leu Ser Lys Ala Asn Pro
100 105 110

Tyr Leu Gly Asn Asp Asn Thr Pro Asp Asn Gln Phe His Ile Gly Asp
115 120 125

Ala Ser Ala Val Glu Ile Lys Phe Ser Asn Gly Ser Gln Asp Ile Leu
130 135 140

Leu Pro Asn Val Ile Ile Met Gly Ala Glu Pro Asp Leu Phe Glu Thr
145 150 155 160

Asn Ser Ser Asn Ile Ser Leu Arg Asn Asn Tyr Met Pro Ser Asn His
165 170 175

Gly Phe Gly Ser Ile Ala Ile Val Thr Phe Ser Pro Glu Tyr Ser Phe
180 185 190

Arg Phe Asn Asp Asn Ser Met Asn Glu Phe Ile Gln Asp Pro Ala Leu
195 200 205

Thr Leu Met His Gln Leu Ile Tyr Ser Leu His Gly Leu Tyr Gly Ala
210 215 220

Lys Gly Ile Thr Thr Lys Tyr Thr Ile Thr Gln Lys Gln Asn Pro Leu
225 230 235 240

Ile Thr Asn Ile Arg Gly Thr Asn Ile Glu Glu Phe Leu Thr Phe Gly
245 250 255

Gly Thr Asp Leu Asn Ile Ile Thr Ser Ala Gln Ser Asn Asp Ile Tyr
260 265 270

Thr Asn Leu Leu Ala Asp Tyr Lys Lys Ile Ala Ser Lys Leu Ser Lys
275 280 285

Val Gln Val Ser Asn Pro Leu Leu Asn Pro Tyr Lys Asp Val Phe Glu

```
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720
```

```
Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050

Leu Asp  Glu Thr Glu Ile Gln  Thr Leu Tyr Ser Asn  Glu Pro Asn
    1055                1060                1065

Thr Asn  Ile Leu Lys Asp Phe  Trp Gly Asn Tyr Leu  Leu Tyr Asp
    1070                1075                1080

Lys Glu  Tyr Tyr Leu Leu Asn  Val Leu Lys Pro Asn  Asn Phe Ile
    1085                1090                1095

Asp Arg  Arg Lys Asp Ser Thr  Leu Ser Ile Asn Asn  Ile Arg Ser
    1100                1105                1110

Thr Ile  Leu Leu Ala Asn Arg  Leu Tyr Ser Gly Ile  Lys Val Lys
    1115                1120                1125
```

```
Ile Gln  Arg Val Asn Asn Ser  Ser Thr Asn Asp Asn  Leu Val Arg
    1130                 1135                 1140

Lys Asn  Asp Gln Val Tyr Ile  Asn Phe Val Ala Ser  Lys Thr His
    1145                 1150                 1155

Leu Phe  Pro Leu Tyr Ala Asp  Thr Ala Thr Thr Asn  Lys Glu Lys
    1160                 1165                 1170

Thr Ile  Lys Ile Ser Ser Ser  Gly Asn Arg Phe Asn  Gln Val Val
    1175                 1180                 1185

Val Met  Asn Ser Val Gly Asn  Asn Cys Thr Met Asn  Phe Lys Asn
    1190                 1195                 1200

Asn Asn  Gly Asn Asn Ile Gly  Leu Leu Gly Phe Lys  Ala Asp Thr
    1205                 1210                 1215

Val Val  Ala Ser Thr Trp Tyr  Tyr Thr His Met Arg  Asp His Thr
    1220                 1225                 1230

Asn Ser  Asn Gly Cys Phe Trp  Asn Phe Ile Ser Glu  Glu His Gly
    1235                 1240                 1245

Trp Gln  Glu Lys
    1250
```

<210> SEQ ID NO 15
<211> LENGTH: 3834
<212> TYPE: DNA
<213> ORGANISM: Artificial Sequence
<220> FEATURE:
<223> OTHER INFORMATION: Nucleotide Sequence of rBoNT/F(0)

<400> SEQUENCE: 15

```
atgccggtgg tcatcaacag cttcaactac aacgacccag taaacgacga cacgatcctg     60

tatatgcaaa tcccgtatga agagaagagc aagaagtact ataaggcctt tgaaatcatg    120

cgcaatgtgt ggattattcc ggagcgtaat acgattggta ctgacccaag cgacttcgat    180

ccacctgcgt ctttggaaaa cggctcgtcc gcatattacg acccgaatta cctgaccacc    240

gatgcggaga aagatcgtta tttgaaaacc accatcaagc tgttcaaacg cattaacagc    300

aatccggcag gtgaggtcct gctgcaagag attagctacg caaagcctta tctgggtaat    360

gagcatacgc ctattaacga gtttcacccg gttacccgca ctaccagcgt taacatcaag    420

tcctcgacca acgtgaagtc tagcattatc ctgaacctgc tggttctggg tgccggtccg    480

gacatcttcg aaaactctag ctacccggtg cgtaaactga tggatagcgg cggtgtttat    540

gacccgagca atgacggttt tggcagcatc aatatcgtga cgtttagccc ggagtacgag    600

tacaccttca atgatatcag cggtggttac aattcttcta ccgagagctt catcgccgac    660

ccggcgatca gcctggcaca ccaactgatc tatgcattgc atggcttgta cggtgcccgt    720

ggtgtgacgt ataaagagac tatcaaggtt aagcaggcac ctctgatgat tgcggaaaag    780

ccgattcgcc tggaagagtt cctgaccttc ggcggtcaag atttgaacat cattacctcg    840

gccatgaaag agaaaatcta taacaatttg ctggccaact atgaaaagat tgcaacgcgc    900

ttgtctcgtg ttaactccgc tccgccggaa tacgacatta atgagtacaa agactacttt    960

caatggaaat atggcctgga caaaaatgcg gatggttctt ataccgtgaa tgaaaacaaa   1020

ttcaatgaaa tctacaagaa actgtacagc ttcaccgaaa tcgatctggc gaacaagttc   1080

aaagtcaaat gtcgtaatac ctacttcatc aaatatggct tcctgaaagt cccgaacctg   1140

ctggacgatg acatctatac cgtcagcgaa ggcttcaaca tcggcaatct ggccgtgaat   1200

aatcgtggtc agaacatcaa actgaatccg aaaatcattg actccatccc agacaagggc   1260
```

-continued

```
ctggttgaga aaatcgtgaa gttctgcaaa agcgttattc cgcgtaaagg tacgaaagca   1320
ccgcctcgcc tgtgcattcg cgttaacaac cgtgagttgt tctttgtggc atctgaaagc   1380
agctacaacg agaacgacat caacacccct aaagaaattg atgataccac gaacctgaat   1440
aacaattatc gcaacaatct ggacgaggtg atcctggatt acaattcgga aaccattccg   1500
caaattagca atcagacgct gaacaccctg gttcaggacg atagctacgt tccgcgttac   1560
gactccaatg gtactagcga gattgaagaa cacaacgtag tggacttgaa cgttttcttt   1620
tatctgcacg cccagaaggt tccggagggc gaaaccaata ttagcctgac cagctcgatc   1680
gacaccgcgc tgtctgagga gagccaagtc tacacctttt tcagcagcga gtttatcaac   1740
actattaaca agccagttca tgctgcattg tttatctctt ggattaacca ggtgattcgc   1800
gactttacga cggaggcgac ccagaagtct accttcgaca aaattgcaga catctccctg   1860
gtcgtcccat acgtcggcct ggcgttgaat attggcaatg aagttcaaaa agagaacttc   1920
aaagaagcgt tcgagctgct gggtgcaggc atcctgctgg agttcgtgcc ggaactgttg   1980
atcccgacca tcctggtgtt caccattaag agcttcattg gatcctccga gaataagaac   2040
aagatcatca aggcgatcaa taacagcctg atggagcgtg aaacgaagtg gaaagaaatc   2100
tatagctgga ttgttagcaa ttggctgact cgtattaaca cgcaattcaa caagcgtaaa   2160
gagcaaatgt accaagccct gcaaaaccaa gttgacgcca tcaaaacggt aattgaatac   2220
aagtacaaca attacacgag cgatgagcgc aaccgcctgg aaagcgaata caacatcaac   2280
aacattcgcg aagaattgaa caagaaagtg agcctggcga tggagaacat tgagcgtttt   2340
atcaccgaaa gcagcatctt ttacctgatg aaattgatta atgaggcgaa agtctcgaaa   2400
ctgcgtgagt acgacgaagg tgtgaaagag tatctgctgg attacattag cgagcaccgt   2460
agcatcttgg gtaactcggt tcaggagctg aacgatctgg tgacctctac cctgaacaat   2520
agcatcccgt tcgaactgag cagctatacc aatgacaaga ttctgattct gtatttcaat   2580
aaactgtata agaagatcaa ggataacagc attctggata tgcgttacga aaacaataag   2640
tttatcgaca tttctggtta cggcagcaac atttccatca atggcgatgt ctacatctac   2700
agcaccaatc gcaaccagtt cggcatctac tctagcaaac cgagcgaagt taacatcgca   2760
cagaacaatg atattattta taacggtcgt tatcaaaact tctctatcag cttttgggtc   2820
cgtatcccga agtacttcaa taaagtcaat ctgaataatg aatacacgat catcgactgc   2880
attcgcaata acaacagcgg ttggaaaatc agcctgaatt acaacaaaat tatttggacc   2940
ctgcaagata cggcgggtaa caatcagaaa ctggtgttta actacacgca aatgatcagc   3000
atttctgact atatcaacaa gtggatcttt gttaccatca ccaataatcg tctgggcaat   3060
agccgtattt acatcaacgg taacctgatt gatgagaaaa gcatcagcaa cctgggcgat   3120
attcacgtca gcgacaacat tctgttcaaa attgttggtt gtaacgatac ccgttacgtc   3180
ggcatccgtt atttcaaggt tttcgatacg gagctgggta aaacggaaat cgaaacgttg   3240
tactccgatg aaccagatcc gagcattctg aaggactttt ggggtaacta cttgctgtac   3300
aataaacgtt actatctgct gaatctgttg cgcaccgaca agagcattac ccaaaacagc   3360
aatttcctga acattaatca gcaacgcggc gtataccaaa aaccgaacat cttcagcaat   3420
acgcgcctgt atactggtgt tgaagtgatc attcgtaaga acggtagcac cgacattagc   3480
aacacggaca atttcgtccg taagaatgac ctggcgtaca ttaacgtcgt ggaccgtgat   3540
gtcgagtatc gtctgtacgc agacatcagc attgcgaaac cggaaaagat tatcaagctg   3600
atccgtacca gcaacagcaa caacagcctg ggtcagatca ttgtgatgga cagcattggt   3660
```

```
aataactgca cgatgaactt ccagaacaac aatggtggta atatcggtct gctgggtttt   3720

cacagcaata atctggttgc ttccagctgg tactacaata acattcgtaa aaacacgtct   3780

agcaatggtt gtttttggag ctttatcagc aaagagcacg gctggcaaga aaat         3834


<210> SEQ ID NO 16
<211> LENGTH: 1278
<212> TYPE: PRT
<213> ORGANISM: Artificial Sequence
<220> FEATURE:
<223> OTHER INFORMATION: Polypeptide Sequence of rBoNT/F(0)

<400> SEQUENCE: 16

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Gln Leu Ile Tyr Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335
```

```
Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Arg Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
        595                 600                 605

Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
            660                 665                 670

Ile Gly Ser Ser Glu Asn Lys Asn Lys Ile Ile Lys Ala Ile Asn Asn
        675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
            740                 745                 750
```

```
Leu Glu Ser Glu Tyr Asn Ile Asn Asn Ile Arg Glu Glu Leu Asn Lys
        755                 760                 765

Lys Val Ser Leu Ala Met Glu Asn Ile Glu Arg Phe Ile Thr Glu Ser
    770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
        835                 840                 845

Tyr Thr Asn Asp Lys Ile Leu Ile Leu Tyr Phe Asn Lys Leu Tyr Lys
    850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
        915                 920                 925

Gly Arg Tyr Gln Asn Phe Ser Ile Ser Phe Trp Val Arg Ile Pro Lys
    930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
            980                 985                 990

Phe Asn Tyr Thr Gln Met Ile Ser  Ile Ser Asp Tyr Ile  Asn Lys Trp
        995                 1000                1005

Ile Phe  Val Thr Ile Thr Asn  Asn Arg Leu Gly Asn  Ser Arg Ile
    1010                1015                1020

Tyr Ile  Asn Gly Asn Leu Ile  Asp Glu Lys Ser Ile  Ser Asn Leu
    1025                1030                1035

Gly Asp  Ile His Val Ser Asp  Asn Ile Leu Phe Lys  Ile Val Gly
    1040                1045                1050

Cys Asn  Asp Thr Arg Tyr Val  Gly Ile Arg Tyr Phe  Lys Val Phe
    1055                1060                1065

Asp Thr  Glu Leu Gly Lys Thr  Glu Ile Glu Thr Leu  Tyr Ser Asp
    1070                1075                1080

Glu Pro  Asp Pro Ser Ile Leu  Lys Asp Phe Trp Gly  Asn Tyr Leu
    1085                1090                1095

Leu Tyr  Asn Lys Arg Tyr Tyr  Leu Leu Asn Leu Leu  Arg Thr Asp
    1100                1105                1110

Lys Ser  Ile Thr Gln Asn Ser  Asn Phe Leu Asn Ile  Asn Gln Gln
    1115                1120                1125

Arg Gly  Val Tyr Gln Lys Pro  Asn Ile Phe Ser Asn  Thr Arg Leu
    1130                1135                1140

Tyr Thr  Gly Val Glu Val Ile  Ile Arg Lys Asn Gly  Ser Thr Asp
    1145                1150                1155

Ile Ser  Asn Thr Asp Asn Phe  Val Arg Lys Asn Asp  Leu Ala Tyr
```

```
    1160                1165                1170

Ile Asn  Val Val Asp Arg Asp  Val Glu Tyr Arg Leu  Tyr Ala Asp
    1175                1180                1185

Ile Ser  Ile Ala Lys Pro Glu  Lys Ile Ile Lys Leu  Ile Arg Thr
    1190                1195                1200

Ser Asn  Ser Asn Asn Ser Leu  Gly Gln Ile Ile Val  Met Asp Ser
    1205                1210                1215

Ile Gly  Asn Asn Cys Thr Met  Asn Phe Gln Asn Asn  Asn Gly Gly
    1220                1225                1230

Asn Ile  Gly Leu Leu Gly Phe  His Ser Asn Asn Leu  Val Ala Ser
    1235                1240                1245

Ser Trp  Tyr Tyr Asn Asn Ile  Arg Lys Asn Thr Ser  Ser Asn Gly
    1250                1255                1260

Cys Phe  Trp Ser Phe Ile Ser  Lys Glu His Gly Trp  Gln Glu Asn
    1265                1270                1275


<210> SEQ ID NO 17
<211> LENGTH: 3942
<212> TYPE: DNA
<213> ORGANISM: Artificial Sequence
<220> FEATURE:
<223> OTHER INFORMATION: Nucleotide Sequence of rBoNT/A(0) (His-tagged)

<400> SEQUENCE: 17

atgccgtttg tgaacaagca gttcaactat aaagatccgg ttaatggtgt ggatatcgcc     60

tatatcaaaa ttccgaatgc aggtcagatg cagccggtta aagcctttaa aatccataac    120

aaaatttggg tgattccgga acgtgatacc tttaccaatc cggaagaagg tgatctgaat    180

ccgcctccgg aagcaaaaca ggttccggtt agctattatg atagcaccta tctgagcacc    240

gataacgaga aagataacta tctgaaaggt gtgaccaaac tgtttgaacg catttatagt    300

accgatctgg gtcgtatgct gctgaccagc attgttcgtg gtattccgtt ttggggtggt    360

agcaccattg ataccgaact gaaagttatt gacaccaact gcattaatgt gattcagccg    420

gatggtagct atcgtagcga agaactgaat ctggttatta ttggtccgag cgcagatatc    480

attcagtttg aatgtaaaag ctttggccac gaagttctga atctgacccg taatggttat    540

ggtagtaccc agtatattcg tttcagtccg gattttacct ttggctttga agaaagcctg    600

gaagttgata caaatccgct gttaggtgca ggtaaatttg caaccgatcc ggcagttacc    660

ctggcacacc agctgattta tgccggtcat cgtctgtatg gtattgccat taatccgaat    720

cgtgtgttca aagtgaatac caacgcctat tatgaaatga gcggtctgga agtgagtttt    780

gaagaactgc gtacctttgg tggtcatgat gccaaattta tcgatagcct gcaagaaaat    840

gaatttcgcc tgtactacta taacaaattc aaggatattg cgagcaccct gaataaagcc    900

aaaagcattg ttggcaccac cgcaagcctg cagtatatga aaatgtgtt taaagaaaaa    960

tatctgctga gcgaagatac cagcggtaaa tttagcgttg acaaactgaa attcgataaa   1020

ctgtacaaga tgctgaccga gatttatacc gaagataact tcgtgaagtt tttcaaagtg   1080

ctgaaccgca aaacctacct gaactttgat aaagccgtgt tcaaaatcaa catcgtgccg   1140

aaagtgaact ataccatcta tgatggtttt aacctgcgca ataccaatct ggcagcaaac   1200

tttaatggtc agaacaccga aatcaacaac atgaacttta ccaaactgaa gaacttcacc   1260

ggtctgttcg aattttacaa actgctgtgt gttcgtggca ttattaccag caaaaccaaa   1320

agtctggata aaggctacaa taaagccctg aatgatctgt gcattaaggt gaataattgg   1380
```

```
gacctgtttt ttagcccgag cgaggataat ttcaccaacg atctgaacaa aggcgaagaa   1440
attaccagcg ataccaatat tgaagcagcc gaagaaaaca ttagcctgga tctgattcag   1500
cagtattatc tgaccttcaa cttcgataat gagccggaaa atatcagcat tgaaaacctg   1560
agcagcgata ttattggcca gctggaactg atgccgaata ttgaacgttt tccgaacggc   1620
aaaaaatacg agctggataa atacaccatg ttccattatc tgcgtgccca agaatttgaa   1680
catggtaaaa gccgtattgc actgaccaat agcgttaatg aagcactgct gaacccgagc   1740
cgtgtttata cctttttttag cagcgattac gtgaaaaagg ttaacaaagc aaccgaagca   1800
gccatgtttt taggttgggt tgaacagctg gtttatgatt tcaccgatga aaccagcgaa   1860
gttagcacca ccgataaaat tgcagatatt accatcatca tcccgtatat cggtccggca   1920
ctgaatattg gcaatatgct gtataaagac gattttgtgg gtgccctgat ttttagcggt   1980
gcagttattc tgctggaatt tattccggaa attgccattc cggttctggg cacctttgca   2040
ctggtgagct atattgcaaa taaagttctg accgtgcaga ccatcgataa tgcactgagc   2100
aaacgtaacg aaaaatggga tgaagtgtac aagtatatcg tgaccaattg gctggcaaaa   2160
gttaacaccc agattgacct gattcgcaag aagatgaaag aagcactgga aaatcaggca   2220
gaagcaacca aagccattat caactatcag tataaccagt acaccgaaga agagaaaaat   2280
aacatcaact tcaacatcga cgatctgtcc agcaaactga acgaaagcat caacaaagcc   2340
atgattaaca ttaacaaatt tctgaaccag tgcagcgtga gctatctgat gaatagcatg   2400
attccgtatg gtgtgaaacg tctggaagat tttgatgcaa gcctgaaaga tgccctgctg   2460
aaatatatct atgataatcg tggcaccctg attggtcagg ttgatcgtct gaaagataaa   2520
gtgaacaaca ccctgagtac cgatattcct tttcagctga gcaaatatgt ggataatcag   2580
cgtctgctgt caacctttac cgaatacatt aagaacatca tcaacaccag cattctgaac   2640
ctgcgttatg aaagcaatca tctgattgat ctgagccgtt atgccagcaa aatcaatata   2700
ggcagcaagg ttaacttcga cccgattgac aaaaatcaga tacagctgtt taatctggaa   2760
agcagcaaaa ttgaggtgat cctgaaaaac gccattgtgt ataatagcat gtacgagaat   2820
ttctcgacca gcttttggat tcgtatcccg aaatacttta atagcatcag cctgaacaac   2880
gagtacacca ttattaactg catggaaaac aatagcggct ggaaagttag cctgaattat   2940
ggcgaaatta tctggaccct gcaggatacc caagaaatca aacagcgtgt ggttttcaaa   3000
tacagccaga tgattaatat cagcgactat atcaaccgct ggatttttgt gaccattacc   3060
aataatcgcc tgaataacag caagatctat attaacggtc gtctgattga ccagaaaccg   3120
attagtaatc tgggtaatat tcatgcgagc aacaacatca tgtttaaact ggatggttgt   3180
cgtgataccc atcgttatat ttggatcaag tacttcaacc tgttcgataa agagttgaac   3240
gaaaaagaaa ttaaagacct gtatgataac cagagcaaca gcggtattct gaaggatttt   3300
tggggagatt atctgcagta tgacaaaccg tattatatgc tgaatctgta cgacccgaat   3360
aaatacgtgg atgtgaataa tgttggcatc cgtggttata tgtacctgaa aggtccgcgt   3420
ggtagcgtta tgaccacaaa catttatctg aatagcagcc tgtatcgcgg aaccaaattc   3480
atcattaaaa agtatgccag cggcaacaag gataatattg tgcgtaataa tgatcgcgtg   3540
tacattaacg ttgtggtgaa gaataaagaa tatcgcctgg caaccaatgc aagccaggca   3600
ggcgttgaaa aaattctgag tgccctggaa attccggatg ttggtaatct gagccaggtt   3660
gttgtgatga aaagcaaaaa tgatcagggc atcaccaaca agtgcaaaat gaatctgcag   3720
gacaataacg gcaacgatat tggtttttatt ggcttccacc agttcaacaa tattgcgaaa   3780
```

```
ctggttgcaa gcaattggta taatcgtcag attgaacgta gcagtcgtac cctgggttgt   3840

agctgggaat ttatccctgt ggatgatggt tggggtgaac gtccgctgga aaacctgtat   3900

tttcaaggtg caagtcatca tcaccatcac caccatcatt aa                      3942


<210> SEQ ID NO 18
<211> LENGTH: 1313
<212> TYPE: PRT
<213> ORGANISM: Artificial Sequence
<220> FEATURE:
<223> OTHER INFORMATION: Polypeptide Sequence of rBoNT/A(0) (His-tagged)

<400> SEQUENCE: 18

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335
```

```
Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750
```

```
Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                 1015                 1020

Leu Asn  Asn Ser Lys Ile Tyr  Ile Asn Gly Arg Leu  Ile Asp Gln
    1025                 1030                 1035

Lys Pro  Ile Ser Asn Leu Gly  Asn Ile His Ala Ser  Asn Asn Ile
    1040                 1045                 1050

Met Phe  Lys Leu Asp Gly Cys  Arg Asp Thr His Arg  Tyr Ile Trp
    1055                 1060                 1065

Ile Lys  Tyr Phe Asn Leu Phe  Asp Lys Glu Leu Asn  Glu Lys Glu
    1070                 1075                 1080

Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
```

```
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Gln Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290

Arg Pro  Leu Glu Asn Leu Tyr  Phe Gln Gly Ala Ser  His His His
    1295                1300                1305

His His  His His His
    1310
```

<210> SEQ ID NO 19
<211> LENGTH: 2649
<212> TYPE: DNA
<213> ORGANISM: Artificial Sequence
<220> FEATURE:
<223> OTHER INFORMATION: Nucleotide Sequence of rLHN/A (His-tagged)

<400> SEQUENCE: 19

```
atgccgtttg tgaacaagca gttcaactat aaagatccgg ttaatggtgt ggatatcgcc     60

tatatcaaaa ttccgaatgc aggtcagatg cagccggtta aagcctttaa aatccataac    120

aaaatttggg tgattccgga acgtgatacc tttaccaatc cggaagaagg tgatctgaat    180

ccgcctccgg aagcaaaaca ggttccggtt agctattatg atagcaccta tctgagcacc    240

gataacgaga aagataacta tctgaaaggt gtgaccaaac tgtttgaacg catttatagt    300

accgatctgg gtcgtatgct gctgaccagc attgttcgtg gtattccgtt ttggggtggt    360

agcaccattg ataccgaact gaaagttatt gacaccaact gcattaatgt gattcagccg    420

gatggtagct atcgtagcga agaactgaat ctggttatta ttggtccgag cgcagatatc    480

attcagtttg aatgtaaatc ctttggccac gaagttctga atctgacccg taatggttat    540

ggtagtaccc agtatattcg tttcagtccg gattttacct ttggctttga agaaagcctg    600

gaagttgata caaatccgct gttaggtgca ggtaaatttg caaccgatcc ggcagttacc    660

ctggcacatg aactgattca tgccggtcat cgtctgtatg gtattgcaat taatccgaac    720

cgtgtgttca aagtgaatac caacgcatat tatgaaatga gcggtctgga agtgtcattt    780

gaagaactgc gtacctttgg tggtcatgat gccaaattta tcgatagcct gcaagaaaat    840

gaatttcgcc tgtactacta taacaaattc aaggatattg cgagcaccct gaataaagcc    900

aaaagcattg ttggcaccac cgcaagcctg cagtatatga aaatgtgttt taaagaaaaa    960

tatctgctga gcgaagatac cagcggtaaa tttagcgttg acaaactgaa attcgataaa   1020

ctgtacaaga tgctgaccga gatttatacc gaagataact tcgtgaagtt tttcaaagtg   1080

ctgaaccgca aaacctacct gaactttgat aaagccgtgt tcaaaatcaa catcgtgccg   1140
```

```
aaagtgaact ataccatcta tgatggtttt aacctgcgca ataccaatct ggcagcaaac   1200

tttaatggtc agaacaccga aatcaacaac atgaacttta ccaaactgaa gaacttcacc   1260

ggtctgttcg aattttacaa actgctgtgt gttcgtggca ttattaccag caaaaccaaa   1320

agtctggata aaggctacaa taaagccctg aatgatctgt gcattaaggt gaataattgg   1380

gacctgtttt ttagcccgag cgaggataat ttcaccaacg atctgaacaa aggcgaagaa   1440

attaccagcg ataccaatat tgaagcagcc gaagaaaaca ttagcctgga tctgattcag   1500

cagtattatc tgaccttcaa cttcgataat gagccggaaa atatcagcat tgaaaacctg   1560

agcagcgata ttattggcca gctggaactg atgccgaata ttgaacgttt tccgaacggc   1620

aaaaaatacg agctggataa atacaccatg ttccattatc tgcgtgccca agaatttgaa   1680

catggtaaaa gccgtattgc actgaccaat agcgttaatg aagcactgct gaacccgagc   1740

cgtgtttata cctttttttag cagcgattac gtgaaaaagg ttaacaaagc aaccgaagca   1800

gccatgtttt taggttgggt tgaacagctg gtttatgatt tcaccgatga aaccagcgaa   1860

gttagcacca ccgataaaat tgcagatatt accatcatca tcccgtatat cggtccggca   1920

ctgaatattg gcaatatgct gtataaagac gattttgtgg gtgccctgat ttttagcggt   1980

gcagttattc tgctggaatt tattccggaa attgccattc cggttctggg cacctttgca   2040

ctggtgagct atattgcaaa taaagttctg accgtgcaga ccatcgataa tgcactgagc   2100

aaacgtaacg aaaaatggga tgaagtgtac aagtatatcg tgaccaattg gctggcaaaa   2160

gttaacaccc agattgacct gattcgcaag aagatgaaag aagcactgga aaatcaggca   2220

gaagcaacca aagccattat caactatcag tataaccagt acaccgaaga agagaaaaat   2280

aacatcaact tcaacatcga cgatctgtcc agcaaactga acgaaagcat caacaaagcc   2340

atgattaaca ttaacaaatt tctgaaccag tgcagcgtga gctatctgat gaatagcatg   2400

attccgtatg gtgtgaaacg tctggaagat tttgatgcaa gcctgaaaga tgccctgctg   2460

aaatatatct atgataatcg tggcaccctg attggtcagg ttgatcgtct gaaagataaa   2520

gtgaacaaca ccctgagtac cgatattcct tttcagctga gcaaatatgt ggataatcag   2580

cgtctgctgt caaccgaaaa tctgtatttc cagggtgcaa gtcatcatca ccatcaccac   2640

catcattaa                                                           2649
```

<210> SEQ ID NO 20
<211> LENGTH: 882
<212> TYPE: PRT
<213> ORGANISM: Artificial Sequence
<220> FEATURE:
<223> OTHER INFORMATION: Polypeptide Sequence of rLHN/A (His-tagged)

<400> SEQUENCE: 20

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
```

-continued

```
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510
```

```
Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Glu Asn Leu Tyr Phe Gln Gly Ala Ser His His His His His His
865                 870                 875                 880

His His
```

<210> SEQ ID NO 21
<211> LENGTH: 1323
<212> TYPE: DNA
<213> ORGANISM: Artificial Sequence
<220> FEATURE:
<223> OTHER INFORMATION: Nucleotide Sequence of rHC/A (His-tagged)

<400> SEQUENCE: 21

```
atgcatcatc accatcacca cgaaaatcta tacttccaag gaaaaaacat catcaatact     60
agcattctga acctgcgtta cgagagcaat catctgattg atctgagccg ttatgcaagc    120
aagatcaaca tcggtagcaa ggtcaatttt gacccgatcg ataagaacca gatccagctg    180
tttaatctgg aatcgagcaa aattgaggtt atcctgaaaa acgccattgt ctacaactcc    240
atgtacgaga atttctccac cagcttctgg attcgcatcc cgaaatactt caacagcatt    300
agcctgaaca acgagtatac tatcatcaac tgtatggaga acaacagcgg ttggaaggtg    360
tctctgaact atggtgagat catttggacc ttgcaggaca cccaagagat caagcagcgc    420
gtcgtgttca agtactctca aatgatcaac atttccgatt acattaatcg ttggatcttc    480
gtgaccatta cgaataaccg tctgaataac agcaagattt acatcaatgg tcgcttgatc    540
gatcagaaac cgattagcaa cctgggtaat atccacgcaa gcaacaacat tatgttcaaa    600
ttggacggtt gccgcgatac ccatcgttat atctggatca agtatttcaa cctgtttgat    660
aaagaactga atgagaagga gatcaaagat ttgtatgaca accaatctaa cagcggcatt    720
ttgaaggact tctggggcga ttatctgcaa tacgataagc cgtactatat gctgaacctg    780
tatgatccga acaaatatgt ggatgtcaat aatgtgggta ttcgtggtta catgtatttg    840
aagggtccgc gtggcagcgt tatgacgacc aacatttacc tgaactctag cctgtaccgt    900
ggtacgaaat tcatcattaa gaaatatgcc agcggcaaca aagataacat tgtgcgtaat    960
aacgatcgtg tctacatcaa cgtggtcgtg aagaataaag agtaccgtct ggcgaccaac   1020
gcttcgcagg cgggtgttga gaaaattctg agcgcgttgg agatccctga tgtcggtaat   1080
ctgagccaag tcgtggttat gaagagcaag aacgaccagg gtatcactaa caagtgcaag   1140
atgaacctgc aagacaacaa tggtaacgac atcggcttta ttggtttcca ccagttcaac   1200
aatattgcta aactggtagc gagcaattgg tacaatcgtc agattgagcg cagcagccgt   1260
actttgggct gtagctggga gtttatcccg gtcgatgatg gttggggcga acgtccgctg   1320
taa                                                                 1323
```

<210> SEQ ID NO 22
<211> LENGTH: 440
<212> TYPE: PRT
<213> ORGANISM: Artificial Sequence
<220> FEATURE:
<223> OTHER INFORMATION: Polypeptide Sequence of rHC/A (His-tagged)

<400> SEQUENCE: 22

```
Met His His His His His His Glu Asn Leu Tyr Phe Gln Gly Lys Asn
1               5                   10                  15

Ile Ile Asn Thr Ser Ile Leu Asn Leu Arg Tyr Glu Ser Asn His Leu
            20                  25                  30

Ile Asp Leu Ser Arg Tyr Ala Ser Lys Ile Asn Ile Gly Ser Lys Val
        35                  40                  45

Asn Phe Asp Pro Ile Asp Lys Asn Gln Ile Gln Leu Phe Asn Leu Glu
    50                  55                  60

Ser Ser Lys Ile Glu Val Ile Leu Lys Asn Ala Ile Val Tyr Asn Ser
65                  70                  75                  80

Met Tyr Glu Asn Phe Ser Thr Ser Phe Trp Ile Arg Ile Pro Lys Tyr
                85                  90                  95

Phe Asn Ser Ile Ser Leu Asn Asn Glu Tyr Thr Ile Ile Asn Cys Met
            100                 105                 110
```

```
Glu Asn Asn Ser Gly Trp Lys Val Ser Leu Asn Tyr Gly Glu Ile Ile
        115                 120                 125

Trp Thr Leu Gln Asp Thr Gln Glu Ile Lys Gln Arg Val Val Phe Lys
    130                 135                 140

Tyr Ser Gln Met Ile Asn Ile Ser Asp Tyr Ile Asn Arg Trp Ile Phe
145                 150                 155                 160

Val Thr Ile Thr Asn Asn Arg Leu Asn Asn Ser Lys Ile Tyr Ile Asn
                165                 170                 175

Gly Arg Leu Ile Asp Gln Lys Pro Ile Ser Asn Leu Gly Asn Ile His
            180                 185                 190

Ala Ser Asn Asn Ile Met Phe Lys Leu Asp Gly Cys Arg Asp Thr His
        195                 200                 205

Arg Tyr Ile Trp Ile Lys Tyr Phe Asn Leu Phe Asp Lys Glu Leu Asn
    210                 215                 220

Glu Lys Glu Ile Lys Asp Leu Tyr Asp Asn Gln Ser Asn Ser Gly Ile
225                 230                 235                 240

Leu Lys Asp Phe Trp Gly Asp Tyr Leu Gln Tyr Asp Lys Pro Tyr Tyr
                245                 250                 255

Met Leu Asn Leu Tyr Asp Pro Asn Lys Tyr Val Asp Val Asn Asn Val
            260                 265                 270

Gly Ile Arg Gly Tyr Met Tyr Leu Lys Gly Pro Arg Gly Ser Val Met
        275                 280                 285

Thr Thr Asn Ile Tyr Leu Asn Ser Ser Leu Tyr Arg Gly Thr Lys Phe
    290                 295                 300

Ile Ile Lys Lys Tyr Ala Ser Gly Asn Lys Asp Asn Ile Val Arg Asn
305                 310                 315                 320

Asn Asp Arg Val Tyr Ile Asn Val Val Val Lys Asn Lys Glu Tyr Arg
                325                 330                 335

Leu Ala Thr Asn Ala Ser Gln Ala Gly Val Glu Lys Ile Leu Ser Ala
            340                 345                 350

Leu Glu Ile Pro Asp Val Gly Asn Leu Ser Gln Val Val Val Met Lys
        355                 360                 365

Ser Lys Asn Asp Gln Gly Ile Thr Asn Lys Cys Lys Met Asn Leu Gln
    370                 375                 380

Asp Asn Asn Gly Asn Asp Ile Gly Phe Ile Gly Phe His Gln Phe Asn
385                 390                 395                 400

Asn Ile Ala Lys Leu Val Ala Ser Asn Trp Tyr Asn Arg Gln Ile Glu
                405                 410                 415

Arg Ser Ser Arg Thr Leu Gly Cys Ser Trp Glu Phe Ile Pro Val Asp
            420                 425                 430

Asp Gly Trp Gly Glu Arg Pro Leu
        435                 440
```

<210> SEQ ID NO 23
<211> LENGTH: 1326
<212> TYPE: DNA
<213> ORGANISM: Artificial Sequence
<220> FEATURE:
<223> OTHER INFORMATION: Nucleotide Sequence of rLC/A (His-tagged)

<400> SEQUENCE: 23

```
atgccgtttg tgaacaagca gttcaactat aaagatccgg ttaatggtgt ggatatcgcc      60

tatatcaaaa ttccgaatgc aggtcagatg cagccggtta aagcctttaa aatccataac     120

aaaatttggg tgattccgga acgtgatacc tttaccaatc cggaagaagg tgatctgaat     180
```

```
ccgcctccgg aagcaaaaca ggttccggtt agctattatg atagcaccta tctgagcacc    240

gataacgaga aagataacta tctgaaaggt gtgaccaaac tgtttgaacg catttatagt    300

accgatctgg gtcgtatgct gctgaccagc attgttcgtg gtattccgtt ttggggtggt    360

agcaccattg ataccgaact gaaagttatt gacaccaact gcattaatgt gattcagccg    420

gatggtagct atcgtagcga agaactgaat ctggttatta ttggtccgag cgcagatatc    480

attcagtttg aatgtaaatc ctttggccac gaagttctga atctgacccg taatggttat    540

ggtagtaccc agtatattcg tttcagtccg gattttacct ttggctttga agaaagcctg    600

gaagttgata caaatccgct gttaggtgca ggtaaatttg caaccgatcc ggcagttacc    660

ctggcacatg aactgattca tgccggtcat cgtctgtatg gtattgcaat taatccgaac    720

cgtgtgttca aagtgaatac caacgcatat tatgaaatga gcggtctgga agtgtcattt    780

gaagaactgc gtacctttgg tggtcatgat gccaaattta tcgatagcct gcaagaaaat    840

gaatttcgcc tgtactacta taacaaattc aaggatattg cgagcaccct gaataaagcc    900

aaaagcattg ttggcaccac cgcaagcctg cagtatatga aaatgtgttt taaagaaaaa    960

tatctgctga gcgaagatac cagcggtaaa tttagcgttg acaaactgaa attcgataaa   1020

ctgtacaaga tgctgaccga gatttatacc gaagataact tcgtgaagtt tttcaaagtg   1080

ctgaaccgca aaacctacct gaactttgat aaagccgtgt tcaaaatcaa catcgtgccg   1140

aaagtgaact ataccatcta tgatggtttt aacctgcgca ataccaatct ggcagcaaac   1200

tttaatggtc agaacaccga aatcaacaac atgaacttta ccaaactgaa gaacttcacc   1260

ggtctgtttg aagagaatct gtatttccag ggtgcaagtc atcatcacca tcaccaccat   1320

cattaa                                                               1326
```

```
<210> SEQ ID NO 24
<211> LENGTH: 441
<212> TYPE: PRT
<213> ORGANISM: Artificial Sequence
<220> FEATURE:
<223> OTHER INFORMATION: Polypeptide Sequence of rLC/A (His-tagged)

<400> SEQUENCE: 24

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
```

```
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Glu Asn Leu Tyr Phe Gln Gly Ala
            420                 425                 430

Ser His His His His His His His His
        435                 440
```

<210> SEQ ID NO 25
<211> LENGTH: 3918
<212> TYPE: DNA
<213> ORGANISM: Artificial Sequence
<220> FEATURE:
<223> OTHER INFORMATION: Nucleotide Sequence of rBoNT/FA(0) (His-tagged)

<400> SEQUENCE: 25

```
atgccggttg tgattaacag cttcaattat gatgatccgg tgaacgataa caccatcatt     60

tatatccgtc cgccttatta tgaaaccagc aacacctatt tcaaagcctt ccagattatg    120

gataacgtgt ggattattcc ggaacgttat cgtctgggta ttgatccgag cctgtttaat    180

ccgcctgtta gcctgaaagc aggtagtgat ggttattttg atccgaatta tctgagcacc    240

aacaccgaga aaaacaaata cctgcagatt atgatcaagc tgttcaaacg cattaatagc    300

aaaccggcag gtcagattct gctggaagaa atcaaaaatg caattccgta tctgggcaac    360

agctataccc aagaagaaca gtttaccacc aataatcgta ccgtgagctt taatgttaaa    420
```

```
ctggccaatg gtaatatcgt tcagcagatg gcaaatctga ttatttgggg tccgggtcct    480
gatctgacca caaataaaac cggtggtatc atctatagcc cgtatcagag catggaagca    540
accccgtata aagatggttt tggtagcatt atgaccgtgg aatttagtcc ggaatatgca    600
accgccttta acgatatttc aattgcaagc catagtccgt cgctgtttat caaagatccg    660
gcactgattc tgatgcacca gctgatttat gttctgcatg gtctgtatgg cacctatatc    720
accgaataca aaattacccc gaatgtggtt cagagctata tgaaagttac caaaccgatt    780
accagcgcag aatttctgac ctttggtggt cgtgatcgca atattgttcc gcagagcatt    840
cagagccagc tgtataacaa agttctgagc gattataaac gtattgccag ccgtctgaat    900
aaagttaata ccgcaaccgc actgatcaac atcgatgaat tcaaaaacct gtacgagtgg    960
aaataccagt ttgccaaaga tagcaatggt gtgtatagcg tggatctgaa caaatttgag   1020
cagctgtaca aaaaaatcta tagcttcacc gaattcaacc tggcctatga gtttaaaatc   1080
aaaacccgtc tgggttatct ggccgaaaat tttggtccgt tttatctgcc gaatctgctg   1140
gatgatagca tttataccga agtggatggt tttaacattg gtgcactgag cattaactat   1200
cagggtcaga atattggcag cgatatcaac agcatcaaaa aactgcaagg tcagggtgtt   1260
gttagccgtg ttgttcgtct gtgtagcaat agcaatacca aaaacagcct gtgcattacc   1320
gttaataatc gcgacctgtt ttttatcgca agccaagaaa gctatggcga gaataccatt   1380
aacacctata aagagattga cgataccacc acactggatc cgagctttga agatattctg   1440
gataaagtga tcctgaactt caacgaacag gttattccgc agatgccgaa tcgtaatgtt   1500
agcaccgata ttcagaaaga caactacatc ccgaaatacg attataaccg caccgacatt   1560
atcgatagct atgaagttgg tcgcaactac aacacctttt tctatctgaa tgcccagaaa   1620
tttagcccga acgaaagcaa tattaccctg accagcagct ttgatacagg tctgttagaa   1680
ggtagcaaag tgtatacctt tttcagcagc gatttcatta acaacatcaa caaaccggtt   1740
caggccctgc tgtttattga atgggttaaa caggtgattc gcgattttac caccgaagca   1800
accaaaacct caaccgttga taaactgaaa gatattagcc tggtggtgcc gtatattggt   1860
ctggcactga atattggtga tgagatctac aaacagcatt ttgcagaagc agttgaactg   1920
gttggtgcag gtctgctgct ggaattttca ccggaatttc ttattccgac gctgctgatt   1980
tttaccatca aggttatctt gaccggtagc attcgcgata aagacaaaat cattaaaacc   2040
ctggataacg ccctgaatgt tcgtgatcag aaatggaaag aactgtatcg ttgggttgtt   2100
agcaaatggc tgaccaccat taatacgcag ttcaacaaac gcaaagaaca aatgtacaaa   2160
gccctgaaaa atcaggccac cgccattaaa aagatcatcg agaacaaata taacaactat   2220
accaccgatg aaaaaagcaa gatcgatagc agctataaca tcaacgaaat tgaacgcacc   2280
ctgaacgaaa aaatcaatct ggccatgaaa aacatcgagc agtttattac cgaaagcagc   2340
attgcctatc tgatcaatat catcaacaac gaaacgatcc agaaactgaa aagctatgat   2400
gacctggttc gtcgttatct gctgggttat attcgtaatc atagcagcat tctgggcaat   2460
agcgttgaag aactgaattc caaagtgaac aaccatctgg ataatggcat tccgtttgaa   2520
ctgagcagtt ataccaatga tagcctgctg atccgctact tcaataaaaa ctatggcgaa   2580
ctgaagtaca actgcattct gaacatcaaa tatgagatgg atcgtgacaa actggttgat   2640
agcagcggtt atcgtagccg tatcaatatt ggtacaggcg tcaaatttag cgagatcgat   2700
aaaaatcaag tgcagctgag caatctggaa tccagcaaaa ttgaagtcat tctgaataac   2760
```

```
ggcgtcatct ataacagcat gtatgaaaac ttttcgacca gcttttggat tcgcattccg   2820
aaatactttc gcaacatcaa taacgagtac aagatcatca gctgtatgca gaataatagc   2880
ggttgggaag tgagcctgaa ttttagcaat atgaactcga aaatcatctg gaccctgcag   2940
gataccgaag gtatcaaaaa aaccgttgtg tttcagtaca cccagaacat taacattagc   3000
gactatatca accgctggat ctttgtgacc attacaaata atcgtctgag caacagcaaa   3060
atctacatta atggtcgcct gatcaacgaa gaaagcatta gcgatctggg taatatccat   3120
gccagcaaca acattatgtt taaactggat ggttgccgtg atccgcatcg ttatatctgg   3180
attaaatact ttaacctgtt tgacaaagag ctgaacaaga aagaaattaa agatctgtac   3240
gacaaccaga gcaatagcgg tattctgaaa gatttctggg gtgattatct gcagtatgac   3300
aaaccgtatt atatgctgaa tctgtatgac ccgaataagt atctggatgt gaataatgtt   3360
ggcatccgtg gctatatgta tctgaaaggt ccgcgtggtc gtattgtgac caccaacatt   3420
tatctgaata gcaccctgta tatgggcacc aaattcatca ttaagaaata tgccagcggc   3480
aacaaagata acattgtgcg taataatgat cgcgtgtata ttaacgtggt ggtgaagaat   3540
aaagaatatc gcctggcaac caatgcaagc caggcaggcg ttgaaaaaat tctgagcgca   3600
gttgaaatcc cggatgttgg taatctgagc caggttgttg tgatgaaaag cgaaaatgat   3660
cagggcattc gcaacaagtg taaaatgaat ctgcaagaca ataacggcaa cgatattggc   3720
tttatcggct ttcaccagtt taataacatt gcaaaactgg tggccagcaa ctggtataac   3780
cgtcagattg gtaaagcaag ccgtaccttt ggttgtagct gggaatttat cccggttgat   3840
gatggttggg gtgaaagcag cctggaaaat ctgtatttcc agggtgccag tcatcatcac   3900
caccatcacc atcactga                                                 3918
```

<210> SEQ ID NO 26
<211> LENGTH: 1305
<212> TYPE: PRT
<213> ORGANISM: Artificial Sequence
<220> FEATURE:
<223> OTHER INFORMATION: Polypeptide Sequence of rBoNT/FA(0) (His-tagged)

<400> SEQUENCE: 26

```
Met Pro Val Val Ile Asn Ser Phe Asn Tyr Asp Asp Pro Val Asn Asp
1               5                   10                  15

Asn Thr Ile Ile Tyr Ile Arg Pro Pro Tyr Tyr Glu Thr Ser Asn Thr
            20                  25                  30

Tyr Phe Lys Ala Phe Gln Ile Met Asp Asn Val Trp Ile Ile Pro Glu
        35                  40                  45

Arg Tyr Arg Leu Gly Ile Asp Pro Ser Leu Phe Asn Pro Pro Val Ser
    50                  55                  60

Leu Lys Ala Gly Ser Asp Gly Tyr Phe Asp Pro Asn Tyr Leu Ser Thr
65                  70                  75                  80

Asn Thr Glu Lys Asn Lys Tyr Leu Gln Ile Met Ile Lys Leu Phe Lys
                85                  90                  95

Arg Ile Asn Ser Lys Pro Ala Gly Gln Ile Leu Leu Glu Glu Ile Lys
            100                 105                 110

Asn Ala Ile Pro Tyr Leu Gly Asn Ser Tyr Thr Gln Glu Glu Gln Phe
        115                 120                 125

Thr Thr Asn Asn Arg Thr Val Ser Phe Asn Val Lys Leu Ala Asn Gly
    130                 135                 140

Asn Ile Val Gln Gln Met Ala Asn Leu Ile Ile Trp Gly Pro Gly Pro
```

```
145                 150                 155                 160

Asp Leu Thr Thr Asn Lys Thr Gly Gly Ile Ile Tyr Ser Pro Tyr Gln
                165                 170                 175

Ser Met Glu Ala Thr Pro Tyr Lys Asp Gly Phe Gly Ser Ile Met Thr
            180                 185                 190

Val Glu Phe Ser Pro Glu Tyr Ala Thr Ala Phe Asn Asp Ile Ser Ile
        195                 200                 205

Ala Ser His Ser Pro Ser Leu Phe Ile Lys Asp Pro Ala Leu Ile Leu
    210                 215                 220

Met His Gln Leu Ile Tyr Val Leu His Gly Leu Tyr Gly Thr Tyr Ile
225                 230                 235                 240

Thr Glu Tyr Lys Ile Thr Pro Asn Val Val Gln Ser Tyr Met Lys Val
                245                 250                 255

Thr Lys Pro Ile Thr Ser Ala Glu Phe Leu Thr Phe Gly Gly Arg Asp
            260                 265                 270

Arg Asn Ile Val Pro Gln Ser Ile Gln Ser Gln Leu Tyr Asn Lys Val
        275                 280                 285

Leu Ser Asp Tyr Lys Arg Ile Ala Ser Arg Leu Asn Lys Val Asn Thr
    290                 295                 300

Ala Thr Ala Leu Ile Asn Ile Asp Glu Phe Lys Asn Leu Tyr Glu Trp
305                 310                 315                 320

Lys Tyr Gln Phe Ala Lys Asp Ser Asn Gly Val Tyr Ser Val Asp Leu
                325                 330                 335

Asn Lys Phe Glu Gln Leu Tyr Lys Lys Ile Tyr Ser Phe Thr Glu Phe
            340                 345                 350

Asn Leu Ala Tyr Glu Phe Lys Ile Lys Thr Arg Leu Gly Tyr Leu Ala
        355                 360                 365

Glu Asn Phe Gly Pro Phe Tyr Leu Pro Asn Leu Leu Asp Asp Ser Ile
    370                 375                 380

Tyr Thr Glu Val Asp Gly Phe Asn Ile Gly Ala Leu Ser Ile Asn Tyr
385                 390                 395                 400

Gln Gly Gln Asn Ile Gly Ser Asp Ile Asn Ser Ile Lys Lys Leu Gln
                405                 410                 415

Gly Gln Gly Val Val Ser Arg Val Val Arg Leu Cys Ser Asn Ser Asn
            420                 425                 430

Thr Lys Asn Ser Leu Cys Ile Thr Val Asn Asn Arg Asp Leu Phe Phe
        435                 440                 445

Ile Ala Ser Gln Glu Ser Tyr Gly Glu Asn Thr Ile Asn Thr Tyr Lys
    450                 455                 460

Glu Ile Asp Asp Thr Thr Thr Leu Asp Pro Ser Phe Glu Asp Ile Leu
465                 470                 475                 480

Asp Lys Val Ile Leu Asn Phe Asn Glu Gln Val Ile Pro Gln Met Pro
                485                 490                 495

Asn Arg Asn Val Ser Thr Asp Ile Gln Lys Asp Asn Tyr Ile Pro Lys
            500                 505                 510

Tyr Asp Tyr Asn Arg Thr Asp Ile Ile Asp Ser Tyr Glu Val Gly Arg
        515                 520                 525

Asn Tyr Asn Thr Phe Phe Tyr Leu Asn Ala Gln Lys Phe Ser Pro Asn
    530                 535                 540

Glu Ser Asn Ile Thr Leu Thr Ser Ser Phe Asp Thr Gly Leu Leu Glu
545                 550                 555                 560

Gly Ser Lys Val Tyr Thr Phe Phe Ser Ser Asp Phe Ile Asn Asn Ile
                565                 570                 575
```

```
Asn Lys Pro Val Gln Ala Leu Leu Phe Ile Glu Trp Val Lys Gln Val
            580                 585                 590

Ile Arg Asp Phe Thr Thr Glu Ala Thr Lys Thr Ser Thr Val Asp Lys
        595                 600                 605

Leu Lys Asp Ile Ser Leu Val Val Pro Tyr Ile Gly Leu Ala Leu Asn
    610                 615                 620

Ile Gly Asp Glu Ile Tyr Lys Gln His Phe Ala Glu Ala Val Glu Leu
625                 630                 635                 640

Val Gly Ala Gly Leu Leu Leu Glu Phe Ser Pro Glu Phe Leu Ile Pro
                645                 650                 655

Thr Leu Leu Ile Phe Thr Ile Lys Gly Tyr Leu Thr Gly Ser Ile Arg
            660                 665                 670

Asp Lys Asp Lys Ile Ile Lys Thr Leu Asp Asn Ala Leu Asn Val Arg
        675                 680                 685

Asp Gln Lys Trp Lys Glu Leu Tyr Arg Trp Val Val Ser Lys Trp Leu
    690                 695                 700

Thr Thr Ile Asn Thr Gln Phe Asn Lys Arg Lys Glu Gln Met Tyr Lys
705                 710                 715                 720

Ala Leu Lys Asn Gln Ala Thr Ala Ile Lys Lys Ile Ile Glu Asn Lys
                725                 730                 735

Tyr Asn Asn Tyr Thr Thr Asp Glu Lys Ser Lys Ile Asp Ser Ser Tyr
            740                 745                 750

Asn Ile Asn Glu Ile Glu Arg Thr Leu Asn Glu Lys Ile Asn Leu Ala
        755                 760                 765

Met Lys Asn Ile Glu Gln Phe Ile Thr Glu Ser Ser Ile Ala Tyr Leu
    770                 775                 780

Ile Asn Ile Ile Asn Asn Glu Thr Ile Gln Lys Leu Lys Ser Tyr Asp
785                 790                 795                 800

Asp Leu Val Arg Arg Tyr Leu Leu Gly Tyr Ile Arg Asn His Ser Ser
                805                 810                 815

Ile Leu Gly Asn Ser Val Glu Glu Leu Asn Ser Lys Val Asn Asn His
            820                 825                 830

Leu Asp Asn Gly Ile Pro Phe Glu Leu Ser Ser Tyr Thr Asn Asp Ser
        835                 840                 845

Leu Leu Ile Arg Tyr Phe Asn Lys Asn Tyr Gly Glu Leu Lys Tyr Asn
    850                 855                 860

Cys Ile Leu Asn Ile Lys Tyr Glu Met Asp Arg Asp Lys Leu Val Asp
865                 870                 875                 880

Ser Ser Gly Tyr Arg Ser Arg Ile Asn Ile Gly Thr Gly Val Lys Phe
                885                 890                 895

Ser Glu Ile Asp Lys Asn Gln Val Gln Leu Ser Asn Leu Glu Ser Ser
            900                 905                 910

Lys Ile Glu Val Ile Leu Asn Asn Gly Val Ile Tyr Asn Ser Met Tyr
        915                 920                 925

Glu Asn Phe Ser Thr Ser Phe Trp Ile Arg Ile Pro Lys Tyr Phe Arg
    930                 935                 940

Asn Ile Asn Asn Glu Tyr Lys Ile Ile Ser Cys Met Gln Asn Asn Ser
945                 950                 955                 960

Gly Trp Glu Val Ser Leu Asn Phe Ser Asn Met Asn Ser Lys Ile Ile
                965                 970                 975

Trp Thr Leu Gln Asp Thr Glu Gly Ile Lys Lys Thr Val Val Phe Gln
            980                 985                 990
```

```
Tyr Thr Gln Asn Ile Asn Ile Ser  Asp Tyr Ile Asn Arg  Trp Ile Phe
        995                 1000                 1005

Val Thr  Ile Thr Asn Asn Arg  Leu Ser Asn Ser Lys  Ile Tyr Ile
    1010                 1015                 1020

Asn Gly  Arg Leu Ile Asn Glu  Glu Ser Ile Ser Asp  Leu Gly Asn
    1025                 1030                 1035

Ile His  Ala Ser Asn Asn Ile  Met Phe Lys Leu Asp  Gly Cys Arg
    1040                 1045                 1050

Asp Pro  His Arg Tyr Ile Trp  Ile Lys Tyr Phe Asn  Leu Phe Asp
    1055                 1060                 1065

Lys Glu  Leu Asn Lys Lys Glu  Ile Lys Asp Leu Tyr  Asp Asn Gln
    1070                 1075                 1080

Ser Asn  Ser Gly Ile Leu Lys  Asp Phe Trp Gly Asp  Tyr Leu Gln
    1085                 1090                 1095

Tyr Asp  Lys Pro Tyr Tyr Met  Leu Asn Leu Tyr Asp  Pro Asn Lys
    1100                 1105                 1110

Tyr Leu  Asp Val Asn Asn Val  Gly Ile Arg Gly Tyr  Met Tyr Leu
    1115                 1120                 1125

Lys Gly  Pro Arg Gly Arg Ile  Val Thr Thr Asn Ile  Tyr Leu Asn
    1130                 1135                 1140

Ser Thr  Leu Tyr Met Gly Thr  Lys Phe Ile Ile Lys  Lys Tyr Ala
    1145                 1150                 1155

Ser Gly  Asn Lys Asp Asn Ile  Val Arg Asn Asn Asp  Arg Val Tyr
    1160                 1165                 1170

Ile Asn  Val Val Val Lys Asn  Lys Glu Tyr Arg Leu  Ala Thr Asn
    1175                 1180                 1185

Ala Ser  Gln Ala Gly Val Glu  Lys Ile Leu Ser Ala  Val Glu Ile
    1190                 1195                 1200

Pro Asp  Val Gly Asn Leu Ser  Gln Val Val Val Met  Lys Ser Glu
    1205                 1210                 1215

Asn Asp  Gln Gly Ile Arg Asn  Lys Cys Lys Met Asn  Leu Gln Asp
    1220                 1225                 1230

Asn Asn  Gly Asn Asp Ile Gly  Phe Ile Gly Phe His  Gln Phe Asn
    1235                 1240                 1245

Asn Ile  Ala Lys Leu Val Ala  Ser Asn Trp Tyr Asn  Arg Gln Ile
    1250                 1255                 1260

Gly Lys  Ala Ser Arg Thr Phe  Gly Cys Ser Trp Glu  Phe Ile Pro
    1265                 1270                 1275

Val Asp  Asp Gly Trp Gly Glu  Ser Ser Leu Glu Asn  Leu Tyr Phe
    1280                 1285                 1290

Gln Gly  Ala Ser His His His  His His His His His
    1295                 1300                 1305
```

<210> SEQ ID NO 27
<211> LENGTH: 2634
<212> TYPE: DNA
<213> ORGANISM: Artificial Sequence
<220> FEATURE:
<223> OTHER INFORMATION: Nucleotide Sequence of rLHN/FA (His-tagged)

<400> SEQUENCE: 27

```
atgccggttg tgattaacag cttcaattat gatgatccgg tgaacgataa caccatcatt      60

tatatccgtc cgccttatta tgaaaccagc aacacctatt tcaaagcctt ccagattatg     120

gataacgtgt ggattattcc ggaacgttat cgtctgggta ttgatccgag cctgtttaat     180
```

```
ccgcctgtta gcctgaaagc aggtagtgat ggttattttg atccgaatta tctgagcacc    240
aacaccgaga aaaacaaata cctgcagatt atgatcaagc tgttcaaacg cattaatagc    300
aaaccggcag gtcagattct gctggaagaa atcaaaaatg caattccgta tctgggcaac    360
agctataccc aagaagaaca gtttaccacc aataatcgta ccgtgagctt taatgttaaa    420
ctggccaatg gtaatatcgt tcagcagatg gcaaatctga ttatttgggg tccgggtcct    480
gatctgacca caaataaaac cggtggtatc atctatagcc cgtatcagag catggaagca    540
accccgtata aagatggttt tggtagcatt atgaccgtgg aatttagtcc ggaatatgca    600
accgccttta acgatatttc aattgcaagc catagtccgt cgctgtttat caaagatccg    660
gcactgattc tgatgcatga actgattcat gttctgcatg gtctgtatgg cacctatatt    720
accgaataca aaattacccc gaatgtggtg cagagctata tgaaagttac caaaccgatt    780
accagcgcag aatttctgac ctttggtggt cgtgatcgca atattgttcc gcagagcatt    840
cagagccagc tgtataacaa agttctgagc gattataaac gtattgccag ccgtctgaat    900
aaagttaata ccgcaaccgc actgatcaac atcgatgaat tcaaaaacct gtacgagtgg    960
aaataccagt ttgccaaaga tagcaatggt gtgtatagcg tggatctgaa caaatttgag   1020
cagctgtaca aaaaaatcta tagcttcacc gaattcaacc tggcctatga gtttaaaatc   1080
aaaacccgtc tgggttatct ggccgaaaat tttggtccgt tttatctgcc gaatctgctg   1140
gatgatagca tttataccga agtggatggt tttaacattg gtgcactgag cattaactat   1200
cagggtcaga atattggcag cgatatcaac agcatcaaaa aactgcaagg tcagggtgtt   1260
gttagccgtg ttgttcgtct gtgtagcaat agcaatacca aaaacagcct gtgcattacc   1320
gttaataatc gcgacctgtt ttttatcgca agccaagaaa gctatggcga gaataccatt   1380
aacacctata aagagattga cgataccacc acactggatc cgagctttga agatattctg   1440
gataaagtga tcctgaactt caacgaacag gttattccgc agatgccgaa tcgtaatgtt   1500
agcaccgata ttcagaaaga caactacatc ccgaaatacg attataaccg caccgacatt   1560
atcgatagct atgaagttgg tcgcaactac aacacctttt tctatctgaa tgcccagaaa   1620
tttagcccga acgaaagcaa tattaccctg accagcagct ttgatacagg tctgttagaa   1680
ggtagcaaag tgtatacctt tttcagcagc gatttcatta acaacatcaa caaaccggtt   1740
caggccctgc tgtttattga atgggttaaa caggtgattc gcgattttac caccgaagca   1800
accaaaacct caaccgttga taaactgaaa gatattagcc tggtggtgcc gtatattggt   1860
ctggcactga atattggtga tgagatctac aaacagcatt ttgcagaagc agttgaactg   1920
gttggtgcag gtctgctgct ggaattttca ccggaatttc ttattccgac gctgctgatt   1980
tttaccatca aggttatcct gaccggtagc attcgcgata aagacaaaat cattaaaacc   2040
ctggataacg ccctgaatgt tcgtgatcag aaatggaaag aactgtatcg ttgggttgtt   2100
agcaaatggc tgaccaccat taatacgcag ttcaacaaac gcaaagaaca aatgtacaaa   2160
gccctgaaaa atcaggccac cgccattaaa aagatcatcg agaacaaata taacaactat   2220
accaccgatg aaaaaagcaa gatcgatagc agctataaca tcaacgaaat tgaacgcacc   2280
ctgaacgaaa aaatcaatct ggccatgaaa aacatcgagc agtttattac agaaagcagc   2340
attgcctacc tgatcaatat catcaacaac gaaaccattc agaaactgaa aagctatgat   2400
gacctggttc gtcgttatct gctgggttat attcgtaatc atagcagcat tctgggcaat   2460
agcgttgaag aactgaattc caaagtgaac aaccatctgg ataatggcat tccgtttgaa   2520
ctgagcagtt ataccaatga tagcctgctg atccgctact tcaataaaaa ctatggcgaa   2580
```

gagaacctgt atttccaggg tgccagtcat catcaccacc atcaccatca ctga 2634

<210> SEQ ID NO 28
<211> LENGTH: 877
<212> TYPE: PRT
<213> ORGANISM: Artificial Sequence
<220> FEATURE:
<223> OTHER INFORMATION: Polypeptide Sequence of rLHN/FA (His-tagged)

<400> SEQUENCE: 28

Met Pro Val Val Ile Asn Ser Phe Asn Tyr Asp Asp Pro Val Asn Asp
1 5 10 15

Asn Thr Ile Ile Tyr Ile Arg Pro Pro Tyr Tyr Glu Thr Ser Asn Thr
20 25 30

Tyr Phe Lys Ala Phe Gln Ile Met Asp Asn Val Trp Ile Ile Pro Glu
35 40 45

Arg Tyr Arg Leu Gly Ile Asp Pro Ser Leu Phe Asn Pro Pro Val Ser
50 55 60

Leu Lys Ala Gly Ser Asp Gly Tyr Phe Asp Pro Asn Tyr Leu Ser Thr
65 70 75 80

Asn Thr Glu Lys Asn Lys Tyr Leu Gln Ile Met Ile Lys Leu Phe Lys
85 90 95

Arg Ile Asn Ser Lys Pro Ala Gly Gln Ile Leu Leu Glu Glu Ile Lys
100 105 110

Asn Ala Ile Pro Tyr Leu Gly Asn Ser Tyr Thr Gln Glu Glu Gln Phe
115 120 125

Thr Thr Asn Asn Arg Thr Val Ser Phe Asn Val Lys Leu Ala Asn Gly
130 135 140

Asn Ile Val Gln Gln Met Ala Asn Leu Ile Ile Trp Gly Pro Gly Pro
145 150 155 160

Asp Leu Thr Thr Asn Lys Thr Gly Gly Ile Ile Tyr Ser Pro Tyr Gln
165 170 175

Ser Met Glu Ala Thr Pro Tyr Lys Asp Gly Phe Gly Ser Ile Met Thr
180 185 190

Val Glu Phe Ser Pro Glu Tyr Ala Thr Ala Phe Asn Asp Ile Ser Ile
195 200 205

Ala Ser His Ser Pro Ser Leu Phe Ile Lys Asp Pro Ala Leu Ile Leu
210 215 220

Met His Glu Leu Ile His Val Leu His Gly Leu Tyr Gly Thr Tyr Ile
225 230 235 240

Thr Glu Tyr Lys Ile Thr Pro Asn Val Val Gln Ser Tyr Met Lys Val
245 250 255

Thr Lys Pro Ile Thr Ser Ala Glu Phe Leu Thr Phe Gly Gly Arg Asp
260 265 270

Arg Asn Ile Val Pro Gln Ser Ile Gln Ser Gln Leu Tyr Asn Lys Val
275 280 285

Leu Ser Asp Tyr Lys Arg Ile Ala Ser Arg Leu Asn Lys Val Asn Thr
290 295 300

Ala Thr Ala Leu Ile Asn Ile Asp Glu Phe Lys Asn Leu Tyr Glu Trp
305 310 315 320

Lys Tyr Gln Phe Ala Lys Asp Ser Asn Gly Val Tyr Ser Val Asp Leu
325 330 335

Asn Lys Phe Glu Gln Leu Tyr Lys Lys Ile Tyr Ser Phe Thr Glu Phe
340 345 350

```
Asn Leu Ala Tyr Glu Phe Lys Ile Lys Thr Arg Leu Gly Tyr Leu Ala
        355                 360                 365

Glu Asn Phe Gly Pro Phe Tyr Leu Pro Asn Leu Leu Asp Asp Ser Ile
    370                 375                 380

Tyr Thr Glu Val Asp Gly Phe Asn Ile Gly Ala Leu Ser Ile Asn Tyr
385                 390                 395                 400

Gln Gly Gln Asn Ile Gly Ser Asp Ile Asn Ser Ile Lys Lys Leu Gln
                405                 410                 415

Gly Gln Gly Val Val Ser Arg Val Val Arg Leu Cys Ser Asn Ser Asn
            420                 425                 430

Thr Lys Asn Ser Leu Cys Ile Thr Val Asn Asn Arg Asp Leu Phe Phe
        435                 440                 445

Ile Ala Ser Gln Glu Ser Tyr Gly Glu Asn Thr Ile Asn Thr Tyr Lys
    450                 455                 460

Glu Ile Asp Asp Thr Thr Thr Leu Asp Pro Ser Phe Glu Asp Ile Leu
465                 470                 475                 480

Asp Lys Val Ile Leu Asn Phe Asn Glu Gln Val Ile Pro Gln Met Pro
                485                 490                 495

Asn Arg Asn Val Ser Thr Asp Ile Gln Lys Asp Asn Tyr Ile Pro Lys
            500                 505                 510

Tyr Asp Tyr Asn Arg Thr Asp Ile Ile Asp Ser Tyr Glu Val Gly Arg
        515                 520                 525

Asn Tyr Asn Thr Phe Phe Tyr Leu Asn Ala Gln Lys Phe Ser Pro Asn
    530                 535                 540

Glu Ser Asn Ile Thr Leu Thr Ser Ser Phe Asp Thr Gly Leu Leu Glu
545                 550                 555                 560

Gly Ser Lys Val Tyr Thr Phe Phe Ser Ser Asp Phe Ile Asn Asn Ile
                565                 570                 575

Asn Lys Pro Val Gln Ala Leu Leu Phe Ile Glu Trp Val Lys Gln Val
            580                 585                 590

Ile Arg Asp Phe Thr Thr Glu Ala Thr Lys Thr Ser Thr Val Asp Lys
        595                 600                 605

Leu Lys Asp Ile Ser Leu Val Val Pro Tyr Ile Gly Leu Ala Leu Asn
    610                 615                 620

Ile Gly Asp Glu Ile Tyr Lys Gln His Phe Ala Glu Ala Val Glu Leu
625                 630                 635                 640

Val Gly Ala Gly Leu Leu Leu Glu Phe Ser Pro Glu Phe Leu Ile Pro
                645                 650                 655

Thr Leu Leu Ile Phe Thr Ile Lys Gly Tyr Leu Thr Gly Ser Ile Arg
            660                 665                 670

Asp Lys Asp Lys Ile Ile Lys Thr Leu Asp Asn Ala Leu Asn Val Arg
        675                 680                 685

Asp Gln Lys Trp Lys Glu Leu Tyr Arg Trp Val Val Ser Lys Trp Leu
    690                 695                 700

Thr Thr Ile Asn Thr Gln Phe Asn Lys Arg Lys Glu Gln Met Tyr Lys
705                 710                 715                 720

Ala Leu Lys Asn Gln Ala Thr Ala Ile Lys Lys Ile Ile Glu Asn Lys
                725                 730                 735

Tyr Asn Asn Tyr Thr Thr Asp Glu Lys Ser Lys Ile Asp Ser Ser Tyr
            740                 745                 750

Asn Ile Asn Glu Ile Glu Arg Thr Leu Asn Glu Lys Ile Asn Leu Ala
        755                 760                 765

Met Lys Asn Ile Glu Gln Phe Ile Thr Glu Ser Ser Ile Ala Tyr Leu
```

```
    770                 775                 780

Ile Asn Ile Ile Asn Asn Glu Thr Ile Gln Lys Leu Lys Ser Tyr Asp
785                 790                 795                 800

Asp Leu Val Arg Arg Tyr Leu Leu Gly Tyr Ile Arg Asn His Ser Ser
                805                 810                 815

Ile Leu Gly Asn Ser Val Glu Glu Leu Asn Ser Lys Val Asn Asn His
            820                 825                 830

Leu Asp Asn Gly Ile Pro Phe Glu Leu Ser Ser Tyr Thr Asn Asp Ser
        835                 840                 845

Leu Leu Ile Arg Tyr Phe Asn Lys Asn Tyr Gly Glu Glu Asn Leu Tyr
    850                 855                 860

Phe Gln Gly Ala Ser His His His His His His His His
865                 870                 875


<210> SEQ ID NO 29
<211> LENGTH: 1341
<212> TYPE: DNA
<213> ORGANISM: Artificial Sequence
<220> FEATURE:
<223> OTHER INFORMATION: Nucleotide Sequence of rHC/FA (His-tagged)

<400> SEQUENCE: 29

atgctgaagt ataactgcat cctgaacatc aaatatgaga tggatcgtga taaactggtt     60

gatagcagcg gttatcgtag ccgtatcaat attggcaccg gtgtgaaatt tagcgagatc    120

gataaaaatc aggtgcagct gagcaatctg gaaagcagca aaattgaagt gattctgaat    180

aacggcgtga tctacaatag catgtatgaa aacttttcga ccagcttctg gattcgcatt    240

ccgaaatact ttcgcaacat caacaacgag tacaagatta tcagctgtat gcagaataat    300

agcggttggg aagttagcct gaatttcagc aatatgaaca gcaaaatcat ttggaccctg    360

caggataccg aaggtatcaa aaaaaccgtt gtgtttcagt acacccagaa cattaacatc    420

agcgattaca ttaaccgctg gatctttgtg accattacca ataatcgtct gagcaacagc    480

aagatctata ttaacggtcg cctgattaac gaagagagca ttagcgatct gggtaatatt    540

catgccagca acaacatcat gtttaaactg gatggttgtc gtgatccgca tcgttatatt    600

tggatcaaat acttcaacct gtttgataaa gaactgaaca aaaaagaaat caaagacctg    660

tatgataacc agagcaatag cggcattctg aaagattttt ggggtgatta tctgcagtat    720

gacaaaccgt attacatgct gaatctgtac gatccgaaca aatatctgga tgtgaataat    780

gtgggtatcc gtggctatat gtatctgaaa ggtccgcgtg gtcgtattgt taccaccaac    840

atttatctga atagcaccct gtatatgggc accaaattca tcattaaaaa gtatgccagc    900

ggcaacaaag ataacattgt gcgtaataat gatcgcgtgt atatcaatgt ggtggtgaag    960

aataaagaat atcgtctggc caccaatgca agccaggcag gcgttgaaaa aattctgagc   1020

gcagttgaaa ttccggatgt tggtaatctg agccaggttg ttgttatgaa aagcgaaaat   1080

gatcagggca ttcgcaacaa atgcaaaatg aatctgcagg acaataacgg caacgatatt   1140

ggttttattg gcttccacca gttcaacaac attgcaaaac tggtggcgag caattggtat   1200

aatcgtcaga ttggtaaagc aagccgtacc tttggttgta gctgggaatt tattccggtt   1260

gatgatggtt ggggtgaaag cagcctggaa aatctgtatt ttcagggtgc aagtcatcat   1320

caccaccatc accatcatta a                                              1341


<210> SEQ ID NO 30
<211> LENGTH: 446
```

```
<212> TYPE: PRT
<213> ORGANISM: Artificial Sequence
<220> FEATURE:
<223> OTHER INFORMATION: Polypeptide Sequence of rHC/FA (His-tagged)

<400> SEQUENCE: 30

Met Leu Lys Tyr Asn Cys Ile Leu Asn Ile Lys Tyr Glu Met Asp Arg
1               5                   10                  15

Asp Lys Leu Val Asp Ser Ser Gly Tyr Arg Ser Arg Ile Asn Ile Gly
            20                  25                  30

Thr Gly Val Lys Phe Ser Glu Ile Asp Lys Asn Gln Val Gln Leu Ser
        35                  40                  45

Asn Leu Glu Ser Ser Lys Ile Glu Val Ile Leu Asn Asn Gly Val Ile
    50                  55                  60

Tyr Asn Ser Met Tyr Glu Asn Phe Ser Thr Ser Phe Trp Ile Arg Ile
65                  70                  75                  80

Pro Lys Tyr Phe Arg Asn Ile Asn Asn Glu Tyr Lys Ile Ile Ser Cys
                85                  90                  95

Met Gln Asn Asn Ser Gly Trp Glu Val Ser Leu Asn Phe Ser Asn Met
            100                 105                 110

Asn Ser Lys Ile Ile Trp Thr Leu Gln Asp Thr Glu Gly Ile Lys Lys
        115                 120                 125

Thr Val Val Phe Gln Tyr Thr Gln Asn Ile Asn Ile Ser Asp Tyr Ile
    130                 135                 140

Asn Arg Trp Ile Phe Val Thr Ile Thr Asn Asn Arg Leu Ser Asn Ser
145                 150                 155                 160

Lys Ile Tyr Ile Asn Gly Arg Leu Ile Asn Glu Glu Ser Ile Ser Asp
                165                 170                 175

Leu Gly Asn Ile His Ala Ser Asn Asn Ile Met Phe Lys Leu Asp Gly
            180                 185                 190

Cys Arg Asp Pro His Arg Tyr Ile Trp Ile Lys Tyr Phe Asn Leu Phe
        195                 200                 205

Asp Lys Glu Leu Asn Lys Lys Glu Ile Lys Asp Leu Tyr Asp Asn Gln
    210                 215                 220

Ser Asn Ser Gly Ile Leu Lys Asp Phe Trp Gly Asp Tyr Leu Gln Tyr
225                 230                 235                 240

Asp Lys Pro Tyr Tyr Met Leu Asn Leu Tyr Asp Pro Asn Lys Tyr Leu
                245                 250                 255

Asp Val Asn Asn Val Gly Ile Arg Gly Tyr Met Tyr Leu Lys Gly Pro
            260                 265                 270

Arg Gly Arg Ile Val Thr Thr Asn Ile Tyr Leu Asn Ser Thr Leu Tyr
        275                 280                 285

Met Gly Thr Lys Phe Ile Ile Lys Lys Tyr Ala Ser Gly Asn Lys Asp
    290                 295                 300

Asn Ile Val Arg Asn Asn Asp Arg Val Tyr Ile Asn Val Val Val Lys
305                 310                 315                 320

Asn Lys Glu Tyr Arg Leu Ala Thr Asn Ala Ser Gln Ala Gly Val Glu
                325                 330                 335

Lys Ile Leu Ser Ala Val Glu Ile Pro Asp Val Gly Asn Leu Ser Gln
            340                 345                 350

Val Val Val Met Lys Ser Glu Asn Asp Gln Gly Ile Arg Asn Lys Cys
        355                 360                 365

Lys Met Asn Leu Gln Asp Asn Asn Gly Asn Asp Ile Gly Phe Ile Gly
    370                 375                 380
```

```
Phe His Gln Phe Asn Asn Ile Ala Lys Leu Val Ala Ser Asn Trp Tyr
385                 390                 395                 400

Asn Arg Gln Ile Gly Lys Ala Ser Arg Thr Phe Gly Cys Ser Trp Glu
                405                 410                 415

Phe Ile Pro Val Asp Asp Gly Trp Gly Glu Ser Ser Leu Glu Asn Leu
            420                 425                 430

Tyr Phe Gln Gly Ala Ser His His His His His His His His
        435                 440                 445
```

<210> SEQ ID NO 31
<211> LENGTH: 1347
<212> TYPE: DNA
<213> ORGANISM: Artificial Sequence
<220> FEATURE:
<223> OTHER INFORMATION: Nucleotide Sequence of rLC/FA (His-tagged)

<400> SEQUENCE: 31

```
atgccggttg tgattaacag cttcaattat gatgatccgg tgaacgataa caccatcatt      60

tatatccgtc cgccttatta tgaaaccagc aacacctatt tcaaagcctt ccagattatg     120

gataacgtgt ggattattcc ggaacgttat cgtctgggta ttgatccgag cctgtttaat     180

ccgcctgtta gcctgaaagc aggtagtgat ggttattttg atccgaatta tctgagcacc     240

aacaccgaga aaaacaaata cctgcagatt atgatcaagc tgttcaaacg cattaatagc     300

aaaccggcag gtcagattct gctggaagaa atcaaaaatg caattccgta tctgggcaac     360

agctataccc aagaagaaca gtttaccacc aataatcgta ccgtgagctt taatgttaaa     420

ctggccaatg gtaatatcgt tcagcagatg gcaaatctga ttatttgggg tccgggtcct     480

gatctgacca caaataaaac cggtggtatc atctatagcc cgtatcagag catggaagca     540

accccgtata aagatggttt tggtagcatt atgaccgtgg aatttagtcc ggaatatgca     600

accgccttta acgatatttc aattgcaagc catagtccgt cgctgtttat caaagatccg     660

gcactgattc tgatgcatga actgattcat gttctgcatg gtctgtatgg cacctatatt     720

accgaataca aaattacccc gaatgtggtg cagagctata tgaaagttac caaaccgatt     780

accagcgcag aatttctgac ctttggtggt cgtgatcgca atattgttcc gcagagcatt     840

cagagccagc tgtataacaa agttctgagc gattataaac gtattgccag ccgtctgaat     900

aaagttaata ccgcaaccgc actgatcaac atcgatgaat tcaaaaacct gtacgagtgg     960

aaataccagt ttgccaaaga tagcaatggt gtgtatagcg tggatctgaa caaatttgag    1020

cagctgtaca aaaaaatcta tagcttcacc gaattcaacc tggcctatga gtttaaaatc    1080

aaaacccgtc tgggttatct ggccgaaaat tttggtccgt tttatctgcc gaatctgctg    1140

gatgatagca tttataccga agtggatggt tttaacattg gtgcactgag cattaactat    1200

cagggtcaga atattggcag cgatatcaac agcatcaaaa aactgcaagg tcagggtgtt    1260

gttagccgtg ttgttcgtct gtgtagcaat agcgaaaatc tgtattttca gggtgccagt    1320

catcatcacc accatcacca tcactga                                        1347
```

<210> SEQ ID NO 32
<211> LENGTH: 448
<212> TYPE: PRT
<213> ORGANISM: Artificial Sequence
<220> FEATURE:
<223> OTHER INFORMATION: Polypeptide Sequence of rLC/FA (His-tagged)

<400> SEQUENCE: 32

```
Met Pro Val Val Ile Asn Ser Phe Asn Tyr Asp Asp Pro Val Asn Asp
```

```
1               5                   10                  15

Asn Thr Ile Ile Tyr Ile Arg Pro Pro Tyr Tyr Glu Thr Ser Asn Thr
            20                  25                  30

Tyr Phe Lys Ala Phe Gln Ile Met Asp Asn Val Trp Ile Ile Pro Glu
        35                  40                  45

Arg Tyr Arg Leu Gly Ile Asp Pro Ser Leu Phe Asn Pro Pro Val Ser
    50                  55                  60

Leu Lys Ala Gly Ser Asp Gly Tyr Phe Asp Pro Asn Tyr Leu Ser Thr
65                  70                  75                  80

Asn Thr Glu Lys Asn Lys Tyr Leu Gln Ile Met Ile Lys Leu Phe Lys
                85                  90                  95

Arg Ile Asn Ser Lys Pro Ala Gly Gln Ile Leu Leu Glu Glu Ile Lys
            100                 105                 110

Asn Ala Ile Pro Tyr Leu Gly Asn Ser Tyr Thr Gln Glu Glu Gln Phe
        115                 120                 125

Thr Thr Asn Asn Arg Thr Val Ser Phe Asn Val Lys Leu Ala Asn Gly
    130                 135                 140

Asn Ile Val Gln Gln Met Ala Asn Leu Ile Ile Trp Gly Pro Gly Pro
145                 150                 155                 160

Asp Leu Thr Thr Asn Lys Thr Gly Gly Ile Ile Tyr Ser Pro Tyr Gln
                165                 170                 175

Ser Met Glu Ala Thr Pro Tyr Lys Asp Gly Phe Gly Ser Ile Met Thr
            180                 185                 190

Val Glu Phe Ser Pro Glu Tyr Ala Thr Ala Phe Asn Asp Ile Ser Ile
        195                 200                 205

Ala Ser His Ser Pro Ser Leu Phe Ile Lys Asp Pro Ala Leu Ile Leu
    210                 215                 220

Met His Glu Leu Ile His Val Leu His Gly Leu Tyr Gly Thr Tyr Ile
225                 230                 235                 240

Thr Glu Tyr Lys Ile Thr Pro Asn Val Val Gln Ser Tyr Met Lys Val
                245                 250                 255

Thr Lys Pro Ile Thr Ser Ala Glu Phe Leu Thr Phe Gly Gly Arg Asp
            260                 265                 270

Arg Asn Ile Val Pro Gln Ser Ile Gln Ser Gln Leu Tyr Asn Lys Val
        275                 280                 285

Leu Ser Asp Tyr Lys Arg Ile Ala Ser Arg Leu Asn Lys Val Asn Thr
    290                 295                 300

Ala Thr Ala Leu Ile Asn Ile Asp Glu Phe Lys Asn Leu Tyr Glu Trp
305                 310                 315                 320

Lys Tyr Gln Phe Ala Lys Asp Ser Asn Gly Val Tyr Ser Val Asp Leu
                325                 330                 335

Asn Lys Phe Glu Gln Leu Tyr Lys Lys Ile Tyr Ser Phe Thr Glu Phe
            340                 345                 350

Asn Leu Ala Tyr Glu Phe Lys Ile Lys Thr Arg Leu Gly Tyr Leu Ala
        355                 360                 365

Glu Asn Phe Gly Pro Phe Tyr Leu Pro Asn Leu Leu Asp Asp Ser Ile
    370                 375                 380

Tyr Thr Glu Val Asp Gly Phe Asn Ile Gly Ala Leu Ser Ile Asn Tyr
385                 390                 395                 400

Gln Gly Gln Asn Ile Gly Ser Asp Ile Asn Ser Ile Lys Lys Leu Gln
                405                 410                 415

Gly Gln Gly Val Val Ser Arg Val Val Arg Leu Cys Ser Asn Ser Glu
            420                 425                 430
```

```
Asn Leu Tyr Phe Gln Gly Ala Ser His His His His His His His His
        435                 440                 445


<210> SEQ ID NO 33
<211> LENGTH: 3888
<212> TYPE: DNA
<213> ORGANISM: Artificial Sequence
<220> FEATURE:
<223> OTHER INFORMATION: Nucleotide Sequence of rBoNT/F(0) (His-tagged)

<400> SEQUENCE: 33

atgccggttg tgattaacag cttcaattat aacgatccgg tgaacgatga taccatcctg     60

tatatgcaga ttccgtatga agagaaaagc aaaaagtact acaaagcctt tgagatcatg    120

cgcaacgttt ggattattcc ggaacgtaat accattggca ccgatccgag cgattttgat    180

ccgcctgcaa gcctggaaaa tggtagcagc gcatattatg atccgaatta tctgaccacc    240

gatgccgaaa aagatcgtta tctgaaaacc accatcaaac tgttcaaacg cattaatagc    300

aatccggcag gcgaagttct gctgcaagaa attagctatg caaaaccgta tctgggcaat    360

gaacataccc cgattaatga atttcatccg gttacacgta ccacgagcgt taacattaaa    420

agcagcacca atgtgaagtc cagcattatt ctgaatctgc tggttttagg tgcaggtccg    480

gatatttttg aaaattcaag ctatccggtg cgcaaactga tggatagcgg tggtgtgtat    540

gatccgtcaa atgatggttt tggcagcatt aacattgtga cctttagtcc ggaatatgaa    600

tacaccttca acgatattag cggtggctat aatagcagca ccgaaagttt tattgcagat    660

ccggcaatta gcctggcaca ccagctgatt tatgcactgc atggtctgta tggtgcacgt    720

ggtgttacct ataaagaaac cattaaagtt aaacaggcac cgctgatgat tgcggaaaaa    780

ccgattcgtc tggaagaatt tctgaccttt ggtggtcagg atctgaacat tattaccagc    840

gcaatgaaag agaaaatcta taataacctg ctggccaact atgagaaaat tgcaacccgt    900

ctgagccgtg ttaatagcgc acctcctgaa tatgatatca acgagtataa agactatttt    960

cagtggaaat acggcctgga taaaaatgca gatggtagct ataccgtgaa cgagaacaaa   1020

tttaacgaga tctacaaaaa actgtatagc ttcaccgaaa tcgatctggc caacaaattc   1080

aaagtgaaat gccgcaacac ctacttcatc aaatatggct ttctgaaagt tccgaacctg   1140

cttgatgatg atatctatac cgttagcgaa ggctttaaca ttggtaatct ggccgttaat   1200

aatcgcggtc agaacattaa actgaacccg aaaattatcg atagcatccc ggataaaggc   1260

ctggttgaaa aaattgtgaa attctgcaaa agcgtgattc cgcgtaaagg caccaaagca   1320

ccgcctcgtc tgtgtattcg tgtgaataat cgtgaactgt tttttgttgc aagcgagagc   1380

agctataacg agaatgatat taacaccccg aaagagattg acgataccac caatctgaat   1440

aacaactatc gcaacaatct ggatgaagtg atcctggatt ataacagcga aaccattccg   1500

cagattagca atcagaccct gaataccctg gttcaggatg atagctatgt tccgcgttat   1560

gatagcaatg gcaccagcga aattgaagaa cataatgtgg ttgatctgaa cgtgttcttt   1620

tatctgcatg cacagaaagt gccggaaggt gaaaccaata ttagcctgac cagcagcatt   1680

gataccgcac tgagcgaaga aagccaggtt tatacctttt ttagcagcga attcatcaac   1740

accattaaca aaccggttca tgcagcactg tttattagct ggattaatca ggtgattcgc   1800

gattttacca ccgaagcaac ccagaaaagc acctttgata aaattgccga tattagtctg   1860

gtggtgccgt atgttggtct ggcactgaat attggtaatg aagtgcagaa agagaacttt   1920

aaagaagcct tcgaactgtt aggtgccggt attctgctgg aatttgtgcc ggaactgctg   1980
```

```
attccgacca ttctggtttt taccattaag agctttattg gcagcagcga gaacaagaac   2040
aaaatcatta aagccatcaa caacagcctg atggaacgcg aaaccaaatg gaaagaaatt   2100
tacagctgga ttgtgagcaa ttggctgacc cgtatcaata cccagtttaa caaacgcaaa   2160
gaacaaatgt atcaggccct gcagaatcag gttgatgcaa ttaaaaccgt gatcgaatac   2220
aaatacaaca actataccag cgacgaacgt aatcgcctgg aaagcgaata caacattaat   2280
aacattcgcg aagaactgaa caaaaaagtg agcctggcaa tggaaaacat cgaacgtttt   2340
attaccgaaa gcagcatctt ctacctgatg aaactgatta acgaagccaa agttagcaaa   2400
ctgcgcgaat atgatgaagg cgttaaagaa tatctgctgg actatattag cgaacatcgt   2460
agcattctgg gtaatagcgt tcaagagctg aatgatctgg ttaccagcac actgaataat   2520
agcattccgt ttgaactgag cagctacacc aacgataaaa tcctgatcct gtacttcaac   2580
aaactgtaca agaagatcaa ggacaacagc atactggata tgcgctatga aaacaacaag   2640
ttcattgata tcagcggcta tggtagcaac attagcatta atggtgatgt gtatatctac   2700
agcaccaacc gcaatcagtt tggtatttat agcagcaaac cgagcgaagt taatattgcg   2760
cagaataacg atatcatcta caacggtcgc tatcagaact ttagcattag cttttgggtt   2820
cgcattccga aatactttaa caaggtgaac ctgaacaacg agtacaccat tattgattgc   2880
attcgcaata ataacagcgg ctggaaaatc agcctgaact ataacaaaat tatctggacc   2940
ctgcaggata ccgcaggtaa taatcagaaa ctggtgttta actacaccca gatgattagc   3000
atcagcgact atatcaacaa atggatcttt gtgaccatta ccaacaatcg tctgggtaac   3060
agccgcattt atatcaatgg caatctgatc gacgaaaaaa gcatttcaaa tctgggcgat   3120
attcacgtga gcgataacat tctgttcaaa attgttggct gcaacgatac ccgttatgtt   3180
ggtattcgtt acttcaaagt gtttgatacg gaactgggca aaacggaaat tgaaaccctg   3240
tatagtgatg aaccggatcc gagcattctg aaagattttt ggggtaatta tctgctgtac   3300
aacaaacgct actatctgct gaacctgctg cgtaccgata aaagcattac acagaatagc   3360
aactttctga acatcaatca gcagcgtggt gtttatcaga aaccgaacat tttagcaac    3420
acccgtctgt ataccggtgt ggaagttatt attcgtaaaa acggtagcac cgatatcagc   3480
aacaccgata actttgtgcg taaaaatgac ctggcctata ttaacgttgt tgatcgtgat   3540
gttgagtatc gtctgtatgc ggatattagc attgccaaac cggaaaagat tatcaaactg   3600
atccgtacca gcaacagcaa taattcactg ggtcagatta tcgtgatgga cagcattggt   3660
aacaattgca ccatgaattt ccagaacaat aacggtggta atattggcct gctgggcttt   3720
catagcaata atctggttgc aagcagctgg tattacaaca acatccgtaa aaataccagc   3780
agtaatggtt gcttttggag ctttatcagt aaagaacatg gctggcaaga aaacgagaac   3840
ctgtattttc agggtgcaag tcatcatcac catcaccacc atcattaa               3888
```

<210> SEQ ID NO 34
<211> LENGTH: 1295
<212> TYPE: PRT
<213> ORGANISM: Artificial Sequence
<220> FEATURE:
<223> OTHER INFORMATION: Polypeptide Sequence of rBoNT/F(0) (His-tagged)

<400> SEQUENCE: 34

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
```

```
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Gln Leu Ile Tyr Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445
```

```
Asn Asn Arg Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
        595                 600                 605

Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
            660                 665                 670

Ile Gly Ser Ser Glu Asn Lys Asn Lys Ile Ile Lys Ala Ile Asn Asn
        675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
            740                 745                 750

Leu Glu Ser Glu Tyr Asn Ile Asn Asn Ile Arg Glu Glu Leu Asn Lys
        755                 760                 765

Lys Val Ser Leu Ala Met Glu Asn Ile Glu Arg Phe Ile Thr Glu Ser
    770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
        835                 840                 845

Tyr Thr Asn Asp Lys Ile Leu Ile Leu Tyr Phe Asn Lys Leu Tyr Lys
    850                 855                 860
```

```
Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
                885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
        915                 920                 925

Gly Arg Tyr Gln Asn Phe Ser Ile Ser Phe Trp Val Arg Ile Pro Lys
    930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
            980                 985                 990

Phe Asn Tyr Thr Gln Met Ile Ser  Ile Ser Asp Tyr Ile  Asn Lys Trp
        995                 1000                1005

Ile Phe  Val Thr Ile Thr Asn  Asn Arg Leu Gly Asn  Ser Arg Ile
    1010                 1015                1020

Tyr Ile  Asn Gly Asn Leu Ile  Asp Glu Lys Ser Ile  Ser Asn Leu
    1025                 1030                1035

Gly Asp  Ile His Val Ser Asp  Asn Ile Leu Phe Lys  Ile Val Gly
    1040                 1045                1050

Cys Asn  Asp Thr Arg Tyr Val  Gly Ile Arg Tyr Phe  Lys Val Phe
    1055                 1060                1065

Asp Thr  Glu Leu Gly Lys Thr  Glu Ile Glu Thr Leu  Tyr Ser Asp
    1070                 1075                1080

Glu Pro  Asp Pro Ser Ile Leu  Lys Asp Phe Trp Gly  Asn Tyr Leu
    1085                 1090                1095

Leu Tyr  Asn Lys Arg Tyr Tyr  Leu Leu Asn Leu Leu  Arg Thr Asp
    1100                 1105                1110

Lys Ser  Ile Thr Gln Asn Ser  Asn Phe Leu Asn Ile  Asn Gln Gln
    1115                 1120                1125

Arg Gly  Val Tyr Gln Lys Pro  Asn Ile Phe Ser Asn  Thr Arg Leu
    1130                 1135                1140

Tyr Thr  Gly Val Glu Val Ile  Ile Arg Lys Asn Gly  Ser Thr Asp
    1145                 1150                1155

Ile Ser  Asn Thr Asp Asn Phe  Val Arg Lys Asn Asp  Leu Ala Tyr
    1160                 1165                1170

Ile Asn  Val Val Asp Arg Asp  Val Glu Tyr Arg Leu  Tyr Ala Asp
    1175                 1180                1185

Ile Ser  Ile Ala Lys Pro Glu  Lys Ile Ile Lys Leu  Ile Arg Thr
    1190                 1195                1200

Ser Asn  Ser Asn Asn Ser Leu  Gly Gln Ile Ile Val  Met Asp Ser
    1205                 1210                1215

Ile Gly  Asn Asn Cys Thr Met  Asn Phe Gln Asn Asn  Asn Gly Gly
    1220                 1225                1230

Asn Ile  Gly Leu Leu Gly Phe  His Ser Asn Asn Leu  Val Ala Ser
    1235                 1240                1245

Ser Trp  Tyr Tyr Asn Asn Ile  Arg Lys Asn Thr Ser  Ser Asn Gly
    1250                 1255                1260

Cys Phe  Trp Ser Phe Ile Ser  Lys Glu His Gly Trp  Gln Glu Asn
```

```
    1265                1270                1275

Glu Asn  Leu Tyr Phe Gln Gly  Ala Ser His His His  His His His
    1280                1285                1290

His His
    1295
```

<210> SEQ ID NO 35
<211> LENGTH: 2649
<212> TYPE: DNA
<213> ORGANISM: Artificial Sequence
<220> FEATURE:
<223> OTHER INFORMATION: Nucleotide Sequence of rLHN/F (His-tagged)

<400> SEQUENCE: 35

```
atgccggttg tgattaacag cttcaattat aacgatccgg tgaacgatga taccatcctg     60
tatatgcaga ttccgtatga agagaaaagc aaaaagtact acaaagcctt tgagatcatg    120
cgcaacgttt ggattattcc ggaacgtaat accattggca ccgatccgag cgattttgat    180
ccgcctgcaa gcctggaaaa tggtagcagc gcatattatg atccgaatta tctgaccacc    240
gatgccgaaa aagatcgtta tctgaaaacc accatcaaac tgttcaaacg cattaatagc    300
aatccggcag gcgaagttct gctgcaagaa attagctatg caaaaccgta tctgggcaat    360
gaacataccc cgattaatga atttcatccg gttacacgta ccacgagcgt taacattaaa    420
agcagcacca atgtgaagtc cagcattatt ctgaatctgc tggttttagg tgcaggtccg    480
gatatttttg aaaattcaag ctatccggtg cgcaaactga tggatagcgg tggtgtgtat    540
gatccgtcaa atgatggttt tggcagcatt aacattgtga cctttagtcc ggaatatgaa    600
tacaccttca acgatattag cggtggctat aatagcagca ccgaaagttt tattgcagat    660
ccggcaatta gcctggcaca tgaactgatt catgcactgc atggtctgta tggtgcacgt    720
ggtgttacct ataaagaaac cattaaagtt aaacaggcac cgctgatgat tgcggaaaaa    780
ccgattcgtc tggaagaatt tctgaccttt ggtggtcagg atctgaacat tattaccagc    840
gcaatgaaag agaaaatcta taataacctg ctggccaact atgagaaaat tgcaacccgt    900
ctgagccgtg ttaatagcgc acctcctgaa tatgatatca acgagtataa agactatttt    960
cagtggaaat acggcctgga taaaaatgca gatggtagct ataccgtgaa cgagaacaaa   1020
tttaacgaga tctacaaaaa actgtatagc ttcaccgaaa tcgatctggc caacaaattc   1080
aaagtgaaat gccgcaacac ctacttcatc aaatatggct ttctgaaagt tccgaacctg   1140
cttgatgatg atatctatac cgttagcgaa ggctttaaca ttggtaatct ggccgttaat   1200
aatcgcggtc agaacattaa actgaacccg aaaattatcg atagcatccc ggataaaggc   1260
ctggttgaaa aaattgtgaa attctgcaaa agcgtgattc cgcgtaaagg caccaaagca   1320
ccgcctcgtc tgtgtattcg tgtgaataat cgtgaactgt tttttgttgc aagcgagagc   1380
agctataacg agaatgatat taacaccccg aaagagattg acgataccac caatctgaat   1440
aacaactatc gcaacaatct ggatgaagtg atcctggatt ataacagcga aaccattccg   1500
cagattagca atcagaccct gaataccctg gttcaggatg atagctatgt tccgcgttat   1560
gatagcaatg gcaccagcga aattgaagaa cataatgtgg ttgatctgaa cgtgttcttt   1620
tatctgcatg cacagaaagt gccggaaggt gaaaccaata ttagcctgac cagcagcatt   1680
gataccgcac tgagcgaaga aagccaggtt tatacctttt ttagcagcga attcatcaac   1740
accattaaca aaccggttca tgcagcactg tttattagct ggattaatca ggtgattcgc   1800
gattttacca ccgaagcaac ccagaaaagc acctttgata aaattgccga tattagtctg   1860
```

```
gtggtgccgt atgttggtct ggcactgaat attggtaatg aagtgcagaa agagaacttt   1920

aaagaagcct tcgaactgtt aggtgccggt attctgctgg aatttgtgcc ggaactgctg   1980

attccgacca ttctggtttt taccattaag agctttattg gcagcagcga gaacaagaac   2040

aaaatcatta aagccatcaa caacagcctg atggaacgcg aaaccaaatg gaaagaaatt   2100

tacagctgga ttgtgagcaa ttggctgacc cgtatcaata cccagtttaa caaacgcaaa   2160

gaacaaatgt atcaggccct gcagaatcag gttgatgcaa ttaaaaccgt gatcgaatac   2220

aaatacaaca actataccag cgacgaacgt aatcgcctgg aaagcgaata caacattaat   2280

aacattcgcg aagaactgaa caaaaaagtg agcctggcaa tggaaaacat cgaacgtttt   2340

attaccgaaa gcagcatctt ctacctgatg aaactgatta acgaagccaa agttagcaaa   2400

ctgcgcgaat atgatgaagg cgttaaagaa tatctgctgg actatattag cgaacatcgt   2460

agcattctgg gtaatagcgt tcaagagctg aatgatctgg ttaccagcac actgaataat   2520

agcattccgt ttgaactgag cagctacacc aacgataaaa tcctgatcct gtacttcaac   2580

aaactgtaca agaaagaaaa cctgtatttt cagggtgcaa gccatcatca ccaccatcac   2640

catcattaa                                                           2649
```

<210> SEQ ID NO 36
<211> LENGTH: 882
<212> TYPE: PRT
<213> ORGANISM: Artificial Sequence
<220> FEATURE:
<223> OTHER INFORMATION: Polypeptide Sequence of rLHN/F (His-tagged)

<400> SEQUENCE: 36

```
Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
```

```
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Arg Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
        595                 600                 605

Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640
```

```
Lys Glu Ala Phe Glu Leu Leu Gly Ala Gly Ile Leu Leu Glu Phe Val
            645                 650                 655

Pro Glu Leu Leu Ile Pro Thr Ile Leu Val Phe Thr Ile Lys Ser Phe
        660                 665                 670

Ile Gly Ser Ser Glu Asn Lys Asn Lys Ile Ile Lys Ala Ile Asn Asn
    675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Val Ile Glu Tyr Lys Tyr Asn Asn Tyr Thr Ser Asp Glu Arg Asn Arg
        740                 745                 750

Leu Glu Ser Glu Tyr Asn Ile Asn Asn Ile Arg Glu Glu Leu Asn Lys
    755                 760                 765

Lys Val Ser Leu Ala Met Glu Asn Ile Glu Arg Phe Ile Thr Glu Ser
    770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
            805                 810                 815

Ser Glu His Arg Ser Ile Leu Gly Asn Ser Val Gln Glu Leu Asn Asp
        820                 825                 830

Leu Val Thr Ser Thr Leu Asn Asn Ser Ile Pro Phe Glu Leu Ser Ser
    835                 840                 845

Tyr Thr Asn Asp Lys Ile Leu Ile Leu Tyr Phe Asn Lys Leu Tyr Lys
    850                 855                 860

Lys Glu Asn Leu Tyr Phe Gln Gly Ala Ser His His His His His His
865                 870                 875                 880

His His
```

<210> SEQ ID NO 37
<211> LENGTH: 1296
<212> TYPE: DNA
<213> ORGANISM: Artificial Sequence
<220> FEATURE:
<223> OTHER INFORMATION: Nucleotide Sequence of rHC/F (His-tagged)

<400> SEQUENCE: 37

```
atgatcaagg ataacagcat tctggatatg cgctatgaga acaacaaatt cattgatatt      60

agcggctatg gcagcaacat tagcattaat ggtgatgtgt atatctacag caccaaccgt     120

aatcagtttg gcatttatag cagcaaaccg agcgaagtta atattgccca gaacaacgat     180

atcatctata acggtcgcta tcagaacttc agcattagct tttgggttcg cattccgaaa     240

tacttcaata aggtgaacct gaacaacgag tataccatca ttgattgcat tcgcaataat     300

aacagcggct ggaaaattag cctgaactac aacaaaatta tctggaccct gcaggatacc     360

gcaggtaata atcagaaact ggtgtttaac tacacccaga tgattagcat cagcgactat     420

atcaacaaat ggatctttgt gaccattacc aataatcgcc tgggtaatag ccgcatttat     480

atcaatggta acctgatcga tgagaaaagc attagcaatc tgggtgatat tcatgtgagc     540

gataacatcc tgtttaaaat cgtgggttgt aacgataccc gttatgttgg tattcgctac     600

ttcaaagtgt ttgataccga actgggtaaa accgaaattg aaaccctgta tagtgatgaa     660
```

```
ccggatccga gcattctgaa agatttttgg ggtaattatc tgctgtacaa caaacgctac    720

tatctgctga atctgctgcg taccgataaa tcaattaccc agaatagcaa cttcctgaac    780

attaatcagc agcgtggtgt ttatcagaaa ccgaacattt ttagcaacac ccgtctgtat    840

accggtgtgg aagttattat tcgtaaaaat ggcagcaccg atatcagcaa caccgataac    900

tttgttcgca aaaatgatct ggcgtatatc aacgttgttg atcgtgatgt tgaatatcgt    960

ctgtatgccg atattagcat tgccaaaccg gaaaaaatca tcaaactgat ccgtaccagc   1020

aacagcaata attcactggg tcagattatt gtgatggata gcattggtaa taactgcacc   1080

atgaactttc agaacaataa cggtggtaat attggtctgc tgggctttca tagtaataat   1140

ctggttgcaa gcagctggta ttataacaac atccgtaaaa ataccagcag caatggttgc   1200

ttttggagct ttattagcaa agaacatggc tggcaagaaa acgagaatct gtattttcag   1260

ggtgcaagtc atcatcacca ccatcaccat cattaa                              1296
```

<210> SEQ ID NO 38
<211> LENGTH: 431
<212> TYPE: PRT
<213> ORGANISM: Artificial Sequence
<220> FEATURE:
<223> OTHER INFORMATION: Polypeptide Sequence of rHC/F (His-tagged)

<400> SEQUENCE: 38

```
Met Ile Lys Asp Asn Ser Ile Leu Asp Met Arg Tyr Glu Asn Asn Lys
1               5                   10                  15

Phe Ile Asp Ile Ser Gly Tyr Gly Ser Asn Ile Ser Ile Asn Gly Asp
            20                  25                  30

Val Tyr Ile Tyr Ser Thr Asn Arg Asn Gln Phe Gly Ile Tyr Ser Ser
        35                  40                  45

Lys Pro Ser Glu Val Asn Ile Ala Gln Asn Asn Asp Ile Ile Tyr Asn
    50                  55                  60

Gly Arg Tyr Gln Asn Phe Ser Ile Ser Phe Trp Val Arg Ile Pro Lys
65                  70                  75                  80

Tyr Phe Asn Lys Val Asn Leu Asn Asn Glu Tyr Thr Ile Ile Asp Cys
                85                  90                  95

Ile Arg Asn Asn Asn Ser Gly Trp Lys Ile Ser Leu Asn Tyr Asn Lys
            100                 105                 110

Ile Ile Trp Thr Leu Gln Asp Thr Ala Gly Asn Asn Gln Lys Leu Val
        115                 120                 125

Phe Asn Tyr Thr Gln Met Ile Ser Ile Ser Asp Tyr Ile Asn Lys Trp
    130                 135                 140

Ile Phe Val Thr Ile Thr Asn Asn Arg Leu Gly Asn Ser Arg Ile Tyr
145                 150                 155                 160

Ile Asn Gly Asn Leu Ile Asp Glu Lys Ser Ile Ser Asn Leu Gly Asp
                165                 170                 175

Ile His Val Ser Asp Asn Ile Leu Phe Lys Ile Val Gly Cys Asn Asp
            180                 185                 190

Thr Arg Tyr Val Gly Ile Arg Tyr Phe Lys Val Phe Asp Thr Glu Leu
        195                 200                 205

Gly Lys Thr Glu Ile Glu Thr Leu Tyr Ser Asp Glu Pro Asp Pro Ser
    210                 215                 220

Ile Leu Lys Asp Phe Trp Gly Asn Tyr Leu Leu Tyr Asn Lys Arg Tyr
225                 230                 235                 240

Tyr Leu Leu Asn Leu Leu Arg Thr Asp Lys Ser Ile Thr Gln Asn Ser
```

```
                245                 250                 255

Asn Phe Leu Asn Ile Asn Gln Gln Arg Gly Val Tyr Gln Lys Pro Asn
            260                 265                 270

Ile Phe Ser Asn Thr Arg Leu Tyr Thr Gly Val Glu Val Ile Ile Arg
        275                 280                 285

Lys Asn Gly Ser Thr Asp Ile Ser Asn Thr Asp Asn Phe Val Arg Lys
    290                 295                 300

Asn Asp Leu Ala Tyr Ile Asn Val Val Asp Arg Asp Val Glu Tyr Arg
305                 310                 315                 320

Leu Tyr Ala Asp Ile Ser Ile Ala Lys Pro Glu Lys Ile Ile Lys Leu
                325                 330                 335

Ile Arg Thr Ser Asn Ser Asn Asn Ser Leu Gly Gln Ile Ile Val Met
            340                 345                 350

Asp Ser Ile Gly Asn Asn Cys Thr Met Asn Phe Gln Asn Asn Asn Gly
        355                 360                 365

Gly Asn Ile Gly Leu Leu Gly Phe His Ser Asn Asn Leu Val Ala Ser
    370                 375                 380

Ser Trp Tyr Tyr Asn Asn Ile Arg Lys Asn Thr Ser Ser Asn Gly Cys
385                 390                 395                 400

Phe Trp Ser Phe Ile Ser Lys Glu His Gly Trp Gln Glu Asn Glu Asn
                405                 410                 415

Leu Tyr Phe Gln Gly Ala Ser His His His His His His His His
            420                 425                 430
```

<210> SEQ ID NO 39
<211> LENGTH: 1347
<212> TYPE: DNA
<213> ORGANISM: Artificial Sequence
<220> FEATURE:
<223> OTHER INFORMATION: Nucleotide Sequence of rLC/F (His-tagged)

<400> SEQUENCE: 39

```
atgccggttg tgattaacag cttcaattat aacgatccgg tgaacgatga taccatcctg      60

tatatgcaga ttccgtatga agagaaaagc aaaaagtact acaaagcctt tgagatcatg     120

cgcaacgttt ggattattcc ggaacgtaat accattggca ccgatccgag cgattttgat     180

ccgcctgcaa gcctggaaaa tggtagcagc gcatattatg atccgaatta tctgaccacc     240

gatgccgaaa aagatcgtta tctgaaaacc accatcaaac tgttcaaacg cattaatagc     300

aatccggcag gcgaagttct gctgcaagaa attagctatg caaaaccgta tctgggcaat     360

gaacataccc cgattaatga atttcatccg gttacacgta ccacgagcgt taacattaaa     420

agcagcacca atgtgaagtc cagcattatt ctgaatctgc tggttttagg tgcaggtccg     480

gatatttttg aaaattcaag ctatccggtg cgcaaactga tggatagcgg tggtgtgtat     540

gatccgtcaa atgatggttt tggcagcatt aacattgtga cctttagtcc ggaatatgaa     600

tacaccttca acgatattag cggtggctat aatagcagca ccgaaagttt tattgcagat     660

ccggcaatta gcctggcaca tgaactgatt catgcactgc atggtctgta tggtgcacgt     720

ggtgttacct ataaagaaac cattaaagtt aaacaggcac cgctgatgat tgcggaaaaa     780

ccgattcgtc tggaagaatt tctgaccttt ggtggtcagg atctgaacat tattaccagc     840

gcaatgaaag agaaaatcta taataacctg ctggccaact atgagaaaat tgcaacccgt     900

ctgagccgtg ttaatagcgc acctcctgaa tatgatatca acgagtataa agactatttt     960

cagtggaaat acggcctgga taaaaatgca gatggtagct ataccgtgaa cgagaacaaa    1020
```

```
tttaacgaga tctacaaaaa actgtatagc ttcaccgaaa tcgatctggc caacaaattc   1080

aaagtgaaat gccgcaacac ctacttcatc aaatatggct ttctgaaagt tccgaacctg   1140

cttgatgatg atatctatac cgttagcgaa ggctttaaca ttggtaatct ggccgttaat   1200

aatcgcggtc agaacattaa actgaacccg aaaattatcg atagcatccc ggataaaggc   1260

ctggttgaaa aaattgtgaa attctgcaaa agcgagaacc tgtattttca gggtgcaagt   1320

catcatcacc atcaccacca tcattaa                                       1347
```

```
<210> SEQ ID NO 40
<211> LENGTH: 448
<212> TYPE: PRT
<213> ORGANISM: Artificial Sequence
<220> FEATURE:
<223> OTHER INFORMATION: Polypeptide Sequence of rLC/F (His-tagged)

<400> SEQUENCE: 40

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300
```

```
Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Glu
            420                 425                 430

Asn Leu Tyr Phe Gln Gly Ala Ser His His His His His His His His
        435                 440                 445


<210> SEQ ID NO 41
<211> LENGTH: 1317
<212> TYPE: DNA
<213> ORGANISM: Artificial Sequence
<220> FEATURE:
<223> OTHER INFORMATION: Nucleotide Sequence of Cationic rHC/A (His-
      tagged)

<400> SEQUENCE: 41

atgatcatca acaccagcat tctgaacctg cgttatgaaa gcaaacatct gattgatctg     60

agccgttatg ccagcaaaat caatataggc agcaaggtta acttcgaccc gattgacaaa    120

aatcagatac agctgtttaa tctggaaagc agcaaaattg aggtgatcct gaaaaaagcg    180

atcgtgtata atagcatgta cgagaatttt tcgaccagct tttggattcg catcccgaaa    240

tactttaaca agattagcct gaacaacgag tataccatca ttaactgcat ggaaaacaat    300

agcggttgga aagtcagcct gaattatggc gaaattatct ggaccctgca ggataccaaa    360

gaaatcaaac agcgtgtggt gttcaaatac agccagatga ttaatatcag cgactatatc    420

aaccgctgga tttttgtgac cattaccaat aatcggctga acaagagcaa gatctatatt    480

aacggtcgtc tgattgacca gaaaccgatt agtaatctgg gtaatattca tgcgagcaac    540

aaaatcatgt ttaaactgga tggttgccgt gatacccatc gttatatttg gatcaaatac    600

ttcaacctgt tcgataaaga gttgaacgaa aaagaaatta aagacctgta cgataaccag    660

agcaatagcg gcatactgaa agatttttgg ggagattatc tgcagtatga caaaccgtat    720

tatatgctga atctgtacga cccgaataaa tacgtggatg ttaataatgt gggcatccgt    780

ggttatatgt acctgaaagg tccgcgtggt agcgttatga ccacaaacat ttatctgaat    840

agcagcctgt atcgcggaac caaattcatc attaaaaagt atgccagcgg caacaaggat    900

aatattgtgc gtaataatga tcgcgtgtac attaacgttg tggtgaagaa taaagaatat    960

cgcctggcaa ccaatgcaag ccaggcaggc gttgaaaaaa ttctgagtgc cctggaaatt   1020

ccggatgttg gtaatctgag ccaggttgtt gtgatgaaaa gcaaaaacga taaaggcatc   1080

accaacaaat gcaagatgaa tctgcaggac aataacggca atgatattgg cttcattggc   1140

tttcaccagt ttaacaacat tgcaaaactg gttgcgagca attggtataa tcgtcagatt   1200

gaacgtagca gtcgtaccct gggttgtagc tgggaattta tccctgtgga tgatggttgg   1260
```

ggtgaacgtc cgctgaagct tgcggccgca ctcgagcacc accaccacca ccactga 1317

<210> SEQ ID NO 42
<211> LENGTH: 438
<212> TYPE: PRT
<213> ORGANISM: Artificial Sequence
<220> FEATURE:
<223> OTHER INFORMATION: Polypeptide Sequence of Cationic rHC/A (His-tagged)

<400> SEQUENCE: 42

```
Met Ile Ile Asn Thr Ser Ile Leu Asn Leu Arg Tyr Glu Ser Lys His
1               5                   10                  15

Leu Ile Asp Leu Ser Arg Tyr Ala Ser Lys Ile Asn Ile Gly Ser Lys
            20                  25                  30

Val Asn Phe Asp Pro Ile Asp Lys Asn Gln Ile Gln Leu Phe Asn Leu
        35                  40                  45

Glu Ser Ser Lys Ile Glu Val Ile Leu Lys Lys Ala Ile Val Tyr Asn
    50                  55                  60

Ser Met Tyr Glu Asn Phe Ser Thr Ser Phe Trp Ile Arg Ile Pro Lys
65                  70                  75                  80

Tyr Phe Asn Lys Ile Ser Leu Asn Asn Glu Tyr Thr Ile Ile Asn Cys
                85                  90                  95

Met Glu Asn Asn Ser Gly Trp Lys Val Ser Leu Asn Tyr Gly Glu Ile
            100                 105                 110

Ile Trp Thr Leu Gln Asp Thr Lys Glu Ile Lys Gln Arg Val Val Phe
        115                 120                 125

Lys Tyr Ser Gln Met Ile Asn Ile Ser Asp Tyr Ile Asn Arg Trp Ile
    130                 135                 140

Phe Val Thr Ile Thr Asn Asn Arg Leu Asn Lys Ser Lys Ile Tyr Ile
145                 150                 155                 160

Asn Gly Arg Leu Ile Asp Gln Lys Pro Ile Ser Asn Leu Gly Asn Ile
                165                 170                 175

His Ala Ser Asn Lys Ile Met Phe Lys Leu Asp Gly Cys Arg Asp Thr
            180                 185                 190

His Arg Tyr Ile Trp Ile Lys Tyr Phe Asn Leu Phe Asp Lys Glu Leu
        195                 200                 205

Asn Glu Lys Glu Ile Lys Asp Leu Tyr Asp Asn Gln Ser Asn Ser Gly
    210                 215                 220

Ile Leu Lys Asp Phe Trp Gly Asp Tyr Leu Gln Tyr Asp Lys Pro Tyr
225                 230                 235                 240

Tyr Met Leu Asn Leu Tyr Asp Pro Asn Lys Tyr Val Asp Val Asn Asn
                245                 250                 255

Val Gly Ile Arg Gly Tyr Met Tyr Leu Lys Gly Pro Arg Gly Ser Val
            260                 265                 270

Met Thr Thr Asn Ile Tyr Leu Asn Ser Ser Leu Tyr Arg Gly Thr Lys
        275                 280                 285

Phe Ile Ile Lys Lys Tyr Ala Ser Gly Asn Lys Asp Asn Ile Val Arg
    290                 295                 300

Asn Asn Asp Arg Val Tyr Ile Asn Val Val Val Lys Asn Lys Glu Tyr
305                 310                 315                 320

Arg Leu Ala Thr Asn Ala Ser Gln Ala Gly Val Glu Lys Ile Leu Ser
                325                 330                 335

Ala Leu Glu Ile Pro Asp Val Gly Asn Leu Ser Gln Val Val Val Met
            340                 345                 350
```

```
Lys Ser Lys Asn Asp Lys Gly Ile Thr Asn Lys Cys Lys Met Asn Leu
        355                 360                 365

Gln Asp Asn Asn Gly Asn Asp Ile Gly Phe Ile Gly Phe His Gln Phe
    370                 375                 380

Asn Asn Ile Ala Lys Leu Val Ala Ser Asn Trp Tyr Asn Arg Gln Ile
385                 390                 395                 400

Glu Arg Ser Ser Arg Thr Leu Gly Cys Ser Trp Glu Phe Ile Pro Val
                405                 410                 415

Asp Asp Gly Trp Gly Glu Arg Pro Leu Lys Leu Ala Ala Ala Leu Glu
            420                 425                 430

His His His His His His
        435
```

<210> SEQ ID NO 43
<211> LENGTH: 1341
<212> TYPE: DNA
<213> ORGANISM: Artificial Sequence
<220> FEATURE:
<223> OTHER INFORMATION: Nucleotide Sequence of rHC/AB (His-tagged)

<400> SEQUENCE: 43

```
atgattctga acaatattat cctgaacctg cgttacaaag acaacaatct gatcgatctg     60

agcggctatg gtgcaaaagt tgaagtctac gacggtgtcg aactgaacga taaaaaccag    120

ttcaaactga cctcatcggc taactcaaaa attcgtgtga cgcagaacca aaacatcatc    180

ttcaactcgg tctttctgga cttcagcgtg tctttctgga ttcgcatccc gaaatataaa    240

aatgatggca tccagaacta catccataac gaatacacca tcatcaactg tatgaaaaac    300

aacagtggtt ggaaaatttc catccgtggc aaccgcatta tctggaccct gattgatatc    360

aatggtaaaa cgaaaagcgt gtttttcgaa tacaacatcc gtgaagatat ctctgaatac    420

atcaatcgct ggtttttcgt gaccattacg aacaatctga acaatgcgaa aatctatatc    480

aacggcaaac tggaaagtaa taccgacatc aaagatattc gtgaagttat cgccaacggt    540

gaaatcatct tcaaactgga tggcgacatc gatcgcaccc agttcatttg gatgaaatac    600

ttctccatct tcaacacgga actgagtcag tccaatatcg aagaacgcta caaaatccaa    660

tcatactcgg aatacctgaa agatttctgg ggtaacccgc tgatgtacaa caaagaatac    720

tacatgttca acgcgggcaa caaaaactca tacatcaaac tgaaaaaaga ttcgccggtg    780

ggtgaaatcc tgacccgtag caaatacaac cagaactcta aatacatcaa ctatcgcgat    840

ctgtacattg gcgaaaaatt tattatccgt cgcaaaagca actctcagag tattaatgat    900

gacatcgtgc gtaaagaaga ctacatctat ctggatttct ttaatctgaa ccaagaatgg    960

cgcgtttata cctacaaata cttcaaaaaa gaagaaatga aactgttcct ggccccgatt   1020

tacgacagcg atgaatttta caacaccatc cagatcaaag aatacgatga acagccgacg   1080

tatagttgcc aactgctgtt caaaaaagac gaagaatcca ccgatgaaat tggcctgatt   1140

ggtatccacc gtttctatga aagcggtatc gttttcgaag aatacaaaga ttacttctgt   1200

atctctaaat ggtatctgaa agaagtcaaa cgcaaaccgt acaacctgaa actgggctgc   1260

aactggcaat ttatcccgaa agacgaaggc tggaccgaaa agcttgcggc cgcactcgag   1320

caccaccacc accaccactg a                                               1341
```

<210> SEQ ID NO 44
<211> LENGTH: 446
<212> TYPE: PRT

```
<213> ORGANISM: Artificial Sequence
<220> FEATURE:
<223> OTHER INFORMATION: Polypeptide Sequence of rHC/AB (His-tagged)

<400> SEQUENCE: 44

Met Ile Leu Asn Asn Ile Ile Leu Asn Leu Arg Tyr Lys Asp Asn Asn
1               5                   10                  15

Leu Ile Asp Leu Ser Gly Tyr Gly Ala Lys Val Glu Val Tyr Asp Gly
            20                  25                  30

Val Glu Leu Asn Asp Lys Asn Gln Phe Lys Leu Thr Ser Ser Ala Asn
        35                  40                  45

Ser Lys Ile Arg Val Thr Gln Asn Gln Asn Ile Ile Phe Asn Ser Val
    50                  55                  60

Phe Leu Asp Phe Ser Val Ser Phe Trp Ile Arg Ile Pro Lys Tyr Lys
65                  70                  75                  80

Asn Asp Gly Ile Gln Asn Tyr Ile His Asn Glu Tyr Thr Ile Ile Asn
                85                  90                  95

Cys Met Lys Asn Asn Ser Gly Trp Lys Ile Ser Ile Arg Gly Asn Arg
            100                 105                 110

Ile Ile Trp Thr Leu Ile Asp Ile Asn Gly Lys Thr Lys Ser Val Phe
        115                 120                 125

Phe Glu Tyr Asn Ile Arg Glu Asp Ile Ser Glu Tyr Ile Asn Arg Trp
    130                 135                 140

Phe Phe Val Thr Ile Thr Asn Asn Leu Asn Asn Ala Lys Ile Tyr Ile
145                 150                 155                 160

Asn Gly Lys Leu Glu Ser Asn Thr Asp Ile Lys Asp Ile Arg Glu Val
                165                 170                 175

Ile Ala Asn Gly Glu Ile Ile Phe Lys Leu Asp Gly Asp Ile Asp Arg
            180                 185                 190

Thr Gln Phe Ile Trp Met Lys Tyr Phe Ser Ile Phe Asn Thr Glu Leu
        195                 200                 205

Ser Gln Ser Asn Ile Glu Glu Arg Tyr Lys Ile Gln Ser Tyr Ser Glu
    210                 215                 220

Tyr Leu Lys Asp Phe Trp Gly Asn Pro Leu Met Tyr Asn Lys Glu Tyr
225                 230                 235                 240

Tyr Met Phe Asn Ala Gly Asn Lys Asn Ser Tyr Ile Lys Leu Lys Lys
                245                 250                 255

Asp Ser Pro Val Gly Glu Ile Leu Thr Arg Ser Lys Tyr Asn Gln Asn
            260                 265                 270

Ser Lys Tyr Ile Asn Tyr Arg Asp Leu Tyr Ile Gly Glu Lys Phe Ile
        275                 280                 285

Ile Arg Arg Lys Ser Asn Ser Gln Ser Ile Asn Asp Asp Ile Val Arg
    290                 295                 300

Lys Glu Asp Tyr Ile Tyr Leu Asp Phe Phe Asn Leu Asn Gln Glu Trp
305                 310                 315                 320

Arg Val Tyr Thr Tyr Lys Tyr Phe Lys Lys Glu Glu Met Lys Leu Phe
                325                 330                 335

Leu Ala Pro Ile Tyr Asp Ser Asp Glu Phe Tyr Asn Thr Ile Gln Ile
            340                 345                 350

Lys Glu Tyr Asp Glu Gln Pro Thr Tyr Ser Cys Gln Leu Leu Phe Lys
        355                 360                 365

Lys Asp Glu Glu Ser Thr Asp Glu Ile Gly Leu Ile Gly Ile His Arg
    370                 375                 380

Phe Tyr Glu Ser Gly Ile Val Phe Glu Glu Tyr Lys Asp Tyr Phe Cys
```

-continued

```
385                 390                 395                 400

Ile Ser Lys Trp Tyr Leu Lys Glu Val Lys Arg Lys Pro Tyr Asn Leu
                405                 410                 415

Lys Leu Gly Cys Asn Trp Gln Phe Ile Pro Lys Asp Glu Gly Trp Thr
            420                 425                 430

Glu Lys Leu Ala Ala Ala Leu Glu His His His His His His
        435                 440                 445


<210> SEQ ID NO 45
<211> LENGTH: 1306
<212> TYPE: DNA
<213> ORGANISM: Artificial Sequence
<220> FEATURE:
<223> OTHER INFORMATION: Nucleotide Sequence of rHC/A Variant Y1117V
      H1253K (His-tagged)

<400> SEQUENCE: 45

atgatcatca atactagcat tctgaacctg cgttacgaga gcaatcatct gattgatctg     60

agccgttatg caagcaagat caacatcggt agcaaggtca attttgaccc gatcgataag    120

aaccagatcc agctgtttaa tctggaatcg agcaaaattg aggttatcct gaaaaacgcc    180

attgtctaca actccatgta cgagaatttc tccaccagct tctggattcg catcccgaaa    240

tacttcaaca gcattagcct gaacaacgag tatactatca tcaactgtat ggagaacaac    300

agcggttgga aggtgtctct gaactatggt gagatcattt ggaccttgca ggacacccaa    360

gagatcaagc agcgcgtcgt gttcaagtac tctcaaatga tcaacatttc cgattacatt    420

aatcgttgga tcttcgtgac cattacgaat aaccgtctga ataacagcaa gatttacatc    480

aatggtcgct tgatcgatca gaaaccgatt agcaacctgg gtaatatcca cgcaagcaac    540

aacattatgt tcaaattgga cggttgccgc gatacccatc gttatatctg gatcaagtat    600

ttcaacctgt ttgataaaga actgaatgag aaggagatca aagatttgta tgacaaccaa    660

tctaacagcg gcattttgaa ggacttctgg ggcgattatc tgcaatacga taagccgtac    720

tatatgctga acctggttga tccgaacaaa tatgtggatg tcaataatgt gggtattcgt    780

ggttacatgt atttgaaggg tccgcgtggc agcgttatga cgaccaacat ttacctgaac    840

tctagcctgt accgtggtac gaaattcatc attaagaaat atgccagcgg caacaaagat    900

aacattgtgc gtaataacga tcgtgtctac atcaacgtgg tcgtgaagaa taaagagtac    960

cgtctggcga ccaacgcttc gcaggcgggt gttgagaaaa ttctgagcgc gttggagatc   1020

cctgatgtcg gtaatctgag ccaagtcgtg gttatgaaga gcaagaacga ccagggtatc   1080

actaacaagt gcaagatgaa cctgcaagac aacaatggta acgacatcgg ctttattggt   1140

ttcaaacagt tcaacaatat tgctaaactg gtagcgagca attggtacaa tcgtcagatt   1200

gagcgcagca gccgtacttt gggctgtagc tgggagttta tcccggtcga tgatggttgg   1260

ggcgaacgtc cgctgcacca tcaccatcac catcaccatc accatt                  1306


<210> SEQ ID NO 46
<211> LENGTH: 435
<212> TYPE: PRT
<213> ORGANISM: Artificial Sequence
<220> FEATURE:
<223> OTHER INFORMATION: Polypeptide Sequence of rHC/A Variant Y1117V
      H1253K (His-tagged)

<400> SEQUENCE: 46

Met Ile Ile Asn Thr Ser Ile Leu Asn Leu Arg Tyr Glu Ser Asn His
1               5                   10                  15
```

```
Leu Ile Asp Leu Ser Arg Tyr Ala Ser Lys Ile Asn Ile Gly Ser Lys
            20                  25                  30

Val Asn Phe Asp Pro Ile Asp Lys Asn Gln Ile Gln Leu Phe Asn Leu
        35                  40                  45

Glu Ser Ser Lys Ile Glu Val Ile Leu Lys Asn Ala Ile Val Tyr Asn
    50                  55                  60

Ser Met Tyr Glu Asn Phe Ser Thr Ser Phe Trp Ile Arg Ile Pro Lys
65                  70                  75                  80

Tyr Phe Asn Ser Ile Ser Leu Asn Asn Glu Tyr Thr Ile Ile Asn Cys
                85                  90                  95

Met Glu Asn Asn Ser Gly Trp Lys Val Ser Leu Asn Tyr Gly Glu Ile
            100                 105                 110

Ile Trp Thr Leu Gln Asp Thr Gln Glu Ile Lys Gln Arg Val Val Phe
        115                 120                 125

Lys Tyr Ser Gln Met Ile Asn Ile Ser Asp Tyr Ile Asn Arg Trp Ile
    130                 135                 140

Phe Val Thr Ile Thr Asn Asn Arg Leu Asn Asn Ser Lys Ile Tyr Ile
145                 150                 155                 160

Asn Gly Arg Leu Ile Asp Gln Lys Pro Ile Ser Asn Leu Gly Asn Ile
                165                 170                 175

His Ala Ser Asn Asn Ile Met Phe Lys Leu Asp Gly Cys Arg Asp Thr
            180                 185                 190

His Arg Tyr Ile Trp Ile Lys Tyr Phe Asn Leu Phe Asp Lys Glu Leu
        195                 200                 205

Asn Glu Lys Glu Ile Lys Asp Leu Tyr Asp Asn Gln Ser Asn Ser Gly
    210                 215                 220

Ile Leu Lys Asp Phe Trp Gly Asp Tyr Leu Gln Tyr Asp Lys Pro Tyr
225                 230                 235                 240

Tyr Met Leu Asn Leu Val Asp Pro Asn Lys Tyr Val Asp Val Asn Asn
                245                 250                 255

Val Gly Ile Arg Gly Tyr Met Tyr Leu Lys Gly Pro Arg Gly Ser Val
            260                 265                 270

Met Thr Thr Asn Ile Tyr Leu Asn Ser Ser Leu Tyr Arg Gly Thr Lys
        275                 280                 285

Phe Ile Ile Lys Lys Tyr Ala Ser Gly Asn Lys Asp Asn Ile Val Arg
    290                 295                 300

Asn Asn Asp Arg Val Tyr Ile Asn Val Val Val Lys Asn Lys Glu Tyr
305                 310                 315                 320

Arg Leu Ala Thr Asn Ala Ser Gln Ala Gly Val Glu Lys Ile Leu Ser
                325                 330                 335

Ala Leu Glu Ile Pro Asp Val Gly Asn Leu Ser Gln Val Val Val Met
            340                 345                 350

Lys Ser Lys Asn Asp Gln Gly Ile Thr Asn Lys Cys Lys Met Asn Leu
        355                 360                 365

Gln Asp Asn Asn Gly Asn Asp Ile Gly Phe Ile Gly Phe Lys Gln Phe
    370                 375                 380

Asn Asn Ile Ala Lys Leu Val Ala Ser Asn Trp Tyr Asn Arg Gln Ile
385                 390                 395                 400

Glu Arg Ser Ser Arg Thr Leu Gly Cys Ser Trp Glu Phe Ile Pro Val
                405                 410                 415

Asp Asp Gly Trp Gly Glu Arg Pro Leu His His His His His His His
            420                 425                 430
```

His His His
        435

<210> SEQ ID NO 47
<211> LENGTH: 1308
<212> TYPE: DNA
<213> ORGANISM: Artificial Sequence
<220> FEATURE:
<223> OTHER INFORMATION: Nucleotide Sequence of rHC/A Variant Y1117V
      F1252Y H1253K L1278F (His-tagged)

<400> SEQUENCE: 47

```
atgatcatca atactagcat tctgaacctg cgttacgaga gcaatcatct gattgatctg     60

agccgttatg caagcaagat caacatcggt agcaaggtca attttgaccc gatcgataag    120

aaccagatcc agctgtttaa tctggaatcg agcaaaattg aggttatcct gaaaaacgcc    180

attgtctaca actccatgta cgagaatttc tccaccagct tctggattcg catcccgaaa    240

tacttcaaca gcattagcct gaacaacgag tatactatca tcaactgtat ggagaacaac    300

agcggttgga aggtgtctct gaactatggt gagatcattt ggaccttgca ggacacccaa    360

gagatcaagc agcgcgtcgt gttcaagtac tctcaaatga tcaacatttc cgattacatt    420

aatcgttgga tcttcgtgac cattacgaat aaccgtctga ataacagcaa gatttacatc    480

aatggtcgct tgatcgatca gaaaccgatt agcaacctgg gtaatatcca cgcaagcaac    540

aacattatgt tcaaattgga cggttgccgc gatacccatc gttatatctg gatcaagtat    600

ttcaacctgt ttgataaaga actgaatgag aaggagatca aagatttgta tgacaaccaa    660

tctaacagcg gcattttgaa ggacttctgg ggcgattatc tgcaatacga taagccgtac    720

tatatgctga acctggttga tccgaacaaa tatgtggatg tcaataatgt gggtattcgt    780

ggttacatgt atttgaaggg tccgcgtggc agcgttatga cgaccaacat ttacctgaac    840

tctagcctgt accgtggtac gaaattcatc attaagaaat atgccagcgg caacaaagat    900

aacattgtgc gtaataacga tcgtgtctac atcaacgtgg tcgtgaagaa taaagagtac    960

cgtctggcga ccaacgcttc gcaggcgggt gttgagaaaa ttctgagcgc gttggagatc   1020

cctgatgtcg gtaatctgag ccaagtcgtg gttatgaaga gcaagaacga ccagggtatc   1080

actaacaagt gcaagatgaa cctgcaagac aacaatggta acgacatcgg ctttattggt   1140

tacaaacagt tcaacaatat tgctaaactg gtagcgagca attggtacaa tcgtcagatt   1200

gagcgcagca gccgtacttt tggctgtagc tgggagttta tcccggtcga tgatggttgg   1260

ggcgaacgtc cgctgcacca tcaccatcac catcaccatc accattaa                1308
```

<210> SEQ ID NO 48
<211> LENGTH: 435
<212> TYPE: PRT
<213> ORGANISM: Artificial Sequence
<220> FEATURE:
<223> OTHER INFORMATION: Polypeptide Sequence of rHC/A Variant Y1117V
      F1252Y H1253K L1278F (His-tagged)

<400> SEQUENCE: 48

```
Met Ile Ile Asn Thr Ser Ile Leu Asn Leu Arg Tyr Glu Ser Asn His
1               5                   10                  15

Leu Ile Asp Leu Ser Arg Tyr Ala Ser Lys Ile Asn Ile Gly Ser Lys
            20                  25                  30

Val Asn Phe Asp Pro Ile Asp Lys Asn Gln Ile Gln Leu Phe Asn Leu
        35                  40                  45

Glu Ser Ser Lys Ile Glu Val Ile Leu Lys Asn Ala Ile Val Tyr Asn
```

```
    50                  55                  60

Ser Met Tyr Glu Asn Phe Ser Thr Ser Phe Trp Ile Arg Ile Pro Lys
65                  70                  75                  80

Tyr Phe Asn Ser Ile Ser Leu Asn Asn Glu Tyr Thr Ile Ile Asn Cys
                85                  90                  95

Met Glu Asn Asn Ser Gly Trp Lys Val Ser Leu Asn Tyr Gly Glu Ile
            100                 105                 110

Ile Trp Thr Leu Gln Asp Thr Gln Glu Ile Lys Gln Arg Val Val Phe
        115                 120                 125

Lys Tyr Ser Gln Met Ile Asn Ile Ser Asp Tyr Ile Asn Arg Trp Ile
    130                 135                 140

Phe Val Thr Ile Thr Asn Asn Arg Leu Asn Asn Ser Lys Ile Tyr Ile
145                 150                 155                 160

Asn Gly Arg Leu Ile Asp Gln Lys Pro Ile Ser Asn Leu Gly Asn Ile
                165                 170                 175

His Ala Ser Asn Asn Ile Met Phe Lys Leu Asp Gly Cys Arg Asp Thr
            180                 185                 190

His Arg Tyr Ile Trp Ile Lys Tyr Phe Asn Leu Phe Asp Lys Glu Leu
        195                 200                 205

Asn Glu Lys Glu Ile Lys Asp Leu Tyr Asp Asn Gln Ser Asn Ser Gly
    210                 215                 220

Ile Leu Lys Asp Phe Trp Gly Asp Tyr Leu Gln Tyr Asp Lys Pro Tyr
225                 230                 235                 240

Tyr Met Leu Asn Leu Val Asp Pro Asn Lys Tyr Val Asp Val Asn Asn
                245                 250                 255

Val Gly Ile Arg Gly Tyr Met Tyr Leu Lys Gly Pro Arg Gly Ser Val
            260                 265                 270

Met Thr Thr Asn Ile Tyr Leu Asn Ser Ser Leu Tyr Arg Gly Thr Lys
        275                 280                 285

Phe Ile Ile Lys Lys Tyr Ala Ser Gly Asn Lys Asp Asn Ile Val Arg
    290                 295                 300

Asn Asn Asp Arg Val Tyr Ile Asn Val Val Val Lys Asn Lys Glu Tyr
305                 310                 315                 320

Arg Leu Ala Thr Asn Ala Ser Gln Ala Gly Val Glu Lys Ile Leu Ser
                325                 330                 335

Ala Leu Glu Ile Pro Asp Val Gly Asn Leu Ser Gln Val Val Val Met
            340                 345                 350

Lys Ser Lys Asn Asp Gln Gly Ile Thr Asn Lys Cys Lys Met Asn Leu
        355                 360                 365

Gln Asp Asn Asn Gly Asn Asp Ile Gly Phe Ile Gly Tyr Lys Gln Phe
    370                 375                 380

Asn Asn Ile Ala Lys Leu Val Ala Ser Asn Trp Tyr Asn Arg Gln Ile
385                 390                 395                 400

Glu Arg Ser Ser Arg Thr Phe Gly Cys Ser Trp Glu Phe Ile Pro Val
                405                 410                 415

Asp Asp Gly Trp Gly Glu Arg Pro Leu His His His His His His His
            420                 425                 430

His His His
        435
```

<210> SEQ ID NO 49
<211> LENGTH: 1293
<212> TYPE: DNA
<213> ORGANISM: Artificial Sequence
<220> FEATURE:
<223> OTHER INFORMATION: Nucleotide Sequence of rHC/A Variant Y1117V
      F1252Y H1253K L1278H (His-tagged)

<400> SEQUENCE: 49

```
atgatcatca atactagcat tctgaacctg cgttacgaga gcaatcatct gattgatctg     60

agccgttatg caagcaagat caacatcggt agcaaggtca attttgaccc gatcgataag    120

aaccagatcc agctgtttaa tctggaatcg agcaaaattg aggttatcct gaaaaacgcc    180

attgtctaca actccatgta cgagaatttc tccaccagct tctggattcg catcccgaaa    240

tacttcaaca gcattagcct gaacaacgag tatactatca tcaactgtat ggagaacaac    300

agcggttgga aggtgtctct gaactatggt gagatcattt ggaccttgca ggacacccaa    360

gagatcaagc agcgcgtcgt gttcaagtac tctcaaatga tcaacatttc cgattacatt    420

aatcgttgga tcttcgtgac cattacgaat aaccgtctga ataacagcaa gatttacatc    480

aatggtcgct tgatcgatca gaaaccgatt agcaacctgg gtaatatcca cgcaagcaac    540

aacattatgt tcaaattgga cggttgccgc gatacccatc gttatatctg gatcaagtat    600

ttcaacctgt ttgataaaga actgaatgag aaggagatca aagatttgta tgacaaccaa    660

tctaacagcg gcattttgaa ggacttctgg ggcgattatc tgcaatacga taagccgtac    720

tatatgctga acctggttga tccgaacaaa tatgtggatg tcaataatgt gggtattcgt    780

ggttacatgt atttgaaggg tccgcgtggc agcgttatga cgaccaacat ttacctgaac    840

tctagcctgt accgtggtac gaaattcatc attaagaaat atgccagcgg caacaaagat    900

aacattgtgc gtaataacga tcgtgtctac atcaacgtgg tcgtgaagaa taaagagtac    960

cgtctggcga ccaacgcttc gcaggcgggt gttgagaaaa ttctgagcgc gttggagatc   1020

cctgatgtcg gtaatctgag ccaagtcgtg gttatgaaga gcaagaacga ccagggtatc   1080

actaacaagt gcaagatgaa cctgcaagac aacaatggta acgacatcgg ctttattggt   1140

tacaaacagt tcaacaatat tgctaaactg gtagcgagca attggtacaa tcgtcagatt   1200

gagcgcagca gccgtactca tggctgtagc tgggagttta tcccggtcga tgatggttgg   1260

ggcgaacgtc cgctgcacca tcaccatcac cat                                1293
```

<210> SEQ ID NO 50
<211> LENGTH: 431
<212> TYPE: PRT
<213> ORGANISM: Artificial Sequence
<220> FEATURE:
<223> OTHER INFORMATION: Polypeptide Sequence of rHC/A Variant Y1117V
      F1252Y H1253K L1278H (His-tagged)

<400> SEQUENCE: 50

```
Met Ile Ile Asn Thr Ser Ile Leu Asn Leu Arg Tyr Glu Ser Asn His
1               5                   10                  15

Leu Ile Asp Leu Ser Arg Tyr Ala Ser Lys Ile Asn Ile Gly Ser Lys
            20                  25                  30

Val Asn Phe Asp Pro Ile Asp Lys Asn Gln Ile Gln Leu Phe Asn Leu
        35                  40                  45

Glu Ser Ser Lys Ile Glu Val Ile Leu Lys Asn Ala Ile Val Tyr Asn
    50                  55                  60

Ser Met Tyr Glu Asn Phe Ser Thr Ser Phe Trp Ile Arg Ile Pro Lys
65                  70                  75                  80

Tyr Phe Asn Ser Ile Ser Leu Asn Asn Glu Tyr Thr Ile Ile Asn Cys
                85                  90                  95
```

```
Met Glu Asn Asn Ser Gly Trp Lys Val Ser Leu Asn Tyr Gly Glu Ile
            100                 105                 110

Ile Trp Thr Leu Gln Asp Thr Gln Glu Ile Lys Gln Arg Val Val Phe
        115                 120                 125

Lys Tyr Ser Gln Met Ile Asn Ile Ser Asp Tyr Ile Asn Arg Trp Ile
    130                 135                 140

Phe Val Thr Ile Thr Asn Asn Arg Leu Asn Asn Ser Lys Ile Tyr Ile
145                 150                 155                 160

Asn Gly Arg Leu Ile Asp Gln Lys Pro Ile Ser Asn Leu Gly Asn Ile
                165                 170                 175

His Ala Ser Asn Asn Ile Met Phe Lys Leu Asp Gly Cys Arg Asp Thr
            180                 185                 190

His Arg Tyr Ile Trp Ile Lys Tyr Phe Asn Leu Phe Asp Lys Glu Leu
        195                 200                 205

Asn Glu Lys Glu Ile Lys Asp Leu Tyr Asp Asn Gln Ser Asn Ser Gly
    210                 215                 220

Ile Leu Lys Asp Phe Trp Gly Asp Tyr Leu Gln Tyr Asp Lys Pro Tyr
225                 230                 235                 240

Tyr Met Leu Asn Leu Val Asp Pro Asn Lys Tyr Val Asp Val Asn Asn
                245                 250                 255

Val Gly Ile Arg Gly Tyr Met Tyr Leu Lys Gly Pro Arg Gly Ser Val
            260                 265                 270

Met Thr Thr Asn Ile Tyr Leu Asn Ser Ser Leu Tyr Arg Gly Thr Lys
        275                 280                 285

Phe Ile Ile Lys Lys Tyr Ala Ser Gly Asn Lys Asp Asn Ile Val Arg
    290                 295                 300

Asn Asn Asp Arg Val Tyr Ile Asn Val Val Val Lys Asn Lys Glu Tyr
305                 310                 315                 320

Arg Leu Ala Thr Asn Ala Ser Gln Ala Gly Val Glu Lys Ile Leu Ser
                325                 330                 335

Ala Leu Glu Ile Pro Asp Val Gly Asn Leu Ser Gln Val Val Val Met
            340                 345                 350

Lys Ser Lys Asn Asp Gln Gly Ile Thr Asn Lys Cys Lys Met Asn Leu
        355                 360                 365

Gln Asp Asn Asn Gly Asn Asp Ile Gly Phe Ile Gly Tyr Lys Gln Phe
    370                 375                 380

Asn Asn Ile Ala Lys Leu Val Ala Ser Asn Trp Tyr Asn Arg Gln Ile
385                 390                 395                 400

Glu Arg Ser Ser Arg Thr His Gly Cys Ser Trp Glu Phe Ile Pro Val
                405                 410                 415

Asp Asp Gly Trp Gly Glu Arg Pro Leu His His His His His His
            420                 425                 430
```

<210> SEQ ID NO 51
<211> LENGTH: 1296
<212> TYPE: PRT
<213> ORGANISM: Clostridium botulinum

<400> SEQUENCE: 51

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45
```

```
Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460
```

```
Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
```

```
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                1015                1020

Leu Asn  Asn Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Asn Ile
    1040                1045                1050

Met Phe  Lys Leu Asp Gly Cys  Arg Asp Thr His Arg  Tyr Ile Trp
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Gln Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290
```

Arg Pro Leu
    1295

<210> SEQ ID NO 52
<211> LENGTH: 1291
<212> TYPE: PRT
<213> ORGANISM: Clostridium botulinum

<400> SEQUENCE: 52

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys

```
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Gly Cys Ser Val Ser Tyr Leu Met
    770                 775                 780
```

```
Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
        835                 840                 845

Leu Ile Glu Met Phe Asn Lys Tyr Asn Ser Glu Ile Leu Asn Asn Ile
    850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn  Arg Trp Phe Phe Val  Thr Ile Thr
        995                 1000                1005

Asn Asn  Leu Asn Asn Ala Lys  Ile Tyr Ile Asn Gly  Lys Leu Glu
    1010                1015                1020

Ser Asn  Thr Asp Ile Lys Asp  Ile Arg Glu Val Ile  Ala Asn Gly
    1025                1030                1035

Glu Ile  Ile Phe Lys Leu Asp  Gly Asp Ile Asp Arg  Thr Gln Phe
    1040                1045                1050

Ile Trp  Met Lys Tyr Phe Ser  Ile Phe Asn Thr Glu  Leu Ser Gln
    1055                1060                1065

Ser Asn  Ile Glu Glu Arg Tyr  Lys Ile Gln Ser Tyr  Ser Glu Tyr
    1070                1075                1080

Leu Lys  Asp Phe Trp Gly Asn  Pro Leu Met Tyr Asn  Lys Glu Tyr
    1085                1090                1095

Tyr Met  Phe Asn Ala Gly Asn  Lys Asn Ser Tyr Ile  Lys Leu Lys
    1100                1105                1110

Lys Asp  Ser Pro Val Gly Glu  Ile Leu Thr Arg Ser  Lys Tyr Asn
    1115                1120                1125

Gln Asn  Ser Lys Tyr Ile Asn  Tyr Arg Asp Leu Tyr  Ile Gly Glu
    1130                1135                1140

Lys Phe  Ile Ile Arg Arg Lys  Ser Asn Ser Gln Ser  Ile Asn Asp
    1145                1150                1155

Asp Ile  Val Arg Lys Glu Asp  Tyr Ile Tyr Leu Asp  Phe Phe Asn
    1160                1165                1170

Leu Asn  Gln Glu Trp Arg Val  Tyr Thr Tyr Lys Tyr  Phe Lys Lys
    1175                1180                1185
```

```
Glu Glu  Glu Lys Leu Phe Leu  Ala Pro Ile Ser Asp  Ser Asp Glu
    1190                 1195                 1200

Phe Tyr  Asn Thr Ile Gln Ile  Lys Glu Tyr Asp Glu  Gln Pro Thr
    1205                 1210                 1215

Tyr Ser  Cys Gln Leu Leu Phe  Lys Lys Asp Glu Glu  Ser Thr Asp
    1220                 1225                 1230

Glu Ile  Gly Leu Ile Gly Ile  His Arg Phe Tyr Glu  Ser Gly Ile
    1235                 1240                 1245

Val Phe  Glu Glu Tyr Lys Asp  Tyr Phe Cys Ile Ser  Lys Trp Tyr
    1250                 1255                 1260

Leu Lys  Glu Val Lys Arg Lys  Pro Tyr Asn Leu Lys  Leu Gly Cys
    1265                 1270                 1275

Asn Trp  Gln Phe Ile Pro Lys  Asp Glu Gly Trp Thr  Glu
    1280                 1285                 1290


<210> SEQ ID NO 53
<211> LENGTH: 1291
<212> TYPE: PRT
<213> ORGANISM: Clostridium botulinum

<400> SEQUENCE: 53

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270
```

```
Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685
```

```
Thr Ile Asp Asn Cys Leu Glu Gln Arg Ile Lys Arg Trp Lys Asp Ser
    690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn  Ala Pro Gly Tyr Asn  Lys Trp Phe
        995                 1000                1005

Phe Val  Thr Val Thr Asn Asn  Met Met Gly Asn Met  Lys Ile Tyr
    1010                1015                1020

Ile Asn  Gly Lys Leu Ile Asp  Thr Ile Lys Val Lys  Glu Leu Thr
    1025                1030                1035

Gly Ile  Asn Phe Ser Lys Thr  Ile Thr Phe Glu Ile  Asn Lys Ile
    1040                1045                1050

Pro Asp  Thr Gly Leu Ile Thr  Ser Asp Ser Asp Asn  Ile Asn Met
    1055                1060                1065

Trp Ile  Arg Asp Phe Tyr Ile  Phe Ala Lys Glu Leu  Asp Gly Lys
    1070                1075                1080

Asp Ile  Asn Ile Leu Phe Asn  Ser Leu Gln Tyr Thr  Asn Val Val
    1085                1090                1095

Lys Asp  Tyr Trp Gly Asn Asp  Leu Arg Tyr Asn Lys  Glu Tyr Tyr
```

```
    1100                1105                1110

Met Val  Asn Ile Asp Tyr Leu  Asn Arg Tyr Met Tyr  Ala Asn Ser
    1115                1120                1125

Arg Gln  Ile Val Phe Asn Thr  Arg Arg Asn Asn Asn  Asp Phe Asn
    1130                1135                1140

Glu Gly  Tyr Lys Ile Ile Ile  Lys Arg Ile Arg Gly  Asn Thr Asn
    1145                1150                1155

Asp Thr  Arg Val Arg Gly Gly  Asp Ile Leu Tyr Phe  Asp Met Thr
    1160                1165                1170

Ile Asn  Asn Lys Ala Tyr Asn  Leu Phe Met Lys Asn  Glu Thr Met
    1175                1180                1185

Tyr Ala  Asp Asn His Ser Thr  Glu Asp Ile Tyr Ala  Ile Gly Leu
    1190                1195                1200

Arg Glu  Gln Thr Lys Asp Ile  Asn Asp Asn Ile Ile  Phe Gln Ile
    1205                1210                1215

Gln Pro  Met Asn Asn Thr Tyr  Tyr Tyr Ala Ser Gln  Ile Phe Lys
    1220                1225                1230

Ser Asn  Phe Asn Gly Glu Asn  Ile Ser Gly Ile Cys  Ser Ile Gly
    1235                1240                1245

Thr Tyr  Arg Phe Arg Leu Gly  Gly Asp Trp Tyr Arg  His Asn Tyr
    1250                1255                1260

Leu Val  Pro Thr Val Lys Gln  Gly Asn Tyr Ala Ser  Leu Leu Glu
    1265                1270                1275

Ser Thr  Ser Thr His Trp Gly  Phe Val Pro Val Ser  Glu
    1280                1285                1290


<210> SEQ ID NO 54
<211> LENGTH: 1276
<212> TYPE: PRT
<213> ORGANISM: Clostridium botulinum

<400> SEQUENCE: 54

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175
```

```
Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
```

```
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
        755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
        835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn  Lys Trp Phe Phe Val  Thr Ile Thr
        995                 1000                1005

Asn Asn  Ile Met Gly Tyr Met  Lys Leu Tyr Ile Asn  Gly Glu Leu
    1010                1015                1020
```

```
Lys Gln  Ser Gln Lys Ile Glu  Asp Leu Asp Glu Val  Lys Leu Asp
    1025                 1030                 1035

Lys Thr  Ile Val Phe Gly Ile  Asp Glu Asn Ile Asp  Glu Asn Gln
    1040                 1045                 1050

Met Leu  Trp Ile Arg Asp Phe  Asn Ile Phe Ser Lys  Glu Leu Ser
    1055                 1060                 1065

Asn Glu  Asp Ile Asn Ile Val  Tyr Glu Gly Gln Ile  Leu Arg Asn
    1070                 1075                 1080

Val Ile  Lys Asp Tyr Trp Gly  Asn Pro Leu Lys Phe  Asp Thr Glu
    1085                 1090                 1095

Tyr Tyr  Ile Ile Asn Asp Asn  Tyr Ile Asp Arg Tyr  Ile Ala Pro
    1100                 1105                 1110

Glu Ser  Asn Val Leu Val Leu  Val Gln Tyr Pro Asp  Arg Ser Lys
    1115                 1120                 1125

Leu Tyr  Thr Gly Asn Pro Ile  Thr Ile Lys Ser Val  Ser Asp Lys
    1130                 1135                 1140

Asn Pro  Tyr Ser Arg Ile Leu  Asn Gly Asp Asn Ile  Ile Leu His
    1145                 1150                 1155

Met Leu  Tyr Asn Ser Arg Lys  Tyr Met Ile Ile Arg  Asp Thr Asp
    1160                 1165                 1170

Thr Ile  Tyr Ala Thr Gln Gly  Gly Glu Cys Ser Gln  Asn Cys Val
    1175                 1180                 1185

Tyr Ala  Leu Lys Leu Gln Ser  Asn Leu Gly Asn Tyr  Gly Ile Gly
    1190                 1195                 1200

Ile Phe  Ser Ile Lys Asn Ile  Val Ser Lys Asn Lys  Tyr Cys Ser
    1205                 1210                 1215

Gln Ile  Phe Ser Ser Phe Arg  Glu Asn Thr Met Leu  Leu Ala Asp
    1220                 1225                 1230

Ile Tyr  Lys Pro Trp Arg Phe  Ser Phe Lys Asn Ala  Tyr Thr Pro
    1235                 1240                 1245

Val Ala  Val Thr Asn Tyr Glu  Thr Lys Leu Leu Ser  Thr Ser Ser
    1250                 1255                 1260

Phe Trp  Lys Phe Ile Ser Arg  Asp Pro Gly Trp Val  Glu
    1265                 1270                 1275


<210> SEQ ID NO 55
<211> LENGTH: 1251
<212> TYPE: PRT
<213> ORGANISM: Clostridium botulinum

<400> SEQUENCE: 55

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
```

```
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525
```

```
Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940
```

```
Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                 1015                1020

His Val  Ser Asp Asn Ile Leu  Phe Lys Ile Val Asn  Cys Ser Tyr
    1025                 1030                1035

Thr Arg  Tyr Ile Gly Ile Arg  Tyr Phe Asn Ile Phe  Asp Lys Glu
    1040                 1045                1050

Leu Asp  Glu Thr Glu Ile Gln  Thr Leu Tyr Ser Asn  Glu Pro Asn
    1055                 1060                1065

Thr Asn  Ile Leu Lys Asp Phe  Trp Gly Asn Tyr Leu  Leu Tyr Asp
    1070                 1075                1080

Lys Glu  Tyr Tyr Leu Leu Asn  Val Leu Lys Pro Asn  Asn Phe Ile
    1085                 1090                1095

Asp Arg  Arg Lys Asp Ser Thr  Leu Ser Ile Asn Asn  Ile Arg Ser
    1100                 1105                1110

Thr Ile  Leu Leu Ala Asn Arg  Leu Tyr Ser Gly Ile  Lys Val Lys
    1115                 1120                1125

Ile Gln  Arg Val Asn Asn Ser  Ser Thr Asn Asp Asn  Leu Val Arg
    1130                 1135                1140

Lys Asn  Asp Gln Val Tyr Ile  Asn Phe Val Ala Ser  Lys Thr His
    1145                 1150                1155

Leu Phe  Pro Leu Tyr Ala Asp  Thr Ala Thr Thr Asn  Lys Glu Lys
    1160                 1165                1170

Thr Ile  Lys Ile Ser Ser Ser  Gly Asn Arg Phe Asn  Gln Val Val
    1175                 1180                1185

Val Met  Asn Ser Val Gly Asn  Cys Thr Met Asn Phe  Lys Asn Asn
    1190                 1195                1200

Asn Gly  Asn Asn Ile Gly Leu  Leu Gly Phe Lys Ala  Asp Thr Val
    1205                 1210                1215

Val Ala  Ser Thr Trp Tyr Tyr  Thr His Met Arg Asp  His Thr Asn
    1220                 1225                1230

Ser Asn  Gly Cys Phe Trp Asn  Phe Ile Ser Glu Glu  His Gly Trp
    1235                 1240                1245

Gln Glu  Lys
    1250


<210> SEQ ID NO 56
<211> LENGTH: 1278
<212> TYPE: PRT
<213> ORGANISM: Clostridium botulinum

<400> SEQUENCE: 56

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45
```

```
Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Arg Glu Leu Phe Phe Val Ala Ser Glu Ser Ser Tyr Asn Glu
    450                 455                 460
```

-continued

```
Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
            580                 585                 590

Ser Trp Ile Asn Gln Val Ile Arg Asp Phe Thr Thr Glu Ala Thr Gln
        595                 600                 605

Lys Ser Thr Phe Asp Lys Ile Ala Asp Ile Ser Leu Val Val Pro Tyr
    610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
            660                 665                 670

Ile Gly Ser Ser Glu Asn Lys Asn Lys Ile Ile Lys Ala Ile Asn Asn
        675                 680                 685

Ser Leu Met Glu Arg Glu Thr Lys Trp Lys Glu Ile Tyr Ser Trp Ile
    690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Asn Tyr Thr Ser Asp Glu Arg Asn Arg
            740                 745                 750

Leu Glu Ser Glu Tyr Asn Ile Asn Asn Ile Arg Glu Glu Leu Asn Lys
        755                 760                 765

Lys Val Ser Leu Ala Met Glu Asn Ile Glu Arg Phe Ile Thr Glu Ser
    770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
                805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
        835                 840                 845

Tyr Thr Asn Asp Lys Ile Leu Ile Leu Tyr Phe Asn Lys Leu Tyr Lys
    850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
```

```
                885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
        915                 920                 925

Gly Arg Tyr Gln Asn Phe Ser Ile Ser Phe Trp Val Arg Ile Pro Lys
    930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
                965                 970                 975

Ile Ile Trp Thr Leu Gln Asp Thr Ala Gly Asn Asn Gln Lys Leu Val
            980                 985                 990

Phe Asn Tyr Thr Gln Met Ile Ser  Ile Ser Asp Tyr Ile  Asn Lys Trp
        995                 1000                1005

Ile Phe  Val Thr Ile Thr Asn  Asn Arg Leu Gly Asn  Ser Arg Ile
    1010                 1015                 1020

Tyr Ile  Asn Gly Asn Leu Ile  Asp Glu Lys Ser Ile  Ser Asn Leu
    1025                 1030                 1035

Gly Asp  Ile His Val Ser Asp  Asn Ile Leu Phe Lys  Ile Val Gly
    1040                 1045                 1050

Cys Asn  Asp Thr Arg Tyr Val  Gly Ile Arg Tyr Phe  Lys Val Phe
    1055                 1060                 1065

Asp Thr  Glu Leu Gly Lys Thr  Glu Ile Glu Thr Leu  Tyr Ser Asp
    1070                 1075                 1080

Glu Pro  Asp Pro Ser Ile Leu  Lys Asp Phe Trp Gly  Asn Tyr Leu
    1085                 1090                 1095

Leu Tyr  Asn Lys Arg Tyr Tyr  Leu Leu Asn Leu Leu  Arg Thr Asp
    1100                 1105                 1110

Lys Ser  Ile Thr Gln Asn Ser  Asn Phe Leu Asn Ile  Asn Gln Gln
    1115                 1120                 1125

Arg Gly  Val Tyr Gln Lys Pro  Asn Ile Phe Ser Asn  Thr Arg Leu
    1130                 1135                 1140

Tyr Thr  Gly Val Glu Val Ile  Ile Arg Lys Asn Gly  Ser Thr Asp
    1145                 1150                 1155

Ile Ser  Asn Thr Asp Asn Phe  Val Arg Lys Asn Asp  Leu Ala Tyr
    1160                 1165                 1170

Ile Asn  Val Val Asp Arg Asp  Val Glu Tyr Arg Leu  Tyr Ala Asp
    1175                 1180                 1185

Ile Ser  Ile Ala Lys Pro Glu  Lys Ile Ile Lys Leu  Ile Arg Thr
    1190                 1195                 1200

Ser Asn  Ser Asn Asn Ser Leu  Gly Gln Ile Ile Val  Met Asp Ser
    1205                 1210                 1215

Ile Gly  Asn Asn Cys Thr Met  Asn Phe Gln Asn Asn  Asn Gly Gly
    1220                 1225                 1230

Asn Ile  Gly Leu Leu Gly Phe  His Ser Asn Asn Leu  Val Ala Ser
    1235                 1240                 1245

Ser Trp  Tyr Tyr Asn Asn Ile  Arg Lys Asn Thr Ser  Ser Asn Gly
    1250                 1255                 1260

Cys Phe  Trp Ser Phe Ile Ser  Lys Glu His Gly Trp  Gln Glu Asn
    1265                 1270                 1275
```

<210> SEQ ID NO 57

<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365
```

```
Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
```

```
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
        915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp  Asn Ile Ser Asp Tyr  Ile Asn Lys
        995                 1000                1005

Trp Phe  Ser Ile Thr Ile Thr  Asn Asp Arg Leu Gly  Asn Ala Asn
    1010                1015                1020

Ile Tyr  Ile Asn Gly Ser Leu  Lys Lys Ser Glu Lys  Ile Leu Asn
    1025                1030                1035

Leu Asp  Arg Ile Asn Ser Ser  Asn Asp Ile Asp Phe  Lys Leu Ile
    1040                1045                1050

Asn Cys  Thr Asp Thr Thr Lys  Phe Val Trp Ile Lys  Asp Phe Asn
    1055                1060                1065

Ile Phe  Gly Arg Glu Leu Asn  Ala Thr Glu Val Ser  Ser Leu Tyr
    1070                1075                1080

Trp Ile  Gln Ser Ser Thr Asn  Thr Leu Lys Asp Phe  Trp Gly Asn
    1085                1090                1095

Pro Leu  Arg Tyr Asp Thr Gln  Tyr Tyr Leu Phe Asn  Gln Gly Met
    1100                1105                1110

Gln Asn  Ile Tyr Ile Lys Tyr  Phe Ser Lys Ala Ser  Met Gly Glu
    1115                1120                1125

Thr Ala  Pro Arg Thr Asn Phe  Asn Asn Ala Ala Ile  Asn Tyr Gln
    1130                1135                1140

Asn Leu  Tyr Leu Gly Leu Arg  Phe Ile Ile Lys Lys  Ala Ser Asn
    1145                1150                1155

Ser Arg  Asn Ile Asn Asn Asp  Asn Ile Val Arg Glu  Gly Asp Tyr
    1160                1165                1170

Ile Tyr  Leu Asn Ile Asp Asn  Ile Ser Asp Glu Ser  Tyr Arg Val
    1175                1180                1185

Tyr Val  Leu Val Asn Ser Lys  Glu Ile Gln Thr Gln  Leu Phe Leu
    1190                1195                1200
```

Ala Pro Ile Asn Asp Asp Pro Thr Phe Tyr Asp Val Leu Gln Ile
1205 1210 1215

Lys Lys Tyr Tyr Glu Lys Thr Thr Tyr Asn Cys Gln Ile Leu Cys
1220 1225 1230

Glu Lys Asp Thr Lys Thr Phe Gly Leu Phe Gly Ile Gly Lys Phe
1235 1240 1245

Val Lys Asp Tyr Gly Tyr Val Trp Asp Thr Tyr Asp Asn Tyr Phe
1250 1255 1260

Cys Ile Ser Gln Trp Tyr Leu Arg Arg Ile Ser Glu Asn Ile Asn
1265 1270 1275

Lys Leu Arg Leu Gly Cys Asn Trp Gln Phe Ile Pro Val Asp Glu
1280 1285 1290

Gly Trp Thr Glu
1295

<210> SEQ ID NO 58
<211> LENGTH: 1315
<212> TYPE: PRT
<213> ORGANISM: Clostridium tetani

<400> SEQUENCE: 58

Met Pro Ile Thr Ile Asn Asn Phe Arg Tyr Ser Asp Pro Val Asn Asn
1 5 10 15

Asp Thr Ile Ile Met Met Glu Pro Pro Tyr Cys Lys Gly Leu Asp Ile
20 25 30

Tyr Tyr Lys Ala Phe Lys Ile Thr Asp Arg Ile Trp Ile Val Pro Glu
35 40 45

Arg Tyr Glu Phe Gly Thr Lys Pro Glu Asp Phe Asn Pro Pro Ser Ser
50 55 60

Leu Ile Glu Gly Ala Ser Glu Tyr Tyr Asp Pro Asn Tyr Leu Arg Thr
65 70 75 80

Asp Ser Asp Lys Asp Arg Phe Leu Gln Thr Met Val Lys Leu Phe Asn
85 90 95

Arg Ile Lys Asn Asn Val Ala Gly Glu Ala Leu Leu Asp Lys Ile Ile
100 105 110

Asn Ala Ile Pro Tyr Leu Gly Asn Ser Tyr Ser Leu Leu Asp Lys Phe
115 120 125

Asp Thr Asn Ser Asn Ser Val Ser Phe Asn Leu Leu Glu Gln Asp Pro
130 135 140

Ser Gly Ala Thr Thr Lys Ser Ala Met Leu Thr Asn Leu Ile Ile Phe
145 150 155 160

Gly Pro Gly Pro Val Leu Asn Lys Asn Glu Val Arg Gly Ile Val Leu
165 170 175

Arg Val Asp Asn Lys Asn Tyr Phe Pro Cys Arg Asp Gly Phe Gly Ser
180 185 190

Ile Met Gln Met Ala Phe Cys Pro Glu Tyr Val Pro Thr Phe Asp Asn
195 200 205

Val Ile Glu Asn Ile Thr Ser Leu Thr Ile Gly Lys Ser Lys Tyr Phe
210 215 220

Gln Asp Pro Ala Leu Leu Leu Met His Glu Leu Ile His Val Leu His
225 230 235 240

Gly Leu Tyr Gly Met Gln Val Ser Ser His Glu Ile Ile Pro Ser Lys
245 250 255

Gln Glu Ile Tyr Met Gln His Thr Tyr Pro Ile Ser Ala Glu Glu Leu

```
        260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685
```

```
Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu  Ile Trp Thr Leu Lys  Asp Ser Ala
        995                 1000                1005

Gly Glu  Val Arg Gln Ile Thr  Phe Arg Asp Leu Pro  Asp Lys Phe
    1010                1015                1020

Asn Ala  Tyr Leu Ala Asn Lys  Trp Val Phe Ile Thr  Ile Thr Asn
    1025                1030                1035

Asp Arg  Leu Ser Ser Ala Asn  Leu Tyr Ile Asn Gly  Val Leu Met
    1040                1045                1050

Gly Ser  Ala Glu Ile Thr Gly  Leu Gly Ala Ile Arg  Glu Asp Asn
    1055                1060                1065

Asn Ile  Thr Leu Lys Leu Asp  Arg Cys Asn Asn Asn  Asn Gln Tyr
    1070                1075                1080

Val Ser  Ile Asp Lys Phe Arg  Ile Phe Cys Lys Ala  Leu Asn Pro
    1085                1090                1095
```

```
Lys Glu  Ile Glu Lys Leu Tyr  Thr Ser Tyr Leu Ser  Ile Thr Phe
    1100                 1105                 1110

Leu Arg  Asp Phe Trp Gly Asn  Pro Leu Arg Tyr Asp  Thr Glu Tyr
    1115                 1120                 1125

Tyr Leu  Ile Pro Val Ala Ser  Ser Ser Lys Asp Val  Gln Leu Lys
    1130                 1135                 1140

Asn Ile  Thr Asp Tyr Met Tyr  Leu Thr Asn Ala Pro  Ser Tyr Thr
    1145                 1150                 1155

Asn Gly  Lys Leu Asn Ile Tyr  Tyr Arg Arg Leu Tyr  Asn Gly Leu
    1160                 1165                 1170

Lys Phe  Ile Ile Lys Arg Tyr  Thr Pro Asn Asn Glu  Ile Asp Ser
    1175                 1180                 1185

Phe Val  Lys Ser Gly Asp Phe  Ile Lys Leu Tyr Val  Ser Tyr Asn
    1190                 1195                 1200

Asn Asn  Glu His Ile Val Gly  Tyr Pro Lys Asp Gly  Asn Ala Phe
    1205                 1210                 1215

Asn Asn  Leu Asp Arg Ile Leu  Arg Val Gly Tyr Asn  Ala Pro Gly
    1220                 1225                 1230

Ile Pro  Leu Tyr Lys Lys Met  Glu Ala Val Lys Leu  Arg Asp Leu
    1235                 1240                 1245

Lys Thr  Tyr Ser Val Gln Leu  Lys Leu Tyr Asp Asp  Lys Asn Ala
    1250                 1255                 1260

Ser Leu  Gly Leu Val Gly Thr  His Asn Gly Gln Ile  Gly Asn Asp
    1265                 1270                 1275

Pro Asn  Arg Asp Ile Leu Ile  Ala Ser Asn Trp Tyr  Phe Asn His
    1280                 1285                 1290

Leu Lys  Asp Lys Ile Leu Gly  Cys Asp Trp Tyr Phe  Val Pro Thr
    1295                 1300                 1305

Asp Glu  Gly Trp Thr Asn Asp
    1310                 1315


<210> SEQ ID NO 59
<211> LENGTH: 1306
<212> TYPE: PRT
<213> ORGANISM: Clostridium botulinum

<400> SEQUENCE: 59

Met Lys Leu Glu Ile Asn Lys Phe Asn Tyr Asn Asp Pro Ile Asp Gly
1               5                   10                  15

Ile Asn Val Ile Thr Met Arg Pro Pro Arg His Ser Asp Lys Ile Asn
            20                  25                  30

Lys Gly Lys Gly Pro Phe Lys Ala Phe Gln Val Ile Lys Asn Ile Trp
        35                  40                  45

Ile Val Pro Glu Arg Tyr Asn Phe Thr Asn Asn Thr Asn Asp Leu Asn
    50                  55                  60

Ile Pro Ser Glu Pro Ile Met Glu Ala Asp Ala Ile Tyr Asn Pro Asn
65                  70                  75                  80

Tyr Leu Asn Thr Pro Ser Glu Lys Asp Glu Phe Leu Gln Gly Val Ile
                85                  90                  95

Lys Val Leu Glu Arg Ile Lys Ser Lys Pro Glu Gly Glu Lys Leu Leu
            100                 105                 110

Glu Leu Ile Ser Ser Ser Ile Pro Leu Pro Leu Val Ser Asn Gly Ala
        115                 120                 125

Leu Thr Leu Ser Asp Asn Glu Thr Ile Ala Tyr Gln Glu Asn Asn Asn
    130                 135                 140
```

```
Ile Val Ser Asn Leu Gln Ala Asn Leu Val Ile Tyr Gly Pro Gly Pro
145                 150                 155                 160

Asp Ile Ala Asn Asn Ala Thr Tyr Gly Leu Tyr Ser Thr Pro Ile Ser
                165                 170                 175

Asn Gly Glu Gly Thr Leu Ser Glu Val Ser Phe Ser Pro Phe Tyr Leu
            180                 185                 190

Lys Pro Phe Asp Glu Ser Tyr Gly Asn Tyr Arg Ser Leu Val Asn Ile
        195                 200                 205

Val Asn Lys Phe Val Lys Arg Glu Phe Ala Pro Asp Pro Ala Ser Thr
    210                 215                 220

Leu Met His Glu Leu Val His Val Thr His Asn Leu Tyr Gly Ile Ser
225                 230                 235                 240

Asn Arg Asn Phe Tyr Tyr Asn Phe Asp Thr Gly Lys Ile Glu Thr Ser
                245                 250                 255

Arg Gln Gln Asn Ser Leu Ile Phe Glu Glu Leu Leu Thr Phe Gly Gly
            260                 265                 270

Ile Asp Ser Lys Ala Ile Ser Ser Leu Ile Ile Lys Lys Ile Ile Glu
        275                 280                 285

Thr Ala Lys Asn Asn Tyr Thr Thr Leu Ile Ser Glu Arg Leu Asn Thr
    290                 295                 300

Val Thr Val Glu Asn Asp Leu Leu Lys Tyr Ile Lys Asn Lys Ile Pro
305                 310                 315                 320

Val Gln Gly Arg Leu Gly Asn Phe Lys Leu Asp Thr Ala Glu Phe Glu
                325                 330                 335

Lys Lys Leu Asn Thr Ile Leu Phe Val Leu Asn Glu Ser Asn Leu Ala
            340                 345                 350

Gln Arg Phe Ser Ile Leu Val Arg Lys His Tyr Leu Lys Glu Arg Pro
        355                 360                 365

Ile Asp Pro Ile Tyr Val Asn Ile Leu Asp Asp Asn Ser Tyr Ser Thr
    370                 375                 380

Leu Glu Gly Phe Asn Ile Ser Ser Gln Gly Ser Asn Asp Phe Gln Gly
385                 390                 395                 400

Gln Leu Leu Glu Ser Ser Tyr Phe Glu Lys Ile Glu Ser Asn Ala Leu
                405                 410                 415

Arg Ala Phe Ile Lys Ile Cys Pro Arg Asn Gly Leu Leu Tyr Asn Ala
            420                 425                 430

Ile Tyr Arg Asn Ser Lys Asn Tyr Leu Asn Asn Ile Asp Leu Glu Asp
        435                 440                 445

Lys Lys Thr Thr Ser Lys Thr Asn Val Ser Tyr Pro Cys Ser Leu Leu
    450                 455                 460

Asn Gly Cys Ile Glu Val Glu Asn Lys Asp Leu Phe Leu Ile Ser Asn
465                 470                 475                 480

Lys Asp Ser Leu Asn Asp Ile Asn Leu Ser Glu Glu Lys Ile Lys Pro
                485                 490                 495

Glu Thr Thr Val Phe Phe Lys Asp Lys Leu Pro Pro Gln Asp Ile Thr
            500                 505                 510

Leu Ser Asn Tyr Asp Phe Thr Glu Ala Asn Ser Ile Pro Ser Ile Ser
        515                 520                 525

Gln Gln Asn Ile Leu Glu Arg Asn Glu Glu Leu Tyr Glu Pro Ile Arg
    530                 535                 540

Asn Ser Leu Phe Glu Ile Lys Thr Ile Tyr Val Asp Lys Leu Thr Thr
545                 550                 555                 560
```

```
Phe His Phe Leu Glu Ala Gln Asn Ile Asp Glu Ser Ile Asp Ser Ser
                565                 570                 575

Lys Ile Arg Val Glu Leu Thr Asp Ser Val Asp Glu Ala Leu Ser Asn
            580                 585                 590

Pro Asn Lys Val Tyr Ser Pro Phe Lys Asn Met Ser Asn Thr Ile Asn
        595                 600                 605

Ser Ile Glu Thr Gly Ile Thr Ser Thr Tyr Ile Phe Tyr Gln Trp Leu
    610                 615                 620

Arg Ser Ile Val Lys Asp Phe Ser Asp Glu Thr Gly Lys Ile Asp Val
625                 630                 635                 640

Ile Asp Lys Ser Ser Asp Thr Leu Ala Ile Val Pro Tyr Ile Gly Pro
                645                 650                 655

Leu Leu Asn Ile Gly Asn Asp Ile Arg His Gly Asp Phe Val Gly Ala
            660                 665                 670

Ile Glu Leu Ala Gly Ile Thr Ala Leu Leu Glu Tyr Val Pro Glu Phe
        675                 680                 685

Thr Ile Pro Ile Leu Val Gly Leu Glu Val Ile Gly Gly Glu Leu Ala
    690                 695                 700

Arg Glu Gln Val Glu Ala Ile Val Asn Asn Ala Leu Asp Lys Arg Asp
705                 710                 715                 720

Gln Lys Trp Ala Glu Val Tyr Asn Ile Thr Lys Ala Gln Trp Trp Gly
                725                 730                 735

Thr Ile His Leu Gln Ile Asn Thr Arg Leu Ala His Thr Tyr Lys Ala
            740                 745                 750

Leu Ser Arg Gln Ala Asn Ala Ile Lys Met Asn Met Glu Phe Gln Leu
        755                 760                 765

Ala Asn Tyr Lys Gly Asn Ile Asp Asp Lys Ala Lys Ile Lys Asn Ala
    770                 775                 780

Ile Ser Glu Thr Glu Ile Leu Leu Asn Lys Ser Val Glu Gln Ala Met
785                 790                 795                 800

Lys Asn Thr Glu Lys Phe Met Ile Lys Leu Ser Asn Ser Tyr Leu Thr
                805                 810                 815

Lys Glu Met Ile Pro Lys Val Gln Asp Asn Leu Lys Asn Phe Asp Leu
            820                 825                 830

Glu Thr Lys Lys Thr Leu Asp Lys Phe Ile Lys Glu Lys Glu Asp Ile
        835                 840                 845

Leu Gly Thr Asn Leu Ser Ser Ser Leu Arg Arg Lys Val Ser Ile Arg
    850                 855                 860

Leu Asn Lys Asn Ile Ala Phe Asp Ile Asn Asp Ile Pro Phe Ser Glu
865                 870                 875                 880

Phe Asp Asp Leu Ile Asn Gln Tyr Lys Asn Glu Ile Glu Asp Tyr Glu
                885                 890                 895

Val Leu Asn Leu Gly Ala Glu Asp Gly Lys Ile Lys Asp Leu Ser Gly
            900                 905                 910

Thr Thr Ser Asp Ile Asn Ile Gly Ser Asp Ile Glu Leu Ala Asp Gly
        915                 920                 925

Arg Glu Asn Lys Ala Ile Lys Ile Lys Gly Ser Glu Asn Ser Thr Ile
    930                 935                 940

Lys Ile Ala Met Asn Lys Tyr Leu Arg Phe Ser Ala Thr Asp Asn Phe
945                 950                 955                 960

Ser Ile Ser Phe Trp Ile Lys His Pro Lys Pro Thr Asn Leu Leu Asn
                965                 970                 975

Asn Gly Ile Glu Tyr Thr Leu Val Glu Asn Phe Asn Gln Arg Gly Trp
```

```
            980                 985                 990

Lys Ile Ser Ile Gln Asp Ser Lys  Leu Ile Trp Tyr Leu  Arg Asp His
        995                 1000                1005

Asn Asn  Ser Ile Lys Ile Val  Thr Pro Asp Tyr Ile  Ala Phe Asn
    1010                 1015                 1020

Gly Trp  Asn Leu Ile Thr Ile  Thr Asn Asn Arg Ser  Lys Gly Ser
    1025                 1030                 1035

Ile Val  Tyr Val Asn Gly Ser  Lys Ile Glu Glu Lys  Asp Ile Ser
    1040                 1045                 1050

Ser Ile  Trp Asn Thr Glu Val  Asp Asp Pro Ile Ile  Phe Arg Leu
    1055                 1060                 1065

Lys Asn  Asn Arg Asp Thr Gln  Ala Phe Thr Leu Leu  Asp Gln Phe
    1070                 1075                 1080

Ser Ile  Tyr Arg Lys Glu Leu  Asn Gln Asn Glu Val  Val Lys Leu
    1085                 1090                 1095

Tyr Asn  Tyr Tyr Phe Asn Ser  Asn Tyr Ile Arg Asp  Ile Trp Gly
    1100                 1105                 1110

Asn Pro  Leu Gln Tyr Asn Lys  Lys Tyr Tyr Leu Gln  Thr Gln Asp
    1115                 1120                 1125

Lys Pro  Gly Lys Gly Leu Ile  Arg Glu Tyr Trp Ser  Ser Phe Gly
    1130                 1135                 1140

Tyr Asp  Tyr Val Ile Leu Ser  Asp Ser Lys Thr Ile  Thr Phe Pro
    1145                 1150                 1155

Asn Asn  Ile Arg Tyr Gly Ala  Leu Tyr Asn Gly Ser  Lys Val Leu
    1160                 1165                 1170

Ile Lys  Asn Ser Lys Lys Leu  Asp Gly Leu Val Arg  Asn Lys Asp
    1175                 1180                 1185

Phe Ile  Gln Leu Glu Ile Asp  Gly Tyr Asn Met Gly  Ile Ser Ala
    1190                 1195                 1200

Asp Arg  Phe Asn Glu Asp Thr  Asn Tyr Ile Gly Thr  Thr Tyr Gly
    1205                 1210                 1215

Thr Thr  His Asp Leu Thr Thr  Asp Phe Glu Ile Ile  Gln Arg Gln
    1220                 1225                 1230

Glu Lys  Tyr Arg Asn Tyr Cys  Gln Leu Lys Thr Pro  Tyr Asn Ile
    1235                 1240                 1245

Phe His  Lys Ser Gly Leu Met  Ser Thr Glu Thr Ser  Lys Pro Thr
    1250                 1255                 1260

Phe His  Asp Tyr Arg Asp Trp  Val Tyr Ser Ser Ala  Trp Tyr Phe
    1265                 1270                 1275

Gln Asn  Tyr Glu Asn Leu Asn  Leu Arg Lys His Thr  Lys Thr Asn
    1280                 1285                 1290

Trp Tyr  Phe Ile Pro Lys Asp  Glu Gly Trp Asp Glu  Asp
    1295                 1300                 1305
```

<210> SEQ ID NO 60
<211> LENGTH: 3888
<212> TYPE: DNA
<213> ORGANISM: Artificial Sequence
<220> FEATURE:
<223> OTHER INFORMATION: Nucleotide Sequence of mrBoNT/A

<400> SEQUENCE: 60

```
atgccattcg tcaacaagca attcaactac aaagacccag tcaacggcgt cgacatcgca      60

tacatcaaga ttccgaacgc cggtcaaatg cagccggtta aggcttttaa gatccacaac     120
```

```
aagatttggg ttatcccgga gcgtgacacc ttcacgaacc cggaagaagg cgatctgaac    180
ccgccaccgg aagcgaagca agtccctgtc agctactacg attcgacgta cctgagcacg    240
gataacgaaa aagataacta cctgaaaggt gtgaccaagc tgttcgaacg tatctacagc    300
acggatctgg gtcgcatgct gctgactagc attgttcgcg gtatcccgtt ctggggtggt    360
agcacgattg acaccgaact gaaggttatc gacactaact gcattaacgt tattcaaccg    420
gatggtagct atcgtagcga agagctgaat ctggtcatca ttggcccgag cgcagacatt    480
atccaattcg agtgcaagag ctttggtcac gaggttctga atctgacccg caatggctat    540
ggtagcaccc agtacattcg tttttcgccg gattttacct tcggctttga agagagcctg    600
gaggttgata ccaatccgtt gctgggtgcg ggcaaattcg ctaccgatcc ggctgtcacg    660
ctggcccatg aactgatcca cgcaggccac cgcctgtacg gcattgccat caacccaaac    720
cgtgtgttca aggttaatac gaatgcatac tacgagatga gcggcctgga agtcagcttc    780
gaagaactgc gcaccttcgg tggccatgac gctaaattca ttgacagctt gcaagagaat    840
gagttccgtc tgtactacta taacaaattc aaagacattg caagcacgtt gaacaaggcc    900
aaaagcatcg ttggtactac cgcgtcgttg cagtatatga agaatgtgtt taaagagaag    960
tacctgctgt ccgaggatac ctccggcaag tttagcgttg ataagctgaa gtttgacaaa   1020
ctgtacaaga tgctgaccga gatttacacc gaggacaact ttgtgaaatt cttcaaagtg   1080
ttgaatcgta aaacctatct gaattttgac aaagcggttt tcaagattaa catcgtgccg   1140
aaggtgaact acaccatcta tgacggtttt aacctgcgta acaccaacct ggcggcgaac   1200
tttaacggtc agaatacgga aatcaacaac atgaatttca cgaagttgaa gaacttcacg   1260
ggtctgttcg agttctataa gctgctgtgc gtgcgcggta tcatcaccag caaaaccaaa   1320
agcctggaca aaggctacaa caaggcgctg aatgacctgt gcattaaggt aaacaattgg   1380
gatctgttct tttcgccatc cgaagataat tttaccaacg acctgaacaa gggtgaagaa   1440
atcaccagcg atacgaatat tgaagcagcg gaagagaata tcagcctgga tctgatccag   1500
cagtactatc tgacctttaa cttcgacaat gaaccggaga acattagcat tgagaatctg   1560
agcagcgaca ttatcggtca gctggaactg atgccgaata tcgaacgttt cccgaacggc   1620
aaaaagtacg agctggacaa gtacactatg ttccattacc tgcgtgcaca ggagtttgaa   1680
cacggtaaaa gccgtatcgc gctgaccaac agcgttaacg aggccctgct gaacccgagc   1740
cgtgtctata ccttcttcag cagcgactat gttaagaaag tgaacaaagc cactgaggcc   1800
gcgatgttcc tgggctgggt ggaacagctg gtatatgact tcacggacga gacgagcgaa   1860
gtgagcacta ccgacaaaat tgctgatatt accatcatta tcccgtatat tggtccggca   1920
ctgaacattg gcaacatgct gtacaaagac gattttgtgg gtgccctgat cttctccggt   1980
gccgtgattc tgctggagtt cattccggag attgcgatcc cggtgttggg taccttcgcg   2040
ctggtgtcct acatcgcgaa taaggttctg acggttcaga ccatcgataa cgcgctgtcg   2100
aaacgtaatg aaaaatggga cgaggtttac aaatacattg ttacgaattg gctggcgaaa   2160
gtcaataccc agatcgacct gatccgtaag aaaatgaaag aggcgctgga gaatcaggcg   2220
gaggccacca aagcaattat caactaccaa tacaaccagt acacggaaga agagaagaat   2280
aacattaact tcaatatcga tgatttgagc agcaagctga atgaatctat caacaaagcg   2340
atgatcaata tcaacaagtt tttgaatcag tgtagcgttt cgtacctgat gaatagcatg   2400
attccgtatg gcgtcaaacg tctggaggac ttcgacgcca gcctgaaaga tgcgttgctg   2460
aaatacattt acgacaatcg tggtacgctg attggccaag ttgaccgctt gaaagacaaa   2520
```

```
gttaacaata ccctgagcac cgacatccca tttcaactga gcaagtatgt tgataatcaa   2580

cgtctgttga gcactttcac cgagtatatc aaaaacatca tcaatactag cattctgaac   2640

ctgcgttacg agagcaagca tctgattgat ctgagccgtt atgctagcaa gatcaacatc   2700

ggtagcaagg tcaattttga cccgatcgat aagaaccaga tccagctgtt taatctggaa   2760

tcgagcaaaa ttgaggttat cctgaaaaag gccattgtct acaactccat gtacgagaat   2820

ttctccacca gcttctggat tcgcatcccg aaatacttca acaagattag cctgaacaac   2880

gagtatacta tcatcaactg tatggagaac aacagcggtt ggaaggtgtc tctgaactat   2940

ggtgagatca tttggacctt gcaggacacc aaagagatca agcagcgcgt cgtgttcaag   3000

tactctcaaa tgatcaacat ttccgattac attaatcgtt ggatcttcgt gaccattacg   3060

aataaccgtc tgaataagag caagatttac atcaatggtc gcttgatcga tcagaaaccg   3120

attagcaacc tgggtaatat ccacgcaagc aacaagatta tgttcaaatt ggacggttgc   3180

cgcgataccc atcgttatat ctggatcaag tatttcaacc tgtttgataa agaactgaat   3240

gagaaggaga tcaaagattt gtatgacaac caatctaaca gcggcatttt gaaggacttc   3300

tggggcgatt atctgcaata cgataagccg tactatatgc tgaacctgta tgatccgaac   3360

aaatatgtgg atgtcaataa tgtgggtatt cgtggttaca tgtatttgaa gggtccgcgt   3420

ggcagcgtta tgacgaccaa catttacctg aactctagcc tgtaccgtgg tacgaaattc   3480

atcattaaga aatatgccag cggcaacaaa gataacattg tgcgtaataa cgatcgtgtc   3540

tacatcaacg tggtcgtgaa gaataaagag taccgtctgg cgaccaacgc ttcgcaggcg   3600

ggtgttgaga aaattctgag cgcgttggag atccctgatg tcggtaatct gagccaagtc   3660

gtggttatga agagcaagaa cgacaagggt atcactaaca agtgcaagat gaacctgcaa   3720

gacaacaatg gtaacgacat cggctttatt ggtttccacc agttcaacaa tattgctaaa   3780

ctggtagcga gcaattggta caatcgtcag attgagcgca gcagccgtac tttgggctgt   3840

agctgggagt ttatcccggt cgatgatggt tggggcgaac gtccgctg                3888
```

```
<210> SEQ ID NO 61
<211> LENGTH: 1296
<212> TYPE: PRT
<213> ORGANISM: Artificial Sequence
<220> FEATURE:
<223> OTHER INFORMATION: Polypeptide Sequence of mrBoNT/A

<400> SEQUENCE: 61

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
```

```
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540
```

```
Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Lys Ile Ser Leu Asn Asn
945                 950                 955                 960
```

```
Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                1015                1020

Leu Asn  Lys Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Lys Ile
    1040                1045                1050

Met Phe  Lys Leu Asp Gly Cys  Arg Asp Thr His Arg  Tyr Ile Trp
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Lys Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260

Ser Asn  Trp Tyr Asn Arg Gln  Ile Glu Arg Ser Ser  Arg Thr Leu
    1265                1270                1275

Gly Cys  Ser Trp Glu Phe Ile  Pro Val Asp Asp Gly  Trp Gly Glu
    1280                1285                1290

Arg Pro  Leu
    1295
```

<210> SEQ ID NO 62
<211> LENGTH: 1296
<212> TYPE: PRT
<213> ORGANISM: Clostridium botulinum

<400> SEQUENCE: 62

```
Met Pro Phe Val Asn Lys Gln Phe Asn Tyr Lys Asp Pro Val Asn Gly
1               5                   10                  15
```

```
Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430
```

```
Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
```

```
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                1015                1020

Leu Asn  Asn Ser Lys Ile Tyr  Ile Asn Gly Arg Leu  Ile Asp Gln
    1025                1030                1035

Lys Pro  Ile Ser Asn Leu Gly  Asn Ile His Ala Ser  Asn Asn Ile
    1040                1045                1050

Met Phe  Lys Leu Asp Gly Cys  Arg Asp Thr His Arg  Tyr Ile Trp
    1055                1060                1065

Ile Lys  Tyr Phe Asn Leu Phe  Asp Lys Glu Leu Asn  Glu Lys Glu
    1070                1075                1080

Ile Lys  Asp Leu Tyr Asp Asn  Gln Ser Asn Ser Gly  Ile Leu Lys
    1085                1090                1095

Asp Phe  Trp Gly Asp Tyr Leu  Gln Tyr Asp Lys Pro  Tyr Tyr Met
    1100                1105                1110

Leu Asn  Leu Tyr Asp Pro Asn  Lys Tyr Val Asp Val  Asn Asn Val
    1115                1120                1125

Gly Ile  Arg Gly Tyr Met Tyr  Leu Lys Gly Pro Arg  Gly Ser Val
    1130                1135                1140

Met Thr  Thr Asn Ile Tyr Leu  Asn Ser Ser Leu Tyr  Arg Gly Thr
    1145                1150                1155

Lys Phe  Ile Ile Lys Lys Tyr  Ala Ser Gly Asn Lys  Asp Asn Ile
    1160                1165                1170

Val Arg  Asn Asn Asp Arg Val  Tyr Ile Asn Val Val  Val Lys Asn
    1175                1180                1185

Lys Glu  Tyr Arg Leu Ala Thr  Asn Ala Ser Gln Ala  Gly Val Glu
    1190                1195                1200

Lys Ile  Leu Ser Ala Leu Glu  Ile Pro Asp Val Gly  Asn Leu Ser
    1205                1210                1215

Gln Val  Val Val Met Lys Ser  Lys Asn Asp Gln Gly  Ile Thr Asn
    1220                1225                1230

Lys Cys  Lys Met Asn Leu Gln  Asp Asn Asn Gly Asn  Asp Ile Gly
    1235                1240                1245

Phe Ile  Gly Phe His Gln Phe  Asn Asn Ile Ala Lys  Leu Val Ala
    1250                1255                1260
```

```
Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295
```

<210> SEQ ID NO 63
<211> LENGTH: 1304
<212> TYPE: PRT
<213> ORGANISM: Artificial Sequence
<220> FEATURE:
<223> OTHER INFORMATION: Polypeptide Sequence of mrBoNT/AB

<400> SEQUENCE: 63

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320
```

```
Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735
```

```
Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                 1005

Ser Glu  Tyr Ile Asn Arg Trp  Phe Phe Val Thr Ile  Thr Asn Asn
    1010                 1015                 1020

Leu Asn  Asn Ala Lys Ile Tyr  Ile Asn Gly Lys Leu  Glu Ser Asn
    1025                 1030                 1035

Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
```

```
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Met Lys  Leu Phe Leu Ala Pro  Ile Tyr Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230

Cys Gln  Leu Leu Phe Lys Lys  Asp Glu Glu Ser Thr  Asp Glu Ile
    1235                1240                1245

Gly Leu  Ile Gly Ile His Arg  Phe Tyr Glu Ser Gly  Ile Val Phe
    1250                1255                1260

Glu Glu  Tyr Lys Asp Tyr Phe  Cys Ile Ser Lys Trp  Tyr Leu Lys
    1265                1270                1275

Glu Val  Lys Arg Lys Pro Tyr  Asn Leu Lys Leu Gly  Cys Asn Trp
    1280                1285                1290

Gln Phe  Ile Pro Lys Asp Glu  Gly Trp Thr Glu
    1295                1300


<210> SEQ ID NO 64
<211> LENGTH: 1304
<212> TYPE: PRT
<213> ORGANISM: Artificial Sequence
<220> FEATURE:
<223> OTHER INFORMATION: Polypeptide Sequence of mrBoNT/AB(0)

<400> SEQUENCE: 64

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
```

```
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620
```

```
Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
                965                 970                 975

Ile Ser Ile Arg Gly Asn Arg Ile Ile Trp Thr Leu Ile Asp Ile Asn
            980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035
```

```
Thr Asp  Ile Lys Asp Ile Arg  Glu Val Ile Ala Asn  Gly Glu Ile
    1040                 1045                 1050

Ile Phe  Lys Leu Asp Gly Asp  Ile Asp Arg Thr Gln  Phe Ile Trp
    1055                 1060                 1065

Met Lys  Tyr Phe Ser Ile Phe  Asn Thr Glu Leu Ser  Gln Ser Asn
    1070                 1075                 1080

Ile Glu  Glu Arg Tyr Lys Ile  Gln Ser Tyr Ser Glu  Tyr Leu Lys
    1085                 1090                 1095

Asp Phe  Trp Gly Asn Pro Leu  Met Tyr Asn Lys Glu  Tyr Tyr Met
    1100                 1105                 1110

Phe Asn  Ala Gly Asn Lys Asn  Ser Tyr Ile Lys Leu  Lys Lys Asp
    1115                 1120                 1125

Ser Pro  Val Gly Glu Ile Leu  Thr Arg Ser Lys Tyr  Asn Gln Asn
    1130                 1135                 1140

Ser Lys  Tyr Ile Asn Tyr Arg  Asp Leu Tyr Ile Gly  Glu Lys Phe
    1145                 1150                 1155

Ile Ile  Arg Arg Lys Ser Asn  Ser Gln Ser Ile Asn  Asp Asp Ile
    1160                 1165                 1170

Val Arg  Lys Glu Asp Tyr Ile  Tyr Leu Asp Phe Phe  Asn Leu Asn
    1175                 1180                 1185

Gln Glu  Trp Arg Val Tyr Thr  Tyr Lys Tyr Phe Lys  Lys Glu Glu
    1190                 1195                 1200

Met Lys  Leu Phe Leu Ala Pro  Ile Tyr Asp Ser Asp  Glu Phe Tyr
    1205                 1210                 1215

Asn Thr  Ile Gln Ile Lys Glu  Tyr Asp Glu Gln Pro  Thr Tyr Ser
    1220                 1225                 1230

Cys Gln  Leu Leu Phe Lys Lys  Asp Glu Glu Ser Thr  Asp Glu Ile
    1235                 1240                 1245

Gly Leu  Ile Gly Ile His Arg  Phe Tyr Glu Ser Gly  Ile Val Phe
    1250                 1255                 1260

Glu Glu  Tyr Lys Asp Tyr Phe  Cys Ile Ser Lys Trp  Tyr Leu Lys
    1265                 1270                 1275

Glu Val  Lys Arg Lys Pro Tyr  Asn Leu Lys Leu Gly  Cys Asn Trp
    1280                 1285                 1290

Gln Phe  Ile Pro Lys Asp Glu  Gly Trp Thr Glu
    1295                 1300
```

<210> SEQ ID NO 65
<211> LENGTH: 1296
<212> TYPE: PRT
<213> ORGANISM: Artificial Sequence
<220> FEATURE:
<223> OTHER INFORMATION: Polypeptide Sequence of mrBoNT/A(0)

<400> SEQUENCE: 65

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80
```

```
Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Gln
    210                 215                 220

Leu Ile Tyr Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
```

```
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
    530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Lys His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925
```

```
Lys Lys Ala Ile Val Tyr Asn Ser Met Tyr Glu Asn Phe Ser Thr Ser
    930                 935                 940

Phe Trp Ile Arg Ile Pro Lys Tyr Phe Asn Lys Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Lys Glu
            980                 985                 990

Ile Lys Gln Arg Val Val Phe Lys  Tyr Ser Gln Met Ile  Asn Ile Ser
        995                 1000                1005

Asp Tyr  Ile Asn Arg Trp Ile  Phe Val Thr Ile Thr  Asn Asn Arg
    1010                 1015                 1020

Leu Asn  Lys Ser Lys Ile Tyr  Ile Asn Gly Arg Leu  Ile Asp Gln
    1025                 1030                 1035

Lys Pro  Ile Ser Asn Leu Gly  Asn Ile His Ala Ser  Asn Lys Ile
    1040                 1045                 1050

Met Phe  Lys Leu Asp Gly Cys  Arg Asp Thr His Arg  Tyr Ile Trp
    1055                 1060                 1065

Ile Lys  Tyr Phe Asn Leu Phe  Asp Lys Glu Leu Asn  Glu Lys Glu
    1070                 1075                 1080

Ile Lys  Asp Leu Tyr Asp Asn  Gln Ser Asn Ser Gly  Ile Leu Lys
    1085                 1090                 1095

Asp Phe  Trp Gly Asp Tyr Leu  Gln Tyr Asp Lys Pro  Tyr Tyr Met
    1100                 1105                 1110

Leu Asn  Leu Tyr Asp Pro Asn  Lys Tyr Val Asp Val  Asn Asn Val
    1115                 1120                 1125

Gly Ile  Arg Gly Tyr Met Tyr  Leu Lys Gly Pro Arg  Gly Ser Val
    1130                 1135                 1140

Met Thr  Thr Asn Ile Tyr Leu  Asn Ser Ser Leu Tyr  Arg Gly Thr
    1145                 1150                 1155

Lys Phe  Ile Ile Lys Lys Tyr  Ala Ser Gly Asn Lys  Asp Asn Ile
    1160                 1165                 1170

Val Arg  Asn Asn Asp Arg Val  Tyr Ile Asn Val Val  Val Lys Asn
    1175                 1180                 1185

Lys Glu  Tyr Arg Leu Ala Thr  Asn Ala Ser Gln Ala  Gly Val Glu
    1190                 1195                 1200

Lys Ile  Leu Ser Ala Leu Glu  Ile Pro Asp Val Gly  Asn Leu Ser
    1205                 1210                 1215

Gln Val  Val Val Met Lys Ser  Lys Asn Asp Lys Gly  Ile Thr Asn
    1220                 1225                 1230

Lys Cys  Lys Met Asn Leu Gln  Asp Asn Asn Gly Asn  Asp Ile Gly
    1235                 1240                 1245

Phe Ile  Gly Phe His Gln Phe  Asn Asn Ile Ala Lys  Leu Val Ala
    1250                 1255                 1260

Ser Asn  Trp Tyr Asn Arg Gln  Ile Glu Arg Ser Ser  Arg Thr Leu
    1265                 1270                 1275

Gly Cys  Ser Trp Glu Phe Ile  Pro Val Asp Asp Gly  Trp Gly Glu
    1280                 1285                 1290

Arg Pro  Leu
    1295
```

<210> SEQ ID NO 66
<211> LENGTH: 7

<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 66

Xaa Asp Xaa Xaa Xaa Leu Leu
1               5

<210> SEQ ID NO 67
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 67

Xaa Glu Xaa Xaa Xaa Leu Leu
1               5

<210> SEQ ID NO 68
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 68

Xaa Glu Xaa Xaa Xaa Ile Leu
1               5

<210> SEQ ID NO 69
<211> LENGTH: 7
<212> TYPE: PRT
<213> ORGANISM: Artificial Sequence
<220> FEATURE:
<223> OTHER INFORMATION: Leucine-Based Motif
<220> FEATURE:
<221> NAME/KEY: SITE
<222> LOCATION: (1)..(1)
<223> OTHER INFORMATION: Xaa can be any naturally occurring amino acid
<220> FEATURE:
<221> NAME/KEY: SITE
<222> LOCATION: (3)..(5)
<223> OTHER INFORMATION: Xaa can be any naturally occurring amino acid

<400> SEQUENCE: 69

Xaa Glu Xaa Xaa Xaa Leu Met 1 5

<210> SEQ ID NO 70
<211> LENGTH: 4
<212> TYPE: PRT
<213> ORGANISM: Artificial Sequence
<220> FEATURE:
<223> OTHER INFORMATION: Tyrosine-Based Motif
<220> FEATURE:
<221> NAME/KEY: SITE
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa is a hydrophobic amino acid

<400> SEQUENCE: 70

Tyr Xaa Xaa Xaa
1

<210> SEQ ID NO 71
<211> LENGTH: 6
<212> TYPE: PRT
<213> ORGANISM: Clostridium botulinum

<400> SEQUENCE: 71

Asn Ile Ile Asn Thr Ser
1 5

<210> SEQ ID NO 72
<211> LENGTH: 6
<212> TYPE: PRT
<213> ORGANISM: Clostridium botulinum

<400> SEQUENCE: 72

Asn Ile Val Asn Thr Ser
1 5

<210> SEQ ID NO 73
<211> LENGTH: 6
<212> TYPE: PRT
<213> ORGANISM: Clostridium botulinum

<400> SEQUENCE: 73

Asn Ile Thr Asn Ala Ser
1 5

<210> SEQ ID NO 74
<211> LENGTH: 6
<212> TYPE: PRT
<213> ORGANISM: Clostridium botulinum

<400> SEQUENCE: 74

Asn Ile Thr Asn Thr Ser
1 5

<210> SEQ ID NO 75
<211> LENGTH: 6
<212> TYPE: PRT
<213> ORGANISM: Clostridium botulinum

<400> SEQUENCE: 75

Glu Ile Leu Asn Asn Ile
1 5

-continued

```
<210> SEQ ID NO 76
<211> LENGTH: 6
<212> TYPE: PRT
<213> ORGANISM: Clostridium botulinum

<400> SEQUENCE: 76

Asp Ile Leu Asn Asn Ile
1               5
```